United States Patent
Zhao et al.

(10) Patent No.: US 9,896,432 B2
(45) Date of Patent: Feb. 20, 2018

(54) SOMATOSTATIN MODULATORS AND USES THEREOF

(71) Applicant: Crinetics Pharmaceuticals, Inc., San Diego, CA (US)

(72) Inventors: Jian Zhao, San Diego, CA (US);
Sangdon Han, San Diego, CA (US);
Sun Hee Kim, San Diego, CA (US);
Shimiao Wang, San Diego, CA (US);
Yunfei Zhu, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/647,758

(22) Filed: Jul. 12, 2017

(65) Prior Publication Data

US 2018/0016252 A1 Jan. 18, 2018

Related U.S. Application Data

(60) Provisional application No. 62/362,493, filed on Jul. 14, 2016, provisional application No. 62/411,338, filed on Oct. 21, 2016.

(51) Int. Cl.
| | |
|---|---|
| *C07D 401/04* | (2006.01) |
| *C07D 471/04* | (2006.01) |
| *C07D 405/14* | (2006.01) |
| *C07D 401/14* | (2006.01) |
| *C07D 498/04* | (2006.01) |
| *C07D 413/14* | (2006.01) |

(52) U.S. Cl.
CPC ......... *C07D 401/04* (2013.01); *C07D 401/14* (2013.01); *C07D 405/14* (2013.01); *C07D 413/14* (2013.01); *C07D 471/04* (2013.01); *C07D 498/04* (2013.01)

(58) Field of Classification Search
CPC ............ C07D 401/0414; C07D 471/04; C07D 405/14; C07D 413/14; C07D 498/04
See application file for complete search history.

(56) References Cited

U.S. PATENT DOCUMENTS

| | | |
|---|---|---|
| 7,115,634 B2 | 10/2006 | Thurieau et al. |
| 7,767,817 B2 | 8/2010 | Wang et al. |
| 9,120,749 B2 | 9/2015 | Matsuo et al. |
| 9,309,222 B2 * | 4/2016 | Leonard ............... C07D 401/06 |
| 2003/0153553 A1 | 8/2003 | Mattei et al. |
| 2005/0009815 A1 | 1/2005 | Devita et al. |
| 2009/0258853 A1 | 10/2009 | Eastman et al. |
| 2015/0232478 A1 | 8/2015 | Ishida et al. |
| 2015/0239900 A1 | 8/2015 | Li et al. |
| 2015/0284337 A1 | 10/2015 | Aubele et al. |
| 2017/0001966 A1 | 1/2017 | Zhao et al. |
| 2017/0002001 A1 | 1/2017 | Zhu et al. |

FOREIGN PATENT DOCUMENTS

| | | |
|---|---|---|
| KR | 20160062023 A | 6/2016 |
| WO | WO-03045920 A1 | 6/2003 |
| WO | WO-2008051272 A2 | 5/2008 |
| WO | WO-2010041054 A1 | 4/2010 |
| WO | WO-2012162254 A1 | 11/2012 |
| WO | WO-2016049568 A1 | 3/2016 |

OTHER PUBLICATIONS

Cescato, Mol Endocrinol, Jan. 2010, 24(1), 240-249.*
Gradiz, Scientific Reports, Feb. 2016, 1-14.*
Prasoon, Neuropeptides, 49, 47-54, 2015.*
SOng, Org Lett, 18, 5328-5331, 2016.*
Berge et al. Pharmaceutical Salts. Journal of Pharmaceutical Sciences 66(1):1-19 (Jan. 1977).
Brazeau et al. Hypothalamic polypeptide that inhibits the secretion of immunoreactive pituitary growth hormone. Science 179:77-79 (1973).
Bundgaard. Advanced Drug Delivery Review 8:1-38 (1992).
Bundgaard. Design and Application of Prodrugs. Textbook of Drug Design and Development. Krosgaard-Larsen and Bundgaard. Chapter 5. pp. 113-191 (1991).
Bundgaard. Design of Prodrugs. Elseview (12 pgs.) (1985).
Esch et al. Primary structure of ovine hypothalamic somatostatin-28 and somatostatin-25. PNAS USA 77:6827-6831 (1980).
Patel et al. Somatostatin receptors. Trends Endocrinol Metab 8:398-405 (1997).
Pradayrol et al. N-terminally extended somatostatin: the primary structure of somatostatin-28. FEBS Letters 109:55-58 (1980).
Reisine et al. Molecular biology of somatostatin receptors. Endocr Rev 16:427-442 (1995).
Science IP CAS Search, May 23, 2016 (291 pgs).
Stahl et al. Handbook of Pharmaceutical Salts. Verlag Helvetica Chimica Acta, Zurich, 2002.
Widder et al. Section III: Prodrugs Kinetics. Method in Enzymology. 112:309-396 (1985).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).
PCT/US2017/041694 International Search Report and Written Opinion dated Dec. 12, 2017.

* cited by examiner

*Primary Examiner* — D M Seaman
(74) *Attorney, Agent, or Firm* — Wilson Sonsini Goodrich & Rosati

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

20 Claims, No Drawings

SOMATOSTATIN MODULATORS AND USES THEREOF

CROSS-REFERENCE

This application claims benefit of U.S. Provisional Patent Application No. 62/362,493, filed on Jul. 14, 2016; and U.S. Provisional Patent Application No. 62/411,338, filed on Oct. 21, 2016; each of which is incoporated herein by reference in its entirety.

STATEMENT AS TO FEDERALLY SPONSORED RESEARCH

This invention was made with the support of the United States government under SBIR Grant No. 1R44NS092231-01 by the National Institutes of Health.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

SUMMARY OF THE INVENTION

Compounds described herein are somatostatin modulator compounds. In some embodiments, compounds described herein modulate one or more of the subtype somatostatin receptor proteins. In some embodiments, compounds described herein modulate two or more of the subtype somatostatin receptor proteins. Somatostatin peptide analogs, such as octreotide and pasireotide, formulated as depot injections, are routinely used to normalize hormone levels for the treatment of GH secreting adenomas, pancreatic neuroendocrine tumors, and carcinoid tumors. Unfortunately, these analogs are only effective in about half of acromegalic patients with GH adenomas, and patients with carcinoid tumors frequently become resistant to therapy due to internalization and desensitization of the SST2A receptor. In addition, these peptide drugs are extremely expensive and require frequent doctor's office visits for painful injections that can lead to injection site reactions. Compounds described herein are molecules that are structurally different from peptide analogs. The compounds described herein are somatostatin modulators that are potent inhibitors of hormone secretion.

In one aspect, described herein is a compound of Formula (A), or a pharmaceutically acceptable salt, pharmaceutically acceptable solvate, diastereomeric mixture, enantiomer or prodrug thereof:

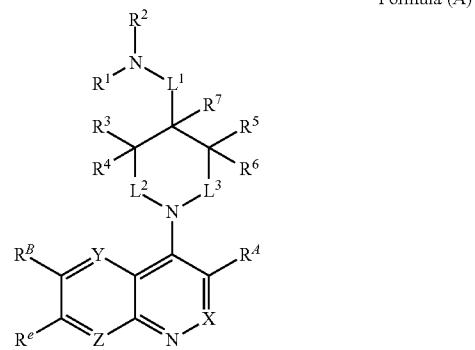

Formula (A)

wherein:

$R^A$ is hydrogen, halogen, unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, or a unsubstituted or substituted ring A that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring A is substituted then the ring A is substituted with m $R^a$ and n $R^b$;

each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$ or —C(=NOR$^{15}$)R$^{15}$;

m is 1 or 2; n is 0, 1 or 2;

or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;

$R^B$ is unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, or a unsubstituted or substituted ring B that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring B is substituted then the ring B is substituted with p $R^c$ and q $R^d$;

each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted monocyclic heterocycle, —CN, —OH, —OR$^{14}$, —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C(=NOR$^{15}$)R$^{15}$, N(R$^{15}$)SO$_2$R$^{14}$, —C(=O)NR$^{15}$S(=O)$_2$R$^{14}$, —S(=O)$_2$NR$^{15}$C(=O)R$^{14}$, —C(=NR$^{15}$)N(R$^{15}$)$_2$, —NR$^{15}$C(=NR$^{15}$)N(R$^{15}$)$_2$, —NR$^{15}$C(=CR$^{14}$R$^{15}$)N(R$^{15}$)$_2$, —C(=O)NR$^{15}$C(=NR$^{15}$)N(R$^{15}$)$_2$ or, —C(=O)NR$^{15}$C(=CR$^{14}$R$^{15}$)N(R$^{15}$)$_2$;

p is 1 or 2; q is 0, 1 or 2;

or if one R$^c$ and one R$^d$ are on adjacent atoms of ring B then the adjacent R$^c$ and R$^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is CR$^f$ or N;
Y is CR$^f$ or N;
Z is CR$^f$ or N;

R$^e$ is hydrogen, halogen, unsubstituted or substituted C$_1$-C$_6$alkyl, unsubstituted or substituted C$_1$-C$_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;

each R$^f$ is independently hydrogen, halogen, unsubstituted or substituted C$_1$-C$_6$alkyl, unsubstituted or substituted C$_1$-C$_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;

R$^1$ and R$^2$ are independently hydrogen, unsubstituted or substituted C$_1$-C$_6$alkyl, unsubstituted or substituted C$_1$-C$_6$heteroalkyl, unsubstituted or substituted C$_1$-C$_6$fluoroalkyl, unsubstituted or substituted C$_3$-C$_6$cycloalkyl or substituted or unsubstituted C$_2$-C$_{10}$heterocycloalkyl;

or R$^1$ and R$^2$ are taken together with the nitrogen atom to which they are attached to form ring C that is an unsubstituted or substituted N-containing C$_2$-C$_8$heterocycloalkyl;

R$^3$ and R$^5$ are each independently selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted C$_1$-C$_6$alkyl, unsubstituted or substituted C$_1$-C$_6$heteroalkyl, and unsubstituted or substituted C$_1$-C$_6$fluoroalkyl;

or R$^3$ and R$^5$ are taken together to form a bond, or C$_1$-C$_2$alkylene;

or R$^2$ and R$^5$ are taken together with the intervening atoms to which they are attached to form an unsubstituted or substituted 4-7 membered saturated N-containing heterocyclic ring;

R$^4$ and R$^6$ are each independently selected from the group consisting of hydrogen, unsubstituted or substituted C$_1$-C$_6$alkyl, and unsubstituted or substituted C$_1$-C$_6$fluoroalkyl;

R$^7$ is hydrogen, unsubstituted or substituted C$_1$-C$_6$alkyl, or unsubstituted or substituted C$_1$-C$_6$fluoroalkyl;

or R$^2$ and R$^7$ are taken together with the intervening atoms to which they are attached to form an unsubstituted or substituted N-containing C$_2$-C$_8$heterocycloalkyl;

L$^1$ is absent or —CR$^8$R$^9$—;
L$^2$ is —CR$^{10}$R$^{11}$— or absent;
L$^3$ is —(CR$^{12}$R$^{13}$)$_t$- or absent;

t is 1 or 2;

each R$^8$, R$^9$, R$^{10}$, R$^{11}$, R$^{12}$, and R$^{13}$ is independently selected from the group consisting of hydrogen, unsubstituted or substituted C$_1$-C$_6$alkyl, and unsubstituted or substituted C$_1$-C$_6$fluoroalkyl;

or R$^5$ and R$^8$ are taken together with the intervening atoms to which they are attached to form an unsubstituted or substituted monocyclic carbocyclic or unsubstituted or substituted monocyclic heterocyclic ring;

or R$^5$ and R$^{13}$ are taken together with the intervening atoms to which they are attached to form an unsubstituted or substituted monocyclic carbocyclic or unsubstituted or substituted monocyclic heterocyclic ring;

or R$^7$ and R$^8$ are taken together with the intervening atoms to which they are attached to form an unsubstituted or substituted monocyclic carbocyclic or unsubstituted or substituted monocyclic heterocyclic ring;

each R$^{14}$ is independently selected from unsubstituted or substituted C$_1$-C$_6$alkyl, unsubstituted or substituted C$_1$-C$_6$heteroalkyl, unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

each R$^{15}$ is independently selected from hydrogen, unsubstituted or substituted C$_1$-C$_6$alkyl, unsubstituted or substituted C$_1$-C$_6$heteroalkyl, unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

or two R$^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more R$^5$ groups independently selected from the group consisting of halogen, C$_1$-C$_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

each R$^{16}$ is independently selected from hydrogen, C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl; or two R$^{16}$ groups are taken together with the N atom to which they are attached to form a N-containing heterocycle;

each R$^{17}$ is independently selected from C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl.

In one aspect, the compound of Formula (A) has the structure of Formula (I), or a pharmaceutically acceptable salt, pharmaceutically acceptable solvate, diastereomeric mixture, enantiomer or prodrug thereof:

Formula (I)

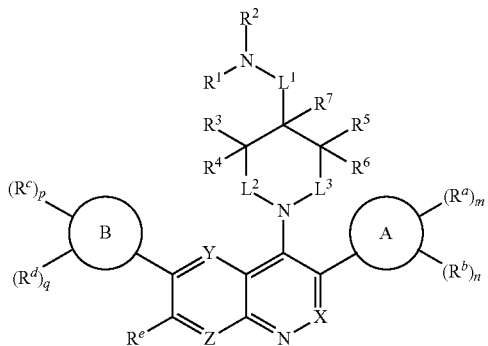

wherein:
ring A is a monocyclic carbocycle, bicyclic carbocycle, monocyclic heterocycle, or bicyclic heterocycle;
  each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$ or —C(=NOR$^{15}$)R$^{15}$;
  m is 1 or 2; n is 0, 1 or 2;
  or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;
ring B is a monocyclic carbocycle, bicyclic carbocycle, monocyclic heterocycle, or bicyclic heterocycle;
  each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —OR$^{14}$, —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C(=NOR$^{15}$)R$^{15}$, N(R$^{15}$)SO$_2$R$^{14}$, —C(=O)NR$^{15}$S(=O)$_2$R$^{14}$, —S(=O)$_2$NR$^{15}$C(=O)R$^{14}$, —C(=NR$^{15}$)N(R$^{15}$)$_2$, —NR$^{15}$C(=NR$^{15}$)N(R$^{15}$)$_2$, —NR$^{15}$C(=CR$^{14}$R$^{15}$)N(R$^{15}$)$_2$, —C(=O)NR$^{15}$C(=NR$^{15}$)N(R$^{15}$)$_2$ or, —C(=O)NR$^{15}$C(=CR$^{14}$R$^{15}$)N(R$^{15}$)$_2$;
  p is 1 or 2; q is 0, 1 or 2;
  or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is CR$^f$ or N;
Y is CR$^f$ or N;
Z is CR$^f$ or N;
$R^e$ is hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;
each $R^f$ is independently hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;
$R^1$ and $R^2$ are independently hydrogen, unsubstituted or substituted $C_1$-$C_6$alkyl, unsubstituted or substituted $C_1$-$C_6$heteroalkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;
or $R^1$ and $R^2$ are taken together with the nitrogen atom to which they are attached to form ring C that is an unsubstituted or substituted N-containing $C_2$-$C_8$heterocycloalkyl;
$R^3$ and $R^5$ are each independently selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted $C_1$-$C_6$alkyl, unsubstituted or substituted $C_1$-$C_6$heteroalkyl, and unsubstituted or substituted $C_1$-$C_6$fluoroalkyl;
or $R^3$ and $R^5$ are taken together to form a bond, or $C_1$-$C_2$alkylene;
or $R^2$ and $R^5$ are taken together with the intervening atoms to which they are attached to form an unsubstituted or substituted 4-7 membered saturated N-containing heterocyclic ring;
$R^4$ and $R^6$ are each independently selected from the group consisting of hydrogen, unsubstituted or substituted $C_1$-$C_6$alkyl, and unsubstituted or substituted $C_1$-$C_6$fluoroalkyl;
$R^7$ is hydrogen, unsubstituted or substituted $C_1$-$C_6$alkyl, or unsubstituted or substituted $C_1$-$C_6$fluoroalkyl;
or $R^2$ and $R^7$ are taken together with the intervening atoms to which they are attached to form an unsubstituted or substituted N-containing $C_2$-$C_8$heterocycloalkyl;
$L^1$ is absent or —CR$^8$R$^9$—;
$L^2$ is —CR$^{10}$R$^{11}$— or absent;
$L^3$ is —(CR$^{12}$R$^{13}$)$_t$- or absent;
t is 1 or 2;
each $R^8$, $R^9$, $R^{10}$, $R^{11}$, $R^{12}$, and $R^{13}$ is independently selected from the group consisting of hydrogen, unsubstituted or substituted $C_1$-$C_6$alkyl, and unsubstituted or substituted $C_1$-$C_6$fluoroalkyl;
or $R^5$ and $R^8$ are taken together with the intervening atoms to which they are attached to form an unsubstituted or substituted monocyclic carbocyclic or unsubstituted or substituted monocyclic heterocyclic ring;
or $R^5$ and $R^{13}$ are taken together with the intervening atoms to which they are attached to form an unsubstituted or substituted monocyclic carbocyclic or unsubstituted or substituted monocyclic heterocyclic ring;
or $R^7$ and $R^8$ are taken together with the intervening atoms to which they are attached to form an unsubstituted or substituted monocyclic carbocyclic or unsubstituted or substituted monocyclic heterocyclic ring;
each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

or two $R^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more $R^5$ groups independently selected from the group consisting of halogen, $C_1$-$C_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;

each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of somatostatin receptor activity comprising administering a small molecule non-peptidyl compound, or pharmaceutically acceptable salt, or solvate thereof, to the mammal in need thereof In some embodiments, the small molecule non-peptidyl compound is orally administered. In some embodiments, the small molecule non-peptidyl compound is a compound as described herein, or a pharmaceutically acceptable salt or solvate thereof . In some embodiments, the small molecule non-peptidyl compound is a SSTR2 modulator as described herein, or a pharmaceutically acceptable salt or solvate thereof. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Somatostatin (SST), also known as somatotropin release inhibiting factor (SRIF) was initially isolated as a 14-amino acid peptide from ovine hypothalamii (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous sstem (CNS) and gut and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily. SST2A receptor is the most widely expressed subtype in human tumors and is the dominant receptor by which GH secretion is suppressed. Unless otherwise stated, the term SSTR2 means SSTR2a.

It is possible to selectively modulate any one of the somatostatin receptor subtypes, or combination thereof In some embodiments, selectively modulating any one of the somatostatin receptor subtypes relative to the other somatostatin receptor subtypes, or combination thereof, in useful in a variety of clinical applications. In some embodiments, selectively modulating any one of the somatostatin receptor subtypes relative to the other somatostatin receptor subtypes reduces unwanted side effects in a variety of clinical applications.

For example, modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, gut neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In some embodiments, SSTR4 agonists exhibit anti-inflammatory and anti-nociceptive effects.

In some embodiments, SSTR3 agonists inhibit insulin secretion.

In some embodiments, SSTR5 agonists inhibit insulin secretion. In addition, SSTR5 has also been implicated to modulate the release of growth hormone.

Somatostatin peptide and its receptor subtypes are also widely expressed in the brain and disruption or diminishment of their activity is potentially involved in several psychiatric and neurodegenerative diseases. For example, concentrations of somatostatin in the cerebral cortex and hippocampus are reduced in schizophrenics and one of the most consistent neuropathologic findings in this patient group is a deficit in cortical inhibitory interneurons expressing somatostatin. Somatostatin is also highly expressed in brain regions associated with seizures and has also been implicated as having an important role in epilepsy. Somatostatin levels are diminished in the hippocampi of Alzheimer's and Parkinson's patients, suggesting that restoration of its signaling as a potential drug target for neurodegeneration.

In one aspect, compounds described herein are modulators of SSTR2. In some embodiments, compounds described herein selectively modulate the activity of SSTR2 relative to the other somatostatin receptors.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, somatostatin receptor modulators described herein are used in the treatment of acromegaly in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, insulin, glucagon and prolactin. The suppression of certain endocrine secretions is useful in the treatment of disorders such as acromegaly; endocrine tumors such as carcinoids, VIPomas, insulinomas and glucagonomas; or diabetes and diabetes-related pathologies, including retinopathy, neuropathy and nephropathy. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, colon and pancreatic adenocarcinomas (ductal type), chondrosarcomas, and melanomas, diabetic retinopathy, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

Compounds

Compounds of Formula (A), including pharmaceutically acceptable salts, prodrugs, active metabolites and pharmaceutically acceptable solvates thereof, are somatostatin receptor modulators. In some embodiments, the compounds of Formula (A), including pharmaceutically acceptable salts, prodrugs, active metabolites and pharmaceutically acceptable solvates thereof, are SSTR2 receptor modulators. In some embodiments, the somatostatin receptor modulators are somatostatin receptor agonists.

In one aspect, described herein is a compound of Formula (A), or a pharmaceutically acceptable salt, pharmaceutically acceptable solvate, diastereomeric mixture, enantiomer or prodrug thereof:

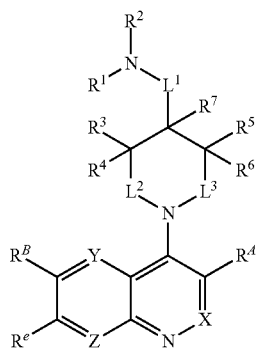

Formula (A)

wherein:
$R^A$ is hydrogen, halogen, unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, or a unsubstituted or substituted ring A that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring A is substituted then the ring A is substituted with m $R^a$ and n $R^b$;

each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$ or —C(=NOR$^{15}$)R$^{15}$;

m is 1 or 2; n is 0, 1 or 2;
or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;

$R^B$ is unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, or a unsubstituted or substituted ring B that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring B is substituted then the ring B is substituted with p $R^c$ and q $R^d$;

each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —OR$^{14}$, —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C(=NOR$^{15}$)R$^{15}$, N(R$^{15}$)SO$_2$R$^{14}$, —C(=O)NR$^{15}$S(=O)$_2$R$^{14}$, —S(=O)$_2$NR$^{15}$C(=O)R$^{14}$, —C(=NR$^{15}$)N(R$^{15}$)$_2$, —NR$^{15}$C(=NR$^{15}$)N(R$^{15}$)$_2$, —NR$^{15}$C(=CR$^{14}$R$^{15}$)N(R$^{15}$)$_2$, —C(=O)NR$^{15}$C(=NR$^{15}$)N(R$^{15}$)$_2$ or, —C(=O)NR$^{15}$C(=CR$^{14}$R$^{15}$)N(R$^{15}$)$_2$;

p is 1 or 2; q is 0, 1 or 2;
or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is CR$^f$ or N;
Y is CR$^f$ or N;
Z is CR$^f$ or N;
$R^e$ is hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;
each $R^f$ is independently hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;
$R^1$ and $R^2$ are independently hydrogen, unsubstituted or substituted $C_1$-$C_6$alkyl, unsubstituted or substituted $C_1$-$C_6$heteroalkyl, unsubstituted or substituted $C_1$-$C_6$fluoroalkyl, unsubstituted or substituted $C_3$-$C_6$cycloalkyl or substituted or unsubstituted $C_2$-$C_{10}$heterocycloalkyl;
or $R^1$ and $R^2$ are taken together with the nitrogen atom to which they are attached to form ring C that is an unsubstituted or substituted N-containing $C_2$-$C_8$heterocycloalkyl;
$R^3$ and $R^5$ are each independently selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted $C_1$-$C_6$alkyl, unsubstituted or substituted $C_1$-$C_6$heteroalkyl, and unsubstituted or substituted $C_1$-$C_6$fluoroalkyl;
or $R^3$ and $R^5$ are taken together to form a bond, or $C_1$-$C_2$alkylene;
or $R^2$ and $R^5$ are taken together with the intervening atoms to which they are attached to form an unsubstituted or substituted 4-7 membered saturated N-containing heterocyclic ring;
$R^4$ and $R^6$ are each independently selected from the group consisting of hydrogen, unsubstituted or substituted $C_1$-$C_6$alkyl, and unsubstituted or substituted $C_1$-$C_6$fluoroalkyl;
$R^7$ is hydrogen, unsubstituted or substituted $C_1$-$C_6$alkyl, or unsubstituted or substituted $C_1$-$C_6$fluoroalkyl;
or $R^2$ and $R^7$ are taken together with the intervening atoms to which they are attached to form an unsubstituted or substituted N-containing $C_2$-$C_8$heterocycloalkyl;
$L^1$ is absent or —CR$^8$R$^9$—;
$L^2$ is —CR$^{10}$R$^{11}$— or absent;
$L^3$ is —(CR$^{12}$R$^{13}$)$_r$— or absent;

t is 1 or 2;
each $R^8$, $R^9$, $R^{10}$, $R^{11}$, $R^{12}$, and $R^{13}$ is independently selected from the group consisting of hydrogen, unsubstituted or substituted $C_1$-$C_6$alkyl, and unsubstituted or substituted $C_1$-$C_6$fluoroalkyl;
or $R^5$ and $R^8$ are taken together with the intervening atoms to which they are attached to form an unsubstituted or substituted monocyclic carbocyclic or unsubstituted or substituted monocyclic heterocyclic ring;
or $R^5$ and $R^{13}$ are taken together with the intervening atoms to which they are attached to form an unsubstituted or substituted monocyclic carbocyclic or unsubstituted or substituted monocyclic heterocyclic ring;
or $R^7$ and $R^8$ are taken together with the intervening atoms to which they are attached to form an unsubstituted or substituted monocyclic carbocyclic or unsubstituted or substituted monocyclic heterocyclic ring;
each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;
each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;
or two $R^{15}$ on the same N atom are taken together with the N atom to which they are attached to form an unsubstituted or substituted N-containing heterocycle;
wherein each substituted alkyl, substituted fluoroalkyl, substituted heteroalkyl, substituted carbocycle, and substituted heterocycle is substituted with one or more $R^s$ groups independently selected from the group consisting of halogen, $C_1$-$C_6$alkyl, monocyclic carbocycle, monocyclic heterocycle, —CN, —$OR^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;
each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;
each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

In some embodiments of the compound of Formula (A):
$R^A$ is hydrogen, halogen, unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, or a substituted ring A that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring A is substituted then the ring A is substituted with m $R^a$ and n $R^b$;
each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —$OR^{14}$, —$CO_2R^{15}$, —$CH_2CO_2R^{15}$, —C(=O)N($R^{15}$)$_2$, —$CH_2$C(=O)N($R^{15}$)$_2$, —N($R^{15}$)$_2$, —$CH_2$N($R^{15}$)$_2$, —$NR^{15}$C(=O)$R^{14}$, —$CH_2NR^{15}$C(=O)$R^{14}$, —$SR^{14}$, —S(=O)$R^{14}$, —$SO_2R^{14}$, or —$SO_2$N($R^{15}$)$_2$;
m is 1 or 2; n is 0, 1 or 2;
or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;
$R^B$ is unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, or a unsubstituted or substituted ring B that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring B is substituted then the ring B is substituted with p $R^c$ and q $R^d$;
each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —$OR^{14}$, —$CO_2R^{15}$, —$CH_2CO_2R^{15}$, —C(=O)N($R^{15}$)$_2$, —$CH_2$C(=O)N($R^{15}$)$_2$, —N($R^{15}$)$_2$, —$CH_2$N($R^{15}$)$_2$, —$NR^{15}$C(=O)$R^{14}$, —$CH_2NR^{15}$C(=O)$R^{14}$, —$SR^{14}$, —S(=O)$R^{14}$, —$SO_2R^{14}$, or —$SO_2$N($R^{15}$)$_2$;
p is 1 or 2; q is 0, 1 or 2;
or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;
X is $CR^f$ or N;
Y is $CR^f$ or N;
Z is $CR^f$ or N;
$R^e$ is hydrogen, halogen, unsubstituted or substituted $C_1$-$C_6$alkyl, unsubstituted or substituted $C_1$-$C_6$fluoroalkyl, —CN, —OH, —$OR^{14}$, —$CO_2R^{15}$, —C(=O)N($R^{15}$)$_2$, —N($R^{15}$)$_2$, —$NR^{15}$C(=O)$R^{14}$, —$SR^{14}$, —S(=O)$R^{14}$, —$SO_2R^{14}$, or —$SO_2$N($R^{15}$)$_2$;
each $R^f$ is independently hydrogen, halogen, unsubstituted or substituted $C_1$-$C_6$alkyl, unsubstituted or substituted $C_1$-$C_6$fluoroalkyl, —CN, —OH, —$OR^{14}$, —$CO_2R^{15}$, —C(=O)N($R^{15}$)$_2$, —N($R^{15}$)$_2$, —$NR^{15}$C(=O)$R^{14}$, —$SR^{14}$, —S(=O)$R^{14}$, —$SO_2R^{14}$, or —$SO_2$N($R^{15}$)$_2$;
$R^1$ and $R^2$ are independently hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_{10}$heterocycloalkyl;
or $R^1$ and $R^2$ are taken together with the nitrogen atom to which they are attached to form ring C that is an unsubstituted or substituted N-containing $C_2$-$C_8$heterocycloalkyl;
$R^3$ and $R^5$ are each independently selected from the group consisting of hydrogen, halogen, —OH, —$OR^{14}$, —$SR^{14}$, —S(=O)$R^{14}$, —S(=O)$_2R^{14}$, —N($R^{15}$)$_2$, —CN, unsubstituted or substituted $C_1$-$C_6$alkyl, and unsubstituted or substituted $C_1$-$C_6$fluoroalkyl;
or $R^3$ and $R^5$ are taken together to form a bond, or $C_1$-$C_2$alkylene;

or $R^2$ and $R^5$ are taken together with the intervening atoms to which they are attached to form an unsubstituted or substituted 4-7 membered saturated N-containing heterocyclic ring;

$R^4$ and $R^6$ are each independently selected from the group consisting of hydrogen, unsubstituted or substituted $C_1$-$C_6$alkyl, and unsubstituted or substituted $C_1$-$C_6$fluoroalkyl;

$R^7$ is hydrogen, unsubstituted or substituted $C_1$-$C_6$alkyl, or unsubstituted or substituted $C_1$-$C_6$fluoroalkyl;

or $R^2$ and $R^7$ are taken together with the intervening atoms to which they are attached to form an unsubstituted or substituted N-containing $C_2$-$C_8$heterocycloalkyl;

$L^1$ is absent or —$CR^8R^9$—;

$L^2$ is —$CR^{10}R^{11}$— or absent;

$L^3$ is —$(CR^{12}R^{13})_t$- or absent;

t is 1 or 2;

each $R^8$, $R^9$, $R^{10}$, $R^{11}$, $R^{12}$, and $R^{13}$ is independently selected from the group consisting of hydrogen, unsubstituted or substituted $C_1$-$C_6$alkyl, and unsubstituted or substituted $C_1$-$C_6$fluoroalkyl;

or $R^5$ and $R^8$ are taken together with the intervening atoms to which they are attached to form an unsubstituted or substituted monocyclic carbocyclic or unsubstituted or substituted monocyclic heterocyclic ring;

or $R^5$ and $R^{13}$ are taken together with the intervening atoms to which they are attached to form an unsubstituted or substituted monocyclic carbocyclic or unsubstituted or substituted monocyclic heterocyclic ring;

or $R^7$ and $R^8$ are taken together with the intervening atoms to which they are attached to form an unsubstituted or substituted monocyclic carbocyclic or unsubstituted or substituted monocyclic heterocyclic ring;

each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

or two $R^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, substituted heterocycloalkyl and substituted heterocycle is substituted with one or more $R^s$ groups independently selected from the group consisting of halogen, $C_1$-$C_6$alkyl, monocyclic carbocycle, monocyclic heterocycle, —CN, —$OR^{16}$, —$CO_2R^{16}$, —C(=O)N($R^{16}$)$_2$, —N($R^{16}$)$_2$, —$NR^{16}C$(=O)$R^{17}$, —$SR^{16}$, —S(=O)$R^{17}$, —$SO_2R^{17}$, or —$SO_2N(R^{16})_2$;

each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;

each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

In one aspect, the compound of Formula (A) has the structure of Formula (AI), or a pharmaceutically acceptable salt, pharmaceutically acceptable solvate, diastereomeric mixture, enantiomer or prodrug thereof:

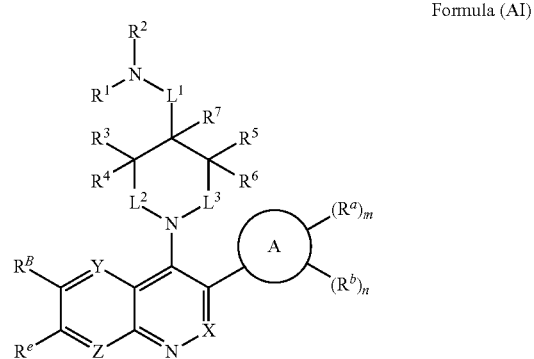

Formula (AI)

wherein:

$R^B$ is an unsubstituted or substituted ring B that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if the ring B is substituted then the ring B is substituted with p $R^c$ and q $R^d$; p is 1 or 2; q is 0, 1 or 2.

In one aspect, the compound of Formula (A) or Formula (AI) has the structure of Formula (I), or a pharmaceutically acceptable salt, pharmaceutically acceptable solvate, diastereomeric mixture, enantiomer or prodrug thereof:

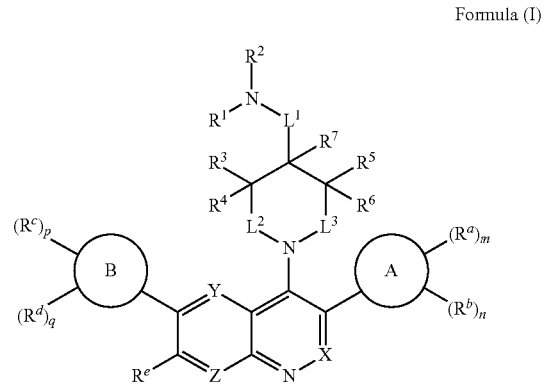

Formula (I)

wherein:

ring A is a monocyclic carbocycle, bicyclic carbocycle, monocyclic heterocycle, or bicyclic heterocycle;

each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —$OR^{14}$, —$CO_2R^{15}$, —$CH_2CO_2R^{15}$, —C(=O)N($R^{15}$)$_2$, —$CH_2C$(=O)N($R^{15}$)$_2$, —N($R^{15}$)$_2$, —$CH_2N(R^{15})_2$, —$CH(CF_3)N(R^{15})_2$, —$NR^{15}C$(=O)$R^{14}$, —$CH_2NR^{15}C$(=O)$R^{14}$, —$SR^{14}$, —S(=O)$R^{14}$, —$SO_2R^{14}$, —$SO_2N(R^{15})_2$ or —C(=$NOR^{15}$)$R^{15}$;

m is 1 or 2; n is 0, 1 or 2;

or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;

ring B is a monocyclic carbocycle, bicyclic carbocycle, monocyclic heterocycle, or bicyclic heterocycle;

each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —OR$^{14}$, —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C(=NOR$^{15}$)R$^{15}$, —N(R$^{15}$)SO$_2$R$^{14}$, —C(=O)NR$^{15}$S(=O)$_2$R$^{14}$, —S(=O)$_2$NR$^{15}$C(=O)R$^{14}$, —C(=NR$^{15}$)N(R$^{15}$)$_2$, —NR$^{15}$C(=NR$^{15}$)N(R$^{15}$)$_2$, —NR$^{15}$C(=CR$^{14}$R$^{15}$)N(R$^{15}$)$_2$, —C(=O)NR$^{15}$C(=NR$^{15}$)N(R$^{15}$)$_2$ or, —C(=O)NR$^{15}$C(=CR$^{14}$R$^{15}$)N(R$^{15}$)$_2$;

p is 1 or 2; q is 0, 1 or 2;

or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is CR$^f$ or N;

Y is CR$^f$ or N;

Z is CR$^f$ or N;

$R^e$ is hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;

each $R^f$ is independently hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;

$R^1$ and $R^2$ are independently hydrogen, unsubstituted or substituted $C_1$-$C_6$alkyl, unsubstituted or substituted $C_1$-$C_6$heteroalkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;

or $R^1$ and $R^2$ are taken together with the nitrogen atom to which they are attached to form ring C that is an unsubstituted or substituted N-containing $C_2$-$C_8$heterocycloalkyl;

$R^3$ and $R^5$ are each independently selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted $C_1$-$C_6$alkyl, unsubstituted or substituted $C_1$-$C_6$heteroalkyl, and unsubstituted or substituted $C_1$-$C_6$fluoroalkyl;

or $R^3$ and $R^5$ are taken together to form a bond, or $C_1$-$C_2$alkylene;

or $R^2$ and $R^5$ are taken together with the intervening atoms to which they are attached to form an unsubstituted or substituted 4-7 membered saturated N-containing heterocyclic ring;

$R^4$ and $R^6$ are each independently selected from the group consisting of hydrogen, unsubstituted or substituted $C_1$-$C_6$alkyl, and unsubstituted or substituted $C_1$-$C_6$fluoroalkyl;

$R^7$ is hydrogen, unsubstituted or substituted $C_1$-$C_6$alkyl, or unsubstituted or substituted $C_1$-$C_6$fluoroalkyl;

or $R^2$ and $R^7$ are taken together with the intervening atoms to which they are attached to form an unsubstituted or substituted N-containing $C_2$-$C_8$heterocycloalkyl;

$L^1$ is absent or —CR$^8$R$^9$—;

$L^2$ is —CR$^{10}$R$^{11}$— or absent;

$L^3$ is —(CR$^{12}$R$^{13}$)$_t$— or absent;

t is 1 or 2;

each $R^8$, $R^9$, $R^{10}$, $R^{11}$, $R^{12}$, and $R^{13}$ is independently selected from the group consisting of hydrogen, unsubstituted or substituted $C_1$-$C_6$alkyl, and unsubstituted or substituted $C_1$-$C_6$fluoroalkyl;

or $R^5$ and $R^8$ are taken together with the intervening atoms to which they are attached to form an unsubstituted or substituted monocyclic carbocyclic or unsubstituted or substituted monocyclic heterocyclic ring;

or $R^5$ and $R^{13}$ are taken together with the intervening atoms to which they are attached to form an unsubstituted or substituted monocyclic carbocyclic or unsubstituted or substituted monocyclic heterocyclic ring;

or $R^7$ and $R^8$ are taken together with the intervening atoms to which they are attached to form an unsubstituted or substituted monocyclic carbocyclic or unsubstituted or substituted monocyclic heterocyclic ring;

each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

or two $R^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more $R^s$ groups independently selected from the group consisting of halogen, $C_1$-$C_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;

each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

In some embodiments of the compound of Formula (I):

ring A is a monocyclic carbocycle, bicyclic carbocycle, monocyclic heterocycle, or bicyclic heterocycle;

each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, or —SO$_2$N(R$^{15}$)$_2$;

m is 1 or 2; n is 0, 1 or 2;

or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;

ring B is a monocyclic carbocycle, bicyclic carbocycle, monocyclic heterocycle, or bicyclic heterocycle;

each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, or —SO$_2$N(R$^{15}$)$_2$;

p is 1 or 2; q is 0, 1 or 2;

or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is CR$^f$ or N;

Y is CR$^f$ or N;

Z is CR$^f$ or N;

$R^e$ is hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;

each $R^f$ is independently hydrogen, halogen, unsubstituted or substituted $C_1$-$C_6$alkyl, unsubstituted or substituted $C_1$-$C_6$fluoroalkyl, —CN, —OH, —OR$^{14}$, —CO$_2$R$^{15}$, —C(=O)N(R$^{15}$)$_2$, —N(R$^{15}$)$_2$, —NR$^{15}$C(=O)R$^{14}$, —SR$^{14}$, —S(=O)R$^{14}$, —SO$_2$R$^{14}$, or —SO$_2$N(R$^{15}$)$_2$;

$R^1$ and $R^2$ are independently hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;

or $R^1$ and $R^2$ are taken together with the nitrogen atom to which they are attached to form ring C that is an unsubstituted or substituted N-containing $C_2$-$C_8$heterocycloalkyl;

$R^3$ and $R^5$ are each independently selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, unsubstituted or substituted $C_1$-$C_6$alkyl, and unsubstituted or substituted $C_1$-$C_6$fluoroalkyl;

or $R^3$ and $R^5$ are taken together to form a bond, or $C_1$-$C_2$alkylene;

or $R^2$ and $R^5$ are taken together with the intervening atoms to which they are attached to form an unsubstituted or substituted 4-7 membered saturated N-containing heterocyclic ring;

$R^4$ and $R^6$ are each independently selected from the group consisting of hydrogen, unsubstituted or substituted $C_1$-$C_6$alkyl, and unsubstituted or substituted $C_1$-$C_6$fluoroalkyl;

$R^7$ is hydrogen, unsubstituted or substituted $C_1$-$C_6$alkyl, or unsubstituted or substituted $C_1$-$C_6$fluoroalkyl;

or $R^2$ and $R^7$ are taken together with the intervening atoms to which they are attached to form an unsubstituted or substituted N-containing $C_2$-$C_8$heterocycloalkyl;

$L^1$ is absent or —CR$^8$R$^9$—;

$L^2$ is —CR$^{10}$R$^{11}$— or absent;

$L^3$ is —(CR$^{12}$R$^{13}$)$_t$- or absent;

t is 1 or 2;

each $R^8$, $R^9$, $R^{10}$, $R^{11}$, $R^{12}$, and $R^{13}$ is independently selected from the group consisting of hydrogen, unsubstituted or substituted $C_1$-$C_6$alkyl, and unsubstituted or substituted $C_1$-$C_6$fluoroalkyl;

or $R^5$ and $R^8$ are taken together with the intervening atoms to which they are attached to form an unsubstituted or substituted monocyclic carbocyclic or unsubstituted or substituted monocyclic heterocyclic ring;

or $R^5$ and $R^{13}$ are taken together with the intervening atoms to which they are attached to form an unsubstituted or substituted monocyclic carbocyclic or unsubstituted or substituted monocyclic heterocyclic ring;

or $R^7$ and $R^8$ are taken together with the intervening atoms to which they are attached to form an unsubstituted or substituted monocyclic carbocyclic or unsubstituted or substituted monocyclic heterocyclic ring;

each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

or two on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more $R^s$ groups independently selected from the group consisting of halogen, $C_1$-$C_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;

each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

For any and all of the embodiments, substituents are selected from among a subset of the listed alternatives. For example, in some embodiments, m is 1 or 2. In other embodiments, m is 1. In some other embodiments, m is 2.

In some embodiments, n is 0, 1, or 2. In some embodiments, n is 1, or 2. In some embodiments, n is 0 or 1. In some embodiments, n is 0. In some embodiments, n is 1. In some embodiments, n is 2.

In some embodiments, p is 1 or 2. In some embodiments, p is 1. In some embodiments, p is is 2.

In some embodiments, q is 0, 1, or 2. In some embodiments, q is 1 or 2. In some embodiments, q is 0 or 1. In some embodiments, q is 0. In some embodiments, q is 1. In some embodiments, q is 2.

In some embodiments, $R^4$ and $R^6$ are each independently selected from the group consisting of hydrogen and —$CH_3$; $R^7$ is hydrogen, —$CH_3$, or —$CH_2CH_3$; or $R^2$ and $R^7$ are taken together with the intervening atoms to which they are attached to form an unsubstituted or substituted N-containing $C_2$-$C_8$heterocycloalkyl; each $R^8$, $R^9$, $R^{10}$, $R^{11}$, $R^{12}$, and $R^{13}$ is independently selected from the group consisting of hydrogen and —$CH_3$.

In some embodiments, $L^1$ is absent, —$CH_2$—, —$CHCH_3$— or —$CH(CH_2CH_3)$—; $L^2$ is —$CH_2$— or absent; $L^3$ is —$CH_2$—, —$CH_2CH_2$— or absent. In some embodiments, $L^1$ is absent or —$CH_2$—; $L^2$ is —$CH_2$— or absent; $L^3$ is —$CH_2$—, —$CH_2CH_2$— or absent.

In some embodiments, X is $CR^f$; Y is $CR^f$; and Z is $CR^f$.

In some embodiments, X is N; Y is $CR^f$; and Z is $CR^f$.

In some embodiments, X is $CR^f$; Y is N; and Z is $CR^f$.

In some embodiments, X is $CR^f$; Y is $CR^f$; and Z is N.

In some embodiments, X is N; Y is N; and Z is $CR^f$.

In some embodiments, X is $CR^f$; Y is N; and Z is N.

In some embodiments, X is N; Y is N; and Z is N.

In some embodiments, the compound of Formula (I) has the structure of Formula (Ia), or a pharmaceutically acceptable salt, solvate, diastereomeric mixture, individual enantiomers or prodrug thereof:

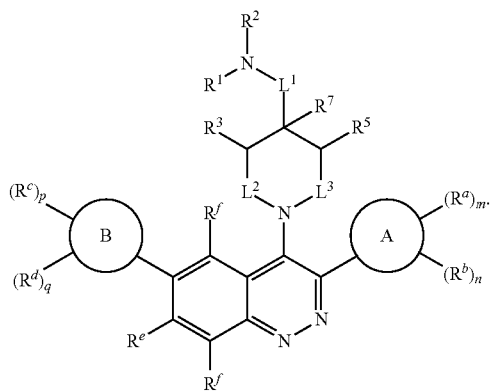

Formula (Ia)

In some embodiments, the compound of Formula (I) has the structure of Formula (Ib), or a pharmaceutically acceptable salt, solvate, diastereomeric mixture, individual enantiomers or prodrug thereof:

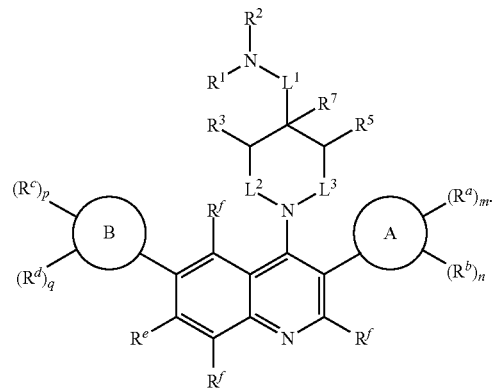

Formula (Ib)

In some embodiments, the compound of Formula (I) has the structure of Formula (Ic), or a pharmaceutically acceptable salt, solvate, diastereomeric mixture, individual enantiomers or prodrug thereof:

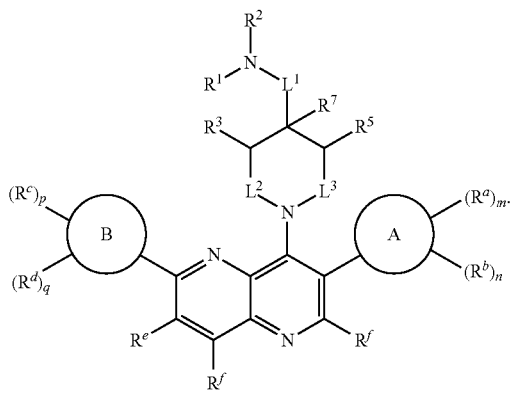

Formula (Ic)

In some embodiments, the compound of Formula (I) has the structure of Formula (Id), or a pharmaceutically acceptable salt, solvate, diastereomeric mixture, individual enantiomers or prodrug thereof:

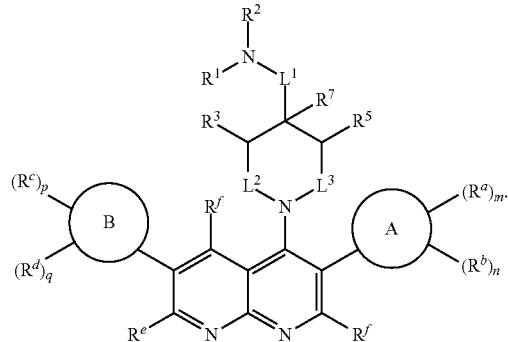

Formula (Id)

In some embodiments, the compound of Formula (I) has the structure of Formula (Ie), or a pharmaceutically acceptable salt, solvate, diastereomeric mixture, individual enantiomers or prodrug thereof:

Formula (Ie)

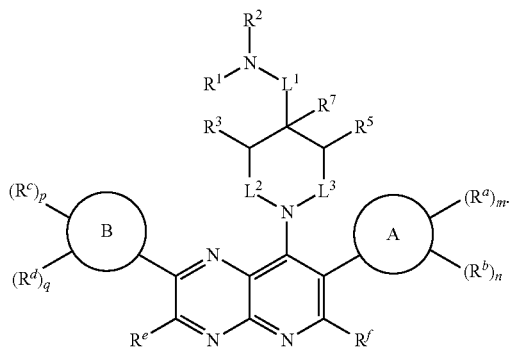

In some embodiments, the compound of Formula (I) has the structure of Formula (If), or a pharmaceutically acceptable salt, solvate, diastereomeric mixture, individual enantiomers or prodrug thereof:

Formula (If)

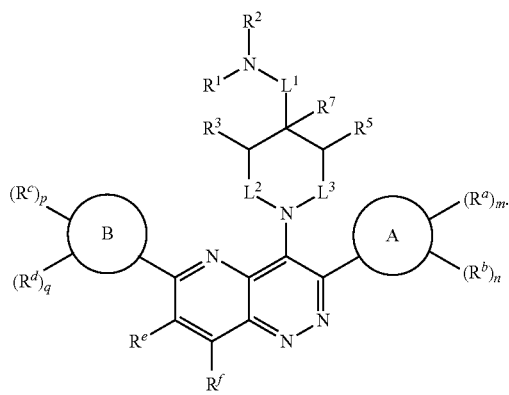

In some embodiments, $R^e$ is hydrogen, halogen, $C_1$-$C_4$alkyl, $C_1$-$C_4$fluoroalkyl, —CN, —OH, or —OR$^{14}$; and each $R^f$ is independently hydrogen, halogen, $C_1$-$C_4$alkyl, $C_1$-$C_4$fluoroalkyl, —CN, —OH, or —OR$^{14}$.

In some embodiments, $R^e$ is hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$F, —CHF$_2$, —CF$_3$, —CN, —OH, —OCH$_3$, —OCH$_2$CH$_3$, or —OCF$_3$; each $R^f$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$F, —CHF$_2$, —CF$_3$, —CN, —OH, —OCH$_3$, —OCH$_2$CH$_3$, or —OCF$_3$.

In some embodiments, ring A is a monocyclic carbocycle or a monocyclic heterocycle.

In some embodiments, ring A is a monocyclic carbocycle that is phenyl, $C_3$-$C_6$cycloalkyl, or $C_5$-$C_6$cycloalkenyl.

In some embodiments, ring A is phenyl.

In some embodiments, $R^A$ is 

In some embodiments, $R^A$ is  is 

In some embodiments,

 is 

In some embodiments,

 is 

In some embodiments, ring A is cyclopropyl, cyclobutyl, cyclopentyl, cyclopentenyl, cyclohexyl or cyclohexenyl.

In some embodiments,

 is 

n is 0, 1, or 2.

In some embodiments, ring A is a bicyclic carbocycle that is naphthyl, indanyl, indenyl, or tetrahyodronaphthyl.

In some embodiments, ring A is a monocyclic heterocycle containing 1-4 N atoms and 0 or 1 O or S atom, or a monocyclic heterocycle containing 0-4 N atoms and 1 O or S atoms.

In some embodiments, ring A is a monocyclic heterocycle that is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, ring A is a monocyclic heterocycle that is pyridinyl, pyrimidinyl, pyrazinyl, or pyridazinyl.

In some embodiments,

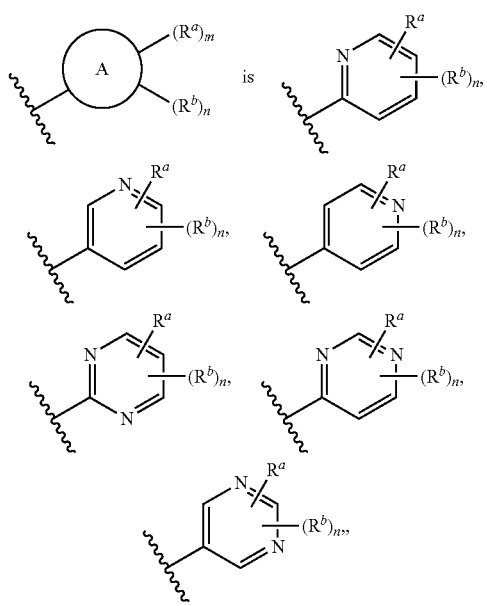

or; n is 0, 1, or 2.

In some embodiments,

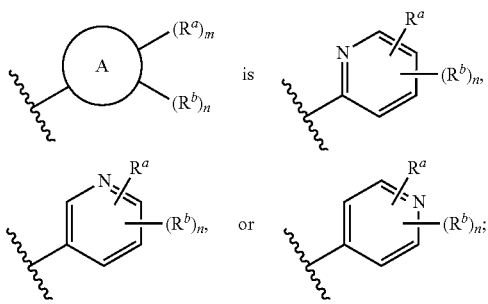

n is 0, 1, or 2.

In some embodiments,

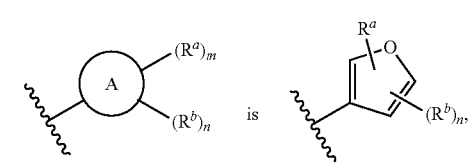

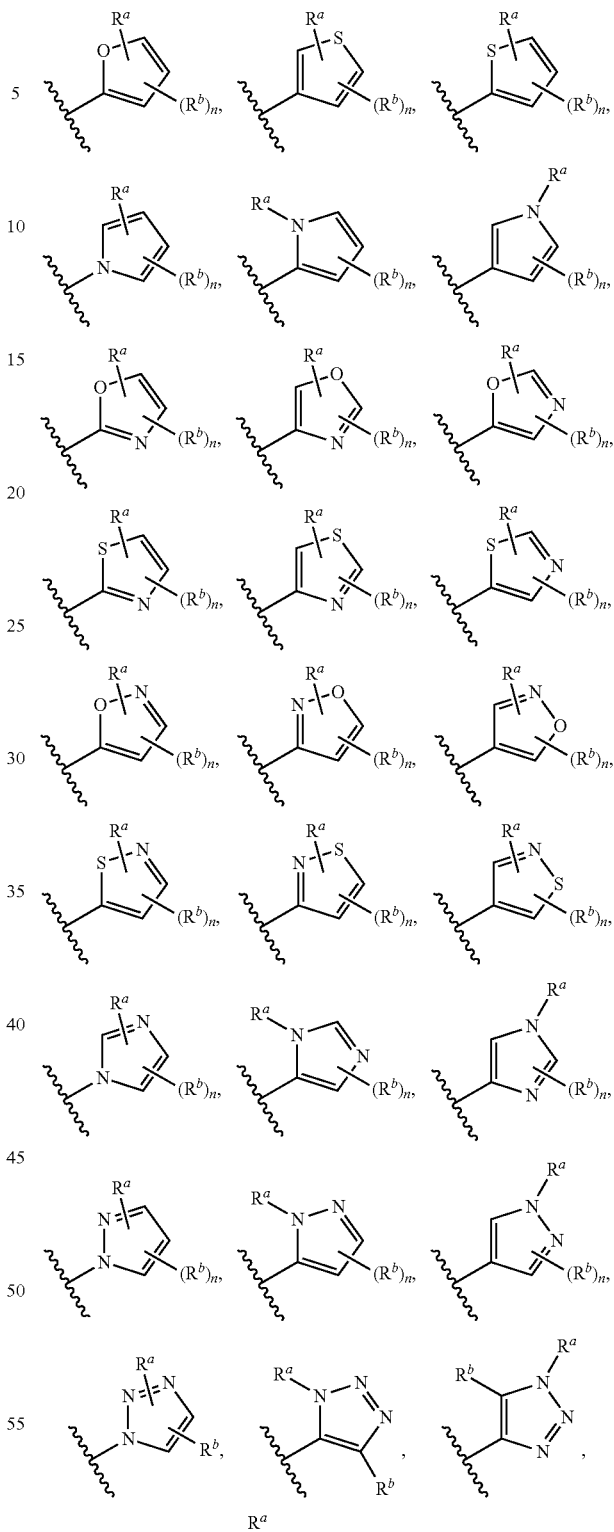

n is 0, 1, or 2.

In some embodiments,

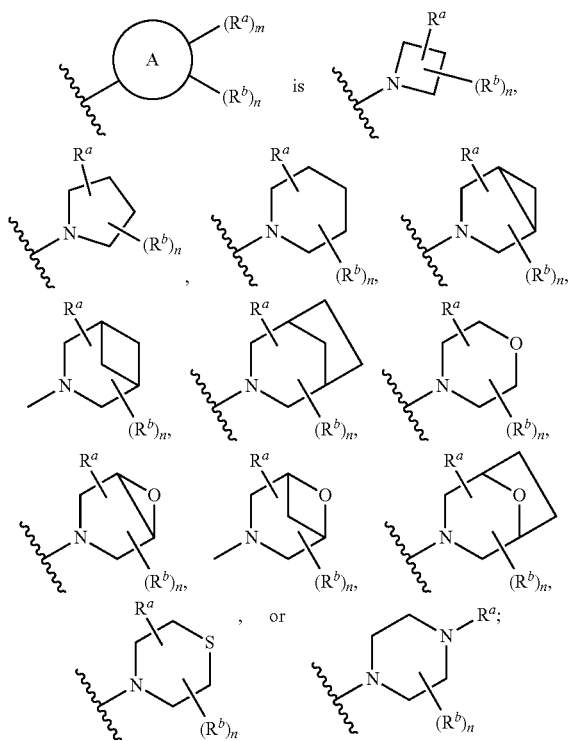

n is 0, 1, or 2.

In some embodiments, ring A is a bicyclic heterocycle containing 1-4 N atoms and 0 or 1 O or S atoms, or a bicyclic heterocycle containing 0-4 N atoms and 1 O or S atoms.

In some embodiments, ring A is a bicyclic heterocycle that is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, azaindolyl, indolinyl, isoindolinyl, indolinonyl, isoindolinonyl, or quinolinonyl.

In some embodiments, each $R^a$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, or —SO$_2$N(R$^{15}$)$_2$; and each $R^b$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —O-(unsubstituted or substituted $C_1$-$C_4$alkyl), or —O-(unsubstituted or substituted $C_1$-$C_4$fluoroalkyl).

In some embodiments, each $R^a$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —NR$^{15}$C(=O)R$^{14}$, or —CH$_2$NR$^{15}$C(=O)R$^{14}$; and each $R^b$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —O-(unsubstituted or substituted $C_1$-$C_4$alkyl), or —O-(unsubstituted or substituted $C_1$-$C_4$fluoroalkyl).

In some embodiments, each $R^a$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, or —C(=NOR$^{15}$)R$^{15}$; and each $R^b$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —O-(unsubstituted or substituted $C_1$-$C_4$alkyl), or —O-(unsubstituted or substituted $C_1$-$C_4$fluoroalkyl).

In some embodiments, each $R^a$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, or —CH$_2$NR$^{15}$C(=O)R$^{14}$; and each $R^b$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —O-(unsubstituted or substituted $C_1$-$C_4$alkyl), or —O-(unsubstituted or substituted $C_1$-$C_4$fluoroalkyl).

In some embodiments, each $R^a$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, —OCF$_3$, —CH$_2$OH, —CH$_2$CH$_2$OH, —CO$_2$H, —CO$_2$CH$_3$, —CO$_2$CH$_2$CH$_3$, —CH$_2$CO$_2$H, —CH$_2$CO$_2$CH$_3$, —CH$_2$CO$_2$CH$_2$CH$_3$, —C(=O)NH$_2$, —C(=O)NHCH$_3$, —C(=O)N(CH$_3$)$_2$, —CH$_2$C(=O)NH$_2$, —CH$_2$C(=O)NHCH$_3$, —CH$_2$C(=O)N(CH$_3$)$_2$, —NH$_2$, —NHCH$_3$, —N(CH$_3$)$_2$, —CH$_2$NH$_2$, —CH$_2$NHCH$_3$, or —CH$_2$N(CH$_3$)$_2$; each $R^b$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —N, —OH, —OCH$_3$, —OCH$_2$CH$_3$, or —OCF$_3$.

In some embodiments, each $R^a$ is independently hydrogen, F, Cl, Br, —CH$_3$, —CH$_2$F, —CHF$_2$, —CF$_3$, —CN, —OH, —OCH$_3$, —OCF$_3$, —CH$_2$CH$_2$OH; each $R^b$ is independently hydrogen, F, Cl, Br, —CH$_3$, —CH$_2$F, —CHF$_2$, —CF$_3$, —CN, —OH, —OCH$_3$, —OCF$_3$.

In some embodiments, ring B is a monocyclic carbocycle or a monocyclic heterocycle.

In some embodiments, ring B is a monocyclic carbocycle that is phenyl, $C_3$-$C_6$cycloalkyl, or $C_5$-$C_6$cycloalkenyl.

In some embodiments, ring B is phenyl.

In some embodiments,

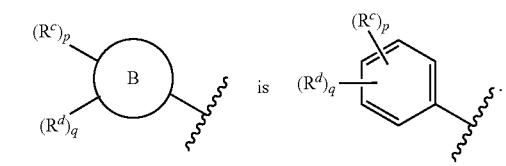

In some embodiments,

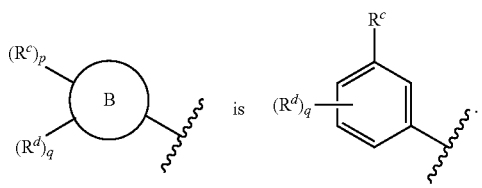

In some embodiments,

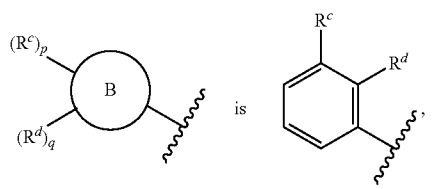

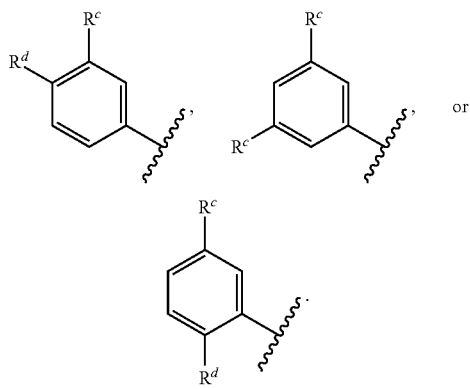

In some embodiments,

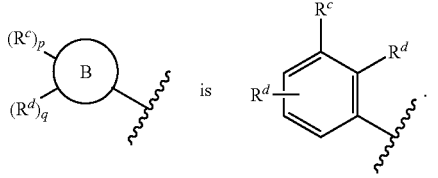

In some embodiments,

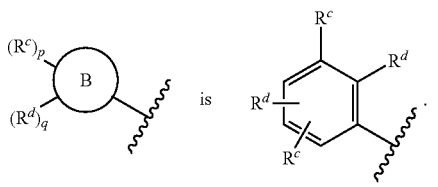

In some embodiments, ring B is cyclopropyl, cyclobutyl, cyclopentyl, cyclopentenyl, cyclohexyl or cyclohexenyl.

In some embodiments,

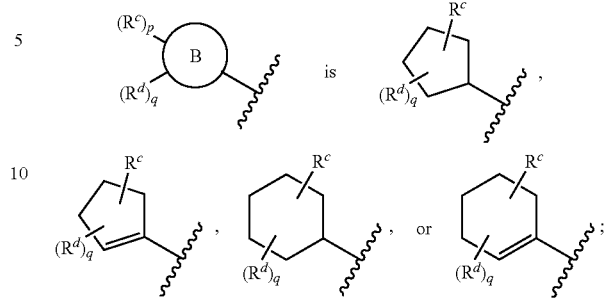

q is 0, 1, or 2.

In some embodiments, ring B is a bicyclic carbocycle that is naphthyl, indanyl, indenyl, or tetrahyodronaphthyl.

In some embodiments, ring B is a monocyclic 5- or 6-membered heterocycle containing 1-4 N atoms and 0 or 1 O or S atom, or a monocyclic heterocycle containing 0-4 N atoms and 1 O or S atoms.

In some embodiments, ring B is a monocyclic 5- or 6-membered heterocycle that is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, ring B is a monocyclic 6-membered heterocycle that is pyridinyl, pyrimidinyl, pyrazinyl, or pyridazinyl.

In some embodiments

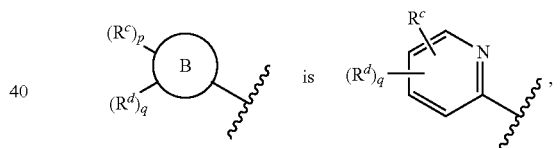

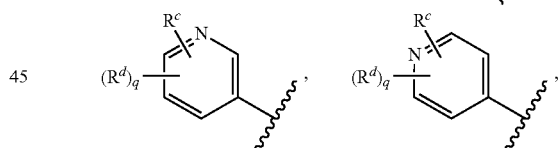

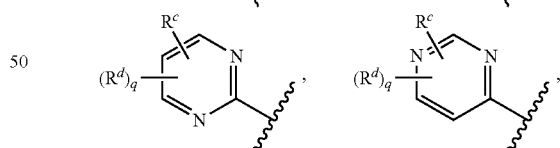

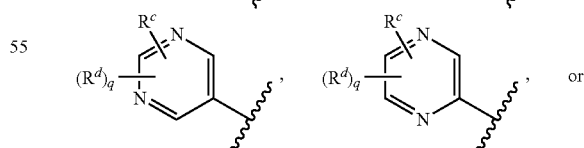

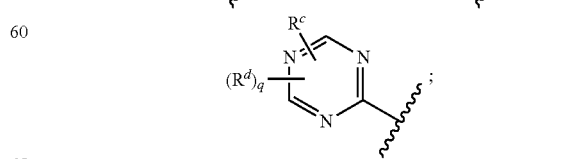

q is 0, 1, or 2. In some embodiments,
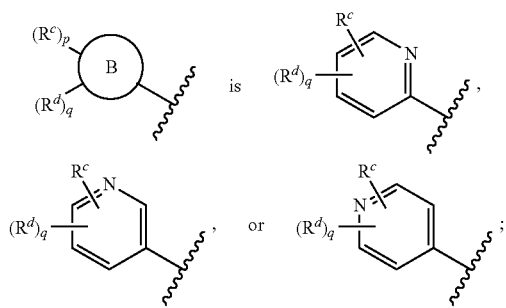
q is 0, 1, or 2.
In some embodiments,
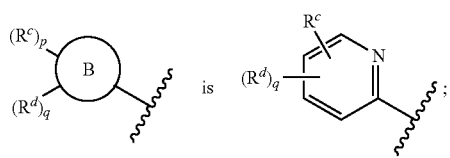
q is 0, 1, or 2.
In some embodiments,
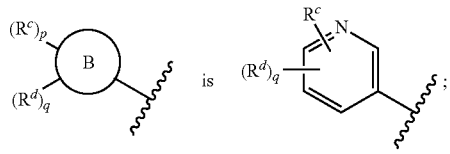
q is 0, 1, or 2.
In some embodiments,
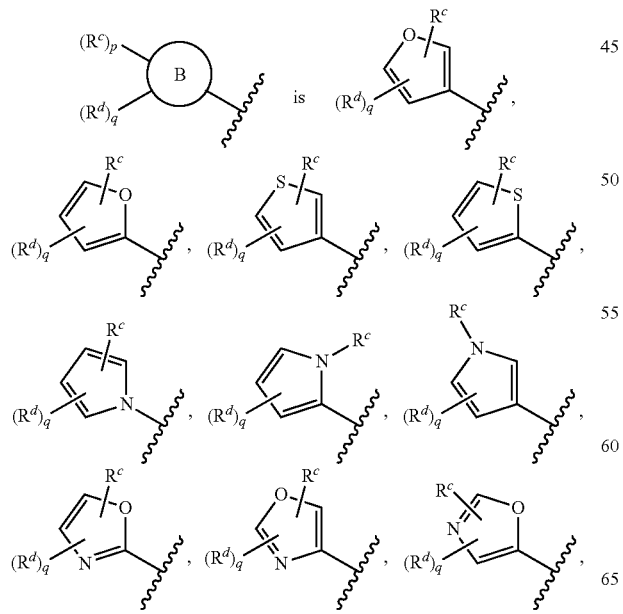
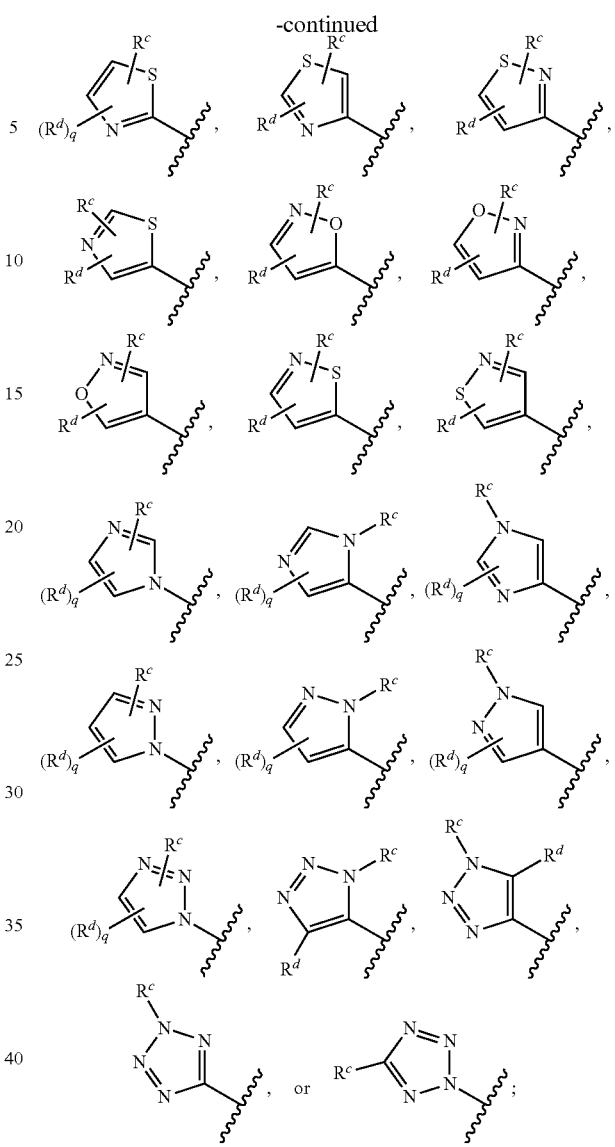
q is 0, 1, or 2.
In some embodiments,
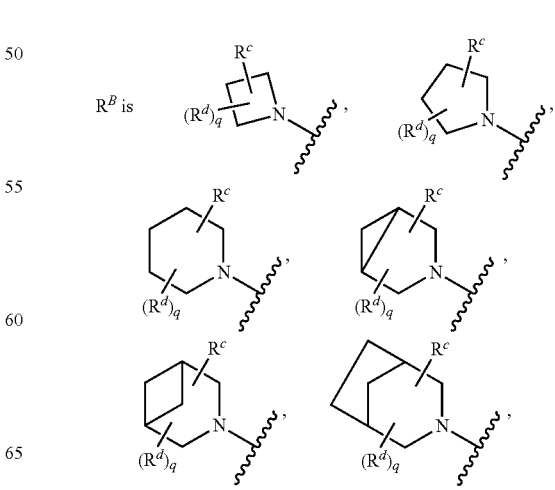

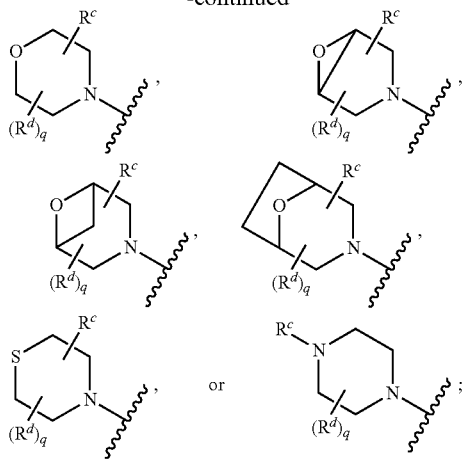

q is 0, 1, or 2.

In some embodiments, ring B is a bicyclic heterocycle containing 1-4 N atoms and 0 or 1 O or S atoms, or a bicyclic heterocycle containing 0-4 N atoms and 1 O or S atoms.

In some embodiments, ring B is a bicyclic heterocycle that is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, azaindolyl, indolinyl, isoindolinyl, indolinonyl, isoindolinonyl, or quinolinonyl.

In some embodiments, each each $R^c$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, or —SO$_2$N(R$^{15}$)$_2$; and each $R^d$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —O-(unsubstituted or substituted $C_1$-$C_4$alkyl), or —O-(unsubstituted or substituted $C_1$-$C_4$fluoroalkyl); or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle.

In some embodiments, each $R^c$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —NR$^{15}$C(=O)NR$^{15}$OR$^{14}$, —C(=O)NR$^{15}$OR$^{15}$,—CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C=N(R$^{14}$)OR$^{15}$ or N(R$^{15}$)SO$_2$R$^{14}$; and $R^d$ is independently hydrogen, halogen, unsubstituted or substituted $C_1$-$C_4$alkyl, unsubstituted or substituted $C_1$-$C_4$fluoroalkyl, unsubstituted or substituted monocyclic 4-7-membered heterocycle, —CN, —OH, —O-(unsubstituted or substituted $C_1$-$C_4$alkyl), —O-(unsubstituted or substituted $C_1$-$C_4$heteroalkyl), —O-(unsubstituted or substituted $C_1$-$C_4$fluoroalkyl), —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —NR$^{15}$C(=O)R$^{14}$, —CH(CF$_3$)N(R$^{15}$)$_2$, —NR$^{15}$C(=O)R$^{14}$, —CH$_2$NR$^{15}$C(=O)R$^{14}$, —SO$_2$N(R$^{15}$)$_2$, —C(=NOR$^{15}$)R$^{15}$, —N(R$^{15}$)SO$_2$R$^{14}$, —C(=O)NR$^{15}$S(=O)$_2$R$^{14}$, or —S(=O)$_2$NR$^{15}$C(=O)R$^{14}$, —C(=NR$^{15}$)N(R$^{15}$)$_2$; or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle.

In some embodiments, each $R^c$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, —OCF$_3$, —CO$_2$H, —CO$_2$CH$_3$, —CO$_2$CH$_2$CH$_3$, —CH$_2$CO$_2$H, —CH$_2$CO$_2$CH$_3$, —CH$_2$CO$_2$CH$_2$CH$_3$, —C(=O)NH$_2$, —C(=O)NHCH$_3$, —C(=O)N(CH$_3$)$_2$, —CH$_2$C(=O)NH$_2$, —CH$_2$C(=O)NHCH$_3$, —CH$_2$C(=O)N(CH$_3$)$_2$, —NH$_2$, —NHCH$_3$, —N(CH$_3$)$_2$, —CH$_2$NH$_2$, —CH$_2$NHCH$_3$, —CH$_2$N(CH$_3$)$_2$, azetidinyl, or pyrrolidinyl; each $R^d$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, or —OCF$_3$; or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic heterocycle.

In some embodiments, each $R^c$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, —OCF$_3$, —CO$_2$H, —CO$_2$CH$_3$, —CO$_2$CH$_2$CH$_3$, —CH$_2$CO$_2$H, —CH$_2$CO$_2$CH$_3$, —CH$_2$CO$_2$CH$_2$CH$_3$, —C(=O)NH$_2$, —C(=O)NHCH$_3$, —C(=O)NHOCH$_3$, —C(=O)N(CH$_3$)$_2$, —SO$_2$N(CH$_3$)$_2$, —C(=NOCH$_3$)H, —C(=O)NH$_2$, —CH$_2$C(=O)NHCH$_3$, —CH$_2$C(=O)N(CH$_3$)$_2$, —NH$_2$, —NHCH$_3$, —N(CH$_3$)$_2$, —NHCO$_2$CH$_3$, —NHSO$_2$CH$_3$, —CH$_2$NH$_2$, —CH$_2$NHCH$_3$, —CH$_2$N(CH$_3$)$_2$, CH(CF$_3$)NH$_2$, azetidinyl, or pyrrolidinyl; each $R^d$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, pyrrolyl, imidazolyl, pyrazolyl, triazolyl, tetrazolyl, —CN, —OH, —OCH$_3$, —OCH$_2$CH$_3$, —OCF$_3$, —OCH$_2$OCH$_3$, —OCH$_2$OCH$_2$CH$_3$, —OCH$_2$CH$_2$OH, —C(=O)NHOCH$_3$, —C(=NOCH$_3$)H, —CH$_2$C(=O)NH$_2$, —NH$_2$, NHCO$_2$CH$_3$, NHSO$_2$CH$_3$, NH(C=O)NHCH$_3$, NH(C=O)NHOCH$_3$, CH(CF$_3$)NH$_2$; or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic heterocycle.

In some embodiments, each $R^c$ is independently hydrogen, F, Cl, Br, —CH$_3$, —CH$_2$F, —CHF$_2$, —CF$_3$, —CN, —OH, —OCH$_3$, —OCF$_3$, —NH$_2$, CONH$_2$, azetidinyl, or pyrrolidinyl; each $R^d$ is independently hydrogen, F, Cl, Br, —CH$_3$, —CH$_2$F, —CHF$_2$, —CF$_3$, —CN, —OH, —OCH$_3$, —OCF$_3$; or if one $R^c$ and one $R^d$ are on adjacent atoms of ring B then the adjacent $R^c$ and $R^d$ groups are taken together with the intervening atoms to which they are attached to form an unsubstituted or substituted 5-membered monocyclic heterocycle.

In some embodiments, each $R^c$ is independently hydrogen, F, Cl, Br, —CH₃, —CH₂F, —CHF₂, —CF₃, —CN, —OH, —OCH₃, —OCF₃, —NH₂, —C(=O)NH₂, —CH(=NOCH₃), —SO₂N(CH₃)₂, azetidinyl, or pyrrolidinyl; each $R^d$ is independently hydrogen, F, Cl, Br, —CH₃, —CH₂F, —CHF₂, —CF₃, —CN, —OH, —OCH₃, —OCH₂OCH₃, —OCF₃, —CH₂OH, —C(=O)NH₂, —CH₂C(=O)NH₂, —NH₂, —NHC(=O)OCH₃, —NHSO₂CH₃; or if one $R^c$ and one $R^d$ are on adjacent atoms of ring B then the adjacent $R^c$ and $R^d$ groups are taken together with the intervening atoms to which they are attached to form an unsubstituted or substituted 5-membered monocyclic heterocycle.

In some embodiments, each $R^c$ is independently hydrogen, F, Cl, Br, —CH₃, —CHF, —CHF₂, —CF₃, pyrrolyl, imidazolyl, pyrazolyl, triazolyl, tetrazolyl, —CN, —OH, —OCH₃, —OCF₃, —NH₂, —C(=O)NH₂, —C(=NOCH₃)H, —SO₂CH₃, —SO₂N(CH₃)₂, azetidinyl, or pyrrolidinyl; each $R^d$ is independently hydrogen, F, Cl, Br, —CH₃, —CHF, —CHF₂, —CF₃, —CN, —OH, —OCH₃, —OCF₃, —OCH₂OCH₃, —CH₂OH, —OCH₂CH₂OH, —C(=O)NH₂, —C(=O)NHOCH₃, NH₂, NHCO₂CH₃, NH(C=O)NHOCH₃, CH₂(C=O)NH₂; or if one $R^c$ and one $R^d$ are on adjacent atoms of ring B then the adjacent $R^c$ and $R^d$ groups are taken together with the intervening atoms to which they are attached to form an unsubstituted or substituted 5-membered monocyclic heterocycle.

In some embodiments, the compound of Formula (AI) has the structure of Formula (AII), or a pharmaceutically acceptable salt, solvate, diastereomeric mixture, individual enantiomers or prodrug thereof:

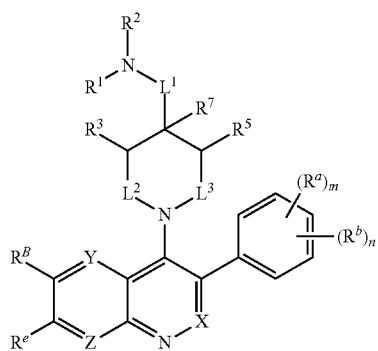

Formula (AII)

wherein:

$R^B$ is an unsubstituted or substituted ring B that is an unsubstituted or substituted monocyclic phenyl, or an unsubstituted or substituted pyridinyl, wherein if the ring B is substituted then the ring B is substituted with p $R^c$ and q $R^d$; p is 1 or 2; q is 0, 1 or 2;

In some embodiments, the compound of Formula (AII) or Formula (I) has the structure of Formula (II), or a pharmaceutically acceptable salt, solvate, diastereomeric mixture, individual enantiomers or prodrug thereof:

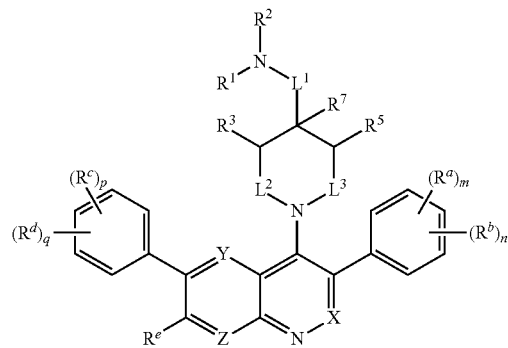

Formula (II)

wherein:
each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —OR¹⁴, —CO₂R¹⁵, —CH₂CO₂R¹⁵, —C(=O)N(R¹⁵)₂, —CH₂C(=O)N(R¹⁵)₂, —N(R¹⁵)₂, —CH₂N(R¹⁵)₂, —CH(CF₃)N(R¹⁵)₂, —NR¹⁵C(=O)R¹⁴, —CH₂NR¹⁵C(=O)R¹⁴, —SR¹⁴, —S(=O)R¹⁴, —SO₂R¹⁴, —SO₂N(R¹⁵)₂ or —C(=NOR¹⁵)R¹⁵;

m is 1 or 2; n is 0, 1 or 2;
or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;

each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —OR¹⁴, —C(=O)R¹⁵, —OC(=O)R¹⁵, —CO₂R¹⁵, —CH₂CO₂R¹⁵, —C(=O)N(R¹⁵)₂, —OC(=O)N(R¹⁵)₂, —NR¹⁵C(=O)N(R¹⁵)₂, —NR¹⁵C(=O)OR¹⁴, —NR¹⁵C(=O)NR¹⁵OR¹⁴, —(=O)NR¹⁵OR¹⁵, —CH₂C(=O)N(R¹⁵)₂, —N(R¹⁵)₂, —CH₂N(R¹⁵)₂, —CH(CF₃)N(R¹⁵)₂, —NR¹⁵C(=O)R¹⁴, —CH₂NR¹⁵C(=O)R¹⁴, —SR¹⁴, —S(=O)R¹⁴, —SO₂R¹⁴, —SO₂N(R¹⁵)₂, —C(=NOR¹⁵)R¹⁵, N(R¹⁵)SO₂R¹⁴, —C(=O)NR¹⁵S(=O)₂R¹⁴, —S(=O)₂NR¹⁵C(=O)R¹⁴, —C(=NR¹⁵)N(R¹⁵)₂, —NR¹⁵C(=NR¹⁵)N(R¹⁵)₂, —NR¹⁵C(=CR¹⁴R¹⁵)N(R¹⁵)₂, —C(=O)NR¹⁵C(=NR¹⁵)N(R¹⁵)₂ or, —C(=O)NR¹⁵C(=CR¹⁴R¹⁵)N(R¹⁵)₂;

p is 1 or 2; q is 0, 1 or 2;
or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is $CR^f$ or N;
Y is $CR^f$ or N;
Z is $CR^f$ or N;

$R^e$ is hydrogen, halogen, $C_1$-$C_4$alkyl, $C_1$-$C_4$fluoroalkyl, —CN, —OH, or —OR¹⁴;

each $R^f$ is independently hydrogen, halogen, $C_1$-$C_4$alkyl, $C_1$-$C_4$fluoroalkyl, —CN, —OH, or —OR¹⁴;

$R^1$ and $R^2$ are independently hydrogen, unsubstituted or substituted $C_1$-$C_6$alkyl, unsubstituted or substituted $C_1$-$C_6$heteroalkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;

or $R^1$ and $R^2$ are taken together with the nitrogen atom to which they are attached to form ring C that is an unsubstituted or substituted N-containing $C_2$-$C_8$heterocycloalkyl;

$R^3$ and $R^5$ are each independently selected from the group consisting of hydrogen, halogen, —OH, —$OR^{14}$, —$SR^{14}$, —S(=O)$R^{14}$, —S(=O)$_2R^{14}$, —N($R^{15}$)$_2$, —CN, —C(=O)O$R^{15}$, —C(=O)N($R^{15}$)$_2$, unsubstituted or substituted $C_1$-$C_6$alkyl, unsubstituted or substituted $C_1$-$C_6$heteroalkyl, and unsubstituted or substituted $C_1$-$C_6$fluoroalkyl;

or $R^3$ and $R^5$ are taken together to form a bond, or $C_1$-$C_2$alkylene;

or $R^2$ and $R^5$ are taken together with the intervening atoms to which they are attached to form an unsubstituted or substituted 4-7 membered saturated N-containing heterocyclic ring;

$R^7$ is hydrogen, or unsubstituted or substituted $C_1$-$C_4$alkyl;

or $R^2$ and $R^7$ are taken together with the intervening atoms to which they are attached to form an unsubstituted or substituted N-containing $C_2$-$C_8$heterocycloalkyl;

$L^1$ is absent or —CH$R^8$—;

$L^2$ is —CH$_2$— or absent;

$L^3$ is —CH$_2$—, —CH$_2$CH$_2$— or absent;

$R^7$ is hydrogen, or $C_1$-$C_4$alkyl;

each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

or two $R^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more $R^s$ groups independently selected from the group consisting of halogen, $C_1$-$C_6$alkyl, monocyclic carbocycle, monocyclic heterocycle, —CN, —$OR^{16}$, —CO$_2R^{16}$, —C(=O)N($R^{16}$)$_2$, —N($R^{16}$)$_2$, —N$R^{16}$C(=O)$R^{17}$, —$SR^{16}$, —S(=O)$R^{17}$, —SO$_2R^{17}$, or —SO$_2$N($R^{16}$)$_2$;

each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;

each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

In some embodiments of the compound of Formula (II):

each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, —CN, —OH, —$OR^{14}$, —CO$_2R^{15}$, —CH$_2$CO$_2R^{15}$, —C(=O)N($R^{15}$)$_2$, —CH$_2$C(=O)N($R^{15}$)$_2$, —N($R^{15}$)$_2$, —CH$_2$N($R^{15}$)$_2$, —N$R^{15}$C(=O)$R^{14}$, —CH$_2$N$R^{15}$C(=O)$R^{14}$, —$SR^{14}$, —S(=O)$R^{14}$, —SO$_2R^{14}$, or —SO$_2$N($R^{15}$)$_2$;

m is 1 or 2; n is 0, 1 or 2;

each $R^c$ and $R^d$ is independently hydrogen, halogen, unsubstituted or substituted $C_1$-$C_6$alkyl, unsubstituted or substituted $C_1$-$C_6$fluoroalkyl, —CN, —OH, —$OR^{14}$, —CO$_2R^{15}$, —CH$_2$CO$_2R^{15}$, —C(=O)N($R^{15}$)$_2$, —CH$_2$C(=O)N($R^{15}$)$_2$, —N($R^{15}$)$_2$, —CH$_2$N($R^{15}$)$_2$, —N$R^{15}$C(=O)$R^{14}$, —CH$_2$N$R^{15}$C(=O)$R^{14}$, —$SR^{14}$, —S(=O)$R^{14}$, —SO$_2R^{14}$, or —SO$_2$N($R^{15}$)$_2$;

p is 1 or 2; q is 0, 1 or 2;

or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is C$R^f$ or N;

Y is C$R^f$ or N;

Z is C$R^f$ or N;

$R^e$ is hydrogen, halogen, $C_1$-$C_4$alkyl, $C_1$-$C_4$fluoroalkyl, —CN, —OH, or —$OR^{14}$;

each $R^f$ is independently hydrogen, halogen, $C_1$-$C_4$alkyl, $C_1$-$C_4$fluoroalkyl, —CN, —OH, or —$OR^{14}$;

$R^1$ and $R^2$ are independently hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;

or $R^1$ and $R^2$ are taken together with the nitrogen atom to which they are attached to form ring C that is an unsubstituted or substituted N-containing $C_2$-$C_8$heterocycloalkyl;

$R^3$ and $R^5$ are each independently selected from the group consisting of hydrogen, halogen, —OH, —$OR^{14}$, —$SR^{14}$, —S(=O)$R^{14}$, —S(=O)$_2R^{14}$, —N($R^{15}$)$_2$, —CN, unsubstituted or substituted $C_1$-$C_6$alkyl, and unsubstituted or substituted $C_1$-$C_6$fluoroalkyl;

or $R^3$ and $R^5$ are taken together to form a bond, or $C_1$-$C_2$alkylene;

or $R^2$ and $R^5$ are taken together with the intervening atoms to which they are attached to form an unsubstituted or substituted 4-7 membered saturated N-containing heterocyclic ring;

$R^7$ is hydrogen, or unsubstituted or substituted $C_1$-$C_4$alkyl;

or $R^2$ and $R^7$ are taken together with the intervening atoms to which they are attached to form an unsubstituted or substituted N-containing $C_2$-$C_8$heterocycloalkyl;

$L^1$ is absent or —CH$R^8$—;

$L^2$ is —CH$_2$— or absent;

$L^3$ is —CH$_2$—, —CH$_2$CH$_2$— or absent;

$R^8$ is hydrogen, or $C_1$-$C_4$alkyl;

each $R^{14}$ is independently selected from unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from hydrogen, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;
or two $R^{15}$ on the same N atom are taken together with the N atom to which they are attached to form an unsubstituted or substituted N-containing heterocycle;
wherein each substituted alkyl, substituted fluoroalkyl, substituted heteroalkyl, substituted carbocycle, and substituted heterocycle is substituted with one or more $R^s$ groups independently selected from the group consisting of halogen, $C_1$-$C_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;
each $R^{16}$ is independently selected from hydrogen, $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{16}$ groups are taken together with the N atom to which they are attached to form a N-containing heterocycle;
each $R^{17}$ is independently selected from $C_1$-$C_6$alkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

In some embodiments, $L^2$ is —CH$_2$—; $L^3$ is —CH$_2$—.
In some embodiments, $L^2$ is absent; $L^3$ is —CH$_2$CH$_2$—.
In some embodiments, $L^2$ is absent; $L^3$ is absent.
In some embodiments, $L^2$ is or absent; $L^3$ is —CH$_2$—.

In some embodiments, $R^1$ hydrogen; $R^2$ is hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl; or $R^1$ and $R^2$ are taken together with the nitrogen atom to which they are attached to form ring C that is an unsubstituted or substituted N-containing $C_2$-$C_8$heterocycloalkyl; $R^3$ is hydrogen; $R^5$ are each independently selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, $C_1$-$C_6$alkyl, and $C_1$-$C_6$fluoroalkyl; or $R^3$ and $R^5$ are taken together to form a bond, or —CH$_2$— or —CH$_2$CH$_2$—; or $R^2$ and $R^5$ are taken together with the intervening atoms to which they are attached to form an unsubstituted or substituted 4- to 7-membered saturated N-containing heterocyclic ring; $R^7$ is hydrogen, or $C_1$-$C_4$alkyl; or $R^2$ and $R^7$ are taken together with the intervening atoms to which they are attached to form an unsubstituted or substituted 4- to 7-membered N-containing $C_2$-$C_8$heterocycloalkyl.

In some embodiments, $R^1$ hydrogen; $R^2$ is hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl; or $R^1$ and $R^2$ are taken together with the nitrogen atom to which they are attached to form ring C that is an unsubstituted or substituted N-containing $C_2$-$C_6$heterocycloalkyl; $R^3$ is hydrogen; $R^5$ are each independently selected from the group consisting of hydrogen, halogen, —OH, —OR$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted $C_1$-$C_6$alkyl, and unsubstituted or substituted $C_1$-$C_6$fluoroalkyl; or $R^3$ and $R^5$ are taken together to form a bond, or —CH$_2$— or —CH$_2$CH$_2$—; or $R^2$ and $R^5$ are taken together with the intervening atoms to which they are attached to form an unsubstituted or substituted 4- to 7-membered saturated N-containing heterocyclic ring; $R^7$ is hydrogen, or $C_1$-$C_4$alkyl; or $R^2$ and $R^7$ are taken together with the intervening atoms to which they are attached to form an unsubstituted or substituted 4- to 7-membered N-containing $C_2$-$C_8$heterocycloalkyl.

In some embodiments, $R^1$ hydrogen; $R^2$ is hydrogen, —CH$_3$, —CH$_2$CH$_3$, —CH$_2$CH$_2$OCH$_3$, CH$_2$CH$_2$F, —CH$_2$CH$_2$NH$_2$, —CH$_2$CH$_2$NHCH$_3$, —CH$_2$CH$_2$N(CH$_3$)$_2$, —CH$_2$CH$_2$CH$_3$, —CH(CH$_3$)$_2$, cyclopropyl, —CH$_2$CH$_2$CH$_2$F, CH$_2$CH$_2$CH$_2$OCH$_3$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, cyclobutyl, cyclopentyl, cyclohexyl, oxetanyl, tetrahydrofuranyl, or tetrahydropyranyl; or $R^1$ and $R^2$ are taken together with the nitrogen atom to which they are attached to form ring C that is an unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl; $R^3$ is hydrogen; $R^5$ is hydrogen, F, Cl, Br, —OH, —OCH$_3$, —NH$_2$, —NHCH$_3$, —N(CH$_3$)$_2$, —OCH$_2$CH$_3$, —OCF$_3$, —CH$_3$, —CH$_2$CH$_3$, —CH$_2$F, —CHF$_2$, or —CF$_3$; or $R^2$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl; $R^7$ is hydrogen, —CH$_3$, or —CH$_2$CH$_3$; or $R^2$ and $R^7$ are taken together with the nitrogen atom to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

In some embodiments, $R^1$ hydrogen; $R^2$ is hydrogen, —CH$_3$, —CH$_2$CH$_3$, —CH$_2$CH$_2$OCH$_3$, CH$_2$CH$_2$F, —CH$_2$CH$_2$NH$_2$, —CH$_2$CH$_2$NHCH$_3$, —CH$_2$CH$_2$N(CH$_3$)$_2$, —CH$_2$CH$_2$CH$_3$, —CH(CH$_3$)$_2$, cyclopropyl, —CH$_2$CH$_2$CH$_2$F, CH$_2$CH$_2$CH$_2$OCH$_3$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, cyclobutyl, cyclopentyl, cyclohexyl, oxetanyl, tetrahydrofuranyl, or tetrahydropyranyl; or $R^1$ and $R^2$ are taken together with the nitrogen atom to which they are attached to form ring C that is an unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl; $R^3$ is hydrogen; $R^5$ is hydrogen, F, Cl, Br, —OH, —OCH$_3$, —NH$_2$, —NHCH$_3$, —N(CH$_3$)$_2$, —OCH$_2$CH$_3$, —OCF$_3$, —CH$_3$, —CH$_2$CH$_3$, —CH$_2$F, —CHF$_2$, or —CF$_3$, —CN, —C(=O)OCH$_3$, —C(=O)NH$_2$, —C(=O)NHCH$_3$, —C(=O)N(CH$_3$)$_2$; or $R^2$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl; $R^7$ is hydrogen, —CH$_3$, or —CH$_2$CH$_3$; or $R^2$ and $R^7$ are taken together with the nitrogen atom to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

In some embodiments, $L^1$ is absent, —CH$_2$—, —CHCH$_3$— or —CH(CH$_2$CH$_3$)—.

In some embodiments, $L^1$ is absent.

In some embodiments, $L^1$ is —CH$_2$—, —CHCH$_3$— or —CH(CH$_2$CH$_3$)—. In some embodiments, $L^1$ is —CH$_2$—.

In some embodiments,

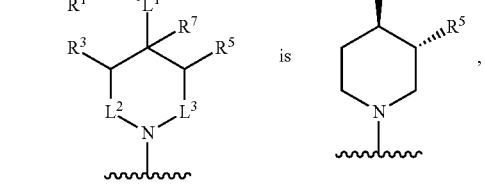

In some embodiments,

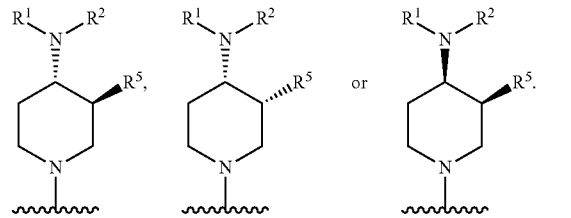

In some embodiments,

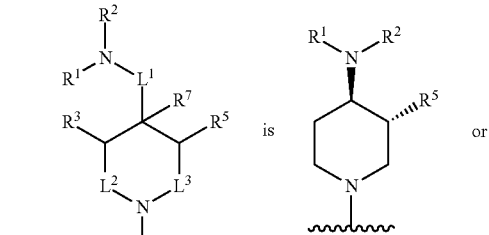

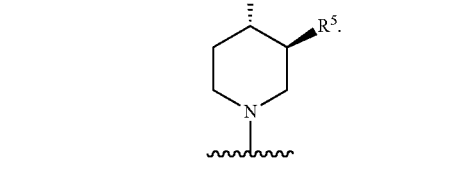

In some embodiments,

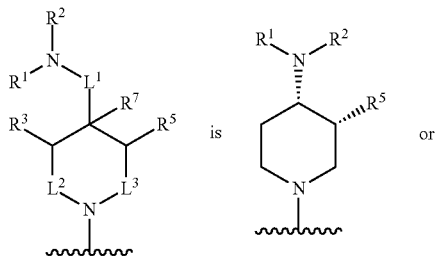

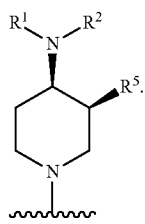

In some embodiments,

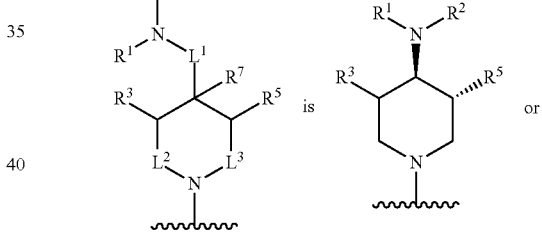

In some embodiments,

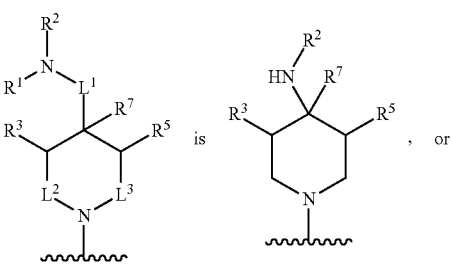

-continued
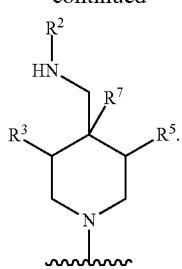
In some embodiments,
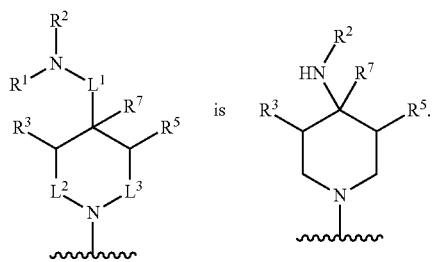 is
In some embodiments,
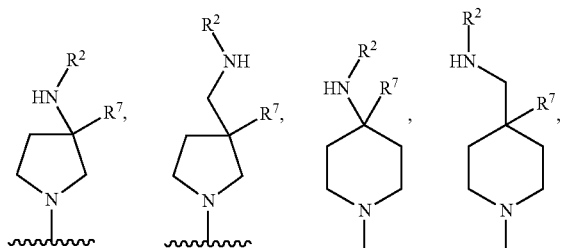 is
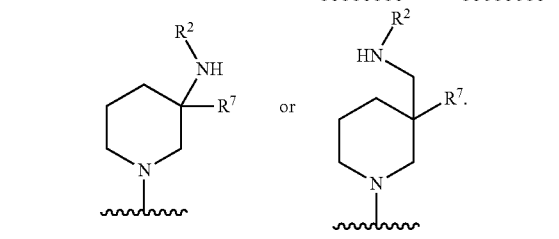
In some embodiments,
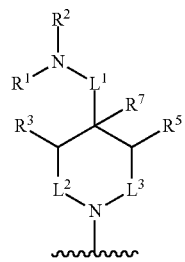
is
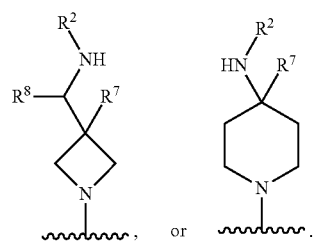
In some embodiments,
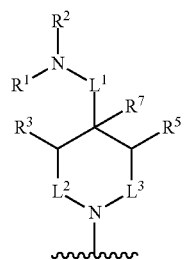 is 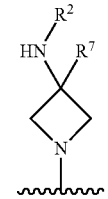,
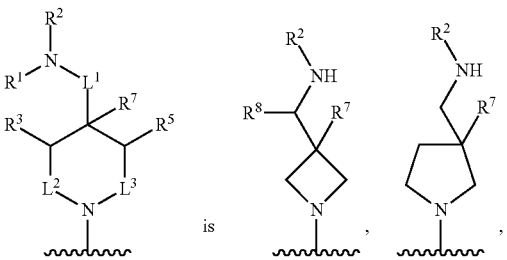
In some embodiments,
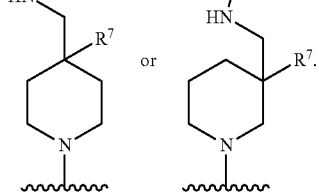
In some embodiments,
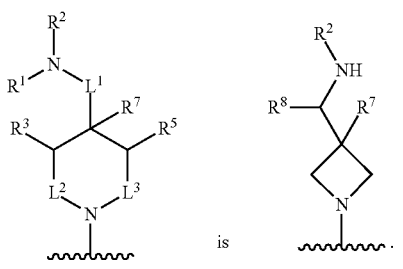

In some embodiments,
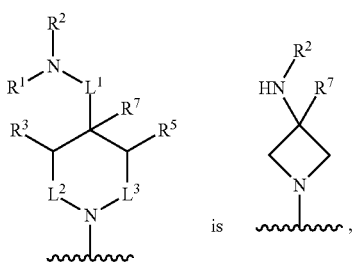
is 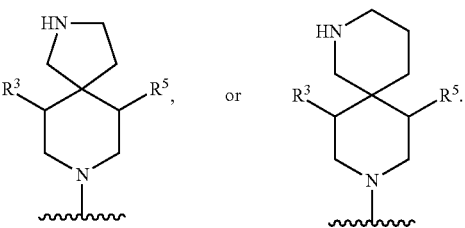,
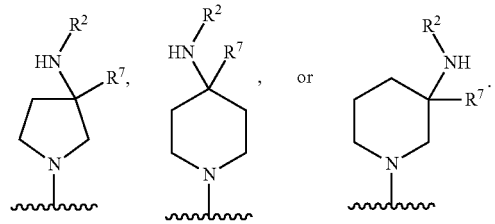
In some embodiments,
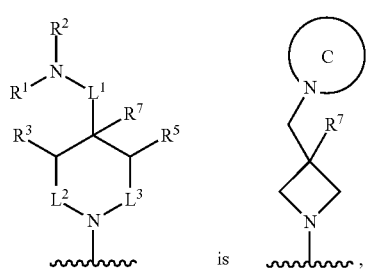
is 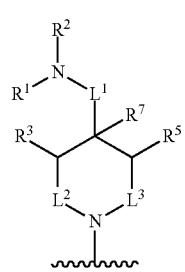,
wherein, ring C that is an unsubstituted or substituted N-containing $C_2$-$C_6$heterocycloalkyl.
In some embodiments,
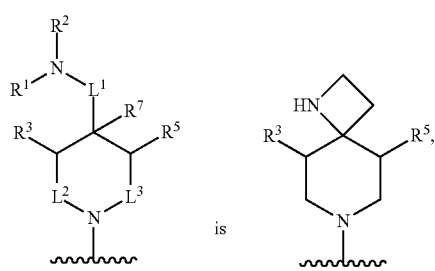
is 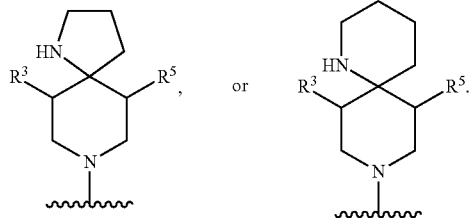
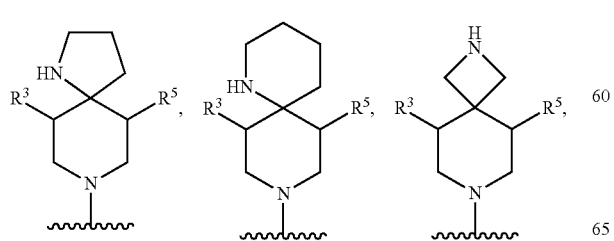
In some embodiments,
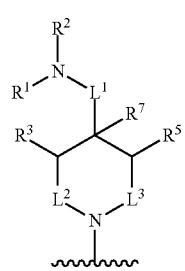
is 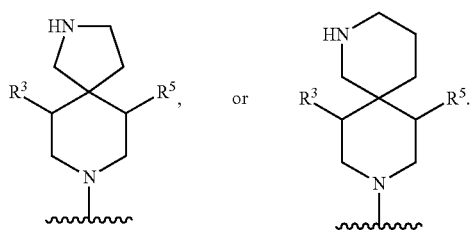

In some embodiments,

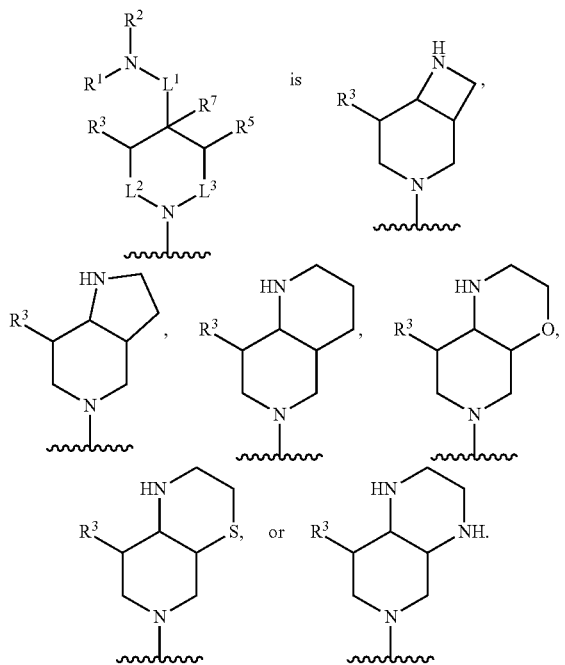

In some embodiments,

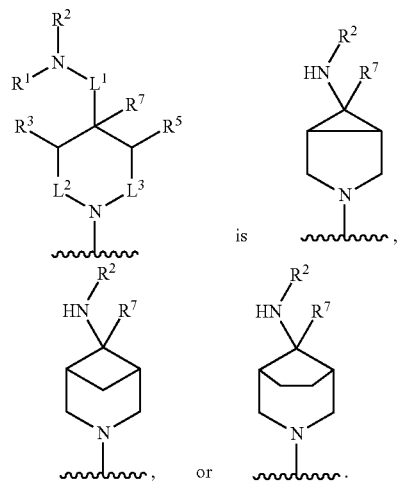

In some embodiments,

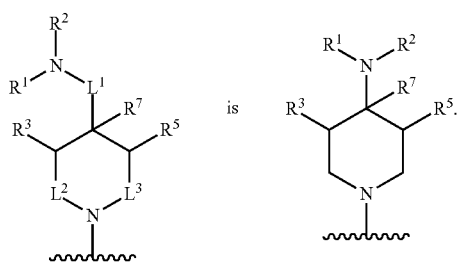

In some embodiments,

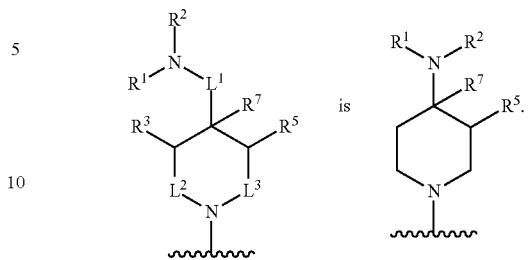

In some embodiments, the compound of Formula (AII) has the following structure of Formula (A2), or a pharmaceutically acceptable salt, solvate, diastereomeric mixture, individual enantiomers or prodrug thereof:

Formula (A2)

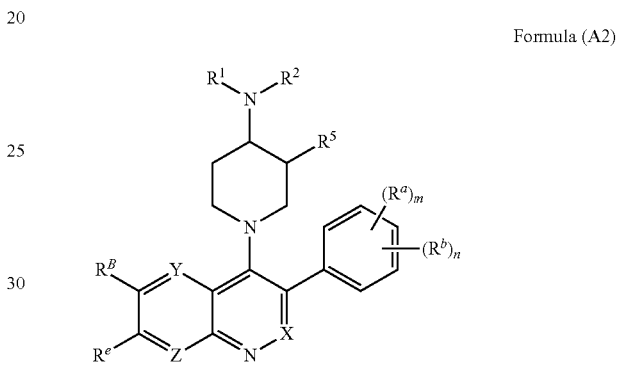

wherein:
each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —$OR^{14}$, —$CO_2R^{15}$, —$CH_2CO_2R^{15}$, —$C(=O)N(R^{15})_2$, —$CH_2C(=O)N(R^{15})_2$, —$N(R^{15})_2$, —$CH_2N(R^{15})_2$, —$CH(CF_3)N(R^{15})_2$, —$NR^{15}C(=O)R^{14}$, —$CH_2NR^{15}C(=O)R^{14}$, —$SR^{14}$, —$S(=O)R^{14}$, —$SO_2R^{14}$, —$SO_2N(R^{15})_2$ or —$C(=NOR^{15})R^{15}$;
m is 1 or 2; n is 0, 1 or 2;
or if one $R^a$ and one $R^b$ are on adjacent atoms of ring A then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;
$R^B$ is an unsubstituted or substituted ring B that is an unsubstituted or substituted phenyl or an unsubstituted or substituted pyridinyl, wherein if the ring B is substituted then the ring B is substituted with p $R^c$ and q $R^d$;
p is 1 or 2; q is 0, 1 or 2;
each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —$OR^{14}$, —$C(=O)R^{15}$, —$OC(=O)R^{15}$, —$CO_2R^{15}$, —$CH_2CO_2R^{15}$, —$C(=O)N(R^{15})_2$, —$OC(=O)N(R^{15})_2$, —$NR^{15}C(=O)N(R^{15})_2$, —$NR^{15}C(=O)OR^{14}$, —$NR^{15}C(=O)NR^{15}OR^{14}$, —$C(=O)NR^{15}OR^{15}$, —$CH_2C(=O)N(R^{15})_2$, —$N(R^{15})_2$, —$CH_2N(R^{15})_2$, —$CH(CF_3)N(R^{15})_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C(=NOR$^{15}$)R$^{15}$, —N(R$^{15}$)SO$_2$R$^{14}$, —C(=O)NR$^{15}$S(=O)$_2$R$^{14}$, —S(=O)$_2$NR$^{15}$C(=O)R$^{14}$, —C(=NR$^{15}$)N(R$^{15}$)$_2$, —NR$^{15}$C(=NR$^{15}$)N(R$^{15}$)$_2$, —NR$^{15}$C(=CR$^{14}$R$^{15}$)N(R$^{15}$)$_2$, —C(=O)NR$^{15}$C(=NR$^{15}$)N(R$^{15}$)$_2$ or, —C(=O)NR$^{15}$C(=CR$^{14}$R$^{15}$)N(R$^{15}$)$_2$;

p is 1 or 2; q is 0, 1 or 2;

or if one R$^c$ and one R$^d$ are on adjacent atoms of ring B then the adjacent R$^c$ and R$^d$ groups are taken together with the intervening atoms to which they are attached to form an unsubstituted or substituted 5- or 6-membered monocyclic carbocycle or an unsubstituted or substituted 5- or 6-membered monocyclic heterocycle;

X is CR$^f$ or N;
Y is CR$^f$ or N;
Z is CR$^f$ or N;

R$^e$ is hydrogen, halogen, C$_1$-C$_4$alkyl, C$_1$-C$_4$fluoroalkyl, —CN, OH, or —OR$^{14}$;

each R$^f$ is independently hydrogen, halogen, C$_1$-C$_4$alkyl, C$_1$-C$_4$fluoroalkyl, —CN, —OH, or —OR$^{14}$;

R$^1$ and R$^2$ are independently hydrogen, unsubstituted or substituted C$_1$-C$_6$alkyl, unsubstituted or substituted C$_1$-C$_6$heteroalkyl, unsubstituted or substituted C$_1$-C$_6$fluoroalkyl, unsubstituted or substituted C$_3$-C$_6$cycloalkyl or substituted or unsubstituted C$_2$-C$_6$heterocycloalkyl;

or R$^1$ and R$^2$ are taken together with the nitrogen atom to which they are attached to form ring C that is an unsubstituted or substituted N-containing C$_2$-C$_8$heterocycloalkyl;

R$^5$ is selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted C$_1$-C$_6$alkyl, unsubstituted or substituted C$_1$-C$_6$heteroalkyl, and unsubstituted or substituted C$_1$-C$_6$fluoroalkyl;

or R$^2$ and R$^5$ are taken together with the intervening atoms to which they are attached to form an unsubstituted or substituted 4-7 membered saturated N-containing heterocyclic ring;

each R$^{14}$ is independently selected from unsubstituted or substituted C$_1$-C$_6$alkyl, unsubstituted or substituted C$_1$-C$_6$heteroalkyl, unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

each R$^{15}$ is independently selected from hydrogen, unsubstituted or substituted C$_1$-C$_6$alkyl, unsubstituted or substituted C$_1$-C$_6$heteroalkyl, unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

or two R$^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more R$^s$ groups independently selected from the group consisting of halogen, C$_1$-C$_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or SO$_2$N(R$^{16}$)$_2$;

each R$^{16}$ is independently selected from hydrogen, C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl; or two R$^{16}$ groups are taken together with the N atom to which they are attached to form a N-containing heterocycle;

each R$^{17}$ is independently selected from C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl.

In some embodiments, the compound of Formula (AII) or Formula (A2) has the structure of Formula (AIIa), Formula (AIIb), Formula (AIIc), Formula (AIId), Formula (AIIe), Formula (AIIf), or a pharmaceutically acceptable salt, solvate, diastereomeric mixture, individual enantiomers or prodrug thereof:

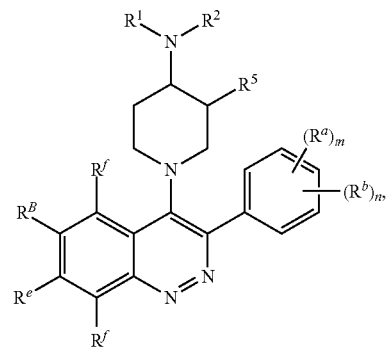

Formula (AIIa)

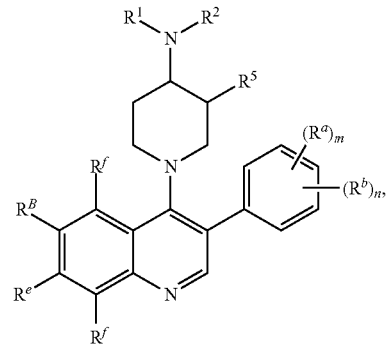

Formula (AIIb)

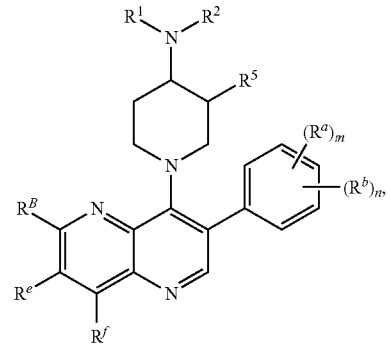

Formula (AIIc)

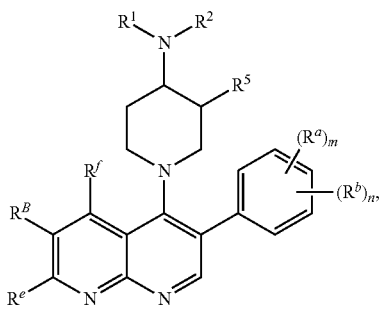

Formula (AIId)

Formula (AIIe)

Formula (AIIf)

In some embodiments, the compound of Formula (AII) or Formula (A2) has the structure of Formula (AIIa), or a pharmaceutically acceptable salt, solvate, diastereomeric mixture, individual enantiomers or prodrug thereof.

In some embodiments, the compound of Formula (AII) or Formula (A2) has the structure of Formula (AIIb), or a pharmaceutically acceptable salt, solvate, diastereomeric mixture, individual enantiomers or prodrug thereof.

In some embodiments, the compound of Formula (AII) or Formula (A2) has the structure of Formula (AIIc), or a pharmaceutically acceptable salt, solvate, diastereomeric mixture, individual enantiomers or prodrug thereof.

In some embodiments, the compound of Formula (AII) or Formula (A2) has the structure of Formula (AIId), or a pharmaceutically acceptable salt, solvate, diastereomeric mixture, individual enantiomers or prodrug thereof.

In some embodiments, the compound of Formula (AII) or Formula (A2) has the structure of Formula (IIe), or a pharmaceutically acceptable salt, solvate, diastereomeric mixture, individual enantiomers or prodrug thereof.

In some embodiments, the compound of Formula (AII) or Formula (A2) has the structure of Formula (AIIf), or a pharmaceutically acceptable salt, solvate, diastereomeric mixture, individual enantiomers or prodrug thereof.

In some embodiments, $R^e$ is hydrogen, F, Cl, Br, —$CH_3$, —$CH_2CH_3$, —$CH_2F$, —$CHF_2$, —$CF_3$, —CN, —OH, —$OCH_3$, —$OCH_2CH_3$, or —$OCF_3$; each $R^f$ is independently hydrogen, F, Cl, Br, —$CH_3$, —$CH_2CH_3$, —$CH_2F$, —$CHF_2$, —$CF_3$, —CN, —OH, —$OCH_3$, —$OCH_2CH_3$, or —$OCF_3$.

In some embodiments, each $R^a$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —$OR^{14}$, —$CO_2R^{15}$, —$CH_2CO_2R^{15}$, —$C(=O)N(R^{15})_2$, —$CH_2C(=O)N(R^{15})_2$, —$N(R^{15})_2$, —$CH_2N(R^{15})_2$, —$CH(CF_3)N(R^{15})_2$, —$NR^{15}C(=O)R^{14}$, —$CH_2NR^{15}C(=O)R^{14}$, —$SR^{14}$, —$S(=O)R^{14}$, —$SO_2R^{14}$, —$SO_2N(R^{15})_2$ or —$C=N(R^{14})OR^{15}$; and each $R^b$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —O-(unsubstituted or substituted $C_1$-$C_4$alkyl), or —O-(unsubstituted or substituted $C_1$-$C_4$fluoroalkyl).

In some embodiments, each $R^a$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —$OR^{14}$, —$CO_2R^{15}$, —$CH_2CO_2R^{15}$, —$C(=O)N(R^{15})_2$, —$CH_2C(=O)N(R^{15})_2$, —$N(R^{15})_2$, or —$CH_2N(R^{15})_2$; and each $R^b$ is independently hydrogen, halogen, unsubstituted or substituted $C_1$-$C_4$alkyl, unsubstituted or substituted $C_1$-$C_4$heteroalkyl, —CN, —O-(unsubstituted or substituted $C_1$-$C_4$alkyl), or —O-(unsubstituted or substituted $C_1$-$C_4$fluoroalkyl).

In some embodiments, each $R^a$ is independently hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2OH$, —$CH_2CN$, —$CH_2F$, —$CHF_2$, —$CF_3$, —CN, —OH, —$OCH_3$, —$OCH_2CH_3$, —$OCF_3$, —$CH_2OH$, —$CH_2CH_2OH$, —$CO_2H$, —$CO_2CH_3$, —$CO_2CH_2CH_3$, —$CH_2CO_2H$, —$CH_2CO_2CH_3$, —$CH_2CO_2CH_2CH_3$, —$C(=O)NH_2$, —$C(=O)NHCH_3$, —$C(=O)N(CH_3)_2$, —$CH_2C(=O)NH_2$, —$CH_2C(=O)NHCH_3$, —$CH_2C(=O)N(CH_3)_2$, —$NH_2$, —$NHCH_3$, —$N(CH_3)_2$, —$CH_2NH_2$, —$CH_2NHCH_3$, or —$CH_2N(CH_3)_2$;

each $R^b$ is independently hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2OH$, —$CH_2CN$, —$CH_2F$, —$CHF_2$, —$CF_3$, —CN, —OH, —$OCH_3$, —$OCH_2CH_3$, —$OCF_3$.

In some embodiments, each $R^a$ is independently hydrogen, F, Cl, Br, —$CH_3$, —$CH_2F$, —$CHF_2$, —$CF_3$, —CN, —OH, —$OCH_3$, —$OCF_3$, or —$CH_2CH_2OH$; each $R^b$ is independently hydrogen, F, Cl, Br, —$CH_3$, —$CH_2F$, —$CHF_2$, —$CF_3$, —CN, —$OCH_3$, —$OCF_3$.

In some embodiments,

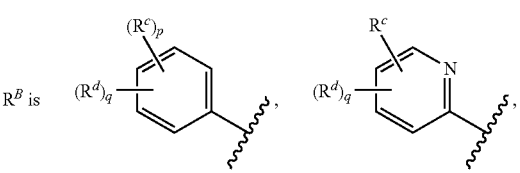

$R^B$ is

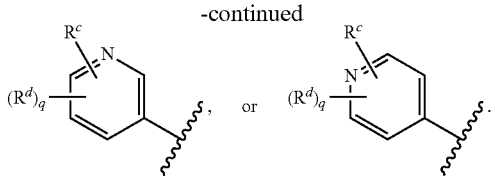

In some embodiments,

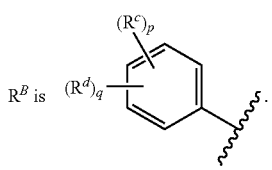

In some embodiments,

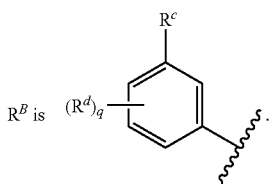

In some embodiments,

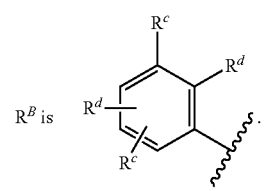

In some embodiments, each $R^c$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$heteroalkyl, —CN, —OH, —OR$^{14}$, —CO$_2$R$^{15}$, —CH$_2$CO$_2$R$^{15}$, —C(=O)N(R$^{15}$)$_2$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C=N(R$^{15}$)OR$^{15}$ or N(R$^{15}$)SO$_2$R$^{14}$; and $R^d$ is independently hydrogen, halogen, unsubstituted or substituted $C_1$-$C_4$alkyl, unsubstituted or substituted $C_1$-$C_4$fluoroalkyl, unsubstituted or substituted monocyclic 4-7-membered heterocycle, —CN, —OH, —O-(unsubstituted or substituted $C_1$-$C_4$alkyl), —O-(unsubstituted or substituted $C_1$-$C_4$heteroalkyl), —O-(unsubstituted or substituted $C_1$-$C_4$fluoroalkyl), —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SO$_2$N(R$^{15}$)$_2$, —C(=NOR$^{15}$)R$^{15}$, —N(R$^{15}$)SO$_2$R$^{14}$, —C(=O)NR$^{15}$S(=O)$_2$R$^{14}$, or —S(=O)$_2$NR$^{15}$C(=O)R$^{14}$, —C(=NR$^{15}$)N(R$^{15}$)$_2$; or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle.

In some embodiments, each $R^c$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, —OCF$_3$, —CO$_2$H, —CO$_2$CH$_3$, —CO$_2$CH$_2$CH$_3$, —CH$_2$CO$_2$H, —CH$_2$CO$_2$CH$_3$, —CH$_2$CO$_2$CH$_2$CH$_3$, —C(=O)NH$_2$, —C(=O)NHCH$_3$, —C(=O)NHOCH$_3$, —C(=O)N(CH$_3$)$_2$, —SO$_2$N(CH$_3$)$_2$, —C(=NOH)H, —C(=NOCH$_3$)H, —CH$_2$C(=O)NH$_2$, —CH$_2$C(=O)NHCH$_3$, —CH$_2$C(=O)N(CH$_3$)$_2$, —NH$_2$, —NHCH$_3$, —N(CH$_3$)$_2$, —NHCO$_2$CH$_3$, —NHSO$_2$CH$_3$, —CH$_2$NH$_2$, —CH$_2$NHCH$_3$, —CH$_2$N(CH$_3$)$_2$, CH(CF$_3$)NH$_2$, azetidinyl, or pyrrolidinyl; each $R^d$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, pyrrolyl, imidazolyl, pyrazolyl, triazolyl, tetrazolyl, —CN, —OH, —OCH$_3$, —OCH$_2$CH$_3$, —OCF$_3$, —OCH$_2$OCH$_3$, —OCH$_2$OCH$_2$CH$_3$, —OCH$_2$CH$_2$OH, —C(=O)NHOCH$_3$, —C(=NOH)H, —C(=NOCH$_3$)H, —CH$_2$C(=O)NH$_2$, —NH$_2$, NHCO$_2$CH$_3$, NHSO$_2$CH$_3$, NH(C=O)NHCH$_3$, NH(C=O)NHOCH$_3$, CH(CF$_3$)NH$_2$; or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic heterocycle.

In some embodiments, each $R^c$ is independently hydrogen, F, Cl, Br, —CH$_3$, —CH$_2$F, —CHF$_2$, —CF$_3$, pyrrolyl, imidazolyl, pyrazolyl, triazolyl, tetrazolyl, —CN, —OH, —OCH$_3$, —OCF$_3$, —NH$_2$, —C(=O)NH$_2$, —CONHCH$_3$, —C(=NOH)H, —C(=NOCH$_3$)H, —SO$_2$CH$_3$, —SO$_2$N(CH$_3$)$_2$, azetidinyl, or pyrrolidinyl; each $R^d$ is independently hydrogen, F, Cl, Br, —CH$_3$, —CH$_2$F, —CHF$_2$, —CF$_3$, —CN, —OH, -OCH$_3$, —OCF$_3$, —OCH$_2$OCH$_3$, —CH$_2$OH, —OCH$_2$CH$_2$OH, —C(=O)NH$_2$, —C(=O)NHOCH$_3$, NH$_2$, NHCO$_2$CH$_3$, NH(C=O)NHOCH$_3$, CH$_2$(C=O)NH$_2$; or if one $R^c$ and one $R^d$ are on adjacent atoms of ring B then the adjacent $R^c$ and $R^d$ groups are taken together with the intervening atoms to which they are attached to form an unsubstituted or substituted 5-membered monocyclic heterocycle.

In some embodiments, the compound of Formula (AI), Formula (AII) or Formula (A2) has the structure of Formula (AIII), or a pharmaceutically acceptable salt, solvate, diastereomeric mixture, individual enantiomers or prodrug thereof:

Formula (AIII)

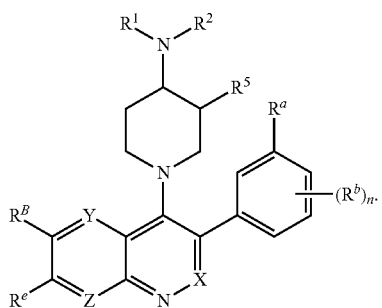

In some embodiments, the compound of Formula (I) or Formula (II) has the structure of Formula (III), or a pharmaceutically acceptable salt, solvate, diastereomeric mixture, individual enantiomers or prodrug thereof:

Formula (III)

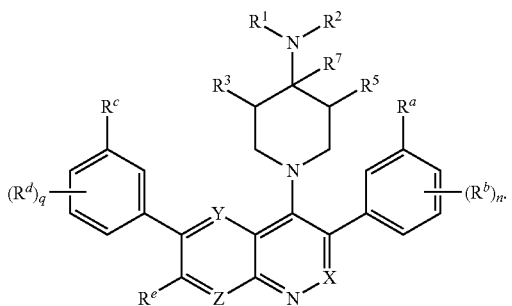

In some embodiments, R⁷ is hydrogen or methyl.

In some embodiments, the compound of Formula (AIII) has the structure of Formula (AIIIa), Formula (AIIIb), Formula (AIIIc), Formula (AIIId), Formula (AIIIe), Formula (AIIIf), or a pharmaceutically acceptable salt, solvate, diastereomeric mixture, individual enantiomers or prodrug thereof:

Formula (AIIIa)

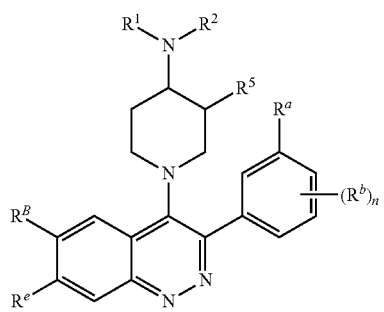

Formula (AIIIb)

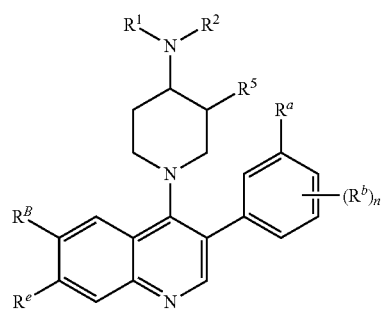

Formula (AIIIc)

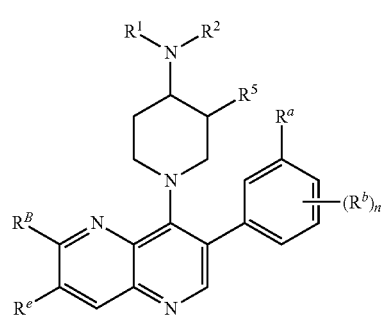

Formula (AIIId)

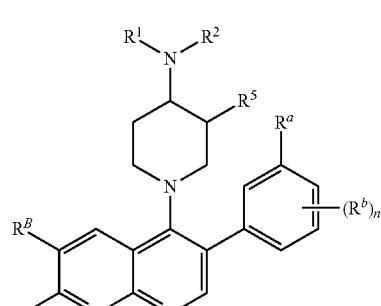

Formula (AIIIe)

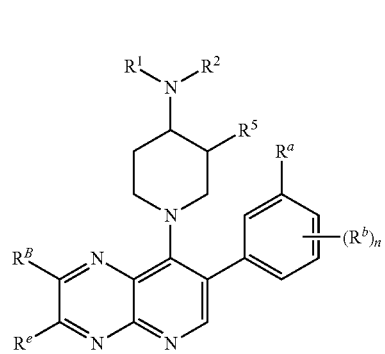

Formula (AIIIf)

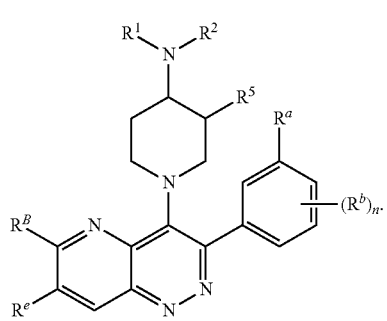

In some embodiments,

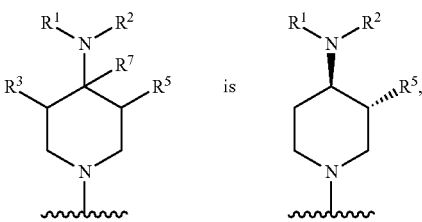 is 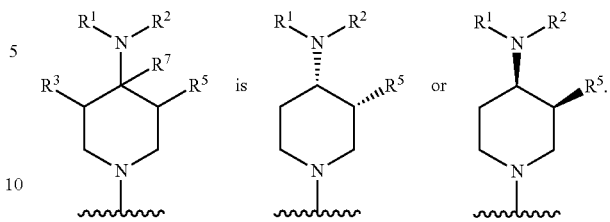

In some embodiments,

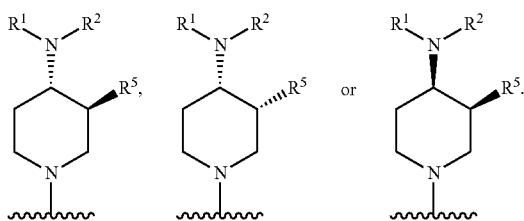

In other embodiments,

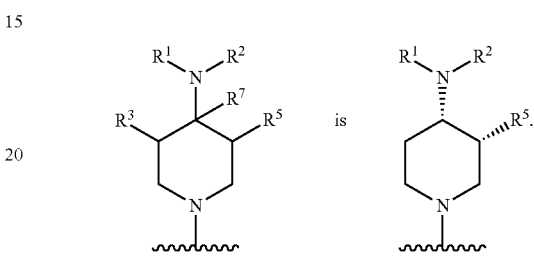

In other embodiments,

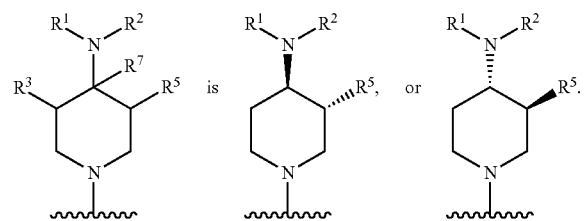

In some embodiments,

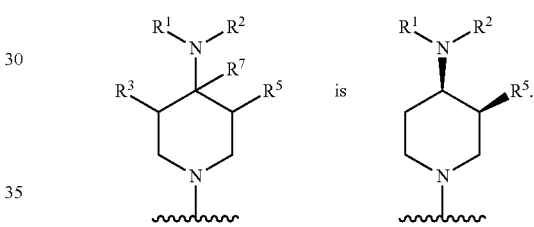

In some embodiments,

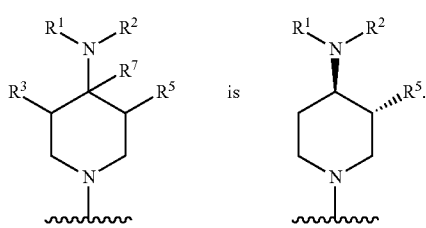

In other embodiments,

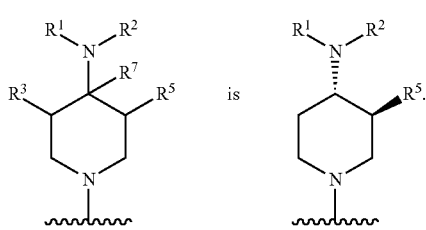

In some embodiments, $R^1$ hydrogen; $R^2$ is hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl; or $R^1$ and $R^2$ are taken together with the nitrogen atom to which they are attached to form ring C that is an unsubstituted or substituted N-containing $C_2$-$C_6$heterocycloalkyl; $R^5$ are each independently selected from the group consisting of hydrogen, halogen, —OH, —OR$^{14}$, —S(=O)$_2$R$^{14}$, N(R$^{15}$)$_2$, —CN, —C(=O)OR$^{15}$, —C(=O)N(R$^{15}$)$_2$, unsubstituted or substituted $C_1$-$C_6$alkyl, and unsubstituted or substituted $C_1$-$C_6$fluoroalkyl; or $R^2$ and $R^5$ are taken together with the intervening atoms to which they are attached to form an unsubstituted or substituted 4- to 7-membered saturated N-containing heterocyclic ring.

In some embodiments, $R^1$ hydrogen; $R^2$ is hydrogen, —CH$_3$, —CH$_2$CH$_3$, —CH$_2$CH$_2$OH, —CH$_2$CH$_2$OCH$_3$, CH$_2$CH$_2$F, —CH$_2$CH$_2$NH$_2$, —CH$_2$CH$_2$NHCH$_3$, —CH$_2$CH$_2$N(CH$_3$)$_2$, —CH$_2$CH$_2$CH$_3$, —CH(CH$_3$)$_2$, cyclopropyl, —CH$_2$CH$_2$CH$_2$F, CH$_2$CH$_2$CH$_2$OH, CH$_2$CH$_2$CH$_2$OCH$_3$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, cyclobutyl, cyclopentyl, cyclohexyl, oxetanyl, tetrahydrofuranyl, or tetrahydropyranyl; or $R^1$ and $R^2$ are taken together with the nitrogen atom to which they are attached to form ring C that is an unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl; R⁵ is hydrogen, F, Cl, Br, —OH, —OCH₃, —NH₂, —NHCH₃, —N(CH₃)₂, —OCH₂CH₃, —OCF₃, —CH₃, —CH₂CH₃, —CH₂F, —CHF₂, or —CF₃, —CN, —C(=O)OCH₃, —C(=O)NH₂, —C(=O)NHCH₃, —C(=O)N(CH₃)₂; or R² and R⁵ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

In some embodiments, the compound of Formula (III) has the structure of Formula (IIIa), or a pharmaceutically acceptable salt, solvate, diastereomeric mixture, individual enantiomers or prodrug thereof:

Formula (IIIa)

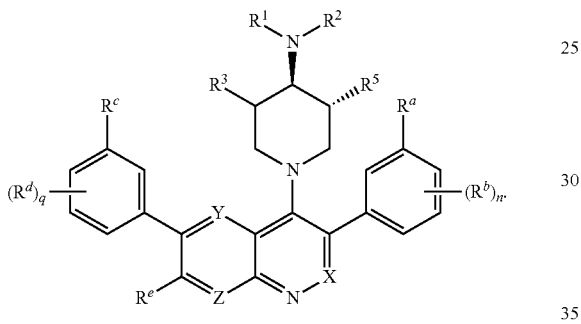

In some embodiments, the compound of Formula (AIII) has one of the following structures, or a pharmaceutically acceptable salt, solvate, diastereomeric mixture, individual enantiomers or prodrug thereof:

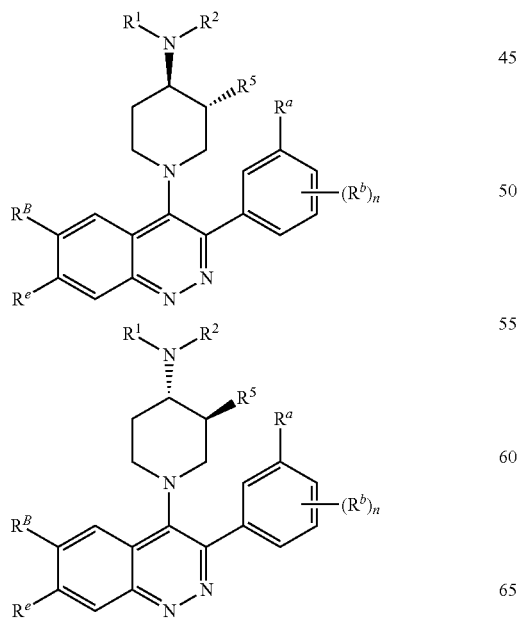

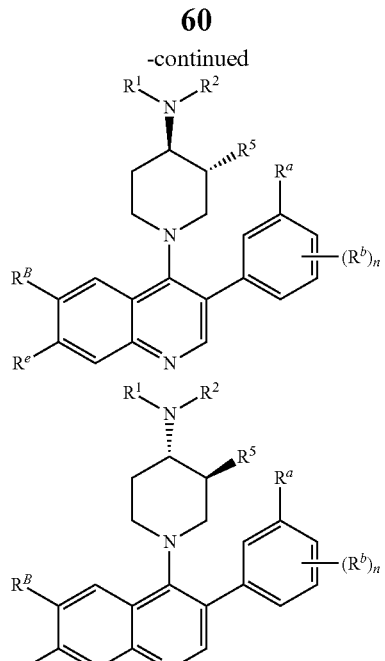

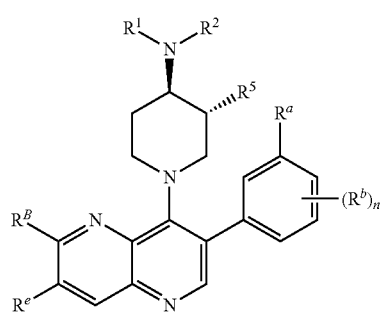

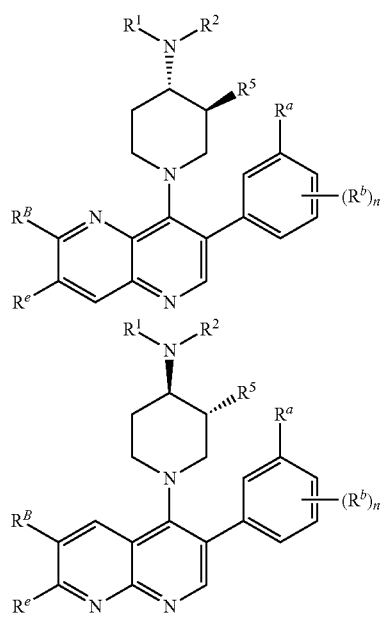

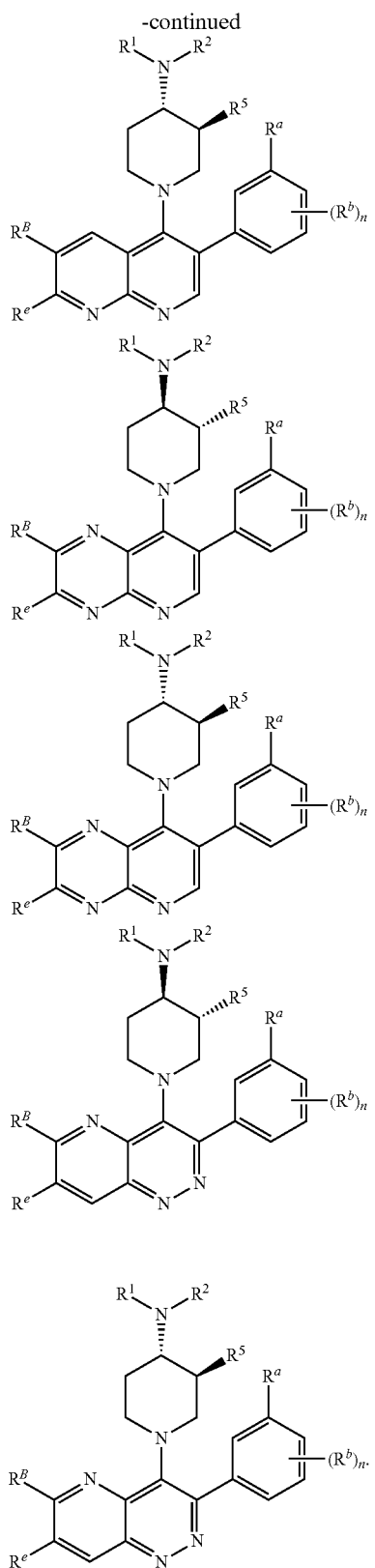

In some embodiments, the compound of Formula (III) has the structure of Formula (IIIb), or a pharmaceutically acceptable salt, solvate, diastereomeric mixture, individual enantiomers or prodrug thereof:

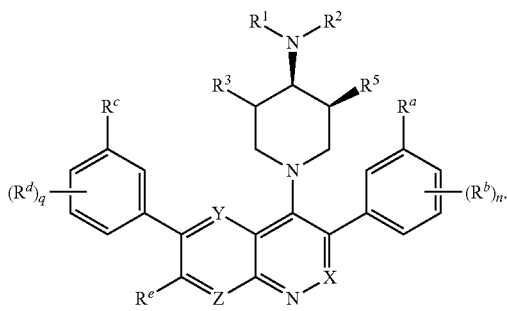

Formula (IIIb)

In some embodiments, the compound of Formula (AIII) has one of the following structures, or a pharmaceutically acceptable salt, solvate, diastereomeric mixture, individual enantiomers or prodrug thereof:

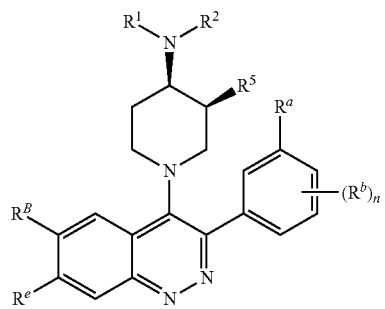

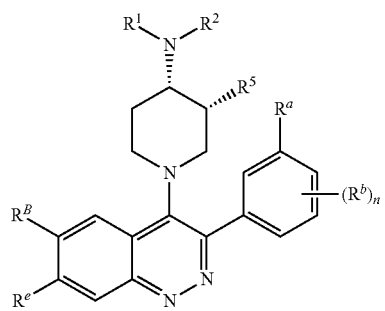

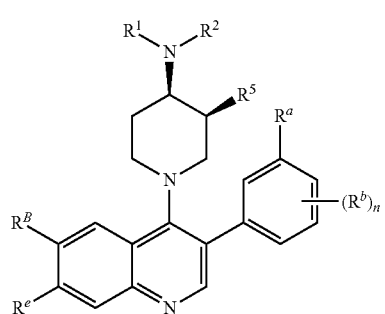

-continued

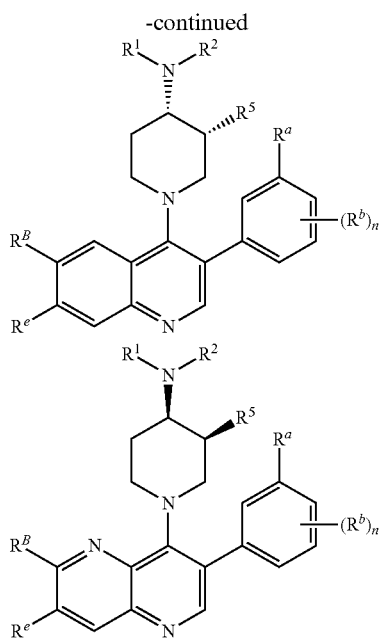

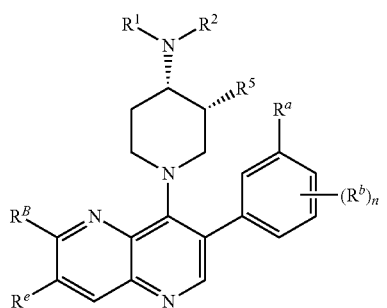

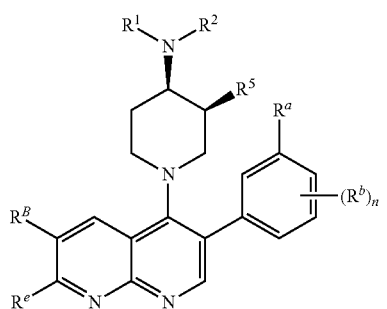

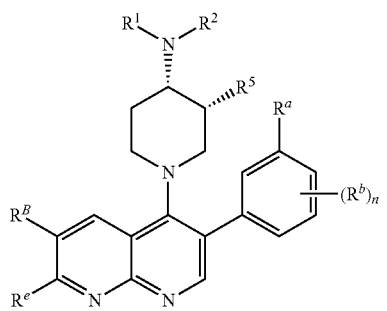

-continued

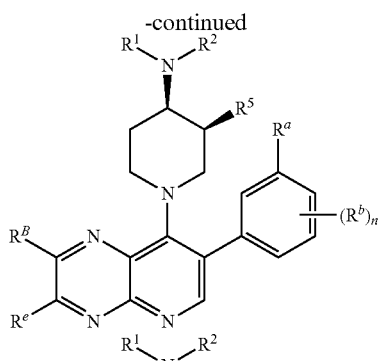

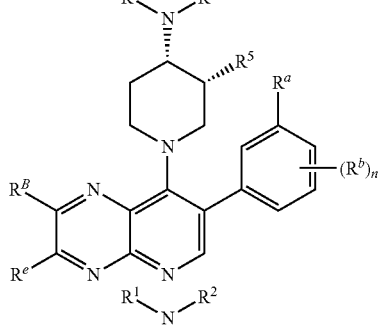

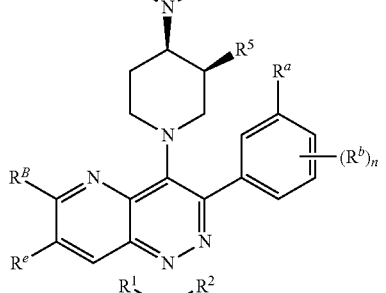

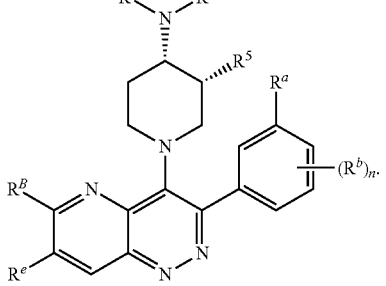

In some embodiments, $R^1$ is hydrogen; and $R^2$ is hydrogen, methyl, ethyl, 2-fluoroethyl, 2-hydroxyethyl, 2-methoxyethyl, n-propyl, i-propyl, n-butyl, i-butyl, sec-butyl, or tert-butyl, or oxetanyl. In some embodiments, $R^2$ is hydrogen; or $R^1$ and $R^2$ are taken together with the nitrogen atom to which they are attached to form ring C that is an unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, or unsubstituted or substituted piperazinyl.

In some embodiments, $R^1$ is hydrogen; and $R^2$ is hydrogen, methyl, ethyl, 2-fluoroethyl, 2-hydroxyethyl, 2-methoxyethyl, n-propyl, i-propyl, n-butyl, i-butyl, sec-butyl, or tert-butyl, or oxetanyl. In some embodiments, $R^2$ is hydrogen.

In some embodiments, the compound of Formula (I) or Formula (II) has the structure of Formula (IV), or a pharmaceutically acceptable salt, solvate, diastereomeric mixture, individual enantiomers or prodrug thereof:

Formula (IV)

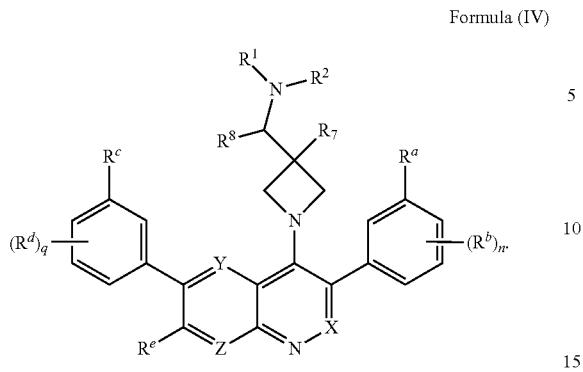

In some embodiments, the compound of Formula (I) or Formula (II) has the structure of Formula (V), or a pharmaceutically acceptable salt, solvate, diastereomeric mixture, individual enantiomers or prodrug thereof:

Formula (V)

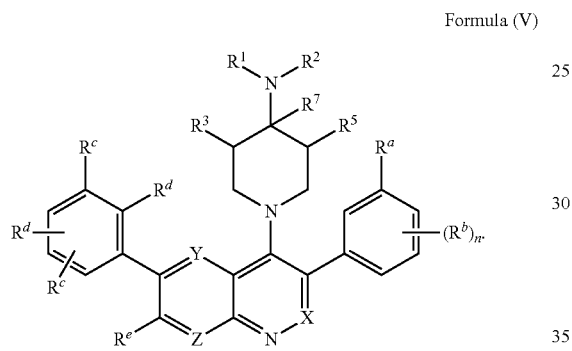

In some embodiments, $R^7$ is hydrogen or methyl.

In some embodiments, $R^8$ is hydrogen or methyl or ethyl.

In some embodiments, the compound of Formula (AI), Formula (AII) or Formula (A2) has the structure of Formula (AV), or a pharmaceutically acceptable salt, solvate, diastereomeric mixture, individual enantiomers or prodrug thereof:

Formula (AV)

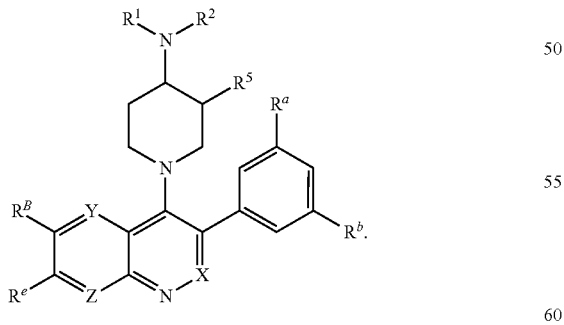

In some embodiments, the compound of Formula (AV) has the following structure of Formula (AVa), Formula (AVb), Formula (AVc), Formula (AVd), Formula (AVe), Formula (AVf), or a pharmaceutically acceptable salt, solvate, diastereomeric mixture, individual enantiomers or prodrug thereof:

Formula (AVa)

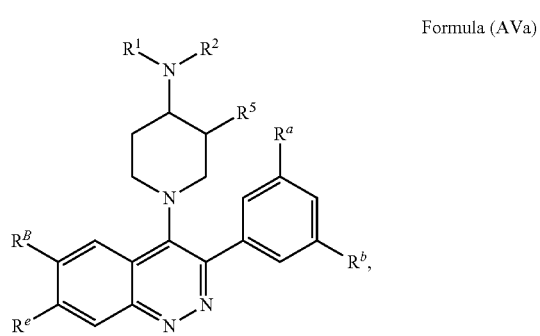

Formula (AVb)

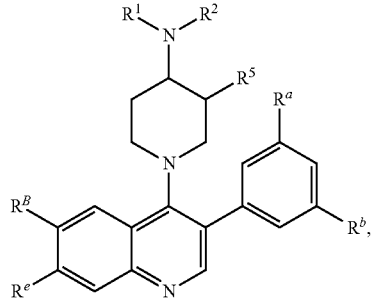

Formula (AVc)

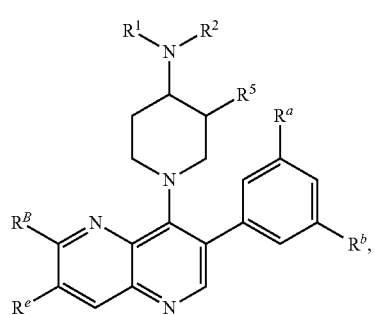

Formula (AVd)

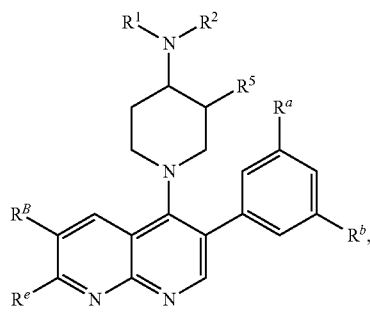

Formula (AVe)

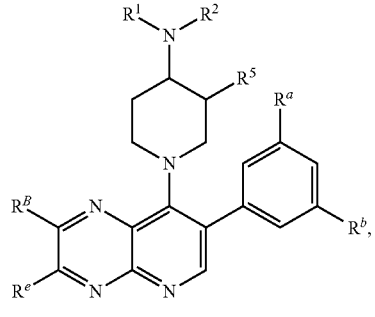

Formula (AVf)
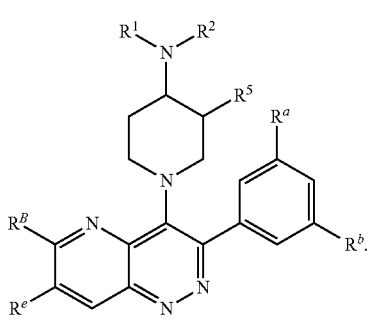
In some embodiments, the compound of Formula (AV) has one of the following structures, or a pharmaceutically acceptable salt, solvate, diastereomeric mixture, individual enantiomers or prodrug thereof:
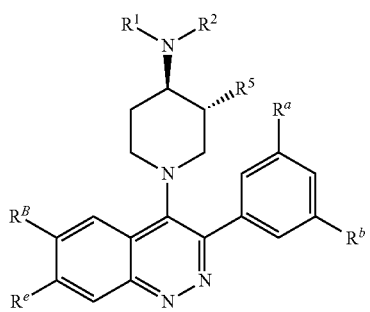
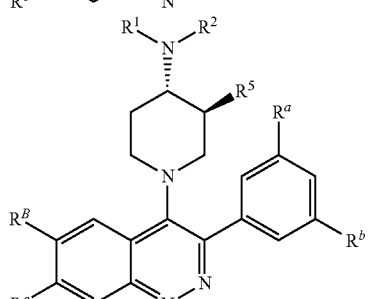
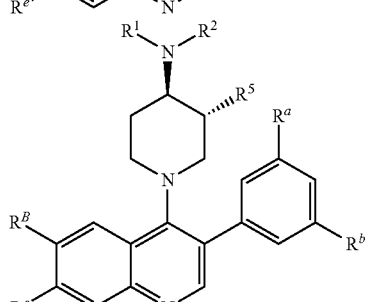
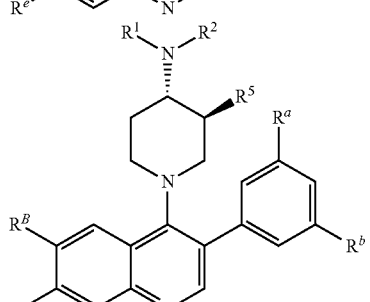
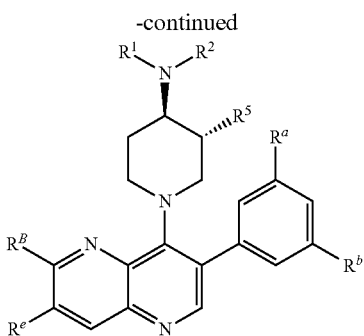
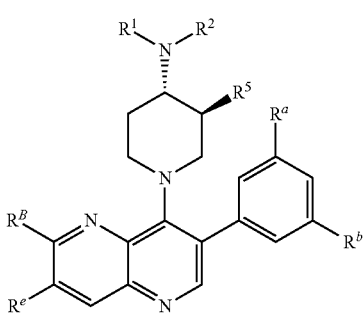
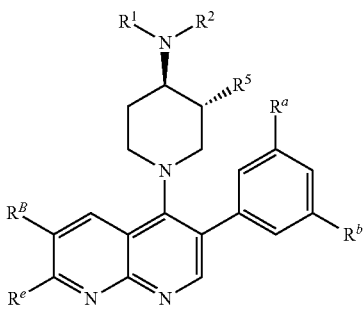
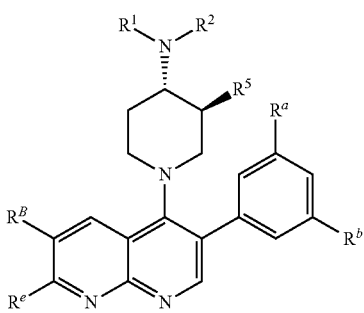
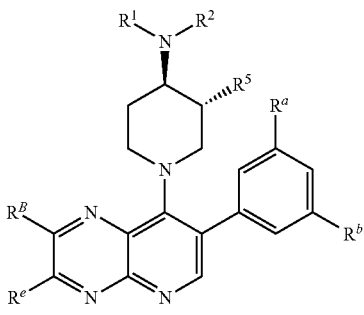

-continued
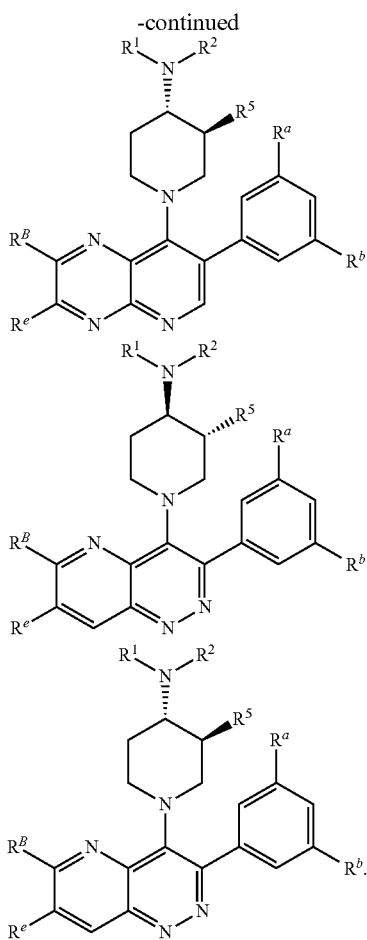
In some embodiments, the compound of Formula (AV) has one of the following structures, or a pharmaceutically acceptable salt, solvate, diastereomeric mixture, individual enantiomers or prodrug thereof:
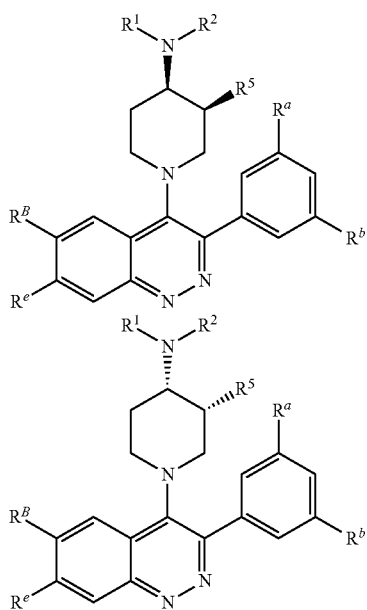
-continued
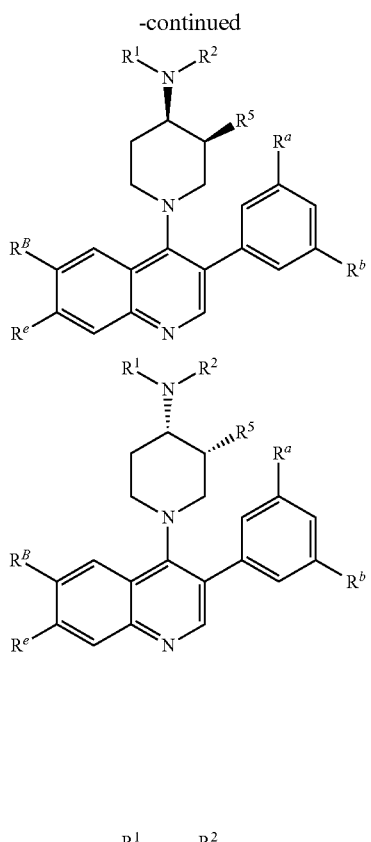
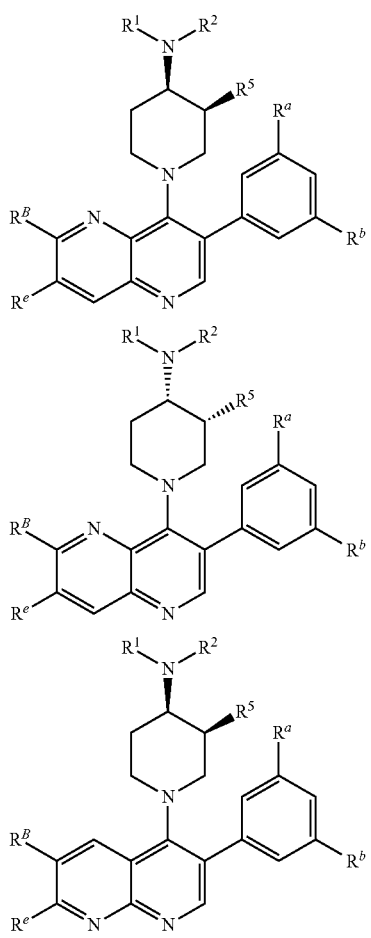

-continued

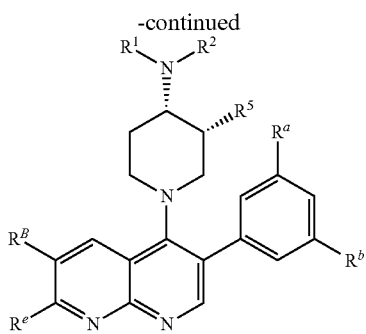

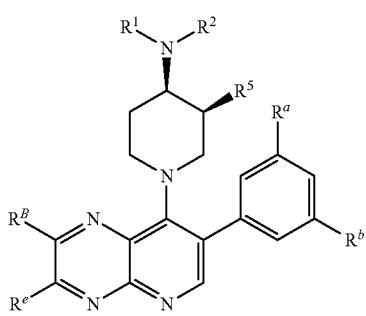

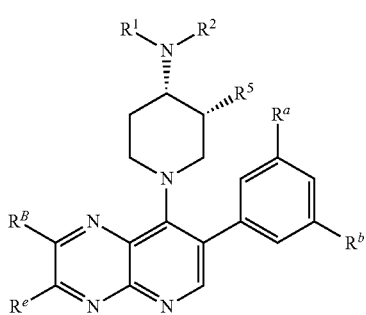

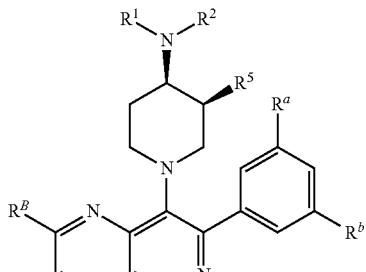

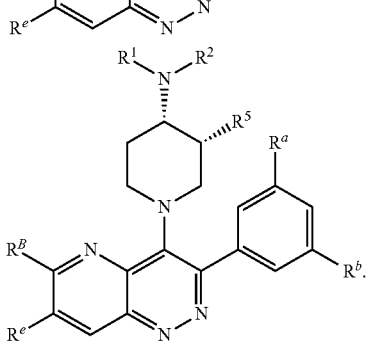

In some embodiments,

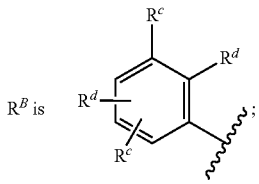

$R^1$ hydrogen; $R^2$ is hydrogen, methyl, ethyl, 2-fluoroethyl, 2-hydroxyethyl, 2-methoxyethyl, n-propyl, i-propyl, cyclopropyl, 3-fluoropropyl, 3-methoxypropyl, n-butyl, i-butyl, sec-butyl, cyclobutyl, or tert-butyl, or oxetanyl;
$R^5$ is hydrogen, F, Cl, Br, —OH, —OCH$_3$, —NH$_2$, —NHCH$_3$, —N(CH$_3$)$_2$, —OCH$_2$CH$_3$, —OCF$_3$, —CH$_3$, —CH$_2$CH$_3$, —CH$_2$F, —CHF$_2$, or —CF$_3$, —CN, —C(=O)OCH$_3$, —C(=O)NH$_2$, —C(=O)NHCH$_3$, —C(=O)N(CH$_3$)$_2$; or $R^2$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

In some embodiments,

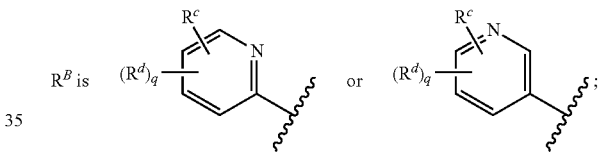

$R^1$ hydrogen; $R^2$ is hydrogen, methyl, ethyl, 2-fluoroethyl, 2-hydroxyethyl, 2-methoxyethyl, n-propyl, i-propyl, cyclopropyl, 3-fluoropropyl, 3-methoxypropyl, n-butyl, i-butyl, sec-butyl, cyclobutyl, or tert-butyl, or oxetanyl; $R^5$ is hydrogen, F, Cl, Br, —OH, —OCH$_3$, —NH$_2$, —NHCH$_3$, —N(CH$_3$)$_2$, —OCH$_2$CH$_3$, —OCF$_3$, —CH$_3$, —CH$_2$CH$_3$, —CH$_2$F, —CHF$_2$, or —CF$_3$, —CN, —C(=O)OCH$_3$, —C(=O)NH$_2$, —C(=O)NHCH$_3$, —C(=O)N(CH$_3$)$_2$; or $R^2$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

In some embodiments, $R^a$ is hydrogen, F, Cl, Br, —CH$_3$, —CH$_2$F, —CHF$_2$, —CF$_3$, —CN, —OH, —OCH$_3$, —OCF$_3$, —CH$_2$OH or —CH$_2$CH$_2$OH; $R^b$ is hydrogen, F, Cl, Br, —CH$_3$, —CH$_2$F, —CHF$_2$, —CF$_3$, —CN, —OH, —OCH$_3$, or —OCF$_3$; each $R^c$ is independently hydrogen, F, Cl, Br, —CH$_3$, —CH$_2$F, —CHF$_2$, —CF$_3$, pyrrolyl, imidazolyl, pyrazolyl, triazolyl, tetrazolyl, —CN, —OH, —OCH$_3$, —OCF$_3$, —NH$_2$, —C(=O)NH$_2$, —C(=NOH)H, —C(=NOCH$_3$)H, —SO$_2$CH$_3$, —SO$_2$N(CH$_3$)$_2$, azetidinyl, or pyrrolidinyl; each $R^d$ is independently hydrogen, F, Cl, Br, —CH$_3$, —CH$_2$F, —CHF$_2$, —CF$_3$, —CN, —OH, —OCH$_3$, —OCF$_3$, —OCH$_2$OCH$_3$, —CH$_2$OH, —OCH$_2$CH$_2$OH, —C(=O)NH$_2$, —C(=O)NHOCH$_3$, —NH$_2$, —NHCO$_2$CH$_3$, —NH(C=O)NHOCH$_3$, —CH$_2$(C=O)NH$_2$; R$^e$ is hydrogen, F, Cl, Br, —CH$_3$, —CH$_2$F, —CHF$_2$, —CF$_3$, —CN, —OH, —OCH$_3$, or —OCF$_3$; R$^1$ hydrogen; R$^2$ is hydrogen; R$^5$ is hydrogen, F, Cl, Br, —OH, —OCH$_3$, —NH$_2$, —NHCH$_3$, —N(CH$_3$)$_2$, —OCH$_2$CH$_3$, —OCF$_3$, —CH$_3$, —CH$_2$CH$_3$, —CH$_2$F, —CHF$_2$, —CF$_3$, —CN, —C(=O)OCH$_3$, —C(=O)NH$_2$, —C(=O)NHCH$_3$, or —C(=O)N(CH$_3$)$_2$; or R$^2$ and R$^5$ are taken together with the intervening atoms to which they are attached to form an unsubstituted or substituted monocyclic 6-membered heterocyclic ring selected from unsubstituted or substituted piperidinyl, unsubstituted or substituted morpholinyl, unsubstituted or substituted thiomorpholinyl, or unsubstituted or substituted piperazinyl.

In some embodiments, R$^a$ is hydrogen, F, Cl, —CH$_3$, —CF$_3$, —CN, —OH, —CH$_2$OH, —CH$_2$CH$_2$OH, —OCH$_3$, or —OCF$_3$; R$^b$ is hydrogen, F, Cl, —CH$_3$, —CF$_3$, —CN, —OH, —OCH$_3$, or —OCF$_3$; each R$^c$ is independently hydrogen, F, Cl, —CH$_3$, —CF$_3$, —CN, —OH, —NH$_2$, —OCH$_3$, —OCF$_3$, —CONH$_2$, —C(C=NOH)H, —C(C=NOCH$_3$)H; each R$^d$ is independently hydrogen, F, Cl, —CH$_3$, —CF$_3$, —CN, —OH, —NH$_2$, —OCH$_3$, —OCF$_3$; R$^1$ hydrogen; R$^2$ is hydrogen; R$^5$ is hydrogen; or R$^2$ and R$^5$ are taken together with the intervening atoms to which they are attached to form an unsubstituted or substituted morpholinyl.

In some embodiments, R$^1$ is hydrogen; and R$^2$ is hydrogen, methyl, ethyl, 2-fluoroethyl, 2-hydroxyethyl, 2-methoxyethyl, 2-aminoethyl, 2-methylaminoethyl, 2-dimethylaminoethyl, 2-carboxyethyl, n-propyl, i-propyl, cyclopropyl, 3-fluoropropyl, 3-methoxypropyl, 3-carboxypropyl, n-butyl, i-butyl, sec-butyl, or tert-butyl, cyclobutyl or oxetanyl. In some other embodiments, R$^1$ is hydrogen; and R$^2$ is methyl, ethyl, 2-fluoroethyl, 2-hydroxyethyl, 2-methoxyethyl, n-propyl, i-propyl, cyclopropyl, n-butyl, i-butyl, sec-butyl, cyclobutyl or tert-butyl or oxetanyl; or R$^1$ and R$^2$ are taken together with the nitrogen atom to which they are attached to form ring C that is an unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, or unsubstituted or substituted piperazinyl.

In some embodiments, R$^1$ is hydrogen; and R$^2$ is hydrogen, methyl, ethyl, 2-fluoroethyl, 2-hydroxyethyl, 2-methoxyethyl, 2-aminoethyl, 2-methylaminoethyl, 2-dimethylaminoethyl, 2-carboxyethyl, n-propyl, i-propyl, cyclopropyl, 3-fluoropropyl, 3-methoxypropyl, 3-carboxypropyl, n-butyl, i-butyl, sec-butyl, or tert-butyl, cyclobutyl or oxetanyl. In some other embodiments, R$^1$ is hydrogen; and R$^2$ is methyl, ethyl, 2-fluoroethyl, 2-hydroxyethyl, 2-methoxyethyl, n-propyl, i-propyl, cyclopropyl, n-butyl, i-butyl, sec-butyl, cyclobutyl or tert-butyl or oxetanyl.

In some embodiments,

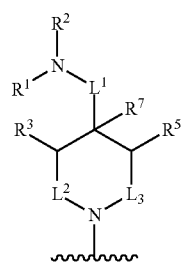

is A as described in Table 1, Table 2, Table 3 or Table 4.

In some embodiments, R$^3$ is hydrogen.

In some embodiments, R$^5$ is hydrogen, —F, —Cl, —Br, —OH, —OCH$_3$, —OCH$_2$CH$_3$, —SH, —SCH$_3$, —SCH$_2$CH$_3$, —SCH(CH$_3$)$_2$, —SCH$_2$CH$_2$CH$_3$, —S(=O)CH$_3$, —S(=O)CH$_2$CH$_3$, —S(=O)CH(CH$_3$)$_2$, —S(=O)CH$_2$CH$_2$CH$_3$, —S(=O)$_2$CH$_3$, —S(=O)$_2$CH$_2$CH$_3$, —S(=O)$_2$CH(CH$_3$)$_2$, —S(=O)$_2$CH$_2$CH$_2$CH$_3$, —NH$_2$, —NH(CH$_3$), —NH(CH$_2$CH$_3$), —N(CH$_3$)$_2$, —N(CH$_2$CH$_3$)$_2$, —CN, methyl, ethyl, fluoroethyl, n-propyl, fluoropropyl, i-propyl, cyclopropyl, n-butyl, i-butyl, sec-butyl, tert-butyl or cyclobutyl. In some embodiments, R$^5$ is hydrogen, fluoro, or methoxy.

In some embodiments,

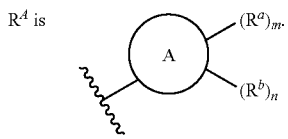

In some embodiments,

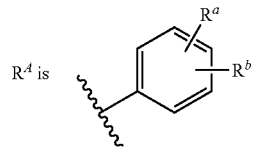

as described in Table 1, Table 2, Table 3 or Table 4. In some embodiments,

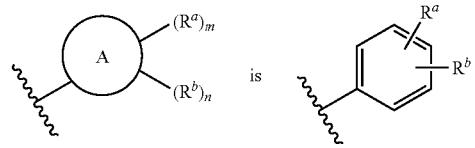

as described in Table 1, Table 2, Table 3 or Table 4.

In some embodiments,

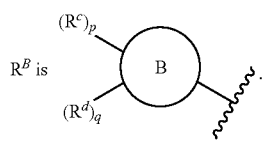

In some embodiments, R$^B$ is as described in Table 1, Table 2, Table 3 or Table 4. In some embodiments,

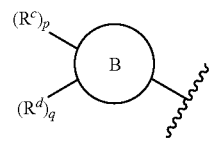

is R$^B$ as described in Table 1, Table 2, Table 3 or Table 4.

In some embodiments, R$^e$ is as described in Table 1.

In some embodiments,

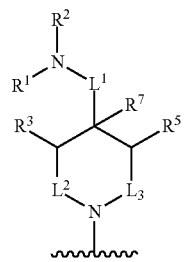

is A as described in Table 1, Table 2, Table 3 or Table 4.

In some embodiments, compounds described herein have the following structure, or a pharmaceutically acceptable salt, solvate, diastereomeric mixture, or individual enantiomers thereof:

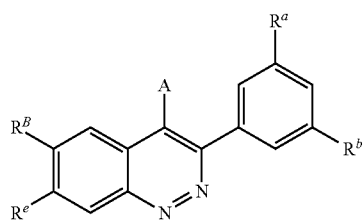

wherein, $R^a$, $R^b$, A, and $R^B$ are as described in Table 1, Table 2, Table 3, or Table 4;

$R^e$ are as described in Table 1.

In some embodiments, $R^a$, $R^b$, A, $R^B$ and $R^e$ are as described in Table 1.

In some embodiments, compounds described herein have the following structure, or a pharmaceutically acceptable salt, solvate, diastereomeric mixture, or individual enantiomers thereof:

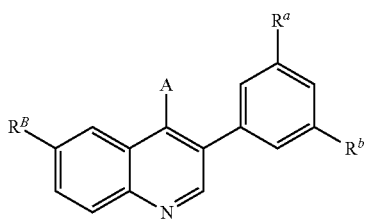

wherein, $R^a$, $R^b$, A, and $R^B$ are as described in Table 1, Table 2, Table 3, or Table 4.

In some embodiments, $R^a$, $R^b$, A, and $R^B$ are as described in Table 2.

In some embodiments, compounds described herein have the following structure, or a pharmaceutically acceptable salt, solvate, diastereomeric mixture, or individual enantiomers thereof:

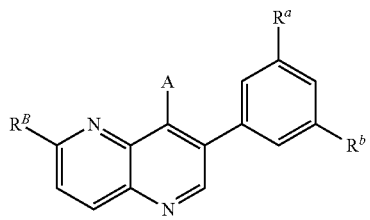

wherein, $R^a$, $R^b$, A, and $R^B$ are as described in Table 1, Table 2, Table 3, or Table 4.

In some embodiments, $R^a$, $R^b$, A, and $R^B$ are as described in Table 3.

In some embodiments, compounds described herein have the following structure, or a pharmaceutically acceptable salt, solvate, diastereomeric mixture, or individual enantiomers thereof:

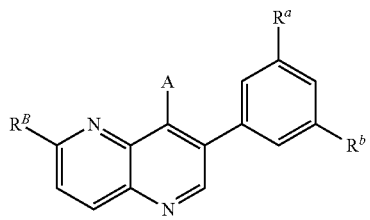

wherein, $R^a$, $R^b$, A, and $R^B$ are as described in Table 1, Table 2, Table 3, or Table 4.

In some embodiments, $R^a$, $R^b$, A, and $R^B$ are as described in Table 4.

Any combination of the groups described above for the various variables is contemplated herein. Throughout the specification, groups and substituents thereof are chosen by one skilled in the field to provide stable moieties and compounds.

Exemplary compounds of Formula (I) include the compounds described in the following Tables:

TABLE 1

| Cpd No. | $R^B$ | $R^c$ | A | $R^a$ | $R^b$ |
|---|---|---|---|---|---|
| 1-1 | 3-carbamoyl-5-fluorophenyl | Cl | 4-aminopiperidin-1-yl | 3-CH₃ | 5-CH₃ |
| 1-2 | 2-cyano-6-hydroxyphenyl | Cl | 4-aminopiperidin-1-yl | 3-CH₃ | 5-CH₃ |
| 1-3 | Cl | Cl | 4-aminopiperidin-1-yl | 3-CH₃ | 5-CH₃ |
| 1-4 | 3-carbamoyl-5-fluorophenyl | Cl | 4-aminopiperidin-1-yl | 3-F | 5-CH₃ |
| 1-5 | 3-carbamoyl-5-fluorophenyl | Cl | (3,4-trans)-4-amino-3-fluoropiperidin-1-yl | 3-F | 5-CH₃ |
| 1-6 | 3-carbamoyl-5-fluorophenyl | Cl | (3,4-trans)-4-amino-3-fluoropiperidin-1-yl (racemic) | 3-F | 5-CH₃ |

TABLE 1-continued

| Cpd No. | $R^B$ | $R^c$ | A | $R^a$ | $R^b$ |
|---|---|---|---|---|---|
| 1-7 | 3-CN, 2-OH phenyl | Cl | 4-aminopiperidin-1-yl | 3-F | 5-CH$_3$ |
| 1-8 | 2-oxo-2,3-dihydro-1H-benzimidazol-5-yl | Cl | 4-aminopiperidin-1-yl | 3-F | 5-CH$_3$ |
| 1-9 | 2-oxo-2,3-dihydro-1H-benzimidazol-4-yl | Cl | 4-aminopiperidin-1-yl | 3-F | 5-CH$_3$ |
| 1-10 | 3-carbamoyl-5-fluorophenyl | Cl | 4-amino-3-methoxypiperidin-1-yl (racemic) | 3-F | 5-CH$_3$ |
| 1-11 | 3-CN, 2-OH phenyl | Cl | 4-aminopiperidin-1-yl | 3-Cl | 5-Cl |
| 1-12 | 3-CN, 2-OH, 5-F phenyl | Cl | 4-aminopiperidin-1-yl | 3-Cl | 5-CH$_3$ |

TABLE 1-continued

| Cpd No. | $R^B$ | $R^c$ | A | $R^a$ | $R^b$ |
|---|---|---|---|---|---|
| 1-13 | 3-carbamoyl-5-fluorophenyl | H | 4-aminopiperidin-1-yl | 3-F | 5-CH$_3$ |
| 1-14 | 3-carbamoyl-5-fluorophenyl | H | 4-aminopiperidin-1-yl | 3-F | 5-F |
| 1-15 | 3-fluoro-5-methylphenyl | H | 4-aminopiperidin-1-yl | 3-F | 5-F |
| 1-16 | 2-oxo-2,3-dihydro-1H-benzimidazol-5-yl | H | 4-aminopiperidin-1-yl | 3-F | 5-CH$_3$ |
| 1-17 | 3-cyano-2-hydroxyphenyl | H | 4-aminopiperidin-1-yl | 3-F | 5-CH$_3$ |
| 1-18 | 3-cyano-2-hydroxyphenyl | H | 4-aminopiperidin-1-yl | 3-Cl | 5-CH$_3$ |

TABLE 1-continued
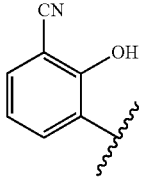 [SMILES: *c1cccc(C#N)c1O]
| Cpd No. | $R^B$ | $R^c$ | A | $R^a$ | $R^b$ |
|---|---|---|---|---|---|
| 1-19 | 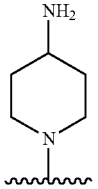 | H | 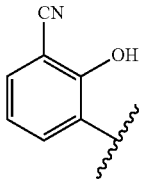 [SMILES: *c1cccc(C#N)c1O] | 3-Cl | 5-F |
| 1-20 | 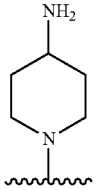 [SMILES: *N1CCC(N)CC1] | H | 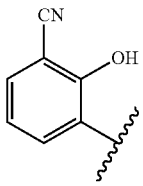 | 3-F | 5-F |
| 1-21 | 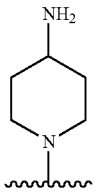 | H | 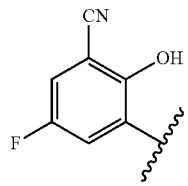 [SMILES: *c1cc(F)cc(C#N)c1O] | 3-Cl | 5-Cl |
| 1-22 | 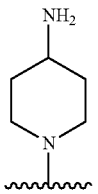 | H | 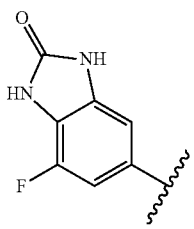 | 3-Cl | 5-$CH_3$ |
| 1-23 | 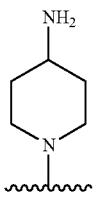 | H | 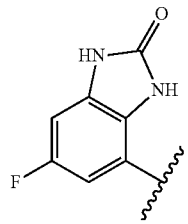 [SMILES: *c1cc(F)cc2[nH]c(=O)[nH]c12] | 3-Cl | 5-$CH_3$ |
| 1-24 | 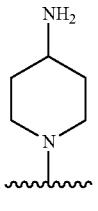 [SMILES: *N1CCC(N)CC1] | H | | 3-Cl | 5-$CH_3$ |

TABLE 1-continued

| Cpd No. | R^B | R^c | A | R^a | R^b |
|---|---|---|---|---|---|
| 1-25 | 3-carbamoyl-5-fluorophenyl | Cl | 2-fluoroethylamino-piperidin-1-yl | 3-F | 5-CH₃ |
| 1-26 | 3-carbamoyl-5-fluorophenyl | Cl | 4-amino-3-hydroxypiperidin-1-yl (racemic) | 3-F | 5-CH₃ |
| 1-27 | 3-cyano-5-fluoro-2-hydroxyphenyl | H | 4-aminopiperidin-1-yl | 3-Cl | 5-Cl |
| 1-28 | 4-fluoro-2-oxo-2,3-dihydro-1H-benzimidazol-6-yl | H | 4-aminopiperidin-1-yl | 3-Cl | 5-Cl |
| 1-29 | 3-fluoro-2-hydroxyphenyl | H | 4-aminopiperidin-1-yl | 3-Cl | 5-CH₃ |
| 1-30 | 3-carbamoyl-5-fluorophenyl | H | 4-aminopiperidin-1-yl | 3-Cl | 5-Cl |

TABLE 1-continued

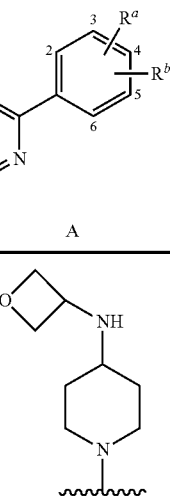

| Cpd No. | $R^B$ | $R^c$ | A | $R^a$ | $R^b$ |
|---|---|---|---|---|---|
| 1-31 | 3-carbamoyl-5-fluorophenyl | H | oxetan-3-yl-amino-piperidinyl | 3-Cl | 5-Cl |
| 1-32 | 3-carbamoyl-5-fluorophenyl | H | (3,3,3-trifluoropropyl)amino-piperidinyl | 3-Cl | 5-Cl |
| 1-33 | 3-carbamoyl-5-fluorophenyl | H | (2-fluoroethyl)amino-piperidinyl | 3-Cl | 5-Cl |
| 1-34 | 3-carbamoyl-5-fluorophenyl | H | 3-(aminomethyl)azetidinyl | 3-Cl | 5-Cl |
| 1-35 | 3-carbamoyl-5-fluorophenyl | Cl | (2-fluoroethyl)amino-piperidinyl | 3-Cl | 5-CH$_3$ |
| 1-36 | 3-cyano-5-fluoro-2-hydroxyphenyl | Cl | (2-fluoroethyl)amino-piperidinyl | 3-Cl | 5-CH$_3$ |

TABLE 1-continued

| Cpd No. | $R^B$ | $R^c$ | A | $R^a$ | $R^b$ |
|---|---|---|---|---|---|
| 1-37 | 3-carbamoyl-5-fluorophenyl | Cl | F₃C-CH₂-CH₂-NH-(piperidin-4-yl) | 3-Cl | 5-CH₃ |
| 1-38 | 3-carbamoyl-5-fluorophenyl | Cl | oxetan-3-yl-NH-(piperidin-4-yl) | 3-Cl | 5-CH₃ |
| 1-39 | 3-cyano-2-hydroxy-5-fluorophenyl | Cl | oxetan-3-yl-NH-(piperidin-4-yl) | 3-Cl | 5-CH₃ |
| 1-40 | 3-cyano-2-hydroxy-5-fluorophenyl | H | oxetan-3-yl-NH-(piperidin-4-yl) | 3-Cl | 5-CH₃ |
| 1-41 | 3-carbamoyl-5-fluorophenyl | Cl | 4-amino-3-fluoropiperidin-1-yl (racemic) | 3-Cl | 5-CH₃ |
| 1-42 | 6-carbamoylpyridin-2-yl | Cl | 4-aminopiperidin-1-yl | 3-Cl | 5-CH₃ |

TABLE 1-continued

| Cpd No. | $R^B$ | $R^c$ | A | $R^a$ | $R^b$ |
| --- | --- | --- | --- | --- | --- |
| 1-43 | 3-carbamoyl-6-chloropyridin-2-yl | Cl | 4-aminopiperidin-1-yl | 3-Cl | 5-CH$_3$ |
| 1-44 | 4-carbamoylpyridin-2-yl | Cl | 4-aminopiperidin-1-yl | 3-Cl | 5-CH$_3$ |
| 1-45 | 2-fluoro-3-hydroxy-4-methylphenyl | H | 4-aminopiperidin-1-yl | 3-Cl | 5-CH$_3$ |
| 1-46 | 3-carbamoyl-5-fluorophenyl | H | (3R)-3-aminopiperidin-1-yl | 3-Cl | 5-CH$_3$ |
| 1-47 | 3-carbamoyl-5-fluorophenyl | H | (3S)-3-aminopiperidin-1-yl | 3-Cl | 5-CH$_3$ |
| 1-48 | 3-carbamoyl-5-fluorophenyl | H | octahydropyrano[3,2-b]pyridine | 3-Cl | 5-CH$_3$ |

TABLE 1-continued

| Cpd No. | $R^B$ | $R^c$ | A | $R^a$ | $R^b$ |
|---|---|---|---|---|---|
| 1-49 | 3-carbamoyl-5-fluorophenyl | H | octahydropyrano[3,2-c]pyridinyl (HN, O) | 3-Cl | 5-CH$_3$ |
| 1-50 | 3-carbamoyl-5-fluorophenyl | H | 2-azaspiro[3.5]nonane (HN-azetidine/piperidine spiro) | 3-Cl | 5-CH$_3$ |
| 1-51 | 3-cyano-2-hydroxyphenyl | H | octahydropyrano[3,2-c]pyridinyl | 3-Cl | 5-CH$_3$ |
| 1-52 | 3-cyano-2-hydroxyphenyl | H | octahydropyrano[3,2-c]pyridinyl | 3-Cl | 5-CH$_3$ |
| 1-53 | 3-cyano-2-hydroxyphenyl | H | octahydropyrano[3,2-c]pyridinyl | 3-F | 5-CH$_3$ |
| 1-54 | 3-cyano-2-hydroxyphenyl | H | octahydropyrano[3,2-c]pyridinyl | 3-F | 5-F |

TABLE 1-continued

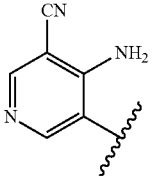 [SMILES: *c1cncc(C#N)c1N]

| Cpd No. | R$^B$ | R$^c$ | A | R$^a$ | R$^b$ |
|---|---|---|---|---|---|
| 1-55 | 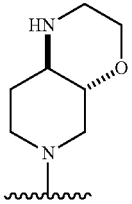 | H | 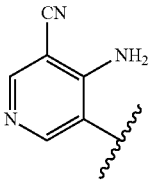 [SMILES: *c1cncc(C#N)c1N] | 3-F | 5-F |
| 1-56 | 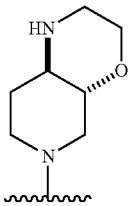 | H | 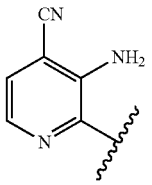 [SMILES: *c1nccc(C#N)c1N] | 3-F | 5-CH$_3$ |
| 1-57 | 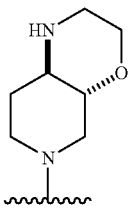 | H | 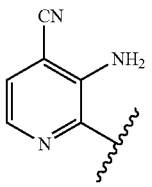 [SMILES: *c1nccc(C#N)c1N] | 3-F | 5-F |
| 1-58 | 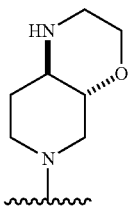 | H | | 3-F | 5-CH$_3$ |

Compounds in Table 1 are Named:
1-1: 3-[4-(4-aminopiperidin-1-yl)-7-chloro-3-(3,5-dimethylphenyl)cinnolin-6-yl]-5-fluorobenzamide;
1-2: 3-[4-(4-aminopiperidin-1-yl)-7-chloro-3-(3,5-dimethylphenyl)cinnolin-6-yl]-2-hydroxybenzonitrile;
1-3: 1-[6,7-dichloro-3-(3,5-dimethylphenyl)cinnolin-4-yl]piperidin-4-amine;
1-4: 3-[4-(4-aminopiperidin-1-yl)-7-chloro-3-(3-fluoro-5-methylphenyl)cinnolin-6-yl]-5-fluorobenzamide;
1-5: 3-{4-[trans-4-amino-3-fluoropiperidin-1-yl]-7-chloro-3-(3-fluoro-5-methylphenyl)cinnolin-6-yl}-5-fluorobenzamide;
1-6: 3-{4-[cis-4-amino-3-fluoropiperidin-1-yl]-7-chloro-3-(3-fluoro-5-methylphenyl)cinnolin-6-yl}-5-fluorobenzamide;
1-7: 3-[4-(4-aminopiperidin-1-yl)-7-chloro-3-(3-fluoro-5-methylphenyl)cinnolin-6-yl]-2-hydroxybenzonitrile;
1-8: 5-[4-(4-aminopiperidin-1-yl)-7-chloro-3-(3-fluoro-5-methylphenyl)cinnolin-6-yl]-2,3-dihydro-1H-1,3-benzodiazol-2-one;
1-9: 4-[4-(4-aminopiperidin-1-yl)-7-chloro-3-(3-fluoro-5-methylphenyl)cinnolin-6-yl]-2,3-dihydro-1H-1,3-benzodiazol-2-one;
1-10: 3-{4-[trans-4-amino-3-methoxypiperidin-1-yl]-7-chloro-3-(3-fluoro-5-methylphenyl)cinnolin-6-yl}-5-fluorobenzamide;
1-11: 3-[4-(4-aminopiperidin-1-yl)-7-chloro-3-(3,5-dichlorophenyl)cinnolin-6-yl]-2-hydroxybenzonitrile;
1-12: 3-[4-(4-aminopiperidin-1-yl)-7-chloro-3-(3-chloro-5-methylphenyl)cinnolin-6-yl]-5-fluoro-2-hydroxybenzonitrile;
1-13: 3-[4-(4-aminopiperidin-1-yl)-3-(3-fluoro-5-methylphenyl)cinnolin-6-yl]-5-fluorobenzamide;
1-14: 3-[4-(4-aminopiperidin-1-yl)-3-(3,5-difluorophenyl)cinnolin-6-yl]-5-fluorobenzamide;
1-15: 3-[4-(4-aminopiperidin-1-yl)-6-(3-fluoro-5-methylphenyl)cinnolin-3-yl]-5-fluorobenzamide;
1-16: 5-[4-(4-aminopiperidin-1-yl)-3-(3-fluoro-5-methylphenyl)cinnolin-6-yl]-2,3-dihydro-1H-1,3-benzodiazol-2-one;

1-17: 3-[4-(4-aminopiperidin-1-yl)-3-(3-fluoro-5-methylphenyl)cinnolin-6-yl]-2-hydroxybenzonitrile;
1-18: 3-[4-(4-aminopiperidin-1-yl)-3-(3-chloro-5-methylphenyl)cinnolin-6-yl]-2-hydroxybenzonitrile;
1-19: 3-[4-(4-aminopiperidin-1-yl)-3-(3-chloro-5-fluorophenyl)cinnolin-6-yl]-2-hydroxybenzonitrile;
1-20: 3-[4-(4-aminopiperidin-1 -yl)-3-(3,5-difluorophenyl)cinnolin-6-yl]-2-hydroxybenzonitrile;
1-21: 3-[4-(4-aminopiperidin-1-yl)-3-(3,5-dichlorophenyl)cinnolin-6-yl]-2-hydroxybenzonitrile;
1-22: 3-[4-(4-aminopiperidin-1-yl)-3-(3-chloro-5-methylphenyl)cinnolin-6-yl]-5-fluoro-2-hydroxybenzonitrile;
1-23: 6-[4-(4-aminopiperidin-1-yl)-3-(3-chloro-5-methylphenyl)cinnolin-6-yl]-4-fluoro-2,3-dihydro-1H-1,3-benzodiazol-2-one;
1-24: 4-[4-(4-aminopiperidin-1-yl)-3-(3-chloro-5-methylphenyl)cinnolin-6-yl]-6-fluoro-2,3-dihydro-1H-1,3-benzodiazol-2-one;
1-25: 3-[7-chloro-3-(3-fluoro-5-methylphenyl)-4-{4-[(2-fluoroethyl)amino]piperidin-1-yl}cinnolin-6-yl]-5-fluorobenzamide;
1-26: 3-{4-[trans-4-amino-3-hydroxypiperidin-1-yl]-7-chloro-3-(3-fluoro-5-methylphenyl)cinnolin-6-yl}-5-fluorobenzamide;
1-27: 3-[4-(4-aminopiperidin-1-yl)-7-chloro-3-(3,5-dichlorophenyl)cinnolin-6-yl]-5-fluoro-2-hydroxybenzonitrile;
1-28: 6-[4-(4-aminopiperidin-1-yl)-3-(3,5-dichlorophenyl)cinnolin-6-yl]-4-fluoro-2,3-dihydro-1H-1,3-benzodiazol-2-one;
1-29: 2-[4-(4-aminopiperidin-1-yl)-3-(3-chloro-5-methylphenyl)cinnolin-6-yl]-6-fluorophenol;
1-30: 3-[4-(4-aminopiperidin-1-yl)-3-(3,5-dichlorophenyl)cinnolin-6-yl]-5-fluorobenzamide;
1-31: 3-[3-(3,5-dichlorophenyl)-4-{4-[(oxetan-3-yl)amino]piperidin-1-yl}cinnolin-6-yl]-5-fluorobenzamide;
1-32: 3-[3-(3,5-dichlorophenyl)-4-{4-[(3,3,3-trifluoropropyl)amino]piperidin-1-yl}cinnolin-6-yl]-5-fluorobenzamide;
1-33: 3-[3-(3,5-dichlorophenyl)-4-{4-[(2-fluoroethyl)amino]piperidin-1-yl }cinnolin-6-yl]-5-fluorobenzamide;
1-34: 3{4-[3-(aminomethyl)azetidin-1-yl]-3-(3,5-dichlorophenyl)cinnolin-6-yl}-5-fluorobenzamide
1-35: 3-[7-chloro-3-(3-chloro-5-methylphenyl)-4-{4-[(2-fluoroethyl)amino]piperidin-1-yl}cinnolin-6-yl]-5-fluorobenzamide;
1-36: 3-[7-chloro-3-(3-chloro-5-methylphenyl)-4-{4-[(2-fluoroethyl)amino]piperidin-1-yl}cinnolin-6-yl]-5-fluoro-2-hydroxybenzonitrile;
1-37: 3-[7-chloro-3-(3-chloro-5-methylphenyl)-4-{4-[(3,3,3-trifluoropropyl)amino]piperidin-1-yl}cinnolin-6-yl]-5-fluorobenzamide;
1-38: 3-[7-chloro-3-(3-chloro-5-methylphenyl)-4-{4-[(oxetan-3-yl)amino]piperidin-1-yl}cinnolin-6-yl]-5-fluorobenzamide;
1-39: 3-[7-chloro-3-(3-chloro-5-methylphenyl)-4-{4-[(oxetan-3 -yl)amino]piperidin-1-yl}cinnolin-6-yl]-5-fluoro-2-hydroxybenzonitrile;
1-40: 3-[3-(3-chloro-5-methylphenyl)-4-{4-[(oxetan-3-yl)amino]piperidin-1-yl}cinnolin-6-yl]-5-fluoro-2-hydroxybenzonitrile;
1-41: 3-{4-[trans-4-amino-3-fluoropiperidin-1-yl]-7-chloro-3-(3-chloro-5-methylphenyl)cinnolin-6-yl}-5-fluorobenzamide;
1-42: 6-[4-(4-aminopiperidin-1-yl)-7-chloro-3-(3-chloro-5-methylphenyl)cinnolin-6-yl]pyridine-2-carboxamide;
1-43: 6-[4-(4-aminopiperidin-1-yl)-7-chloro-3-(3-chloro-5-methylphenyl)cinnolin-6-yl]-5-chloropyridine-2-carboxamide;
1-44: 2-[4-(4-aminopiperidin-1-yl)-7-chloro-3-(3-chloro-5-methylphenyl)cinnolin-6-yl]pyridine-4-carboxamide;
1-45: 2-[4-(4-aminopiperidin-1-yl)-3-(3-chloro-5-methylphenyl)cinnolin-6-yl]-6-fluoro-3-methylphenol;
1-46: 3-{4-[(3S)-3-aminopiperidin-1-yl]-3-(3-chloro-5-methylphenyl)cinnolin-6-yl}-5-fluorobenzamide;
1-47: 3-{4-[(3R)-3-aminopiperidin-1-yl]-3-(3-chloro-5-methylphenyl)cinnolin-6-yl}-5-fluorobenzamide;
1-48: 3-{4-[cis-octahydro-1H-pyrido[3,4-b]morpholin-6-yl]-3-(3-chloro-5-methylphenyl)cinnolin-6-yl}-5-fluorobenzamide;
1-49: 3-{4-[trans-octahydro-1H-pyrido[3,4-b]morpholin-6-yl]-3-(3-chloro-5-methylphenyl)cinnolin-6-yl}-5-fluorobenzamide;
1-50: 3-[3-(3-chloro-5-methylphenyl)-4-{1,7-diazaspiro[3,5]nonan-7-yl}cinnolin-6-yl]-5-fluorobenzamide;
1-51: 3-{4-[trans-octahydro-1H-pyrido[3,4-b]morpholin-6-yl]-3-(3,5-dichlorophenyl)cinnolin-6-yl}-2-hydroxybenzonitrile;
1-52: 3-{4-[trans-octahydro-1H-pyrido[3,4-b]morpholin-6-yl]-3-(3-chloro-5-methylphenyl)cinnolin-6-yl}-2-hydroxybenzonitrile;
1-53: 3-{4-[trans-octahydro-1H-pyrido[3,4-b]morpholin-6-yl]-3-(3-fluoro-5-methylphenyl)cinnolin-6-yl}-2-hydroxybenzonitrile;
1-54: 3-{4-[trans-octahydro-1H-pyrido[3,4-b]morpholin-6-yl]-3-(3,5-difluorophenyl)cinnolin-6-yl}-2-hydroxybenzonitrile;
1-55: 5-{4-[trans-octahydro-1H-pyrido[3,4-b]morpholin-6-yl]-3-(3,5-difluorophenyl)cinnolin-6-yl}-4-aminopyridine-3-carbonitrile;
1-56: 5-{4-[trans-octahydro-1H-pyrido[3,4-b]morpholin-6-yl]-3-(3-fluoro-5-methylphenyl)cinnolin-6-yl}-4-aminopyridine-3-carbonitrile;
1-57: 2-{4-[trans-octahydro-1H-pyrido[3,4-b]morpholin-6-yl]-3-(3,5-difluorophenyl)cinnolin-6-yl}-3-aminopyridine-4-carbonitrile;
1-58: 2-{4-[trans-octahydro-1H-pyrido[3,4-b]morpholin-6-yl]-3-(3-fluoro-5-methylphenyl)cinnolin-6-yl}-3-aminopyridine-4-carbonitrile.

In some embodiments, provided herein is a pharmaceutically acceptable salt of a compound that is described in Table 1.

TABLE 2

| Cpd No. | R^B | A | R^a | R^b |
|---|---|---|---|---|
| 2-1 | 3-cyano-2-hydroxyphenyl | 4-aminopiperidin-1-yl | 3-F | 5-CH₃ |
| 2-2 | 3-cyano-2-hydroxyphenyl | 4-aminopiperidin-1-yl | 3-F | 5-F |
| 2-3 | 3-cyano-2-hydroxyphenyl | 4-amino-3-methoxypiperidin-1-yl (racemic) | 3-F | 5-F |
| 2-4 | 3-cyanophenyl | 4-amino-3-methoxypiperidin-1-yl (racemic) | 3-F | 5-F |
| 2-5 | 3-cyanophenyl | 4-aminopiperidin-1-yl | 3-F | 5-F |
| 2-6 | 2-hydroxyphenyl | 4-aminopiperidin-1-yl | 3-F | 5-F |

TABLE 2-continued
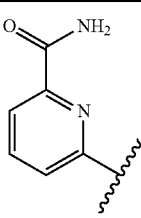
| Cpd No. | R^B | A | R^a | R^b |
|---|---|---|---|---|
| 2-7 | 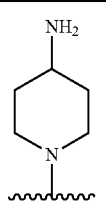 | 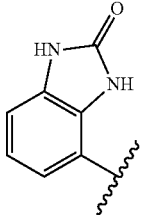 [SMILES: *c1cccc2[nH]c(=O)[nH]c12] | 3-F | 5-CH$_3$ |
| 2-8 | 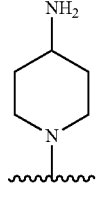 | 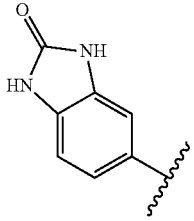 [SMILES: *c1ccc2[nH]c(=O)[nH]c2c1] | 3-F | 5-CH$_3$ |
| 2-9 | 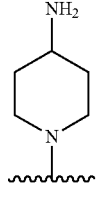 | 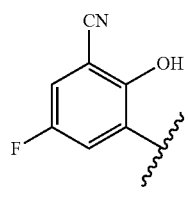 [SMILES: *c1cc(F)cc(C#N)c1O] | 3-F | 5-CH$_3$ |
| 2-10 | 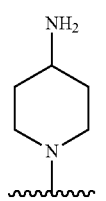 | 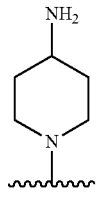 | 3-F | 5-F |
| 2-11 | H | 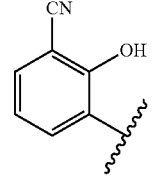 [SMILES: *c1cccc(C#N)c1O] | 3-Cl | 5-Cl |
| 2-12 | 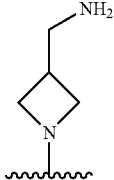 [SMILES: *N1CC(CN)C1] |  | 3-F | 5-CH$_3$ |

TABLE 2-continued

| Cpd No. | $R^B$ | A | $R^a$ | $R^b$ |
| --- | --- | --- | --- | --- |
| 2-13 | 3-cyano-2-hydroxyphenyl | 3-(aminomethyl)azetidin-1-yl | 3-Cl | 5-CH$_3$ |
| 2-14 | 3-carbamoyl-5-fluorophenyl | 3-(aminomethyl)-3-methylazetidin-1-yl | 3-F | 5-CH$_3$ |
| 2-15 | 3-cyano-5-fluoro-2-hydroxyphenyl | 3-(aminomethyl)-3-methylazetidin-1-yl | 3-Cl | 5-CH$_3$ |
| 2-16 | 3-cyano-5-fluoro-2-hydroxyphenyl | 4-aminopiperidin-1-yl | 3-F | 5-CH$_3$ |
| 2-17 | 3-cyano-5-fluoro-2-hydroxyphenyl | 3-(aminomethyl)azetidin-1-yl | 3-F | 5-CH$_3$ |
| 2-18 | 3-cyano-5-fluoro-2-hydroxyphenyl | 3-((ethylamino)methyl)azetidin-1-yl | 3-F | 5-CH$_3$ |

TABLE 2-continued

| Cpd No. | $R^B$ | A | $R^a$ | $R^b$ |
|---|---|---|---|---|
| 2-19 | 3-cyano-2-hydroxyphenyl | octahydropyrido[3,4-b][1,4]oxazine (racemic) | 3-F | 5-F |
| 2-20 | 3-cyano-2-hydroxyphenyl | octahydropyrido[3,4-b][1,4]oxazine (racemic) | 3-Cl | 5-F |
| 2-21 | 3-cyano-5-fluoro-2-hydroxyphenyl | 3-(aminomethyl)azetidin-1-yl | 3-F | 5-F |
| 2-22 | 3-cyano-5-fluoro-2-hydroxyphenyl | 3-(aminomethyl)azetidin-1-yl | 3-Cl | 5-CH$_3$ |
| 2-23 | 3-cyano-5-fluoro-2-hydroxyphenyl | 3-(aminomethyl)azetidin-1-yl | 3-F | 5-F |
| 2-24 | 3-cyano-5-fluoro-2-hydroxyphenyl | 3-{[(2-fluoroethyl)amino]methyl}azetidin-1-yl | 3-F | 5-CH$_3$ |

TABLE 2-continued

| Cpd No. | R^B | A | R^a | R^b |
|---|---|---|---|---|
| 2-25 | 3-cyano-5-fluoro-2-hydroxyphenyl | 1-(azetidin-3-ylmethyl)-N-isopropylamine | 3-F | 5-CH₃ |
| 2-26 | 3-carbamoyl-5-fluorophenyl | 1-(azetidin-3-ylmethyl)-N-ethylamine | 3-F | 5-CH₃ |
| 2-27 | 3-cyano-5-fluoro-2-hydroxyphenyl | 1-(azetidin-3-ylmethyl)-N-(2-methoxyethyl)amine | 3-F | 5-CH₃ |
| 2-28 | 3-cyano-5-fluoro-2-hydroxyphenyl | 1-(azetidin-3-ylmethyl)-N-(3-fluoropropyl)amine | 3-F | 5-CH₃ |
| 2-29 | 3-cyano-5-fluoro-2-hydroxyphenyl | 1-(azetidin-3-ylmethyl)-N-cyclopropylamine | 3-F | 5-CH₃ |
| 2-30 | 3-cyano-5-fluoro-2-hydroxyphenyl | 3-(pyrrolidin-1-ylmethyl)azetidine | 3-F | 5-CH₃ |

TABLE 2-continued

| Cpd No. | R^B | A | R^a | R^b |
|---|---|---|---|---|
| 2-31 | 3-CN, 4-F, 2-OH phenyl | azetidine-3-CH2-NH-propyl | 3-F | 5-CH3 |
| 2-32 | 3-CN, 4-F, 2-OH phenyl | azetidine-3-CH2-NH2 | 3-Cl | 5-CH3 |
| 2-33 | 3-CN, 4-F, 2-OH phenyl | azetidine-3-CH2-NH-oxetan-3-yl | 3-F | 5-CH3 |
| 2-34 | 3-CN, 4-F, 2-OH phenyl | azetidine-3-CH2-NH-cyclopentyl | 3-F | 5-CH3 |
| 2-35 | 3-CN, 4-F, 2-OH phenyl | azetidine-3-CH2-morpholine | 3-F | 5-CH3 |

TABLE 2-continued

| Cpd No. | R^B | A | R^a | R^b |
|---|---|---|---|---|
| 2-36 | 3-cyano-5-fluoro-2-hydroxyphenyl | 1-[(piperazin-1-yl)methyl]azetidin-3-yl | 3-F | 5-CH$_3$ |
| 2-37 | 3-cyano-5-fluoro-2-hydroxyphenyl | 1-{[(tetrahydro-2H-pyran-4-yl)amino]methyl}azetidin-3-yl | 3-F | 5-CH$_3$ |
| 2-38 | 3-fluoro-2-hydroxy-6-methylphenyl | 1-[(ethylamino)methyl]azetidin-3-yl | 3-F | 5-CH$_3$ |
| 2-39 | 3-cyano-5-fluoro-2-hydroxyphenyl | 1-{[(1-methoxy-2-methylpropan-2-yl)amino]methyl}azetidin-3-yl | 3-F | 5-CH$_3$ |
| 2-40 | 3-cyano-5-fluoro-2-hydroxyphenyl | 1-{[(2-hydroxy-2-methylpropyl)amino]methyl}azetidin-3-yl | 3-F | 5-CH$_3$ |

TABLE 2-continued
| Cpd No. | R^B | A | R^a | R^b |
|---|---|---|---|---|
| 2-41 | 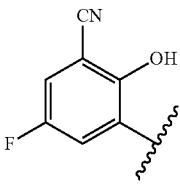 | 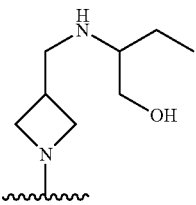 [SMILES: *N1CC(CNC(CC)CO)C1] | 3-F | 5-CH$_3$ |
| 2-42 | 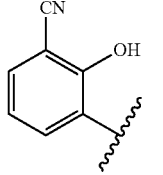 [SMILES: *c1cccc(C#N)c1O] | 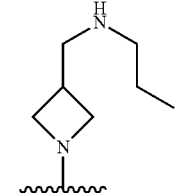 [SMILES: *N1CC(CNCCC)C1] | 3-F | 5-CH$_3$ |
| 2-43 | 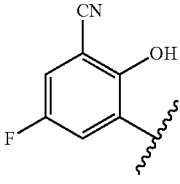 | 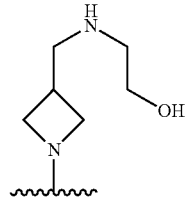 [SMILES: *N1CC(CNCCO)C1] | 3-F | 5-CH$_3$ |
| 2-44 | 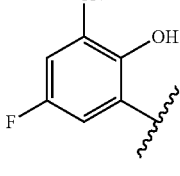 | 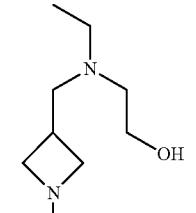 | 3-F | 5-CH$_3$ |
| 2-45 | 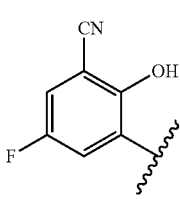 | 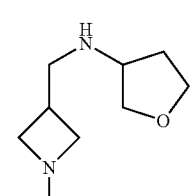 | 3-F | 5-CH$_3$ |
| 2-46 | 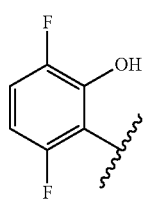 [SMILES: *c1c(F)ccc(F)c1O] | 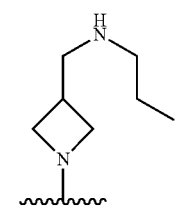 [SMILES: *N1CC(CNCCC)C1] | 3-F | 5-CH$_3$ |

TABLE 2-continued

| Cpd No. | R^B | A | R^a | R^b |
|---|---|---|---|---|
| 2-47 | 3-CN, 2-OH, 5-F phenyl | azetidine-N-CH2-(3,3-difluoropyrrolidin-1-yl) | 3-F | 5-CH₃ |
| 2-48 | 3-CN, 2-OH, 5-F phenyl | azetidine-N-CH2-((S)-3-fluoropyrrolidin-1-yl) | 3-F | 5-CH₃ |
| 2-49 | 3-CN, 2-OH, 5-F phenyl | azetidine-N-CH2-((R)-3-fluoropyrrolidin-1-yl) | 3-F | 5-CH₃ |
| 2-50 | 3-CN, 2-OH, 5-F phenyl | azetidine-N-CH2-(piperidin-1-yl) | 3-F | 5-CH₃ |
| 2-51 | 3-CN, 2-OH, 5-F phenyl | octahydro-1,6-naphthyridinyl-OH | 3-F | 5-CH₃ |

TABLE 2-continued

| Cpd No. | R^B | A | R^a | R^b |
|---|---|---|---|---|
| 2-52 | 3,5-difluoro-4-hydroxyphenyl | 3-((propylamino)methyl)azetidin-1-yl | 3-F | 5-CH$_3$ |
| 2-53 | 3-cyano-5-fluoro-2-(methoxymethoxy)phenyl | 3-(((3-hydroxypropyl)amino)methyl)azetidin-1-yl | 3-F | 5-CH$_3$ |
| 2-54 | 3-cyano-5-fluoro-2-hydroxyphenyl | 3-(((3-hydroxypropyl)amino)methyl)azetidin-1-yl | 3-F | 5-CH$_3$ |
| 2-55 | 7-fluoro-2-oxo-2,3-dihydro-1H-benzo[d]imidazol-5-yl | 3-((propylamino)methyl)azetidin-1-yl | 3-F | 5-CH$_3$ |
| 2-56 | 2-(carboxymethoxy)-3-cyanophenyl (OH of COOH shown) | 4-aminopiperidin-1-yl | 3-F | 3-F |

TABLE 2-continued

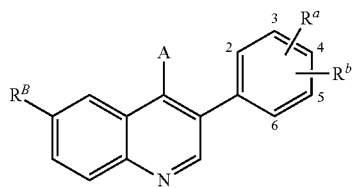

| Cpd No. | $R^B$ | A | $R^a$ | $R^b$ |
|---|---|---|---|---|
| 2-57 | (CN, OH, carboxymethoxy with (CH₂)₃ linker on phenyl) | 4-amino-piperidinyl | 3-F | 3-F |
| 2-58 | (CN, OCH₂OCH₃ on phenyl) | 4-amino-3-hydroxy-piperidinyl, racemic | 3-F | 3-F |
| 2-59 | (CN, OH on phenyl) | 4-amino-3-fluoro-piperidinyl | 3-F | 3-F |
| 2-60 | (CN, OH on phenyl) | 4-amino-3-hydroxy-piperidinyl, racemic | 3-F | 3-F |
| 2-61 | (CN, OH on phenyl) | 4-amino-3-methoxy-piperidinyl | 3-F | 3-F |
| 2-62 | (CN, OCH₂OCH₃ on phenyl) | 4-amino-3-methoxy-piperidinyl | 3-F | 3-F |

TABLE 2-continued

| Cpd No. | R^B | A | R^a | R^b |
|---|---|---|---|---|
| 2-63 | 3-cyano-5-fluoro-2-hydroxyphenyl | 4-amino-3-hydroxypiperidin-1-yl (racemic) | 3-F | 3-F |
| 2-64 | 2-(2-acetoxyethoxy)-3-cyanophenyl | 4-aminopiperidin-1-yl | 3-F | 3-F |
| 2-65 | 3-cyano-2-(2-hydroxyethoxy)phenyl | 4-aminopiperidin-1-yl | 3-F | 3-F |
| 2-66 | 3-cyano-2-hydroxyphenyl | 4-amino-3-methoxypiperidin-1-yl | 3-F | 3-F |
| 2-67 | 3-carbamoyl-2-(1,3-dihydroxypropan-2-yloxy)phenyl | 4-aminopiperidin-1-yl | 3-F | 3-F |

TABLE 2-continued
| Cpd No. | R^B | A | R^a | R^b |
|---|---|---|---|---|
| 2-68 | 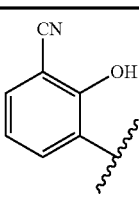 | 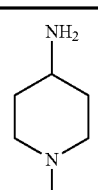 | 3-F | 5-OCH$_2$CH$_2$OCH$_3$ |
| 2-69 | 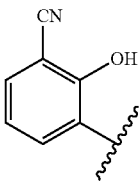 [SMILES: *c1cccc(C#N)c1O] | 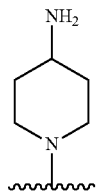 | 3-F | 5: 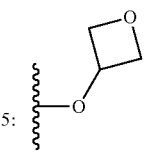 [SMILES: *OC1COC1] |
| 2-70 | 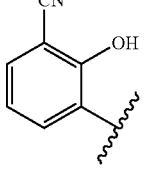 | 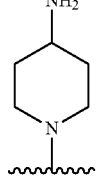 | 3-F | 5: 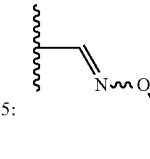 |
| 2-71 | 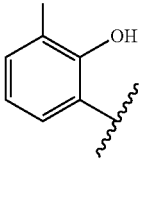 | 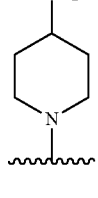 | 3-F | 5: 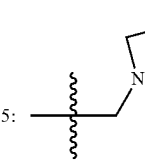 |
| 2-72 | 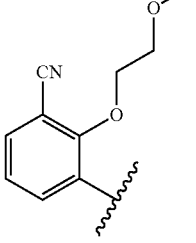 | 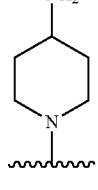 | 3-F | 3-F |
| 2-73 | 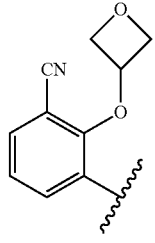 [SMILES: *c1cccc(C#N)c1OC1COC1] | 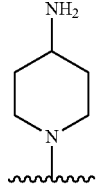 | 3-F | 3-F |

TABLE 2-continued
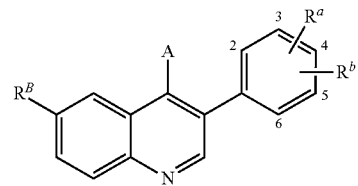
| Cpd No. | R^B | A | R^a | R^b |
|---|---|---|---|---|
| 2-74 | 3-fluoro-4-(oxetan-3-yloxy)pyridinyl | 4-aminopiperidin-1-yl | 3-F | 3-F |
| 2-75 | 6-(azetidin-1-yl)-5-cyanopyridin-3-yl (CN at 5) | 4-aminopiperidin-1-yl | 3-F | 3-F |
| 2-76 | 6-(azetidin-1-yl)-5-carbamoylpyridin-3-yl | 4-aminopiperidin-1-yl | 3-F | 3-F |
| 2-77 | 2-amino-3-cyanophenyl | 4-aminopiperidin-1-yl | 3-F | 3-F |
| 2-78 | 3-cyano-2-(methoxymethoxy)phenyl | 4-aminopiperidin-1-yl | 3-F | 3-F |

TABLE 2-continued
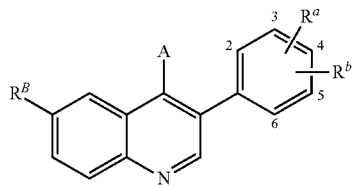
| Cpd No. | $R^B$ | A | $R^a$ | $R^b$ |
|---|---|---|---|---|
| 2-79 | CN, OH phenyl | 4-aminopiperidine (N-linked) | 3-F | =N-O-ethyl |
| 2-80 | fluoro-benzimidazol-2(3H)-one | octahydropyrido[3,4-b][1,4]oxazine (racemic) | 3-F | 5-F |
| 2-81 | methoxyimino-hydroxyphenyl | 4-aminopiperidine (N-linked) | 3-F | 5-F |
| 2-82 | CN, OH, F phenyl | 1-(azetidin-3-yl)propan-1-amine | 3-F | 5-CH$_3$ |
| 2-83 | difluoro-(methoxycarbonylamino)phenyl | 4-aminopiperidine (N-linked) | 3-F | 5-F |

TABLE 2-continued

| Cpd No. | R^B | A | R^a | R^b |
|---|---|---|---|---|
| 2-84 | 2-cyano-6-(methoxymethoxy)phenyl | 4-amino-3-methoxypiperidin-1-yl (racemic) | 3-F | 5-F |
| 2-85 | 6-carbamoylpyridin-2-yl | octahydropyrido[3,4-b][1,4]oxazin-6-yl (racemic) | 3-F | 5-F |
| 2-86 | 2,4-difluoro-6-(methanesulfonamido)phenyl | 4-aminopiperidin-1-yl | 3-F | 5-F |
| 2-87 | 2-cyano-6-((2-methoxyethoxy)methoxy)phenyl | 4-aminopiperidin-1-yl | 3-F | 5-F |
| 2-88 | 3-(azetidine-1-carbonyl)-2-hydroxyphenyl | 4-aminopiperidin-1-yl | 3-F | 5-CH$_3$ |

TABLE 2-continued
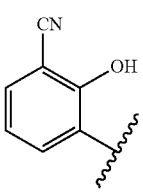 [SMILES: *c1cccc(C#N)c1O]
| Cpd No. | R^B | A | R^a | R^b |
|---|---|---|---|---|
| 2-89 | 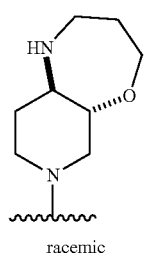 | 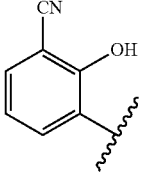 [SMILES: *c1cccc(C#N)c1O]<br>racemic | 3-F | 5-F |
| 2-90 | 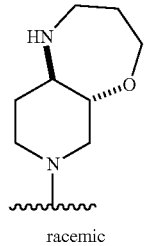 | 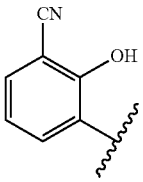 [SMILES: *c1cccc(C#N)c1O]<br>racemic | 3-F | 5-CH$_3$ |
| 2-91 | 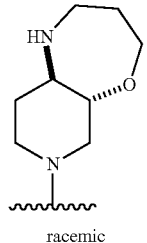 | 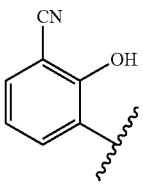 [SMILES: *c1cccc(C#N)c1O]<br>racemic | 3-F | 5-OCH$_3$ |
| 2-92 | 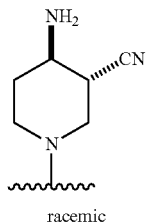 [SMILES: *N1CC[C@@H](N)[C@H](C#N)C1] | 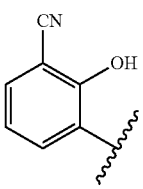 [SMILES: *c1cccc(C#N)c1O]<br>racemic | 3-F | 5-F |
| 2-93 | | 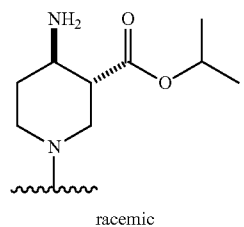 [SMILES: *N1CC[C@@H](N)[C@H](C(=O)OC(C)C)C1]<br>racemic | 3-F | 5-F |

TABLE 2-continued

| Cpd No. | R^B | A | R^a | R^b |
|---|---|---|---|---|
| 2-94 | 3-cyano-2-hydroxyphenyl | 4-amino-3-cyanopiperidin-1-yl, racemic | 3-F | 5-F |
| 2-95 | 3-cyano-2-hydroxyphenyl | 4-amino-3-(2-hydroxyethoxy)piperidin-1-yl, racemic | 3-F | 5-F |
| 2-96 | 3-cyano-2-hydroxyphenyl | 4-amino-3-(2-hydroxyethoxy)piperidin-1-yl, racemic | 3-F | 5-F |
| 2-97 | 3-cyano-2-hydroxyphenyl | 4-amino-3-(2-methoxyethoxy)piperidin-1-yl, racemic | 3-F | 5-F |
| 2-98 | 3-cyano-2-hydroxyphenyl | 4-amino-3-(2-methoxyethoxy)piperidin-1-yl, racemic | 3-F | 5-F |

TABLE 2-continued

| Cpd No. | R^B | A | R^a | R^b |
|---|---|---|---|---|
| 2-99 | CN, OH, F, F (benzonitrile with OH and 2 F) | 4-aminopiperidine (NH₂ on piperidine) | 3-F | 5-F |
| 2-100 | CN, OH, F, F | octahydropyrido-oxazine (HN, O bicyclic), racemic | 3-F | 5-F |
| 2-101 | CN, OH, F, F | octahydropyrido-oxazepine (HN, O bicyclic), racemic | 3-F | 5-F |
| 2-102 | CN, OH, F, F | 4-amino-3-methoxypiperidine (NH₂, OMe), racemic | 3-F | 5-F |
| 2-103 | CN, OH, F, F | 4-aminopiperidine | 3-F | 5-CH₃ |

TABLE 2-continued

| Cpd No. | R^B | A | R^a | R^b |
|---|---|---|---|---|
| 2-104 | 3,4-difluoro-2-hydroxy-6-cyanophenyl | octahydropyrido[3,4-b][1,4]oxazine (racemic) | 3-F | 5-CH₃ |
| 2-105 | 3,4-difluoro-2-hydroxy-6-cyanophenyl | octahydropyrido-oxazepine (racemic) | 3-F | 5-CH₃ |
| 2-106 | 3,4-difluoro-2-hydroxy-6-cyanophenyl | 4-amino-3-methoxypiperidine (racemic) | 3-F | 5-CH₃ |
| 2-107 | 3,4-difluoro-2-hydroxy-6-cyanophenyl | 4-amino-3-hydroxypiperidine (racemic) | 3-F | 5-OCH₃ |
| 2-108 | 3,6-difluoro-2-hydroxy-5-methylphenyl | 4-aminopiperidine | 3-F | 5-F |

TABLE 2-continued

| Cpd No. | R$^B$ | A | R$^a$ | R$^b$ |
|---|---|---|---|---|
| 2-109 | 2,4-difluoro-3-methyl-6-hydroxyphenyl | octahydropyrido[3,4-b][1,4]oxazine (racemic) | 3-F | 5-F |
| 2-110 | 2,4-difluoro-3-methyl-6-hydroxyphenyl | octahydropyrido-oxazepine (racemic) | 3-F | 5-F |
| 2-111 | 2,4-difluoro-3-methyl-6-hydroxyphenyl | 4-amino-3-methoxypiperidinyl (racemic) | 3-F | 5-F |
| 2-112 | 2,4-difluoro-3-methyl-6-hydroxyphenyl | 4-amino-3-methoxypiperidinyl (racemic) | 3-F | 5-CH$_3$ |
| 2-113 | 2,4-difluoro-3-methyl-6-hydroxyphenyl | 4-amino-3-hydroxypiperidinyl (racemic) | 3-F | 5-OCH$_3$ |

TABLE 2-continued

| Cpd No. | R^B | A | R^a | R^b |
|---|---|---|---|---|
| 2-114 | 5-F-3-(methoxyimino-methyl)-2-hydroxyphenyl | 4-aminopiperidin-1-yl | 3-F | 5-F |
| 2-115 | 3-(methoxyimino-methyl)-2-hydroxyphenyl | 4-aminopiperidin-1-yl | 3-F | 5-CH₃ |
| 2-116 | 5-F-3-(methoxyimino-methyl)-2-hydroxyphenyl | 4-aminopiperidin-1-yl | 3-F | 5-CH₃ |
| 2-117 | 4,5-diF-3-(methoxyimino-methyl)-2-hydroxyphenyl | 4-aminopiperidin-1-yl | 3-F | 5-CH₃ |
| 2-118 | 5-F-3-(methoxyimino-methyl)-2-hydroxyphenyl | octahydropyrano[3,2-b]pyridinyl (racemic) | 3-F | 5-CH₃ |

TABLE 2-continued
| Cpd No. | R^B | A | R^a | R^b |
|---|---|---|---|---|
| 2-119 | 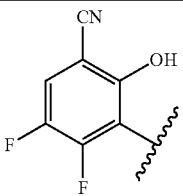 | 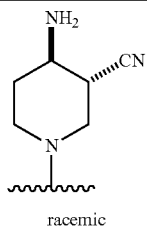<br>racemic | 3-F | 5-F |
| 2-120 | 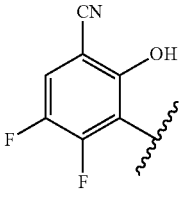 [SMILES: *c1c(O)c(C#N)cc(F)c1F] | 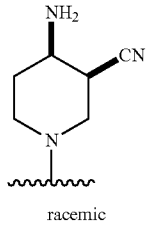 [SMILES: *N1CC[C@@H](N)[C@@H](C#N)C1]<br>racemic | 3-F | 5-F |
| 2-121 | 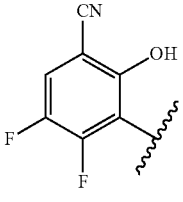 [SMILES: *c1c(O)c(C#N)cc(F)c1F] | 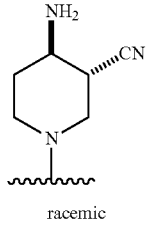<br>racemic | 3-F | 5-CH$_3$ |
| 2-122 | 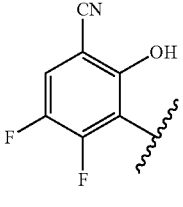 [SMILES: *c1c(O)c(C#N)cc(F)c1F] | 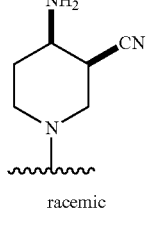<br>racemic | 3-F | 5-CH$_3$ |
| 2-123 | 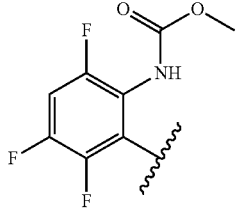 [SMILES: *c1c(F)c(F)cc(F)c1NC(=O)OC] | 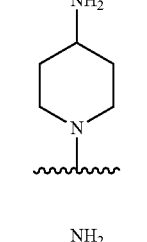 | 3-F | 5-F |
| 2-124 | 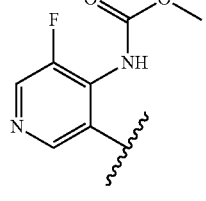 | 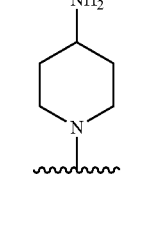 | 3-F | 5-F |

TABLE 2-continued

| Cpd No. | R^B | A | R^a | R^b |
|---|---|---|---|---|
| 2-125 | 3-cyano-4-(methoxycarbonylamino)pyridin-5-yl | 4-amino-piperidin-1-yl | 3-F | 5-F |
| 2-126 | 2-fluoro-6-(hydroxyiminomethyl)phenyl | 4-amino-piperidin-1-yl | 3-F | 5-F |
| 2-127 | 2-chloro-6-(hydroxyiminomethyl)phenyl | 4-amino-piperidin-1-yl | 3-F | 5-F |
| 2-128 | 2-cyano-6-(hydroxyiminomethyl)phenyl | 4-amino-piperidin-1-yl | 3-F | 5-F |
| 2-129 | 2-fluoro-6-(methoxyiminomethyl)phenyl | 4-amino-piperidin-1-yl | 3-F | 5-F |
| 2-130 | 2-chloro-6-(methoxyiminomethyl)phenyl | 4-amino-piperidin-1-yl | 3-F | 5-F |
| 2-131 | 2-cyano-6-(methoxyiminomethyl)phenyl | 4-amino-piperidin-1-yl | 3-F | 5-F |

TABLE 2-continued

| Cpd No. | R^B | A | R^a | R^b |
|---|---|---|---|---|
| 2-132 | 3-(1-amino-2,2,2-trifluoroethyl)phenyl | 4-aminopiperidin-1-yl | 3-F | 5-F |
| 2-133 | 2-(1-amino-2,2,2-trifluoroethyl)-3-fluorophenyl | 4-aminopiperidin-1-yl | 3-F | 5-F |
| 2-134 | 2-chloro-5,6-difluoro-3-hydroxyphenyl | 4-aminopiperidin-1-yl | 3-F | 5-F |
| 2-135 | 2-chloro-5,6-difluoro-3-hydroxyphenyl | octahydropyrido[3,4-b][1,4]oxazinyl (racemic) | 3-F | 5-F |
| 2-136 | 2-chloro-4-fluoro-6-hydroxyphenyl | 4-aminopiperidin-1-yl | 3-F | 5-F |
| 2-137 | 2-chloro-6-hydroxyphenyl | 4-aminopiperidin-1-yl | 3-F | 5-F |

TABLE 2-continued
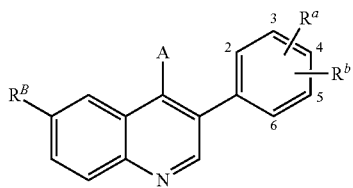
| Cpd No. | R^B | A | R^a | R^b |
|---|---|---|---|---|
| 2-138 | 3-Cl, 2-OH phenyl | racemic hexahydropyrido[3,4-b][1,4]oxazine | 3-F | 5-F |
| 2-139 | 2,4-difluoro-6-[3-methoxyurea]phenyl | 4-amino-piperidine | 3-F | 5-F |
| 2-140 | 2,4,5-trifluoro-6-[3-methoxyurea]phenyl | racemic hexahydropyrido[3,4-b][1,4]oxazine | 3-F | 5-F |
| 2-141 | 4-chloro-2-oxo-benzimidazol-6-yl | 4-amino-piperidine | 3-F | 5-F |
| 2-142 | 2-oxo-benzoxazol-5-yl | 4-amino-piperidine | 3-F | 5-F |
| 2-143 | 3-CN, 2-OH phenyl | methyl 4-amino-piperidine-3-carboxylate | 3-F | 5-F |

TABLE 2-continued
| Cpd No. | R^B | A | R^a | R^b |
|---|---|---|---|---|
| 2-144 | 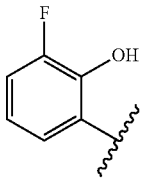 [SMILES: *c1cccc(F)c1O] | 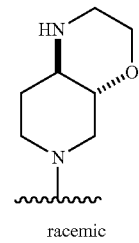<br>racemic | 3-F | 5-F |
| 2-145 |  | <br>racemic | 3-F | 5-F |
| 2-146 | 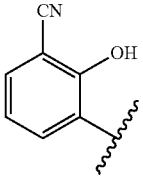 [SMILES: *c1cccc(C#N)c1O] | 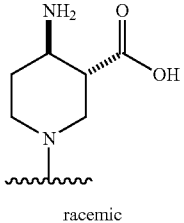<br>racemic | 3-F | 5-F |
| 2-147 |  |  | 3-F | 5-F |
| 2-148 | 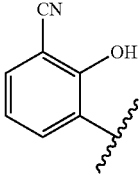 [SMILES: *c1cccc(C#N)c1O] | 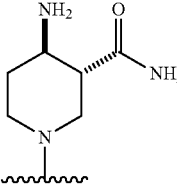 | 3-F | 5-F |

TABLE 2-continued

| Cpd No. | R^B | A | R^a | R^b |
|---|---|---|---|---|
| 2-149 | 3-cyano-2-hydroxyphenyl | 4-amino-3-(N-methylcarbamoyl)piperidin-1-yl (racemic) | 3-F | 5-F |
| 2-150 | 2-hydroxy-3,4,5-trifluorophenyl | 4-aminopiperidin-1-yl | 3-F | 5-F |
| 2-151 | 3-cyano-2-hydroxyphenyl | 4-amino-3-(N,N-dimethylcarbamoyl)piperidin-1-yl (racemic) | 3-F | 5-F |
| 2-152 | 3-fluoro-4-((hydroxyimino)methyl)pyridin-2-yl | 4-aminopiperidin-1-yl | 3-F | 5-F |
| 2-153 | 2-fluoro-6-((hydroxyimino)methyl)phenyl | octahydropyrano[3,2-b]pyridinyl | 3-F | 5-F |
| 2-154 | 2,4-difluoro-6-((hydroxyimino)methyl)phenyl | octahydropyrano[3,2-b]pyridinyl | 3-F | 5-F |

TABLE 2-continued

| Cpd No. | R^B | A | R^a | R^b |
|---|---|---|---|---|
| 2-155 | 2-fluoro-6-(N-hydroxyimino)methyl-phenyl | octahydropyrido[3,4-b][1,4]oxazine (N-linked) | 3-F | 5-OCH₃ |
| 2-156 | 2-fluoro-6-(1H-imidazol-2-yl)phenyl | octahydropyrido[3,4-b][1,4]oxazine (N-linked), racemic | 3-F | 5-OCH₃ |
| 2-157 | 2-fluoro-6-(1H-imidazol-5-yl)phenyl | octahydropyrido[3,4-b][1,4]oxazine (N-linked), racemic | 3-F | 5-OCH₃ |
| 2-158 | 3-cyano-4,5-difluoro-2-hydroxyphenyl | 4-aminopiperidin-1-yl | 3-F | 5-OCH₃ |
| 2-159 | 3-cyano-4,5-difluoro-2-hydroxyphenyl | octahydropyrido[3,4-b][1,4]oxazine (N-linked), racemic | 3-F | 5-OCH₃ |

TABLE 2-continued

| Cpd No. | R^B | A | R^a | R^b |
|---|---|---|---|---|
| 2-160 | 2,3,5-trifluoro-6-hydroxyphenyl | octahydropyrido[3,4-b][1,4]oxazinyl (racemic) | 3-F | 5-OCH₃ |
| 2-161 | 2,3,5-trifluoro-6-hydroxyphenyl | 4-aminopiperidinyl | 3-F | 5-OCH₃ |
| 2-162 | 3-fluoro-4-(3-methoxyureido)pyridinyl | 4-aminopiperidinyl | 3-F | 5-F |
| 2-163 | 3-chloro-4-(3-methoxyureido)pyridinyl | 4-aminopiperidinyl | 3-F | 5-OCH₃ |
| 2-164 | 2,4-difluoro-6-(3-methoxyureido)phenyl | 4-aminopiperidinyl | 3-F | 5-OCH₃ |
| 2-165 | 2,4-difluoro-6-(methoxycarbonylamino)phenyl | 4-aminopiperidinyl | 3-F | 5-OCH₃ |

TABLE 2-continued
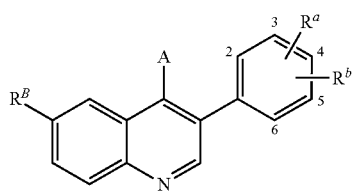
| Cpd No. | $R^B$ | A | $R^a$ | $R^b$ |
|---|---|---|---|---|
| 2-166 | 2-F, 6-(CH=NOH)-phenyl | 4-amino-piperidin-1-yl | 3-F | 5-OCH$_3$ |
| 2-167 | 2-CN, 6-(NHC(O)OCH$_3$)-phenyl | 4-amino-piperidin-1-yl | 3-F | 5-OCH$_3$ |
| 2-168 | 3-F, 4-(CH=NOH)-pyridin-5-yl | 4-amino-piperidin-1-yl | 3-F | 5-CH$_3$ |
| 2-169 | 3-F, 4-NH$_2$-pyridin-5-yl | 4-amino-piperidin-1-yl | 3-F | 5-CH$_3$ |
| 2-170 | 2-CN, 6-OH-phenyl | racemic 4-amino-3-(methoxycarbonyl)-piperidin-1-yl | 3-F | 5-F |
| 2-171 | 3-F, 4-(NHC(O)OCH$_3$)-pyridin-5-yl | 4-amino-piperidin-1-yl | 3-F | 5-CH$_3$ |

TABLE 2-continued

| Cpd No. | R^B | A | R^a | R^b |
|---|---|---|---|---|
| 2-173 | (2-F, 6-methoxycarbonylamino)phenyl | 4-amino-piperidin-1-yl | 3-F | 5-OCH$_3$ |
| 2-174 | (2-F, 6-(N'-methoxyureido))phenyl | 4-amino-piperidin-1-yl | 3-F | 5-OCH$_3$ |
| 2-175 | (2-F, 6-(azetidine-1-carbonylamino))phenyl | 4-amino-piperidin-1-yl | 3-F | 5-OCH$_3$ |
| 2-176 | (3-F, 4-(hydroxyiminomethyl))pyridin-5-yl | 4-amino-piperidin-1-yl | 3-F | 5-CF$_3$ |
| 2-177 | (4-amino-5-cyano)pyridin-3-yl | 4-amino-piperidin-1-yl | 3-F | 5-F |
| 2-178 | (2-amino-5-fluoro)pyridin-3-yl | 4-amino-piperidin-1-yl | 3-F | 5-F |

TABLE 2-continued

| Cpd No. | R^B | A | R^a | R^b |
|---|---|---|---|---|
| 2-179 | 2-amino-3-cyano-5,6-difluorophenyl | 4-aminopiperidin-1-yl | 3-F | 5-F |
| 2-180 | methyl (6-cyano-3,4-difluoro-2-yl)carbamate phenyl | 4-aminopiperidin-1-yl | 3-F | 5-F |
| 2-181 | 4-amino-5-chloropyridin-3-yl | 4-aminopiperidin-1-yl | 3-F | 5-CH$_3$ |
| 2-182 | methyl (5-fluoropyridin-2-yl)carbamate, linked at 3 | 4-aminopiperidin-1-yl | 3-F | 5-CH$_3$ |
| 2-183 | 1-(5-fluoropyridin-2-yl)-3-methoxyurea, linked at 3 | 4-aminopiperidin-1-yl | 3-F | 5-CH$_3$ |
| 2-184 | methyl (5-chloropyridin-4-yl)carbamate, linked at 3 | 4-aminopiperidin-1-yl | 3-F | 5-CH$_3$ |

TABLE 2-continued

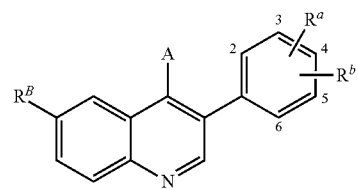

| Cpd No. | R^B | A | R^a | R^b |
|---|---|---|---|---|
| 2-185 | methyl (4-cyano-2-yl)phenylcarbamate | 4-aminopiperidin-1-yl | 3-F | 5-F |
| 2-186 | 3-chloro-N-methoxy-pyridinylurea | 4-aminopiperidin-1-yl | 3-F | 5-CH$_3$ |
| 2-187 | 4-amino-5-cyanopyridin-3-yl | 4-aminopiperidin-1-yl | 3-F | 5-CH$_3$ |
| 2-188 | 4-aminopiperidin-1-yl | 1-methyl-5-((hydroxyimino)methyl)-1H-pyrazol-4-yl | 3-F | 5-F |
| 2-189 | N-methoxy-(4-cyanophenyl)urea | 4-aminopiperidin-1-yl | 3-F | 5-F |
| 2-190 | 3-cyano-2-hydroxyphenyl | octahydropyrano[3,2-b]pyridin-6-yl (Single enantiomer) | 3-F | 5-F |

TABLE 2-continued

| Cpd No. | R^B | A | R^a | R^b |
|---|---|---|---|---|
| 2-191 | [3,4-difluoro-2-(N-methyl-N-methoxycarbamoyl-amino)-6-cyanophenyl] | 4-amino-piperidin-1-yl | 3-F | 5-F |
| 2-192 | [3-chloro-4-(hydroxyiminomethyl)pyridin-5-yl] | 4-amino-piperidin-1-yl | 3-F | 5-F |
| 2-193 | [2-cyano-6-hydroxyphenyl] | octahydropyrido[3,4-b][1,4]oxazin-6-yl (Single enantiomer) | 3-F | 5-F |
| 2-194 | [2-cyano-6-(methoxymethoxy)-4-fluorophenyl] | 4-amino-piperidin-1-yl | 3-F | 5-F |
| 2-195 | [3-(hydroxyiminomethyl)pyridin-2-yl] | 4-amino-piperidin-1-yl | 3-F | 5-F |
| 2-196 | [2-(hydroxyiminomethyl)pyridin-3-yl] | 4-amino-piperidin-1-yl | 3-F | 5-F |

TABLE 2-continued

| Cpd No. | R$^B$ | A | R$^a$ | R$^b$ |
| --- | --- | --- | --- | --- |
| 2-197 | 2,4-difluoro-6-(methoxycarbonylamino)phenyl | 4-amino-piperidin-1-yl | 3-F | 5-CH$_3$ |
| 2-198 | 2,4-difluoro-6-[(N-methoxy-N-methylcarbamoyl)amino]phenyl | 4-amino-piperidin-1-yl | 3-F | 5-CH$_3$ |
| 2-199 | 2,4-difluoro-6-[(N,N-dimethylcarbamoyl)amino]phenyl | 4-amino-piperidin-1-yl | 3-F | 5-CH$_3$ |
| 2-200 | 6-[(hydroxyimino)methyl]pyridin-2-yl | 4-amino-piperidin-1-yl | 3-F | 5-F |
| 2-201 | 2-cyano-6-(methoxycarbonyloxy)phenyl | 4-amino-piperidin-1-yl | 3-F | 5-F |

TABLE 2-continued

| Cpd No. | $R^B$ | A | $R^a$ | $R^b$ |
|---|---|---|---|---|
| 2-202 | (2-F, 3-Me phenyl with CH=N-OH) | 4-amino-piperidin-1-yl | 3-F | 5-F |
| 2-203 | (pyridin-4-yl with CH=N-OH at 2-position) | 4-amino-piperidin-1-yl | 3-F | 5-F |
| 2-204 | (4-F phenyl, CN, O-CH₂CH₂-OCH₃) | 4-amino-piperidin-1-yl | 3-F | 5-CH₃ |
| 2-205 | (3,4-diF phenyl, CN, NH-C(O)-OCH₃) | 4-amino-piperidin-1-yl | 3-F | 5-CH₃ |
| 2-206 | (3,4-diF phenyl, CN, NH-C(O)-N(CH₃)-OCH₃) | 4-amino-piperidin-1-yl | 3-F | 5-CH₃ |

TABLE 2-continued
| Cpd No. | R^B | A | R^a | R^b |
|---|---|---|---|---|
| 2-207 | 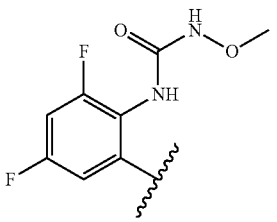 [SMILES: *c1cc(F)cc(F)c1NC(=O)NOC] | 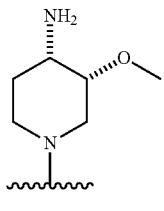 [SMILES: *N1CC[C@H](N)[C@H](OC)C1] | 3-F | 5-CH$_3$ |
| 2-208 | 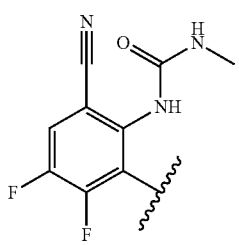 [SMILES: *c1c(F)c(F)cc(C#N)c1NC(=O)NC] | 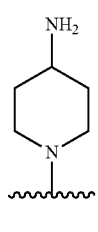 | 3-F | 5-CH$_3$ |
| 2-209 | 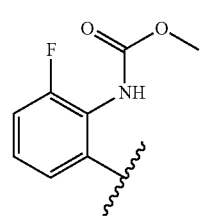 [SMILES: *c1cccc(F)c1NC(=O)OC] | 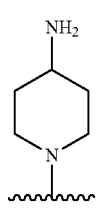 | 3-F | 5-CH$_3$ |
| 2-210 | 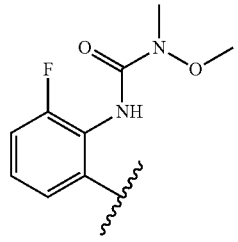 [SMILES: *c1cccc(F)c1NC(=O)N(C)OC] | 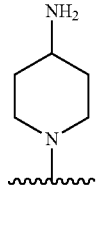 | 3-F | 5-CH$_3$ |
| 2-211 | 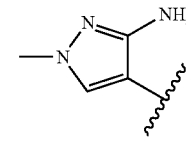 | 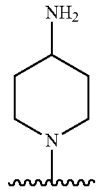 | 3-F | 5-CH$_3$ |
| 2-212 | 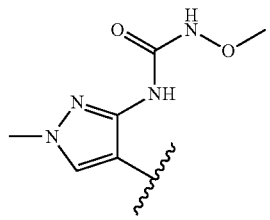 | 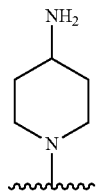 | 3-F | 5-CH$_3$ |

TABLE 2-continued

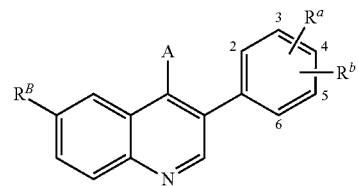

| Cpd No. | R^B | A | R^a | R^b |
|---------|-----|---|-----|-----|
| 2-213 | 2-(methoxyimino)methyl-4-hydroxyphenyl (HO-phenyl with CH=N-OMe) | 4-amino-piperidin-1-yl | 3-F | 5-CH₃ |
| 2-214 | 1-methyl-3-(methoxycarbonylamino)-1H-pyrazol-4-yl | 4-amino-piperidin-1-yl | 3-F | 5-CH₃ |
| 2-215 | 2-(3-methoxyureido)-4-methylpyridin-3-yl | 4-amino-piperidin-1-yl | 3-F | 5-CH₃ |
| 2-216 | 2,4-difluoro-6-(3-isopropoxyureido)phenyl | 4-amino-piperidin-1-yl | 3-F | 5-CH₃ |
| 2-217 | 2-fluoro-6-((hydroxyimino)methyl)phenyl | 4-amino-3-methoxy-piperidin-1-yl (racemic) | 3-F | 5-CH₃ |

TABLE 2-continued

| Cpd No. | R^B | A | R^a | R^b |
|---|---|---|---|---|
| 2-218 | methyl (2-cyano-6-yl)carbamate fragment | 4-amino-3-methoxypiperidinyl (racemic) | 3-F | 5-CH₃ |
| 2-219 | 3-cyano-5-fluoro-2-hydroxyphenyl | 4-amino-3-hydroxypiperidinyl (racemic) | 3-F | 5-CH₃ |
| 2-220 | 3-cyano-5-fluoro-2-(2-methoxyethoxy)phenyl | 4-amino-3-hydroxypiperidinyl (racemic) | 3-F | 5-CH₃ |
| 2-221 | 3-((methoxyimino)methyl)-2-hydroxyphenyl | octahydropyrano[3,2-c]pyridinyl (racemic) | 3-F | 5-CH₃ |
| 2-222 | 4-cyano-2-(3-methoxyureido)phenyl | 4-aminopiperidinyl | 3-F | 5-CH₃ |

TABLE 2-continued

| Cpd No. | R^B | A | R^a | R^b |
|---|---|---|---|---|
| 2-223 | N-(4-fluoro-2-yl)phenyl N'-methoxyurea | 4-aminopiperidin-1-yl | 3-F | 5-CH₃ |
| 2-224 | 3-(2-methoxyethoxy)-2-cyanophenyl | 4-amino-3-hydroxypiperidin-1-yl (racemic) | 3-F | 5-CH₃ |
| 2-225 | 3-(2-methoxyethoxy)-2-cyanophenyl | 4-amino-3-hydroxypiperidin-1-yl (racemic) | 3-F | 5-F |
| 2-226 | N-(pyridin-2-yl) N'-methoxyurea | 4-aminopiperidin-1-yl | 3-F | 5-CH₃ |
| 2-227 | 2-fluoro-6-((hydroxyimino)methyl)phenyl | 4-amino-3-hydroxypiperidin-1-yl (racemic) | 3-F | 5-F |

TABLE 2-continued

| Cpd No. | R^B | A | R^a | R^b |
|---|---|---|---|---|
| 2-228 | 2,4-difluoro-6-[(ethoxyamino)carbonylamino]phenyl | 4-aminopiperidin-1-yl | 3-F | 5-CH₃ |
| 2-229 | 1-methyl-3-[(2-methoxyethyl)amino]pyrazol-4-yl | 4-aminopiperidin-1-yl | 3-F | 5-CH₃ |
| 2-230 | 2,4-difluoro-6-[(methoxyacetyl)amino]phenyl | 4-aminopiperidin-1-yl | 3-F | 5-CH₃ |
| 2-231 | 2-cyano-6-(cyanomethoxy)phenyl | 4-aminopiperidin-1-yl | 3-F | 5-F |
| 2-232 | 2-cyano-4-fluoro-6-(2-methoxyethoxy)phenyl | 4-amino-3-hydroxypiperidin-1-yl (racemic) | 3-F | 5-F |

TABLE 2-continued

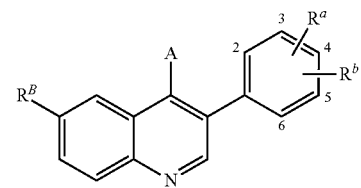

| Cpd No. | R$^B$ | A | R$^a$ | R$^b$ |
|---|---|---|---|---|
| 2-233 | 2,4-difluoro-phenyl with NH-C(O)-NH-O-CH$_2$CF$_3$ | 4-amino-piperidin-1-yl | 3-F | 5-CH$_3$ |
| 2-234 | 5-fluoro-pyridin-2-yl with NH-CH$_2$CH$_2$-OCH$_3$ | 4-amino-piperidin-1-yl | 3-F | 5-CH$_3$ |
| 2-235 | 2,4-difluoro-phenyl with NH-C(O)-OCH$_3$ | 4-amino-3-methoxy-piperidin-1-yl, racemic | 3-F | 5-CH$_3$ |
| 2-236 | 2,4-difluoro-phenyl with NH-C(O)-NH-OCH$_3$ | 4-amino-3-methoxy-piperidin-1-yl, racemic | 3-F | 5-CH$_3$ |
| 2-237 | 2-fluoro-4-cyano-phenyl with NH-C(O)-NH-OCH$_3$ | 4-amino-piperidin-1-yl | 3-F | 5-CH$_3$ |

TABLE 2-continued

| Cpd No. | R^B | A | R^a | R^b |
|---|---|---|---|---|
| 2-238 | 4-cyano-2-{[(2,2,2-trifluoroethoxy)carbamoyl]amino}phenyl | 4-aminopiperidin-1-yl | 3-F | 5-F |
| 2-239 | 6-methyl-2-{[(methoxy)carbamoyl]amino}pyridin-3-yl | 4-aminopiperidin-1-yl | 3-F | 5-CH$_3$ |
| 2-240 | 4-{[(methoxy)carbamoyl]amino}phenyl | 4-aminopiperidin-1-yl | 3-F | 5-CH$_3$ |
| 2-241 | 6-bromo-3,4-difluoro-2-hydroxyphenyl | 4-aminopiperidin-1-yl | 3-F | 5-F |
| 2-242 | 5-cyano-2-{[(2-methoxyethyl)amino]}pyridin-3-yl | 4-aminopiperidin-1-yl | 3-F | 5-CH$_3$ |

TABLE 2-continued

| Cpd No. | R^B | A | R^a | R^b |
|---|---|---|---|---|
| 2-243 | (methoxyimino-methyl)(hydroxy)phenyl | octahydropyrano[3,2-c]pyridine, racemic | 3-F | 5-F |
| 2-244 | (cyano)(amino)pyridinyl | octahydropyrano[3,2-c]pyridine, racemic | 3-F | 5-F |
| 2-245 | (amino)(N-methyl)pyrazolyl | octahydropyrano[3,2-c]pyridine, racemic | 3-F | 5-F |
| 2-246 | (amino)pyridinyl | octahydropyrano[3,2-c]pyridine, racemic | 3-F | 5-F |
| 2-247 | (amino)(methyl)pyridinyl | octahydropyrano[3,2-c]pyridine, racemic | 3-F | 5-F |

TABLE 2-continued
| Cpd No. | R^B | A | R^a | R^b |
|---|---|---|---|---|
| 2-248 | 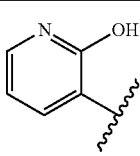 | 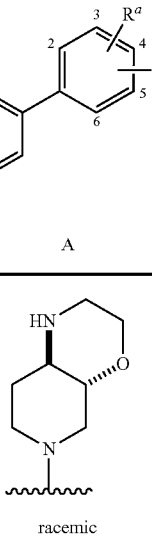 racemic | 3-F | 5-F |
| 2-249 | 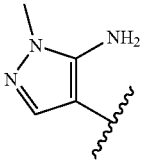 [SMILES: *c1cnn(C)c1N] | 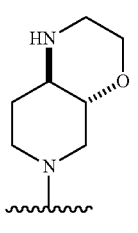 racemic | 3-F | 5-F |
| 2-250 | 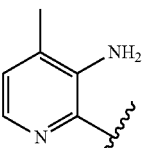 | 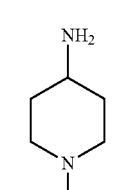 | 3-F | 5-F |
| 2-251 | 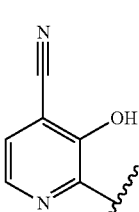 | 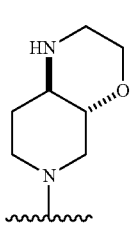 racemic | 3-F | 5-F |
| 2-252 | 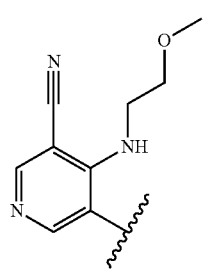 [SMILES: *c1cncc(C#N)c1NCCOC] | 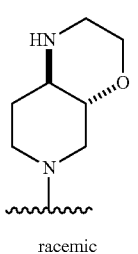 racemic | 3-F | 5-F |

TABLE 2-continued
| Cpd No. | R^B | A | R^a | R^b |
|---|---|---|---|---|
| 2-253 | 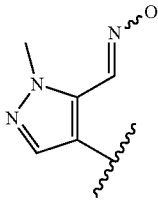 | 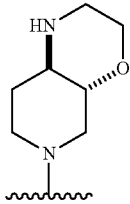 racemic | 3-F | 5-F |
| 2-254 | 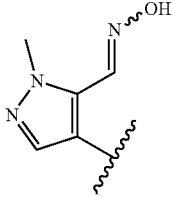 [SMILES: *c1cnn(C)c1C=NO] | 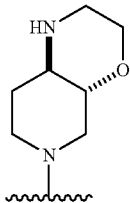 racemic | 3-F | 5-F |
| 2-255 | 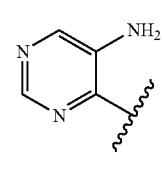 | 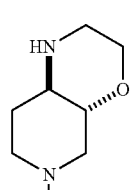 racemic | 3-F | 5-F |
| 2-256 | 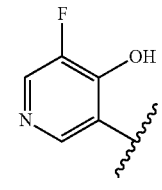 [SMILES: *c1cncc(F)c1O] | 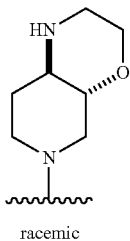 racemic | 3-F | 5-F |
| 2-257 | 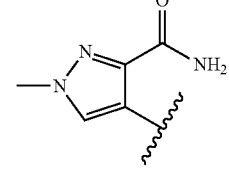 | 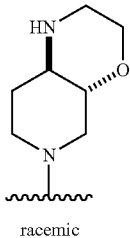 racemic | 3-F | 5-F |

TABLE 2-continued

| Cpd No. | R^B | A | R^a | R^b |
| --- | --- | --- | --- | --- |
| 2-258 | 4-methyl-3-hydroxypyridin-2-yl | octahydro-pyrido[3,4-b][1,4]oxazine (racemic) | 3-F | 5-F |
| 2-259 | 5-fluoro-3-methyl-2-hydroxypyridinyl | octahydro-pyrido[3,4-b][1,4]oxazine (racemic) | 3-F | 5-F |
| 2-260 | 1-methyl-3-((hydroxyimino)methyl)-1H-pyrazol-4-yl | octahydro-pyrido[3,4-b][1,4]oxazine (racemic) | 3-F | 5-F |
| 2-261 | 4-cyano-3-fluoropyridin-2-yl | octahydro-pyrido[3,4-b][1,4]oxazine (racemic) | 3-F | 5-F |
| 2-262 | 4-cyano-3-aminopyridin-2-yl | octahydro-pyrido[3,4-b][1,4]oxazine (racemic) | 3-F | 5-F |

TABLE 2-continued

| Cpd No. | R^B | A | R^a | R^b |
|---|---|---|---|---|
| 2-263 | 3-hydroxypyridin-2-yl | octahydro-2H-pyrido[4,3-b][1,4]oxazine (racemic) | 3-F | 5-F |
| 2-264 | 3-((hydroxyimino)methyl)pyridin-2-yl | octahydro-2H-pyrido[4,3-b][1,4]oxazine (racemic) | 3-F | 5-F |
| 2-265 | 3-amino-5-fluoropyridin-2-yl | octahydro-2H-pyrido[4,3-b][1,4]oxazine (racemic) | 3-F | 5-F |
| 2-266 | 4-amino-5-((methoxyimino)methyl)pyridin-3-yl | octahydro-2H-pyrido[4,3-b][1,4]oxazine (racemic) | 3-F | 5-F |
| 2-267 | 4-amino-5-cyclopropylpyridin-3-yl | octahydro-2H-pyrido[4,3-b][1,4]oxazine (racemic) | 3-F | 5-F |

TABLE 2-continued

| Cpd No. | R^B | A | R^a | R^b |
|---|---|---|---|---|
| 2-268 | 5-amino-1-(oxetan-3-yl)-1H-pyrazol-4-yl | octahydro-2H-pyrido[3,4-b][1,4]oxazine (racemic) | 3-F | 5-F |
| 2-269 | 3-amino-4-((methoxyimino)methyl)pyridin-2-yl | octahydro-2H-pyrido[3,4-b][1,4]oxazine (racemic) | 3-F | 5-F |
| 2-270 | 3-cyano-2-hydroxyphenyl | 3-(morpholin-3-yl)azetidin-1-yl (racemic) | 3-F | 5-Me |
| 2-271 | 3-cyano-2-hydroxyphenyl | 3-(morpholin-3-yl)azetidin-1-yl (racemic) | 3-F | 5-F |
| 2-272 | 4-amino-5-ethynylpyridin-3-yl | octahydro-2H-pyrido[3,4-b][1,4]oxazine (racemic) | 3-F | 5-F |

TABLE 2-continued

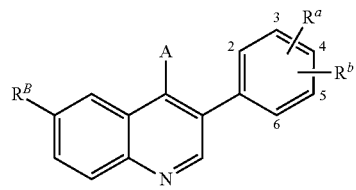

| Cpd No. | $R^B$ | A | $R^a$ | $R^b$ |
|---|---|---|---|---|
| 2-273 | methoxy-NH-C(O)-NH-pyridin-3-yl | hexahydropyrido[3,4-b][1,4]oxazine (racemic) | 3-F | 5-F |
| 2-274 | 5-ethynyl-4-amino-pyridin-3-yl | hexahydropyrido[3,4-b][1,4]oxazine (racemic) | 3-F | 5-F |
| 2-275 | 4-chloro-3-amino-pyridin-2-yl | hexahydropyrido[3,4-b][1,4]oxazine (racemic) | 3-F | 5-F |
| 2-276 | 4-cyclopropyl-3-amino-pyridin-2-yl | hexahydropyrido[3,4-b][1,4]oxazine (racemic) | 3-F | 5-F |
| 2-277 | 4-ethynyl-3-amino-pyridin-2-yl | hexahydropyrido[3,4-b][1,4]oxazine (racemic) | 3-F | 5-F |

TABLE 2-continued
| Cpd No. | $R^B$ | A | $R^a$ | $R^b$ |
|---|---|---|---|---|
| 2-278 | 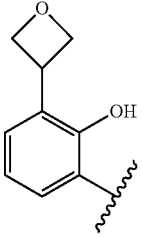 [SMILES: *c1cccc(C2COC2)c1O] | 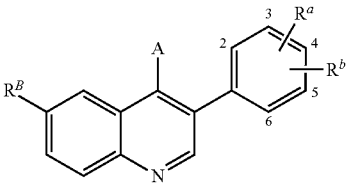 racemic | 3-F | 5-F |
| 2-279 |  |  racemic | 3-F | 5-F |
| 2-280 | 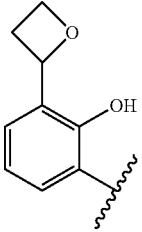 [SMILES: *c1cccc(C2CCO2)c1O] | 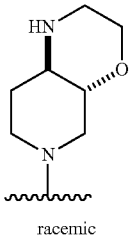 racemic | 3-F | 5-F |
| 2-281 |  |  racemic | 3-F | 5-F |
| 2-282 | 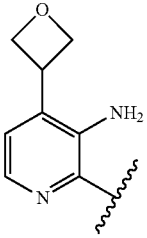 [SMILES: *c1nccc(C2COC2)c1N] | 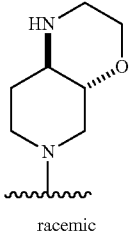 racemic | 3-F | 5-Me |

TABLE 2-continued

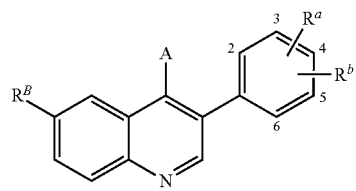

| Cpd No. | R^B | A | R^a | R^b |
|---|---|---|---|---|
| 2-283 | 3-aminopyridin-2-yl | octahydro-2H-pyrano[3,2-c]pyridine (racemic) | 3-F | 5-F |
| 2-284 | 3-amino-4-methoxypyridin-2-yl | octahydro-2H-pyrano[3,2-c]pyridine (racemic) | 3-F | 5-F |
| 2-285 | 2-hydroxy-3-((methoxyimino)methyl)phenyl | octahydro-2H-pyrano[3,2-c]pyridine (Single enantiomer) | 3-F | 5-F |
| 2-286 | octahydro-2H-pyrano[3,2-c]pyridine (racemic) | octahydro-2H-pyrano[3,2-c]pyridine (Single enantiomer) | 3-F | 5-F |
| 2-287 | 3-amino-4-((methoxyimino)methyl)pyridin-2-yl | octahydro-2H-pyrano[3,2-c]pyridine | 3-F | 5-F |

TABLE 2-continued

| Cpd No. | R^B | A | R^a | R^b |
|---|---|---|---|---|
| 2-288 | pyridine with 3-NH2, 2-attachment, 4-CH=N-OMe | hexahydropyrido[3,4-b][1,4]oxazine (Single enantiomer) | 3-F | 5-F |
| 2-289 | 4-cyano-3-amino-pyridin-2-yl | hexahydropyrido[3,4-b][1,4]oxazine (Single enantiomer) | 3-F | 5-F |
| 2-290 | 4-cyano-3-amino-pyridin-2-yl | hexahydropyrido[3,4-b][1,4]oxazine (Single enantiomer) | 3-F | 5-F |
| 2-291 | 5-cyano-4-amino-pyridin-3-yl | hexahydropyrido[3,4-b][1,4]oxazine (Single enantiomer) | 3-F | 5-F |
| 2-292 | 5-cyano-4-amino-pyridin-3-yl | hexahydropyrido[3,4-b][1,4]oxazine (Single enantiomer) | 3-F | 5-F |

TABLE 2-continued

| Cpd No. | $R^B$ | A | $R^a$ | $R^b$ |
|---|---|---|---|---|
| 2-293 | 2-amino-pyridin-3-yl | hexahydro-pyrido[3,4-b][1,4]oxazine (single enantiomer) | 3-F | 5-F |
| 2-294 | 2-amino-pyridin-3-yl | hexahydro-pyrido[3,4-b][1,4]oxazine (single enantiomer) | 3-F | 5-F |
| 2-295 | 3-amino-4-methyl-pyridin-2-yl | hexahydro-pyrido[3,4-b][1,4]oxazine (single enantiomer) | 3-F | 5-F |
| 2-296 | 3-amino-4-methyl-pyridin-2-yl | hexahydro-pyrido[3,4-b][1,4]oxazine (single enantiomer) | 3-F | 5-F |
| 2-297 | 3-hydroxy-4-methyl-pyridin-2-yl | hexahydro-pyrido[3,4-b][1,4]oxazine (single enantiomer) | 3-F | 5-F |

TABLE 2-continued

| Cpd No. | R^B | A | R^a | R^b |
|---|---|---|---|---|
| 2-298 | 4-methyl-3-hydroxypyridin-2-yl | octahydropyrido[3,4-b]morpholin-6-yl (single enantiomer) | 3-F | 5-F |
| 2-299 | 3-cyano-4-fluoro-2-hydroxyphenyl | octahydropyrido[3,4-b]morpholin-6-yl (single enantiomer) | 3-F | 5-F |
| 2-300 | 3-cyano-5-fluoro-2-hydroxyphenyl | octahydropyrido[3,4-b]morpholin-6-yl (single enantiomer) | 3-F | 5-F |

Compounds in Table 2 are Named:

2-1: 3-[4-(4-aminopiperidin-1-yl)-3-(3-fluoro-5-methylphenyl)quinolin-6-yl]-2-hydroxybenzonitrile;
2-2: 3-[4-(4-aminopiperidin-1-yl)-3-(3,5-difluorophenyl)quinolin-6-yl]-2-hydroxybenzonitrile;
2-3: 3-{4-[trans-4-amino-3-methoxypiperidin-1-yl]-3-(3,5-difluorophenyl)quinolin-6-yl}-2-hydroxybenzonitrile;
2-4: 3-{4-[trans-4-amino-3-methoxypiperidin-1-yl]-3-(3,5-difluorophenyl)quinolin-6-yl}benzonitrile;
2-5: 3-[4-(4-aminopiperidin-1-yl)-3-(3,5-difluorophenyl)quinolin-6-yl]benzonitrile;
2-6: 2-[4-(4-aminopiperidin-1-yl)-3-(3,5-difluorophenyl)quinolin-6-yl]phenol;
2-7: 6-[4-(4-aminopiperidin-1-yl)-3-(3-fluoro-5-methylphenyl)quinolin-6-yl]pyridine-2-carboxamide;
2-8: 4-[4-(4-aminopiperidin-1-yl)-3-(3-fluoro-5-methylphenyl)quinolin-6-yl]-2,3-dihydro-1H-1,3-benzodiazol-2-one;
2-9: 5-[4-(4-aminopiperidin-1-yl)-3-(3-fluoro-5-methylphenyl)quinolin-6-yl]-2,3-dihydro-1H-1,3-benzodiazol-2-one;
2-10: 3-[4-(4-aminopiperidin-1-yl)-3-(3,5-difluorophenyl)quinolin-6-yl]-5-fluoro-2-hydroxybenzonitrile;
2-11: 1-[3-(3,5-dichlorophenyl)quinolin-4-yl]piperidin-4-amine;
2-12: 3-{4-[3-(aminomethyl)azetidin-1-yl]-3-(3-fluoro-5-methylphenyl)quinolin-6-yl}-2-hydroxybenzonitrile;
2-13: 3-{4-[3-(aminomethyl)azetidin-1-yl]-3-(3-chloro-5-methylphenyl)quinolin-6-yl}-2-hydroxybenzonitrile;
2-14: 3-{4-[3-(aminomethyl)-3-methylazetidin-1-yl]-3-(3-fluoro-5-methylphenyl)quinolin-6-yl}-5-fluorobenzamide;
2-15: 3-{4-[3-(aminomethyl)-3-methylazetidin-1-yl]-3-(3-chloro-5-methylphenyl)quinolin-6-yl}-5-fluoro-2-hydroxybenzonitrile;
2-16: 3-[4-(4-aminopiperidin-1-yl)-3-(3-fluoro-5-methylphenyl)quinolin-6-yl]-5-fluoro-2-hydroxybenzonitrile;
2-17: 3-{4-[3-(aminomethyl)azetidin-1-yl]-3-(3-fluoro-5-methylphenyl)quinolin-6-yl}-5-fluoro-2-hydroxybenzonitrile;
2-18: 3-(4-{3-[(ethylamino)methyl]azetidin-1-yl}-3-(3-fluoro-5-methylphenyl)quinolin-6-yl)-5-fluoro-2-hydroxybenzonitrile.
2-19: 3-{4-[trans-octahydro-1H-pyrido[3,4-b]morpholin-6-yl]-3-(3,5-difluorophenyl)quinolin-6-yl}-2-hydroxybenzonitrile;

2-20: 3-{4-[trans-octahydro-1H-pyrido[3,4-b]morpholin-6-yl]-3-(3-fluoro-5-methylphenyl)quinolin-6-yl}-2-hydroxybenzonitrile;

2-21: 3-{4-[3-(aminomethyl)azetidin-1-yl]-3-(3-chloro-5-fluorophenyl)quinolin-6-yl}-5-fluoro-2-hydroxybenzonitrile;

2-22: 3-{4-[3-(aminomethyl)azetidin-1-yl]-3-(3-chloro-5-methylphenyl)quinolin-6-yl}-5-fluoro-2-hydroxybenzonitrile;

2-23: 3-{4-[3-(aminomethyl)azetidin-1-yl]-3-(3,5-difluorophenyl)quinolin-6-yl}-5-fluoro-2-hydroxybenzonitrile;

2-24: 5-fluoro-3-[3-(3-fluoro-5-methylphenyl)-4-(3-{[(2-fluoroethyl)amino]methyl}azetidin-1-yl)quinolin-6-yl]-2-hydroxybenzonitrile;

2-25: 5-fluoro-3-[3-(3-fluoro-5-methylphenyl)-4-(3-{[(propan-2-yl)amino]methyl}azetidin-1-yl)quinolin-6-yl]-2-hydroxybenzonitrile;

2-26: 3-(4-{3-[(ethylamino)methyl]azetidin-1-yl}-3-(3-fluoro-5-methylphenyl)quinolin-6-yl)-5-fluorobenzamide;

2-27: 3-[3-(3-fluoro-5-methylphenyl)-4-(3-{[(2-methoxyethyl)amino]methyl}azetidin-1-yl)quinolin-6-yl]-5-fluoro-2-hydroxybenzonitrile;

2-28: 5-fluoro-3-[3-(3-fluoro-5-methylphenyl)-4-(3-{[(3-fluoropropyl)amino]methyl}azetidin-1-yl)quinolin-6-yl]-2-hydroxybenzonitrile;

2-29: 3-(4-{3-[(cyclopropylamino)methyl]azetidin-1-yl}-3-(3-fluoro-5-methylphenyl)quinolin-6-yl)-5-fluoro-2-hydroxybenzonitrile;

2-30: 5-fluoro-3-[3-(3-fluoro-5-methylphenyl)-4-[3-(pyrrolidin-1-ylmethyl)azetidin-1-yl]quinolin-6-yl]-2-hydroxybenzonitrile;

2-31: 5-fluoro-3-[3-(3-fluoro-5-methylphenyl)-4-{3-[(propylamino)methyl]azetidin-1-yl}quinolin-6-yl]-2-hydroxybenzonitrile;

2-32: 3-{4-[3-(aminomethyl)azetidin-1-yl]-3-(3-chloro-5-methylphenyl)quinolin-6-yl}-5-fluoro-2-hydroxybenzonitrile;

2-33: 5-fluoro-3-[3-(3-fluoro-5-methylphenyl)-4-(3-{[(oxetan-3-yl)amino]methyl}azetidin-1-yl)quinolin-6-yl]-2-hydroxybenzonitrile;

2-34: 3-(4-{3-[(cyclopentylamino)methyl]azetidin-1-yl}-3-(3-fluoro-5-methylphenyl)quinolin-6-yl)-5-fluoro-2-hydroxybenzonitrile;

2-35: 5-fluoro-3-[3-(3-fluoro-5-methylphenyl)-4-[3-(morpholin-4-ylmethyl)azetidin-1-yl]quinolin-6-yl]-2-hydroxybenzonitrile;

2-36: 3-[3-(3-fluoro-5-methylphenyl)-4-[3-(piperazin-1-ylmethyl)azetidin-1-yl]quinolin-6-yl]-5-fluoro-2-hydroxybenzonitrile;

2-37: 5-fluoro-3-[3-(3-fluoro-5-methylphenyl)-4-(3-{[(oxan-4-yl)amino]methyl}azetidin-1-yl)quinolin-6-yl]-2-hydroxybenzonitrile;

2-38: 2(4-{3-[(ethylamino)methyl]azetidin-2-yl}-3-(3-fluoro-5-methylphenyl)quinolin-6-yl)-6-fluoro-3-methylphenol;

2-39: 5-fluoro-3-[3-(3-fluoro-5-methylphenyl)-4-(3-{[(1-methoxy-2-methylpropan-2-yl)amino]methyl}azetidin-1-yl)quinolin-6-yl]-2-hydroxybenzonitrile;

2-40: 5-fluoro-3-[3-(3-fluoro-5-methylphenyl)-4-(3-{[(2-hydroxy-2-methylpropyl)amino]methyl}azetidin-1-yl)quinolin-6-yl]-2-hydroxybenzonitrile;

2-41: 5-fluoro-3-[3-(3-fluoro-5-methylphenyl)-4-(3-{[(1-hydroxybutan-2-yl)amino]methyl}azetidin-1-yl)quinolin-6-yl]-2-hydroxybenzonitrile;

2-42: 3-[3-(3-fluoro-5-methylphenyl)-4-{3-[(propylamino)methyl]azetidin-1-yl}quinolin-6-yl]-2-hydroxybenzonitrile;

2-43: 5-fluoro-3-[3-(3-fluoro-5-methylphenyl)-4-(3-{[(2-hydroxyethyl)amino]methyl}azetidin-1-yl)quinolin-6-yl]-2-hydroxybenzonitrile;

2-44: 3-[4-(3-{[ethyl(2-hydroxyethyl)amino]methyl}azetidin-1-yl)-3-(3-fluoro-5-methylphenyl)quinolin-6-yl]-5-fluoro-2-hydroxybenzonitrile;

2-45: 5-fluoro-3-[3-(3-fluoro-5-methylphenyl)-4-(3-{[(oxolan-3-yl)amino]methyl}azetidin-1-yl)quinolin-6-yl]-2-hydroxybenzonitrile;

2-46: 3,6-difluoro-2-[3-(3-fluoro-5-methylphenyl)-4-{3-[(propylamino)methyl]azetidin-1-yl}quinolin-6-yl]phenol;

2-47: 3-(4-{3-[(3,3-difluoropyrrolidin-1-yl)methyl]azetidin-1-yl}-3-(3-fluoro-5-methylphenyl)quinolin-6-yl)-5-fluoro-2-hydroxybenzonitrile;

2-48: 5-fluoro-3-[3-(3-fluoro-5-methylphenyl)-4-(3-{[(3R)-3-fluoropyrrolidin-1-yl]methyl}azetidin-1-yl)quinolin-6-yl]-2-hydroxybenzonitrile;

2-49: 5-fluoro-3-[3-(3-fluoro-5-methylphenyl)-4-(3-{[(3S)-3-fluoropyrrolidin-1-yl]methyl}azetidin-1-yl)quinolin-6-yl]-2-hydroxybenzonitrile;

2-50: 5-fluoro-3-[3-(3-fluoro-5-methylphenyl)-4-[3-(piperidin-1-ylmethyl)azetidin-1-yl]quinolin-6-yl]-2-hydroxybenzonitrile;

2-51: 5-fluoro-3-[3-(3-fluoro-5-methylphenyl)-4-(3-{[(2-hydroxypropyl)amino]methyl}azetidin-1-yl)quinolin-6-yl]-2-hydroxybenzonitrile;

2-52: 2,6-difluoro-4-[3-(3-fluoro-5-methylphenyl)-4-{3-[(propylamino)methyl]azetidin-1-yl}quinolin-6-yl]phenol;

2-53: 5-fluoro-3-[3-(3-fluoro-5-methylphenyl)-4-(3-{[(3-hydroxypropyl)amino]methyl}azetidin-1-yl)quinolin-6-yl]-2-(methoxymethoxy)benzonitrile;

2-54: 5-fluoro-3-[3-(3-fluoro-5-methylphenyl)-4-(3-{[(3-hydroxypropyl)amino]methyl}azetidin-1-yl)quinolin-6-yl]-2-hydroxybenzonitrile;

2-55: 4-fluoro-6-[3-(3-fluoro-5-methylphenyl)-4-{3-[(propylamino)methyl]azetidin-1-yl}quinolin-6-yl]-2,3-dihydro-1H-1,3-benzodiazol-2-one;

2-56: 2-{2-[4-(4-aminopiperidin-1-yl)-3-(3,5-difluorophenyl)quinolin-6-yl]-6-cyanophenoxy}acetic acid;

2-57: 4-{2-[4-(4-aminopiperidin-1-yl)-3-(3,5-difluorophenyl)quinolin-6-yl]-6-cyanophenoxy}butanoic acid;

2-58: 3-{4-[cis-4-amino-3-hydroxypiperidin-1-yl]-3-(3,5-difluorophenyl)quinolin-6-yl}-2-(methoxymethoxy)benzonitrile;

2-59: 3-{4-[(3R,4R)-4-amino-3-fluoropiperidin-1-yl]-3-(3,5-difluorophenyl)quinolin-6-yl}-2-hydroxybenzonitrile;

2-60: 3-{4-[cis-4-amino-3-hydroxypiperidin-1-yl]-3-(3,5-difluorophenyl)quinolin-6-yl}-2-hydroxybenzonitrile;

2-61: 3-{4-[(3S,4R)-4-amino-3-methoxypiperidin-1-yl]-3-(3,5-difluorophenyl)quinolin-6-yl}-2-hydroxybenzonitrile;

2-62: 3-{4-[(3R,4S)-4-amino-3-methoxypiperidin-1-yl]-3-(3,5-difluorophenyl)quinolin-6-yl}-2-(methoxymethoxy)benzonitrile;

2-63: 3-{4-[cis-4-amino-3-hydroxypiperidin-1-yl]-3-(3,5-difluorophenyl)quinolin-6-yl}-5-fluoro-2-hydroxybenzonitrile;

2-64: 2-{2-[4-(4-aminopiperidin-1-yl)-3-(3,5-difluorophenyl)quinolin-6-yl]-6-cyanophenoxy}ethyl acetate;

2-65: 3-[4-(4-aminopiperidin-1-yl)-3-(3,5-difluorophenyl)quinolin-6-yl]-2-(2-hydroxyethoxy)benzonitrile;

2-66: 3-{4-[(3R,4S)-4-amino-3-methoxypiperidin-1-yl]-3-(3,5-difluorophenyl)quinolin-6-yl}-2-hydroxybenzonitrile;

2-67: 3-[4-(4-aminopiperidin-1-yl)-3-(3,5-difluorophenyl)quinolin-6-yl]-2-[(1,3-dihydroxypropan-2-yl)oxy]benzamide;

2-68: 3-[4-(4-aminopiperidin-1-yl)-3-[3-fluoro-5-(2-methoxyethoxy)phenyl]quinolin-6-yl]-2-hydroxybenzonitrile;

2-69: 3-[4-(4-aminopiperidin-1-yl)-3-[3-fluoro-5-(oxetan-3-yloxy)phenyl]quinolin-6-yl]-2-hydroxybenzonitrile;

2-70: 3-[4-(4-aminopiperidin-1-yl)-3-{3-fluoro-5-[(1E)-(methoxyimino)methyl]phenyl}quinolin-6-yl]-2-hydroxybenzonitrile;

2-71: 3-[4-(4-aminopiperidin-1-yl)-3-{3-[(3,3-difluoroazetidin-1-yl)methyl]-5-fluorophenyl}quinolin-6-yl]-2-hydroxybenzonitrile;

2-72: 3-[4-(4-aminopiperidin-1-yl)-3-(3,5-difluorophenyl)quinolin-6-yl]-2-(2-methoxyethoxy)benzonitrile;

2-73: 3-[4-(4-aminopiperidin-1-yl)-3-(3,5-difluorophenyl)quinolin-6-yl]-2-(oxetan-3-yloxy)benzonitrile;

2-74: 1-[3-(3,5-difluorophenyl)-6-[5-fluoro-4-(oxetan-3-yloxy)pyridin-3-yl]quinolin-4-yl]piperidin-4-amine;

2-75: 5-[4-(4-aminopiperidin-1-yl)-3-(3,5-difluorophenyl)quinolin-6-yl]-6-(azetidin-1-yl)pyridine-3-carbonitrile;

2-76: 5-[4-(4-aminopiperidin-1-yl)-3-(3,5-difluorophenyl)quinolin-6-yl]-6-(azetidin-1-yl)pyridine-3-carboxamide;

2-77: 2-amino-3-[4-(4-aminopiperidin-1-yl)-3-(3,5-difluorophenyl)quinolin-6-yl]benzonitrile;

2-78: 3-[4-(4-aminopiperidin-1-yl)-3-(3,5-difluorophenyl)quinolin-6-yl]-2-(methoxymethoxy)benzonitrile;

2-79: 3-[4-(4-aminopiperidin-1-yl)-3-{3-[(ethoxyimino)methyl]-5-fluorophenyl}quinolin-6-yl]-2-hydroxybenzonitrile;

2-80: 6-{4-[trans-octahydro-1H-pyrido[3,4-b]morpholin-6-yl]-3-(3,5-difluorophenyl)quinolin-6-yl}-4-fluoro-2,3-dihydro-1H-1,3-benzodiazol-2-one;

2-81: 2-[4-(4-aminopiperidin-1-yl)-3-(3,5-difluorophenyl)quinolin-6-yl]-6-[-(methoxyimino)methyl]phenol;

2-82: 3-(4-{3-[(1S)-1-aminopropyl]azetidin-1-yl}-3-(3-fluoro-5-methylphenyl)quinolin-6-yl)-5-fluoro-2-hydroxybenzonitrile;

2-83: methyl N-{2-[4-(4-aminopiperidin-1-yl)-3-(3,5-difluorophenyl)quinolin-6-yl]-4,6-difluorophenyl}carbamate;

2-84: 3-{4-[trans-4-amino-3-methoxypiperidin-1-yl]-3-(3,5-difluorophenyl)quinolin-6-yl}-2-(methoxymethoxy)benzonitrile;

2-85: 6-{4-[trans-octahydro-1H-pyrido[3,4-b]morpholin-6-yl]-3-(3,5-difluorophenyl)quinolin-6-yl}pyridine-2-carboxamide;

2-86: N-{2-[4-(4-aminopiperidin-1-yl)-3-(3,5-difluorophenyl)quinolin-6-yl]-4,6-difluorophenyl}methanesulfonamide;

2-87: 3-[4-(4-aminopiperidin-1-yl)-3-(3,5-difluorophenyl)quinolin-6-yl]-2-[(2-methoxyethoxy)methoxy]benzonitrile;

2-88: 2-[4-(4-aminopiperidin-1-yl)-3-(3-fluoro-5-methylphenyl)quinolin-6-yl]-6-(azetidine-1-carbonyl)phenol;

2-89: 3-{4-[trans-decahydropyrido[3,4-b][1,4]oxazepin-7-yl]-3-(3,5-difluorophenyl)quinolin-6-yl}-2-hydroxybenzonitrile;

2-90: 3-{4-[trans-decahydropyrido[3,4-b][1,4]oxazepin-7-yl]-3-(3-fluoro-5-methylphenyl)quinolin-6-yl}-2-hydroxybenzonitrile;

2-91: 3-{4-[trans-decahydropyrido[3,4-b][1,4]oxazepin-7-yl]-3-(3-fluoro-5-methoxyphenyl)quinolin-6-yl}-2-hydroxybenzonitrile;

2-92: trans-4-amino-1-[6-(3-cyano-2-hydroxyphenyl)-3-(3,5-difluorophenyl)quinolin-4-yl]piperidine-3-carbonitrile;

2-93: propan-2-yl trans-4-amino-1-[3-(3,5-difluorophenyl)-6-(3-ethynyl-2-hydroxyphenyl)quinolin-4-yl]piperidine-3-carboxylate;

2-94: cis-4-amino-1-[6-(3-cyano-2-hydroxyphenyl)-3-(3,5-difluorophenyl)quinolin-4-yl]piperidine-3-carbonitrile;

2-95: 3-{4-[trans-4-amino-3-(2-hydroxyethoxy)piperidin-1-yl]-3-(3,5-difluorophenyl)quinolin-6-yl}-2-hydroxybenzonitrile;

2-96: 3-{4-[cis-4-amino-3-(2-hydroxyethoxy)piperidin-1-yl]-3-(3,5-difluorophenyl)quinolin-6-yl}-2-hydroxybenzonitrile;

2-97: 3-{4-[trans-4-amino-3-(2-methoxyethoxy)piperidin-1-yl]-3-(3,5-difluorophenyl)quinolin-6-yl}-2-hydroxybenzonitrile;

2-98: 3-{4-[cis-4-amino-3-(2-methoxyethoxy)piperidin-1-yl]-3-(3,5-difluorophenyl)quinolin-6-yl}-2-hydroxybenzonitrile;

2-99: 3-[4-(4-aminopiperidin-1-yl)-3-(3,5-difluorophenyl)quinolin-6-yl]-4,5-difluoro-2-hydroxybenzonitrile;

2-100: 3-{4-[trans-octahydro-1H-pyrido[3,4-b]morpholin-6-yl]-3-(3,5-difluorophenyl)quinolin-6-yl}-4,5-difluoro-2-hydroxybenzonitrile;

2-101: 3-{4-[trans-decahydropyrido[3,4-b][1,4]oxazepin-7-yl]-3-(3,5-difluorophenyl)quinolin-6-yl}-4,5-difluoro-2-hydroxybenzonitrile;

2-102: 3-{4-[trans-4-amino-3-methoxypiperidin-1-yl]-3-(3,5-difluorophenyl)quinolin-6-yl}-4,5-difluoro-2-hydroxybenzonitrile;

2-103: 3-[4-(4-aminopiperidin-1-yl)-3-(3-fluoro-5-methylphenyl)quinolin-6-yl]-4,5-difluoro-2-hydroxybenzonitrile;

2-104: 3-{4-[trans-octahydro-1H-pyrido[3,4-b]morpholin-6-yl]-3-(3-fluoro-5-methylphenyl)quinolin-6-yl}-4,5-difluoro-2-hydroxybenzonitrile;

2-105: 3-{4-[trans-decahydropyrido[3,4-b][1,4]oxazepin-7-yl]-3-(3-fluoro-5-methylphenyl)quinolin-6-yl}-4,5-difluoro-2-hydroxybenzonitrile;

2-106: 3-{4-[trans-4-amino-3-methoxypiperidin-1-yl]-3-(3-fluoro-5-methylphenyl)quinolin-6-yl}-4,5-difluoro-2-hydroxybenzonitrile;

2-107: 3-{4-[cis-4-amino-3-hydroxypiperidin-1-yl]-3-(3-fluoro-5-methoxyphenyl)quinolin-6-yl}-4,5-difluoro-2-hydroxybenzonitrile;

2-108: 2-[4-(4-aminopiperidin-1-yl)-3-(3,5-difluorophenyl)quinolin-6-yl]-4,6-difluoro-3-methylphenol;

2-109: 2-{4-[trans-octahydro-1H-pyrido[3,4-b]morpholin-6-yl]-3-(3,5-difluorophenyl)quinolin-6-yl}-4,6-difluoro-3-methylphenol;

2-110: 2-{4-[trans-decahydropyrido[3,4-b][1,4]oxazepin-7-yl]-3-(3,5-difluorophenyl)quinolin-6-yl}-4,6-difluoro-3-methylphenol;

2-111: 2-{4-[trans-4-amino-3-methoxypiperidin-1-yl]-3-(3,5-difluorophenyl)quinolin-6-yl}-4,6-difluoro-3-methylphenol;

2-112: 2-{4-[trans-4-amino-3-methoxypiperidin-1-yl]-3-(3-fluoro-5-methylphenyl)quinolin-6-yl}-4,6-difluoro-3-methylphenol;

2-113: cis-4-amino-1-[6-(3,5-difluoro-2-hydroxy-6-methylphenyl)-3-(3-fluoro-5-methoxyphenyl)quinolin-4-yl]piperidin-3-ol;

2-114: 2-[4-(4-aminopiperidin-1-yl)-3-(3,5-difluorophenyl)quinolin-6-yl]-4-fluoro-6-[(methoxyimino)methyl]phenol;

2-115: 2-[4-(4-aminopiperidin-1-yl)-3-(3-fluoro-5-methylphenyl)quinolin-6-yl]-6-[(methoxyimino)methyl]phenol;

2-116: 2-[4-(4-aminopiperidin-1-yl)-3-(3-fluoro-5-methylphenyl)quinolin-6-yl]-4-fluoro-6-[(methoxyimino)methyl]phenol;

2-117: 2-[4-(4-aminopiperidin-1-yl)-3-(3-fluoro-5-methylphenyl)quinolin-6-yl]-3,4-difluoro-6-[(methoxyimino)methyl]phenol;

2-118: 2-{4-[trans-octahydro-1H-pyrido[3,4-b]morpholin-6-yl]-3-(3-fluoro-5-methylphenyl)quinolin-6-yl}-4-fluoro-6-[(1E)-(methoxyimino)methyl]phenol;

2-119: trans-4-amino-1-[6-(3-cyano-5,6-difluoro-2-hydroxyphenyl)-3-(3,5-difluorophenyl)quinolin-4-yl]piperidine-3-carbonitrile;

2-120: cis-4-amino-1-[6-(3-cyano-5,6-difluoro-2-hydroxyphenyl)-3-(3,5-difluorophenyl)quinolin-4-yl]piperidine-3-carbonitrile;

2-121: trans-4-amino-1-[6-(3-cyano-5,6-difluoro-2-hydroxyphenyl)-3-(3-fluoro-5-methylphenyl)quinolin-4-yl]piperidine-3-carbonitrile;

2-122: cis-4-amino-1-[6-(3-cyano-5,6-difluoro-2-hydroxyphenyl)-3-(3-fluoro-5-methylphenyl)quinolin-4-yl]piperidine-3-carbonitrile;

2-123: methyl N-{2-[4-(4-aminopiperidin-1-yl)-3-(3,5-difluorophenyl)quinolin-6-yl]-3,4,6-trifluorophenyl}carbamate;

2-124: methyl N-{3-[4-(4-aminopiperidin-1-yl)-3-(3,5-difluorophenyl)quinolin-6-yl]-5-fluoropyridin-4-yl}carbamate;

2-125: methyl N-{3-[4-(4-aminopiperidin-1-yl)-3-(3,5-difluorophenyl)quinolin-6-yl]-5-cyanopyridin-4-yl}carbamate;

2-126: 1-[3-(3,5-difluorophenyl)-6-{3-fluoro-2-[(hydroxyimino)methyl]phenyl}quinolin-4-yl]piperidin-4-amine;

2-127: 1(6-{3-chloro-2-[(hydroxyimino)methyl]phenyl}-3-(3,5-difluorophenyl)quinolin-4-yl)piperidin-4-amine;

2-128: 3-[4-(4-aminopiperidin-1-yl)-3-(3,5-difluorophenyl)quinolin-6-yl]-2-[(hydroxyimino)methyl]benzonitrile;

2-129: 1-[3-(3,5-difluorophenyl)-6-{3-fluoro-2-[(methoxyimino)methyl]phenyl}quinolin-4-yl]piperidin-4-amine;

2-130: 1-(6-{3-chloro-2-[(methoxyimino)methyl]phenyl}-3-(3,5-difluorophenyl)quinolin-4-yl)piperidin-4-amine;

2-131: 3-[4-(4-aminopiperidin-1-yl)-3-(3,5-difluorophenyl)quinolin-6-yl]-2-[(1E)-(methoxyimino)methyl]benzonitrile;

2-132: 1-{6-[3-(1-amino-2,2,2-trifluoroethyl)phenyl]-3-(3,5-difluorophenyl)quinolin-4-yl}piperidin-4-amine;

2-133: 1-{6-[2-(1-amino-2,2,2-trifluoroethyl)-3-fluorophenyl]-3-(3,5-difluorophenyl)quinolin-4-yl}piperidin-4-amine;

2-134: 2-[4-(4-aminopiperidin-1-yl)-3-(3,5-difluorophenyl)quinolin-6-yl]-6-chloro-3,4-difluorophenol;

2-135: 2-{4-[trans-octahydro-1H-pyrido[3,4-b]morpholin-6-yl]-3-(3,5-difluorophenyl)quinolin-6-yl}-6-chloro-3,4-difluorophenol;

2-136: 2-[4-(4-aminopiperidin-1-yl)-3-(3,5-difluorophenyl)quinolin-6-yl]-6-chloro-4-fluorophenol;

2-137: 2-[4-(4-aminopiperidin-1-yl)-3-(3,5-difluorophenyl)quinolin-6-yl]-6-chlorophenol;

2-138: 2-{4-[trans-octahydro-1H-pyrido[3,4-b]morpholin-6-yl]-3-(3,5-difluorophenyl)quinolin-6-yl}-6-chlorophenol 2-139: 1-{2-[4-(4-aminopiperidin-1-yl)-3-(3,5-difluorophenyl)quinolin-6-yl]-4,6-difluorophenyl}-3-methoxyurea;

2-140: 1-(2-{4-[trans-octahydro-1H-pyrido[3,4-b]morpholin-6-yl]-3-(3,5-difluorophenyl)quinolin-6-yl}-4,6-difluorophenyl)-3-methoxyurea;

2-141: 6-[4-(4-aminopiperidin-1-yl)-3-(3,5-difluorophenyl)quinolin-6-yl]-4-chloro-2,3-dihydro-1H-1,3-benzodiazol-2-one;

2-142: 5-[4-(4-aminopiperidin-1-yl)-3-(3,5-difluorophenyl)quinolin-6-yl]-2,3-dihydro-1,3-benzoxazol-2-one;

2-143: methyl trans-4-amino-1-[6-(3-cyano-2-hydroxyphenyl)-3-(3,5-difluorophenyl)quinolin-4-yl]piperidine-3-carboxylate;

2-144: 2-{4-[trans-octahydro-1H-pyrido[3,4-b]morpholin-6-yl]-3-(3,5-difluorophenyl)quinolin-6-yl}-6-fluorophenol;

2-145: trans-4-amino-1-[6-(3-cyano-2-hydroxyphenyl)-3-(3,5-difluorophenyl)quinolin-4-yl]piperidine-3-carboxylic acid;

2-146: trans-4-amino-1-[6-(3-cyano-2-hydroxyphenyl)-3-(3,5-difluorophenyl)quinolin-4-yl]piperidine-3-carboxamide;

2-147: 3-[4-(4-aminopiperidin-1-yl)-3-(3,5-difluorophenyl)quinolin-6-yl]-5-chloro-4-fluoro-2-hydroxybenzonitrile;

2-148: methyl N-{2-[4-(4-aminopiperidin-1-yl)-3-(3,5-difluorophenyl)quinolin-6-yl]-6-cyanophenyl}carbamate;

2-149: trans-4-amino-1-[6-(3-cyano-2-hydroxyphenyl)-3-(3,5-difluorophenyl)quinolin-4-yl]-N-methylpiperidine-3-carboxamide;

2-150: 2-[4-(4-aminopiperidin-1-yl)-3-(3,5-difluorophenyl)quinolin-6-yl]-3,4,6-trifluorophenol;

2-151: trans-4-amino-1-[6-(3-cyano-2-hydroxyphenyl)-3-(3,5-difluorophenyl)quinolin-4-yl]-N,N-dimethylpiperidine-3-carboxamide;

2-152: 1-[3-(3,5-difluorophenyl)-6-{5-fluoro-4-[(hydroxyimino)methyl]pyridin-3-yl}quinolin-4-yl]piperidin-4-amine;

2-153: N-[(2-{4-[trans-octahydro-1H-pyrido[3,4-b]morpholin-6-yl]-3-(3,5-difluorophenyl)quinolin-6-yl}-6-fluorophenyl)methylidene]hydroxylamine;

2-154: N-[(2-{4-[(trans)-octahydro-1H-pyrido[3,4-b]morpholin-6-yl]-3-(3,5-difluorophenyl)quinolin-6-yl}-4,6-difluorophenyl)methylidene]hydroxylamine;

2-155: N-[(2-{4-[trans-octahydro-1H-pyrido[3,4-b]morpholin-6-yl]-3-(3-fluoro-5-methoxyphenyl)quinolin-6-yl}-6-fluorophenyl)methylidene]hydroxylamine;

2-156: 4-[trans-octahydro-1H-pyrido[3,4-b]morpholin-6-yl]-6-[3-fluoro-2-(1H-imidazol-2-yl)phenyl]-3-(3-fluoro-5-methoxyphenyl)quinoline;

2-157: 4-[trans-octahydro-1H-pyrido[3,4-b]morpholin-6-yl]-6-[3-fluoro-2-(1H-imidazol-5-yl)phenyl]-3-(3-fluoro-5-methoxyphenyl)quinoline;

2-158: 3-{4-[trans-octahydro-1H-pyrido[3,4-b]morpholin-6-yl]-3-(3-fluoro-5-methoxyphenyl)quinolin-6-yl}-4,5-difluoro-2-hydroxybenzonitrile;

2-159: 3-{4-[trans-octahydro-1H-pyrido[3,4-b]morpholin-6-yl]-3-(3-fluoro-5-methoxyphenyl)quinolin-6-yl}-4,5-difluoro-2-hydroxybenzonitrile;

2-160: 2-{4-[trans-octahydro-1H-pyrido[3,4-b]morpholin-6-yl]-3-(3-fluoro-5-methoxyphenyl)quinolin-6-yl}-3,4,6-trifluorophenol;

2-161: 1-[3-(3-fluoro-5-methoxyphenyl)-6-(2,3,5-trifluoro-6-hydroxyphenyl)quinolin-4-yl]piperidin-4-ol;

2-162: 1-{3-[4-(4-aminopiperidin-1-yl)-3-(3,5-difluorophenyl)quinolin-6-yl]-5-hydroxypyridin-4-yl}-3-methoxyurea;

2-163: 1-{2-[4-(4-aminopiperidin-1-yl)-3-(3-fluoro-5-methoxyphenyl)quinolin-6-yl]-6-chlorophenyl}-3-methoxyurea;

2-164: 1-{2-[4-(4-aminopiperidin-1-yl)-3-(3-fluoro-5-methoxyphenyl)quinolin-6-yl]-4,6-difluorophenyl}-3-methoxyurea;

2-165: methyl N-{2-[4-(4-aminopiperidin-1-yl)-3-(3-fluoro-5-methoxyphenyl)quinolin-6-yl]-4,6-difluorophenyl}carbamate;

2-166: 1-(6-{3-fluoro-2-[(hydroxyimino)methyl]phenyl}-3-(3-fluoro-5-methoxyphenyl)quinolin-4-yl)piperidin-4-amine;

2-167: methyl N-{2-[4-(4-aminopiperidin-1-yl)-3-(3-fluoro-5-methoxyphenyl)quinolin-6-yl]-6-cyanophenyl}carbamate;

2-168: 1-(6-{5-fluoro-4-[(hydroxyimino)methyl]pyridin-3-yl}-3-(3-fluoro-5-methylphenyl)quinolin-4-yl)piperidin-4-amine;

2-169: 3-[4-(4-aminopiperidin-1-yl)-3-(3-fluoro-5-methylphenyl)quinolin-6-yl]-5-fluoropyridin-4-amine;

2-170: methyl(trans)-4-amino-1-[6-(3-cyano-2-hydroxyphenyl)-3-(3,5-difluorophenyl)quinolin-4-yl]piperidine-3-carboxylate;

2-171: methyl N-{3-[4-(4-aminopiperidin-1-yl)-3-(3-fluoro-5-methylphenyl)quinolin-6-yl]-5-fluoropyridin-4-yl}carbamate;

2-172: 1-{3-[4-(4-aminopiperidin-1-yl)-3-(3-fluoro-5-methylphenyl)quinolin-6-yl]-5-fluoropyridin-4-yl}-3-methoxyurea;

2-173: methyl N-{2-[4-(4-aminopiperidin-1-yl)-3-(3-fluoro-5-methoxyphenyl)quinolin-6-yl]-6-fluorophenyl}carbamate;

2-174: 1-{2-[4-(4-aminopiperidin-1-yl)-3-(3-fluoro-5-methoxyphenyl)quinolin-6-yl]-6-fluorophenyl}-3-methoxyurea;

2-175: N-{2-[4-(4-aminopiperidin-1-yl)-3-(3-fluoro-5-methoxyphenyl)quinolin-6-yl]-6-fluorophenyl}azetidine-1-carboxamide;

2-176: 1-(6-{5-fluoro-4-[(hydroxyimino)methyl]pyridin-3-yl}-3-[3-fluoro-5-(trifluoromethyl)phenyl]quinolin-4-yl)piperidin-4-amine;

2-177: 4-amino-5-[4-(4-aminopiperidin-1-yl)-3-(3,5-difluorophenyl)quinolin-6-yl]pyridine-3-carbonitrile;

2-178: 3-[4-(4-aminopiperidin-1-yl)-3-(3-fluoro-5-methylphenyl)quinolin-6-yl]-5-fluoropyridin-2-amine;

2-179: 2-amino-3-[4-(4-aminopiperidin-1-yl)-3-(3,5-difluorophenyl)quinolin-6-yl]-4,5-difluorobenzonitrile;

2-180: methyl N-{2-[4-(4-aminopiperidin-1-yl)-3-(3,5-difluorophenyl)quinolin-6-yl]-6-cyano-3,4-difluorophenyl}carbamate;

2-181: 3-[4-(4-aminopiperidin-1-yl)-3-(3-fluoro-5-methylphenyl)quinolin-6-yl]-5-chloropyridin-4-amine;

2-182: methyl N-{3-[4-(4-aminopiperidin-1-yl)-3-(3-fluoro-5-methylphenyl)quinolin-6-yl]-5-fluoropyridin-2-yl}carbamate;

2-183: 1-{3-[4-(4-aminopiperidin-1-yl)-3-(3-fluoro-5-methylphenyl)quinolin-6-yl]-5-fluoropyridin-2-yl}-3-methoxyurea;

2-184: methyl N-{3-[4-(4-aminopiperidin-1-yl)-3-(3-fluoro-5-methylphenyl)quinolin-6-yl]-5-chloropyridin-4-yl}carbamate;

2-185: methyl N-{2-[4-(4-aminopiperidin-1-yl)-3-(3,5-difluorophenyl)quinolin-6-yl]-4-cyanophenyl}carbamate;

2-186: 1-{3-[4-(4-aminopiperidin-1-yl)-3-(3-fluoro-5-methylphenyl)quinolin-6-yl]-5-chloropyridin-4-yl}-3-methoxyurea;

2-187: 4-amino-5-[4-(4-aminopiperidin-1-yl)-3-(3-fluoro-5-methylphenyl)quinolin-6-yl]pyridine-3-carbonitrile;

2-188: 1-[3-(3,5-difluorophenyl)-6-{5-[(hydroxyimino)methyl]-1-methyl-1H-pyrazol-4-yl}quinolin-4-yl]piperidin-4-amine;

2-189: 1-{2-[4-(4-aminopiperidin-1-yl)-3-(3,5-difluorophenyl)quinolin-6-yl]-4-cyanophenyl}-3-methoxyurea;

2-190: 3-{4-[(4αS,8αS)-octahydro-1H-pyrido[3,4-b]morpholin-6-yl]-3-(3,5-difluorophenyl)quinolin-6-yl}-2-hydroxybenzonitrile; 2-191: 1-{2-[4-(4-aminopiperidin-1-yl)-3-(3,5-difluorophenyl)quinolin-6-yl]-6-cyano-3,4-difluorophenyl}-3-methoxy-3-methylurea;

2-192: 1-(6-{5-chloro-4-[(hydroxyimino)methyl]pyridin-3-yl}-3-(3,5-difluorophenyl)quinolin-4-yl)piperidin-4-amine;

2-193: 3-{4-[(4αR,8αR)-octahydro-1H-pyrido[3,4-b]morpholin-6-yl]-3-(3,5-difluorophenyl)quinolin-6-yl}-2-hydroxybenzonitrile;

2-194: 3-[4-(4-aminopiperidin-1-yl)-3-(3,5-difluorophenyl)quinolin-6-yl]-5-fluoro-2-(methoxymethoxy)benzonitrile;

2-195: 1-[3-(3,5-difluorophenyl)-6-{3-[(hydroxyimino)methyl]pyridin-2-yl}quinolin-4-yl]piperidin-4-amine;

2-196: 1-[3-(3,5-difluorophenyl)-6-{2-[(hydroxyimino)methyl]pyridin-3-yl}quinolin-4-yl]piperidin-4-amine;

2-197: methyl N-{2-[4-(4-aminopiperidin-1-yl)-3-(3-fluoro-5-methylphenyl)quinolin-6-yl]-4,6-difluorophenyl}carbamate;

2-198: 1-{2-[4-(4-aminopiperidin-1-yl)-3-(3-fluoro-5-methylphenyl)quinolin-6-yl]-4,6-difluorophenyl}-3-methoxy-3-methylurea;

2-199: 1-{2-[4-(4-aminopiperidin-1-yl)-3-(3-fluoro-5-methylphenyl)quinolin-6-yl]-4,6-difluorophenyl}-3,3-dimethylurea;

2-200: 1-[3-(3,5-difluorophenyl)-6-{6-[(hydroxyimino)methyl]pyridin-2-yl}quinolin-4-yl]piperidin-4-amine;

2-201: 2-[4-(4-aminopiperidin-1-yl)-3-(3,5-difluorophenyl)quinolin-6-yl]-6-cyanophenyl methyl carbonate;

2-202: 1-[3-(3,5-difluorophenyl)-6-{3-fluoro-2-[(hydroxyimino)methyl]-6-methylphenyl}quinolin-4-yl]piperidin-4-amine;

2-203: 1-[3-(3,5-difluorophenyl)-6-{2-[(hydroxyimino)methyl]pyridin-4-yl}quinolin-4-yl]piperidin-4-amine;

2-204: 3-[4-(4-aminopiperidin-1-yl)-3-(3-fluoro-5-methylphenyl)quinolin-6-yl]-5-fluoro-2-(2-methoxyethoxy)benzonitrile;

2-205: methyl N-{2-[4-(4-aminopiperidin-1-yl)-3-(3-fluoro-5-methylphenyl)quinolin-6-yl]-6-cyano-3,4-difluorophenyl}carbamate;

2-206: 1-{2-[4-(4-aminopiperidin-1-yl)-3-(3-fluoro-5-methylphenyl)quinolin-6-yl]-6-cyano-3,4-difluorophenyl}-3-methoxy-3-methylurea;

2-207: 1-(2-{4-[cis-4-amino-3-methoxypiperidin-1-yl]-3-(3-fluoro-5-methylphenyl)quinolin-6-yl}-4,6-difluorophenyl)-3-methoxyurea;

2-208: 1-{2-[4-(4-aminopiperidin-1-yl)-3-(3-fluoro-5-methylphenyl)quinolin-6-yl]-6-cyano-3,4-difluorophenyl}-3-methylurea;

2-209: methyl N-{2-[4-(4-aminopiperidin-1-yl)-3-(3-fluoro-5-methylphenyl)quinolin-6-yl]-6-fluorophenyl}carbamate;

2-210: 1-{2-[4-(4-aminopiperidin-1-yl)-3-(3-fluoro-5-methylphenyl)quinolin-6-yl]-6-fluorophenyl}-3-methoxy-3-methylurea;

2-211: 1-[6-(3-amino-1-methyl-1H-pyrazol-4-yl)-3-(3-fluoro-5-methylphenyl)quinolin-4-yl]piperidin-4-amine;

2-212: 1-{4-[4-(4-aminopiperidin-1-yl)-3-(3-fluoro-5-methylphenyl)quinolin-6-yl]-1-methyl-1H-pyrazol-3-yl}-3-methoxyurea;

2-213: 4-[4-(4-aminopiperidin-1-yl)-3-(3-fluoro-5-methylphenyl)quinolin-6-yl]-2-[(methoxyimino)methyl]phenol;

2-214: methyl N-{4-[4-(4-aminopiperidin-1-yl)-3-(3-fluoro-5-methylphenyl)quinolin-6-yl]-1-methyl-1H-pyrazol-3-yl}carbamate;

2-215: 1-{3-[4-(4-aminopiperidin-1-yl)-3-(3-fluoro-5-methylphenyl)quinolin-6-yl]-4-methylpyridin-2-yl}-3-methoxyurea;

2-216: 1-{2-[4-(4-aminopiperidin-1-yl)-3-(3-fluoro-5-methylphenyl)quinolin-6-yl]-4,6-difluorophenyl}-3-(propan-2-yloxy)urea;

2-217: trans-1-(6-{3-fluoro-2-[(hydroxyimino)methyl]phenyl}-3-(3-fluoro-5-methylphenyl)quinolin-4-yl)-3-methoxypiperidin-4-amine;

2-218: methyl N-(2-{4-[trans-4-amino-3-methoxypiperidin-1-yl]-3-(3-fluoro-5-methylphenyl)quinolin-6-yl}-6-cyanophenyl)carbamate;

2-219: cis-3-{4-[4-amino-3-hydroxypiperidin-1-yl]-3-(3-fluoro-5-methylphenyl)quinolin-6-yl}-5-fluoro-2-hydroxybenzonitrile;

2-220: cis-3-{4-[4-amino-3-hydroxypiperidin-1-yl]-3-(3-fluoro-5-methylphenyl)quinolin-6-yl}-5-fluoro-2-(2-methoxyethoxy)benzonitrile;

2-221: 2-{4-[trans-octahydro-1H-pyrido[3,4-b]morpholin-6-yl]-3-(3-fluoro-5-methylphenyl)quinolin-6-yl}-6-[(methoxyimino)methyl]phenol;

2-222: 1-{2-[4-(4-aminopiperidin-1-yl)-3-(3-fluoro-5-methylphenyl)quinolin-6-yl]-4-cyanophenyl}-3-methoxyurea;

2-223: 1-{3-[4-(4-aminopiperidin-1-yl)-3-(3-fluoro-5-methylphenyl)quinolin-6-yl]-5-fluorophenyl}-3-methoxyurea;

2-224: cis-3-{4-[4-amino-3-hydroxypiperidin-1-yl]-3-(3-fluoro-5-methylphenyl)quinolin-6-yl}-2-(2-methoxyethoxy)benzonitrile;

2-225: cis-3-{4-[4-amino-3-hydroxypiperidin-1-yl]-3-(3,5-difluorophenyl)quinolin-6-yl}-2-(2-methoxyethoxy)benzonitrile;

2-226: 1-{3-[4-(4-aminopiperidin-1-yl)-3-(3-fluoro-5-methylphenyl)quinolin-6-yl]pyridin-2-yl}-3-methoxyurea;

2-227: cis-4-amino-1-(6-{3-fluoro-2-[(hydroxyimino)methyl]phenyl}-3-(3-fluoro-5-methylphenyl)quinolin-4-yl)piperidin-3-ol;

2-228: 1-{2-[4-(4-aminopiperidin-1-yl)-3-(3-fluoro-5-methylphenyl)quinolin-6-yl]-4,6-difluorophenyl}-3-ethoxyurea;

2-229: 1-[3-(3-fluoro-5-methylphenyl)-6-{3-[(2-methoxyethyl)amino]-1-methyl-1H-pyrazol-4-yl}quinolin-4-yl]piperidin-4-amine;

2-230: N-{2-[4-(4-aminopiperidin-1-yl)-3-(3-fluoro-5-methylphenyl)quinolin-6-yl]-4,6-difluorophenyl}-2-methoxyacetamide;

2-231: 3-[4-(4-aminopiperidin-1-yl)-3-(3,5-difluorophenyl)quinolin-6-yl]-2-(cyanomethoxy)benzonitrile;

2-232: cis-3-{4-[4-amino-3-hydroxypiperidin-1-yl]-3-(3,5-difluorophenyl)quinolin-6-yl}-5-fluoro-2-(2-methoxyethoxy)benzonitrile;

2-233: 1-{2-[4-(4-aminopiperidin-1-yl)-3-(3-fluoro-5-methylphenyl)quinolin-6-yl]-4,6-difluorophenyl}-3-(2,2,2-trifluoroethoxy)urea;

2-234: 3-[4-(4-aminopiperidin-1-yl)-3-(3-fluoro-5-methylphenyl)quinolin-6-yl]-5-fluoro-N-(2-methoxyethyl)pyridin-2-amine;

2-235: methyl N-(2-{4-[trans-4-amino-3-methoxypiperidin-1-yl]-3-(3-fluoro-5-methylphenyl)quinolin-6-yl}-4,6-difluorophenyl)carbamate;

2-236: 1-(2-{4-[trans-4-amino-3-methoxypiperidin-1-yl]-3-(3-fluoro-5-methylphenyl)quinolin-6-yl}-4,6-difluorophenyl)-3-methoxyurea;

2-237: 1-{2-[4-(4-aminopiperidin-1-yl)-3-(3-fluoro-5-methylphenyl)quinolin-6-yl]-4-cyano-6-fluorophenyl}-3-methoxyurea;

2-238: 1-{2-[4-(4-aminopiperidin-1-yl)-3-(3,5-difluorophenyl)quinolin-6-yl]-4-cyanophenyl}-3-(2,2,2-trifluoroethoxy)urea;

2-239: 1-{3-[4-(4-aminopiperidin-1-yl)-3-(3-fluoro-5-methylphenyl)quinolin-6-yl]-6-methylpyridin-2-yl}-3-methoxyurea;

2-240: 1-{4-[4-(4-aminopiperidin-1-yl)-3-(3-fluoro-5-methylphenyl)quinolin-6-yl]phenyl}-3-methoxyurea;

2-241: 2-[4-(4-aminopiperidin-1-yl)-3-(3,5-difluorophenyl)quinolin-6-yl]-6-bromo-3,4-difluorophenol;

2-242: 5-[4-(4-aminopiperidin-1-yl)-3-(3-fluoro-5-methylphenyl)quinolin-6-yl]-6-[(2-methoxyethyl)amino]pyridine-3-carbonitrile;

2-243: 2-{4-[trans-octahydro-1H-pyrido[3,4-b]morpholin-6-yl]-3-(3,5-difluorophenyl)quinolin-6-yl}-6-[(1E)-(methoxyimino)methyl]phenol;

2-244: 5-{4-[trans-octahydro-1H-pyrido[3,4-b]morpholin-6-yl]-3-(3,5-difluorophenyl)quinolin-6-yl}-4-aminopyridine-3-carbonitrile;

2-245: 4-{4-[trans-octahydro-1H-pyrido[3,4-b]morpholin-6-yl]-3-(3,5-difluorophenyl)quinolin-6-yl}-1-methyl-1H-pyrazol-3-amine;

2-246: 3-{4-[trans-octahydro-1H-pyrido[3,4-b]morpholin-6-yl]-3-(3,5-difluorophenyl)quinolin-6-yl}pyridin-2-amine;

2-247: 2-{4-[trans-octahydro-1H-pyrido[3,4-b]morpholin-6-yl]-3-(3,5-difluorophenyl)quinolin-6-yl}-4-methylpyridin-3-amine;

2-248: 3-{4-[trans-octahydro-1H-pyrido[3,4-b]morpholin-6-yl]-3-(3,5-difluorophenyl)quinolin-6-yl}pyridin-2-ol;

2-249: 4-{4-[trans-octahydro-1H-pyrido[3,4-b]morpholin-6-yl]-3-(3,5-difluorophenyl)quinolin-6-yl}-1-methyl-1H-pyrazol-5-amine;

2-250: 2-[4-(4-aminopiperidin-1-yl)-3-(3,5-difluorophenyl)quinolin-6-yl]-4-methylpyridin-3-amine;

2-251: 2-{4-[trans-octahydro-1H-pyrido[3,4-b]morpholin-6-yl]-3-(3,5-difluorophenyl)quinolin-6-yl}-3-hydroxypyridine-4-carbonitrile;

2-252: 5-{4-[trans-octahydro-1H-pyrido[3,4-b]morpholin-6-yl]-3-(3,5-difluorophenyl)quinolin-6-yl}-4-[(2-methoxyethyl)amino]pyridine-3-carbonitrile;

2-253: N-[(4-{4-[trans-octahydro-1H-pyrido[3,4-b]morpholin-6-yl]-3-(3,5-difluorophenyl)quinolin-6-yl}-1-methyl-1H-pyrazol-5-yl)methylidene]hydroxylamine 2-254: 5-{4-[trans-octahydro-1H-pyrido[3,4-b]morpholin-6-yl]-3-(3,5-difluorophenyl)quinolin-6-yl}-4-hydroxypyridine-3-carbonitrile;

2-255: 4-{4-[trans-octahydro-1H-pyrido[3,4-b]morpholin-6-yl]-3-(3,5-difluorophenyl)quinolin-6-yl}pyrimidin-5-amine;

2-256: 3-{4-[trans-octahydro-1H-pyrido[3,4-b]morpholin-6-yl]-3-(3,5-difluorophenyl)quinolin-6-yl}-5-fluoropyridin-4-ol;

2-257: 4-{4-[trans-octahydro-1H-pyrido[3,4-b]morpholin-6-yl]-3-(3,5-difluorophenyl)quinolin-6-yl}-1-methyl-1H-pyrazole-3-carboxamide;

2-258: 2-{4-[trans-octahydro-1H-pyrido[3,4-b]morpholin-6-yl]-3-(3,5-difluorophenyl)quinolin-6-yl}-4-methylpyridin-3-ol;

2-259: 3-{4-[trans-octahydro-1H-pyrido[3,4-b]morpholin-6-yl]-3-(3,5-difluorophenyl)quinolin-6-yl}-5-fluoropyridin-2-ol;

2-260: N-[(4-{4-[trans-octahydro-1H-pyrido[3,4-b]morpholin-6-yl]-3-(3,5-difluorophenyl)quinolin-6-yl}-1-methyl-1H-pyrazol-3-yl)methylidene]hydroxylamine;

2-261: 2-{4-[trans-octahydro-1H-pyrido[3,4-b]morpholin-6-yl]-3-(3,5-difluorophenyl)quinolin-6-yl}-3-fluoropyridine-4-carbonitrile;

2-262: 2-{4-[trans-octahydro-1H-pyrido[3,4-b]morpholin-6-yl]-3-(3,5-difluorophenyl)quinolin-6-yl}-3-aminopyridine-4-carbonitrile;

2-263: 2-{4-[trans-octahydro-1H-pyrido[3,4-b]morpholin-6-yl]-3-(3,5-difluorophenyl)quinolin-6-yl}pyridin-3-ol;

2-264: N-[(3-{4-[trans-octahydro-1H-pyrido[3,4-b]morpholin-6-yl]-3-(3,5-difluorophenyl)quinolin-6-yl}pyridin-2-yl)methylidene]hydroxylamine;

2-265: 2-{4-[trans-octahydro-1H-pyrido[3,4-b]morpholin-6-yl]-3-(3,5-difluorophenyl)quinolin-6-yl}-5-fluoropyridin-3-amine;

2-266: 3-{4-[trans-octahydro-1H-pyrido[3,4-b]morpholin-6-yl]-3-(3,5-difluorophenyl)quinolin-6-yl}-5-[(methoxyimino)methyl]pyridin-4-amine;

2-267: 3-{4-[trans-octahydro-1H-pyrido[3,4-b]morpholin-6-yl]-3-(3,5-difluorophenyl)quinolin-6-yl}-5-cyclopropylpyridin-4-amine;

2-268: 4-{4-[trans-octahydro-1H-pyrido[3,4-b]morpholin-6-yl]-3-(3,5-difluorophenyl)quinolin-6-yl}-1-(oxetan-3-yl)-1H-pyrazol-5-amine;

2-269: 2-{4-[trans-octahydro-1H-pyrido[3,4-b]morpholin-6-yl]-3-(3,5-difluorophenyl)quinolin-6-yl}-4-[(methoxyimino)methyl]pyridin-3-amine;

2-270: 3-[3-(3-fluoro-5-methylphenyl)-4-[3-(morpholin-3-yl)azetidin-1-yl]quinolin-6-yl]-2-hydroxybenzonitrile;

2-271: 3-[3-(3,5-difluorophenyl)-4-[3-(morpholin-3-yl)azetidin-1-yl]quinolin-6-yl]-2-hydroxybenzonitrile;

2-272: 3-{4-[trans-octahydro-1H-pyrido[3,4-b]morpholin-6-yl]-3-(3,5-difluorophenyl)quinolin-6-yl}-5-(prop-1-yn-1-yl)pyridin-4-amine;

2-273: 1-(3-{4-[trans-octahydro-1H-pyrido[3,4-b]morpholin-6-yl]-3-(3,5-difluorophenyl)quinolin-6-yl}pyridin-2-yl)-3-methoxyurea;

2-274: 3-{4-[trans-octahydro-1H-pyrido[3,4-b]morpholin-6-yl]-3-(3,5-difluorophenyl)quinolin-6-yl}-5-ethynylpyridin-4-amine;

2-275: 2-{4-[trans-octahydro-1H-pyrido[3,4-b]morpholin-6-yl]-3-(3,5-difluorophenyl)quinolin-6-yl}-4-chloropyridin-3-amine;

2-276: 2-{4-[trans-octahydro-1H-pyrido[3,4-b]morpholin-6-yl]-3-(3,5-difluorophenyl)quinolin-6-yl}-4-cyclopropylpyridin-3-amine;

2-277: 2-{4-[trans-octahydro-1H-pyrido[3,4-b]morpholin-6-yl]-3-(3,5-difluorophenyl)quinolin-6-yl}-4-ethynylpyridin-3-amine;

2-278: 2-{4-[trans-octahydro-1H-pyrido[3,4-b]morpholin-6-yl]-3-(3,5-difluorophenyl)quinolin-6-yl}-6-(oxetan-3-yl)phenol;

2-279: 2-{4-[trans-octahydro-1H-pyrido[3,4-b]morpholin-6-yl]-3-(3,5-difluorophenyl)quinolin-6-yl}-6-(oxetan-2-yl)phenol;

2-280: 2-{4-[trans-octahydro-1H-pyrido[3,4-b]morpholin-6-yl]-3-(3,5-difluorophenyl)quinolin-6-yl}-4-(oxetan-3-yl)pyridin-3-amine;

2-281: 2-{4-[trans-octahydro-1H-pyrido[3,4-b]morpholin-6-yl]-3-(3,5-difluorophenyl)quinolin-6-yl}-4-(oxetan-2-yl)pyridin-3-amine;

2-282: 3-amino-2-[3-(3-fluoro-5-methylphenyl)-4-[3-(morpholin-3-yl)azetidin-1-yl]quinolin-6-yl]pyridine-4-carbonitrile;

2-283: 2-{4-[trans-octahydro-1H-pyrido[3,4-b]morpholin-6-yl]-3-(3,5-difluorophenyl)quinolin-6-yl}pyridin-3-amine;

2-284: 2-{4-[trans-octahydro-1H-pyrido[3,4-b]morpholin-6-yl]-3-(3,5-difluorophenyl)quinolin-6-yl}-4-methoxypyridin-3-amine;

2-285: 2-{4-[(4αR,8αR)-octahydro-1H-pyrido[3,4-b]morpholin-6-yl]-3-(3,5-difluorophenyl)quinolin-6-yl}-6-[(methoxyimino)methyl]phenol;

2-286: 2-{4-[(4αS,8αS)-octahydro-1H-pyrido[3,4-b]morpholin-6-yl]-3-(3,5-difluorophenyl)quinolin-6-yl}-6-[(methoxyimino)methyl]phenol;

2-287: 2-{4-[(4aR,8aR)-octahydro-1H-pyrido[3,4-b]morpholin-6-yl]-3-(3,5-difluorophenyl)quinolin-6-yl}-4-[(methoxyimino)methyl]pyridin-3-amine;

2-288: 2-{4-[(4αS,8αS)-octahydro-1H-pyrido[3,4-b]morpholin-6-yl]-3-(3,5-difluorophenyl)quinolin-6-yl}-4-[(methoxyimino)methyl]pyridin-3-amine;

2-289: 2-{4-[(4αR,8αR)-octahydro-1H-pyrido[3,4-b]morpholin-6-yl]-3-(3,5-difluorophenyl)quinolin-6-yl}-3-aminopyridine-4-carbonitrile;

2-290: 2-{4-[(4αS, 8αS)-octahydro-1H-pyrido[3,4-b]morpholin-6-yl]-3-(3,5-difluorophenyl)quinolin-6-yl}-3-aminopyridine-4-carbonitrile;

2-291: (5-{4-[(4αR, 8αR)-octahydro-1H-pyrido[3,4-b]morpholin-6-yl]-3-(3,5-difluorophenyl)quinolin-6-yl}-4-aminopyridin-3-carbonitrile;

2-292: (5-{4-[(4αS,8αS)-octahydro-1H-pyrido[3,4-b]morpholin-6-yl]-3-(3,5-difluorophenyl)quinolin-6-yl}-4-aminopyridin-3-carbonitrile;

2-293: 3-{4-[(4αR,8αR)-octahydro-1H-pyrido[3,4-b]morpholin-6-yl]-3-(3,5-difluorophenyl)quinolin-6-yl}pyridin-2-amine;

2-294: 3-{4-[(4αS, 8αS)-octahydro-1H-pyrido[3,4-b]morpholin-6-yl]-3-(3,5-difluorophenyl)quinolin-6-yl}pyridin-2-amine;

2-295: 2-{4-[(4αR,8αR)-octahydro-1H-pyrido[3,4-b]morpholin-6-yl]-3-(3,5-difluorophenyl)quinolin-6-yl}-4-methylpyridin-3-amine;

2-296: 2-{4-[(4αS, 8αS)-octahydro-1H-pyrido[3,4-b]morpholin-6-yl]-3-(3,5-difluorophenyl)quinolin-6-yl}-4-methylpyridin-3-amine;

2-297: 2-{4-[(4αR,8αR)-octahydro-1H-pyrido[3,4-b]morpholin-6-yl]-3-(3,5-difluorophenyl)quinolin-6-yl}-4-methylpyridin-3-ol;

2-298: 2-{4-[(4αS, 8αS)-octahydro-1H-pyrido[3,4-b]morpholin-6-yl]-3-(3,5-difluorophenyl)quinolin-6-yl}-4-methylpyridin-3-ol;

2-299: 3-{4-[(4αR,8αR)-octahydro-1H-pyrido[3,4-b]morpholin-6-yl]-3-(3,5-difluorophenyl)quinolin-6-yl}-5-fluoro-2-hydroxybenzonitrile;

2-300: 3-{4-[(4αS, 8αS)-octahydro-1H-pyrido[3,4-b]morpholin-6-yl]-3-(3,5-difluorophenyl)quinolin-6-yl}-5-fluoro-2-hydroxybenzonitrile.

In some embodiments, provided herein is a pharmaceutically acceptable salt of a compound that is described in Table 2.

TABLE 3

| Cpd No. | $R^B$ | A | $R^a$ | $R^b$ |
|---|---|---|---|---|
| 3-1 | 3-fluoro-5-carbamoylphenyl | 4-aminopiperidin-1-yl | 3-F | 5-CH₃ |
| 3-2 | 3-cyano-5-fluoro-2-hydroxyphenyl | 4-aminopiperidin-1-yl | 3-F | 5-CH₃ |
| 3-3 | 4-fluoro-2-oxo-2,3-dihydro-1H-benzimidazol-7-yl | 4-aminopiperidin-1-yl | 3-F | 5-CH₃ |
| 3-4 | 2-oxo-2,3-dihydro-1H-benzimidazol-5-yl | 4-aminopiperidin-1-yl | 3-F | 5-CH₃ |
| 3-5 | 4-fluoro-2-oxo-2,3-dihydro-1H-benzimidazol-6-yl | 4-aminopiperidin-1-yl | 3-F | 5-CH₃ |
| 3-6 | 3-cyano-5-fluoro-2-hydroxyphenyl | 4-aminopiperidin-1-yl | 3-Cl | 5-CH₃ |
| 3-7 | 3-cyano-2-hydroxyphenyl | 4-aminopiperidin-1-yl | 3-F | 5-CH₃ |
| 3-8 | 3-fluoro-2-hydroxyphenyl | 4-aminopiperidin-1-yl | 3-F | 5-CH₃ |
| 3-9 | 4-fluoro-2-oxo-2,3-dihydro-1H-benzimidazol-6-yl | 4-aminopiperidin-1-yl | 3-F | 5-F |
| 3-10 | 4-fluoro-2-oxo-2,3-dihydro-1H-benzimidazol-6-yl | octahydro-pyrido[3,4-b][1,4]oxazinyl (racemic) | 3-F | 5-F |
| 3-11 | 4-fluoro-2-oxo-2,3-dihydro-1H-benzimidazol-6-yl | octahydro-pyrido[3,4-b][1,4]oxazinyl (racemic) | 3-F | 5-CH₃ |
| 3-12 | 2-oxo-2,3-dihydro-1H-imidazo[4,5-b]pyridin-6-yl | octahydro-pyrido[3,4-b][1,4]oxazinyl (racemic) | 3-F | 5-F |

Compounds in Table 3 are Named:
3-1: 3-[8-(4-aminopiperidin-1-yl)-7-(3-fluoro-5-methylphenyl)-1,5-naphthyridin-2-yl]-5-fluorobenzamide;
3-2: 3-[8-(4-aminopiperidin-1-yl)-7-(3-fluoro-5-methylphenyl)-1,5-naphthyridin-2-yl]-5-fluoro-2-hydroxybenzonitrile;
3-3: 4-[8-(4-aminopiperidin-1-yl)-7-(3-fluoro-5-methylphenyl)-1,5-naphthyridin-2-yl]-6-fluoro-2,3-dihydro-1H-1,3-benzodiazol-2-one;
3-4: 5-[8-(4-aminopiperidin-1-yl)-7-(3-fluoro-5-methylphenyl)-1,5-naphthyridin-2-yl]-2,3-dihydro-1H-1,3-benzodiazol-2-one;
3-5: 6-[8-(4-aminopiperidin-1-yl)-7-(3-fluoro-5-methylphenyl)-1,5-naphthyridin-2-yl]-4-fluoro-2,3-dihydro-1H-1,3-benzodiazol-2-one;
3-6: 3-[8-(4-aminopiperidin-1-yl)-7-(3-chloro-5-methylphenyl)-1,5-naphthyridin-2-yl]-5-fluoro-2-hydroxybenzonitrile;
3-7: 3-[8-(4-aminopiperidin-1-yl)-7-(3-fluoro-5-methylphenyl)-1,5-naphthyridin-2-yl]-2-hydroxybenzonitrile;
3-8: 2-[8-(4-aminopiperidin-1-yl)-7-(3-fluoro-5-methylphenyl)-1,5-naphthyridin-2-yl]-6-fluorophenol.
3-9: 6-[8-(4-aminopiperidin-1-yl)-7-(3,5-difluorophenyl)-1,5-naphthyridin-2-yl]-4-fluoro-2,3-dihydro-1H-1,3-benzodiazol-2-one;
3-10: 6-{8-[trans-octahydro-1H-pyrido[3,4-b]morpholin-6-yl]-7-(3,5-difluorophenyl)-1,5-naphthyridin-2-yl}-4-fluoro-2,3-dihydro-1H-1,3-benzodiazol-2-one;
3-11: 4-{8-[trans-octahydro-1H-pyrido[3,4-b]morpholin-6-yl]-7-(3-fluoro-5-methylphenyl)-1,5-naphthyridin-2-yl}-6-fluoro-2,3-dihydro-1H-1,3-benzodiazol-2-one;
3-12: 4-{8-[trans-octahydro-1H-pyrido[3,4-b]morpholin-6-yl]-7-(3,5-difluorophenyl)-1,5-naphthyridin-2-yl}-1H,2H,3H-imidazo[4,5-c]pyridin-2-one.

In some embodiments, provided herein is a pharmaceutically acceptable salt of a compound that is described in Table 3.

TABLE 4

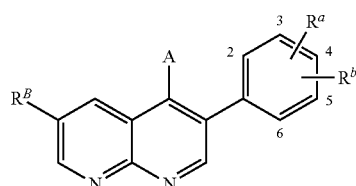

| Cpd No. | $R^B$ | A | $R^a$ | $R^b$ |
|---|---|---|---|---|
| 4-1 | (3-cyano-2-hydroxyphenyl) | (4-aminopiperidin-1-yl) | 3-F | 5-F |
| 4-2 | (3-cyano-2-hydroxyphenyl) | (4-aminopiperidin-1-yl) | 3-F | 5-CH$_3$ |

TABLE 4-continued

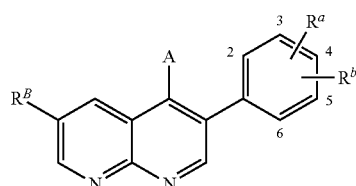

| Cpd No. | $R^B$ | A | $R^a$ | $R^b$ |
|---|---|---|---|---|
| 4-3 | 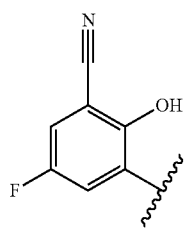 | 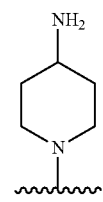 | 3-F | 5-CH$_3$ |
| 4-4 | 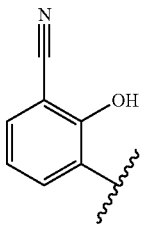 [SMILES: *c1cccc(C#N)c1O] | 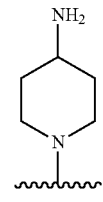 | 3-Cl | 5-CH$_3$ |
| 4-5 | 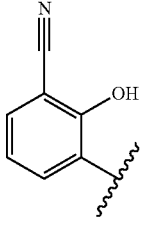 [SMILES: *c1cccc(C#N)c1O] | 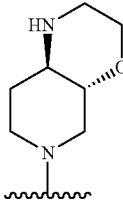 Single enantiomer | 3-F | 5-CH$_3$ |
| 4-6 | 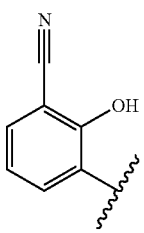 [SMILES: *c1cccc(C#N)c1O] | 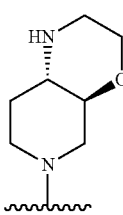 Single enantiomer | 3-F | 5-CH$_3$ |
| 4-7 | 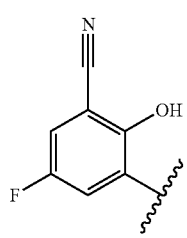 | 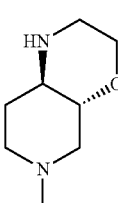 Single enantiomer | 3-F | 5-CH$_3$ |

TABLE 4-continued

| Cpd No. | R^B | A | R^a | R^b |
|---|---|---|---|---|
| 4-8 | 3-cyano-5-fluoro-2-hydroxyphenyl | hexahydropyrano-piperidine (Single enantiomer) | 3-F | 5-CH₃ |
| 4-9 | 3-cyano-5-fluoro-2-hydroxyphenyl | hexahydropyrano-piperidine (Single enantiomer) | 3-F | 5-F |
| 4-10 | 3-cyano-5-fluoro-2-hydroxyphenyl | hexahydropyrano-piperidine (Single enantiomer) | 3-F | 5-F |
| 4-11 | 3-amino-4-cyanopyridinyl | hexahydropyrano-piperidine (Single enantiomer) | 3-F | 5-F |
| 4-12 | 3-amino-4-cyanopyridinyl | hexahydropyrano-piperidine (Single enantiomer) | 3-F | 5-F |
| 4-13 | 4-amino-5-cyanopyridinyl | hexahydropyrano-piperidine (Single enantiomer) | 3-F | 5-F |
| 4-14 | 3-cyano-4-aminopyridinyl | hexahydropyrano-piperidine (Single enantiomer) | 3-F | 5-F |
| 4-15 | 3-amino-4-cyanopyridinyl | hexahydropyrano-piperidine (Single enantiomer) | 3-F | 5-CH₃ |
| 4-16 | 3-amino-4-cyanopyridinyl | hexahydropyrano-piperidine (Single enantiomer) | 3-F | 5-CH₃ |
| 4-17 | 3-amino-4-cyanopyridinyl | hexahydropyrano-piperidine (Single enantiomer) | 3-F | 5-Cl |

TABLE 4-continued

| Cpd No. | R^B | A | R^a | R^b |
|---|---|---|---|---|
| 4-18 | 3-amino-4-cyanopyridin-2-yl | hexahydropyrano[3,2-b]pyridine (Single enantiomer) | 3-F | 5-Cl |
| 4-19 | 3-amino-4-cyanopyridin-2-yl | hexahydropyrano[3,2-b]pyridine (Single enantiomer) | 3-Cl | 5-CH$_3$ |
| 4-20 | 3-amino-4-cyanopyridin-2-yl | hexahydropyrano[3,2-b]pyridine (Single enantiomer) | 3-Cl | 5-CH$_3$ |
| 4-21 | 3-amino-4-((methoxyimino)methyl)pyridin-2-yl | hexahydropyrano[3,2-b]pyridine (Single enantiomer) | 3-F | 5-F |
| 4-22 | 3-amino-4-((methoxyimino)methyl)pyridin-2-yl | hexahydropyrano[3,2-b]pyridine (Single enantiomer) | 3-F | 5-F |
| 4-23 | 3-amino-4-((methoxyimino)methyl)pyridin-2-yl | hexahydropyrano[3,2-b]pyridine (Single enantiomer) | 3-Cl | 5-CH$_3$ |
| 4-24 | 3-amino-4-((methoxyimino)methyl)pyridin-2-yl | hexahydropyrano[3,2-b]pyridine (Single enantiomer) | 3-Cl | 5-CH$_3$ |
| 4-25 | 3-cyano-2-hydroxyphenyl | hexahydropyrano[3,2-b]pyridine (Single enantiomer) | 3-F | 5-F |
| 4-26 | 3-cyano-2-hydroxyphenyl | hexahydropyrano[3,2-b]pyridine (Single enantiomer) | 3-F | 5-F |
| 4-27 | 3-cyano-2-hydroxyphenyl | hexahydropyrano[3,2-b]pyridine (Single enantiomer) | 3-F | 5-Cl |

TABLE 4-continued

| Cpd No. | $R^B$ | A | $R^a$ | $R^b$ |
|---|---|---|---|---|
| 4-28 | 3-cyano-2-hydroxyphenyl | hexahydropyrano-piperidine (single enantiomer) | 3-F | 5-Cl |
| 4-29 | 3-cyano-2-hydroxyphenyl | hexahydropyrano-piperidine (single enantiomer) | 3-F | 5-OCH$_3$ |
| 4-30 | 3-cyano-2-hydroxyphenyl | hexahydropyrano-piperidine (single enantiomer) | 3-F | 5-OCH$_3$ |
| 4-31 | 3-cyano-2-hydroxyphenyl | hexahydropyrano-piperidine (single enantiomer) | 3-Cl | 5-CH$_3$ |
| 4-32 | 3-cyano-2-hydroxyphenyl | hexahydropyrano-piperidine (single enantiomer) | 3-Cl | 5-CH$_3$ |
| 4-33 | 3-cyano-2-hydroxyphenyl | hexahydropyrano-piperidine (single enantiomer) | 3-Cl | 5-Cl |
| 4-34 | 3-cyano-2-hydroxyphenyl | hexahydropyrano-piperidine (single enantiomer) | 3-Cl | 5-Cl |
| 4-35 | 2-amino-pyridin-3-yl | hexahydropyrano-piperidine (single enantiomer) | 3-F | 5-F |
| 4-36 | 2-amino-pyridin-3-yl | hexahydropyrano-piperidine (single enantiomer) | 3-F | 5-F |
| 4-37 | 2-amino-pyridin-3-yl | hexahydropyrano-piperidine (single enantiomer) | 3-F | 5-CH$_3$ |

TABLE 4-continued

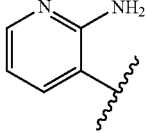

| Cpd No. | $R^B$ | A | $R^a$ | $R^b$ |
|---|---|---|---|---|
| 4-38 | 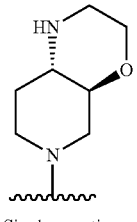 | 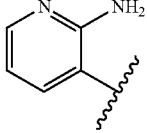<br>Single enantiomer | 3-F | 5-CH₃ |
| 4-39 | 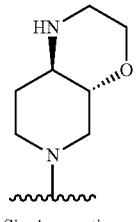 | 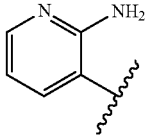<br>Single enantiomer | 3-F | 5-OCH₃ |
| 4-40 | 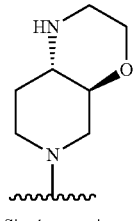 | 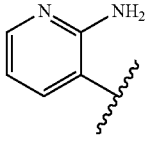 [SMILES: *c1cccnc1N]<br>Single enantiomer | 3-F | 5-OCH₃ |
| 4-41 | 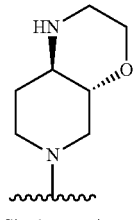 | 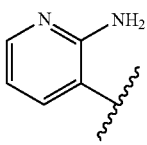 [SMILES: *c1cccnc1N]<br>Single enantiomer | 3-F | 5-Cl |
| 4-42 | 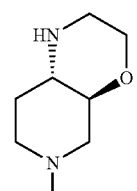 | 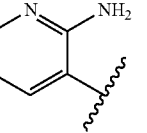<br>Single enantiomer | 3-F | 5-Cl |
| 4-43 | 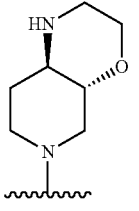 | 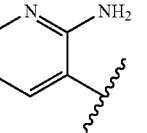<br>Single enantiomer | 3-Cl | 5-CH₃ |
| 4-44 | 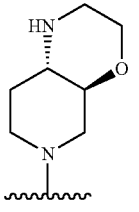 | 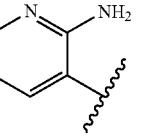<br>Single enantiomer | 3-Cl | 5-CH₃ |
| 4-45 | 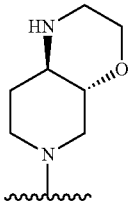 | 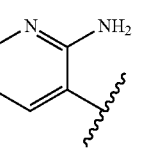<br>Single enantiomer | 3-Cl | 5-Cl |
| 4-46 | 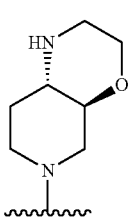 | <br>Single enantiomer | 3-Cl | 5-Cl |

Compounds in Table 4 are Named:
4-1: 3-[5-(4-aminopiperidin-1-yl)-6-(3,5-difluorophenyl)-1,8-naphthyridin-3-yl]-2-hydroxybenzonitrile;
4-2: 3-[5-(4-aminopiperidin-1-yl)-6-(3-fluoro-5-methylphenyl)-1,8-naphthyridin-3-yl]-2-hydroxybenzonitrile;
4-3: 3-[5-(4-aminopiperidin-1-yl)-6-(3-fluoro-5-methylphenyl)-1,8-naphthyridin-3-yl]-5-fluoro-2-hydroxybenzonitrile;
4-4: 3-[5-(4-aminopiperidin-1-yl)-6-(3-chloro-5-methylphenyl)-1,8-naphthyridin-3-yl]-2-hydroxybenzonitrile;
4-5: 3-{5-[(4αR,8αR)-octahydro-1H-pyrido[3,4-b]morpholin-6-yl]-6-(3-fluoro-5-methylphenyl)-1,8-naphthyridin-3-yl}-2-hydroxybenzonitrile;
4-6: 3-{5-[(4αS,8αS)-octahydro-1H-pyrido[3,4-b]morpholin-6-yl]-6-(3-fluoro-5-methylphenyl)-1,8-naphthyridin-3-yl}-2-hydroxybenzonitrile;

4-7: 3-{5-[(4αR,8αR)-octahydro-1H-pyrido[3,4-b]morpholin-6-yl]-6-(3-fluoro-5-methylphenyl)-1,8-naphthyridin-3-yl}-5-fluoro-2-hydroxybenzonitrile;

4-8: 3-{5-[(4αS,8αS)-octahydro-1H-pyrido[3,4-b]morpholin-6-yl]-6-(3-fluoro-5-methylphenyl)-1,8-naphthyridin-3-yl}-5-fluoro-2-hydroxybenzonitrile;

4-9: 3-{5-[(4αR,8αR)-octahydro-1H-pyrido[3,4-b]morpholin-6-yl]-6-(3,5-difluorophenyl)-1,8-naphthyridin-3-yl}-5-fluoro-2-hydroxybenzonitrile;

4-10: 3-{5-[(4αS,8αS)-octahydro-1H-pyrido[3,4-b]morpholin-6-yl]-6-(3,5-difluorophenyl)-1,8-naphthyridin-3-yl}-5-fluoro-2-hydroxybenzonitrile;

4-11: 2-{5-[(4αR,8αR)-octahydro-1H-pyrido[3,4-b]morpholin-6-yl]-6-(3-fluoro-5-methylphenyl)-1,8-naphthyridin-3-yl}-3-aminopyridine-4-carbonitrile;

4-12: 2-{5-[(4αS,8αS)-octahydro-1H-pyrido[3,4-b]morpholin-6-yl]-6-(3-fluoro-5-methylphenyl)-1,8-naphthyridin-3-yl}-3-aminopyridine-4-carbonitrile;

4-13: 5-{5-[(4αR,8αR)-octahydro-1H-pyrido[3,4-b]morpholin-6-yl]-6-(3,5-difluorophenyl)-1,8-naphthyridin-3-yl}-4-aminopyridine-3-carbonitrile;

4-14: 5-{5-[(4αS,8αS)-octahydro-1H-pyrido[3,4-b]morpholin-6-yl]-6-(3,5-difluorophenyl)-1,8-naphthyridin-3-yl}-4-aminopyridine-3-carbonitrile;

4-15: 2-{5-[(4αR,8αR)-octahydro-1H-pyrido[3,4-b][1,4]oxazin-6-yl]-6-(3-fluoro-5-methylphenyl)-1,8-naphthyridin-3-yl}-3-aminopyridine-4-carbonitrile;

4-16: 2-{5-[(4αS, 8αS)-octahydro-1H-pyrido[3,4-b][1,4]oxazin-6-yl]-6-(3-fluoro-5-methylphenyl)-1,8-naphthyridin-3-yl}-3-aminopyridine-4-carbonitrile;

4-17: 2-{5-[(4αR,8αR)-octahydro-1H-pyrido[3,4-b][1,4]oxazin-6-yl]-6-(3-chloro-5-fluorophenyl)-1,8-naphthyridin-3-yl}-3-aminopyridine-4-carbonitrile;

4-18: 2-{5-[(4αS,8αS)-octahydro-1H-pyrido[3,4-b][1,4]oxazin-6-yl]-6-(3-chloro-5-fluorophenyl)-1,8-naphthyridin-3-yl}-3-aminopyridine-4-carbonitrile;

4-19: 2-{5-[(4αR,8αR)-octahydro-1H-pyrido[3,4-b][1,4]oxazin-6-yl]-6-(3-chloro-5-methylphenyl)-1,8-naphthyridin-3-yl}-3-aminopyridine-4-carbonitrile;

4-20: 2-{5-[(4αS,8αS)-octahydro-1H-pyrido[3,4-b][1,4]oxazin-6-yl]-6-(3-chloro-5-methylphenyl)-1,8-naphthyridin-3-yl}-3-aminopyridine-4-carbonitrile;

4-21: 2-{5-[(4αR,8αR)-octahydro-1H-pyrido[3,4-b][1,4]oxazin-6-yl]-6-(3,5-difluorophenyl)-1,8-naphthyridin-3-yl}-4-[(methoxyimino)methyl]pyridin-3-amine;

4-22: 2-{5-[(4αS, 8αS)-octahydro-1H-pyrido[3,4-b][1,4]oxazin-6-yl]-6-(3,5-difluorophenyl)-1,8-naphthyridin-3-yl}-4-[(methoxyimino)methyl]pyridin-3-amine;

4-23: 2-{5-[(4αR,8αR)-octahydro-1H-pyrido[3,4-b][1,4]oxazin-6-yl]-6-(3-chloro-5-methylphenyl)-1,8-naphthyridin-3-yl}-4-[(methoxyimino)methyl]pyridin-3-amine;

4-24: 2-{5-[(4αS,8αS)-octahydro-1H-pyrido[3,4-b][1,4]oxazin-6-yl]-6-(3-chloro-5-methylphenyl)-1,8-naphthyridin-3-yl}-4-[(methoxyimino)methyl]pyridin-3-amine;

4-25: 3-{5-[(4αR,8αR)-octahydro-1H-pyrido[3,4-b][1,4]oxazin-6-yl]-6-(3,5-difluorophenyl)-1,8-naphthyridin-3-yl}-2-hydroxybenzonitrile;

4-26: 3-{5-[(4αS,8αS)-octahydro-1H-pyrido[3,4-b][1,4]oxazin-6-yl]-6-(3,5-difluorophenyl)-1,8-naphthyridin-3-yl}-2-hydroxybenzonitrile;

4-27: 3-{5-[(4αR,8αR)-octahydro-1H-pyrido[3,4-b][1,4]oxazin-6-yl]-6-(3-chloro-5-fluorophenyl)-1,8-naphthyridin-3-yl}-2-hydroxybenzonitrile;

4-28: 3-{5-[(4αS,8αS)-octahydro-1H-pyrido[3,4-b][1,4]oxazin-6-yl]-6-(3-chloro-5-fluorophenyl)-1,8-naphthyridin-3-yl}-2-hydroxybenzonitrile;

4-29: 3-{5-[(4αR,8αR)-octahydro-1H-pyrido[3,4-b][1,4]oxazin-6-yl]-6-(3-fluoro-5-methoxyphenyl)-1,8-naphthyridin-3-yl}-2-hydroxybenzonitrile;

4-30: 3-{5-[(4αS,8αS)-octahydro-1H-pyrido[3,4-b][1,4]oxazin-6-yl]-6-(3-fluoro-5-methoxyphenyl)-1,8-naphthyridin-3-yl}-2-hydroxybenzonitrile;

4-31: 3-{5-[(4αR,8αR)-octahydro-1H-pyrido[3,4-b][1,4]oxazin-6-yl]-6-(3-chloro-5-methylphenyl)-1,8-naphthyridin-3-yl}-2-hydroxybenzonitrile;

4-32: 3-{5-[(4αS,8αS)-octahydro-1H-pyrido[3,4-b][1,4]oxazin-6-yl]-6-(3-chloro-5-methylphenyl)-1,8-naphthyridin-3-yl}-2-hydroxybenzonitrile;

4-33: 3-{5-[(4αR,8αR)-octahydro-1H-pyrido[3,4-b][1,4]oxazin-6-yl]-6-(3,5-dichlorophenyl)-1,8-naphthyridin-3-yl}-2-hydroxybenzonitrile;

4-34: 3-{5-[(4αS,8αS)-octahydro-1H-pyrido[3,4-b][1,4]oxazin-6-yl]-6-(3,5-dichlorophenyl)-1,8-naphthyridin-3-yl}-2-hydroxybenzonitrile;

4-35: 3-{5-[(4αR,8αR)-octahydro-1H-pyrido[3,4-b][1,4]oxazin-6-yl]-6-(3,5-difluorophenyl)-1,8-naphthyridin-3-yl}pyridin-2-amine;

4-36: 3-{5-[(4αS,8αS)-octahydro-1H-pyrido[3,4-b][1,4]oxazin-6-yl]-6-(3,5-difluorophenyl)-1,8-naphthyridin-3-yl}pyridin-2-amine;

4-37: 3-{5-[(4αR,8αR)-octahydro-1H-pyrido[3,4-b][1,4]oxazin-6-yl]-6-(3-fluoro-5-methylphenyl)-1,8-naphthyridin-3-yl}pyridin-2-amine;

4-38: 3-{5-[(4αS,8αS)-octahydro-1H-pyrido[3,4-b][1,4]oxazin-6-yl]-6-(3-fluoro-5-methylphenyl)-1,8-naphthyridin-3-yl}pyridin-2-amine;

4-39: 3-{5-[(4αR,8αR)-octahydro-1H-pyrido[3,4-b][1,4]oxazin-6-yl]-6-(3-fluoro-5-methoxyphenyl)-1,8-naphthyridin-3-yl}pyridin-2-amine;

4-40: 3-{5-[(4αS,8αS)-octahydro-1H-pyrido[3,4-b][1,4]oxazin-6-yl]-6-(3-fluoro-5-methoxyphenyl)-1,8-naphthyridin-3-yl}pyridin-2-amine;

4-41: 3-{5-[(4αR,8αR)-octahydro-1H-pyrido[3,4-b][1,4]oxazin-6-yl]-6-(3-chloro-5-fluorophenyl)-1,8-naphthyridin-3-yl}pyridin-2-amine;

4-42: 3-{5-[(4αS,8αS)-octahydro-1H-pyrido[3,4-b][1,4]oxazin-6-yl]-6-(3-chloro-5-fluorophenyl)-1,8-naphthyridin-3-yl}pyridin-2-amine;

4-43: 3-{5-[(4αR,8αR)-octahydro-1H-pyrido[3,4-b][1,4]oxazin-6-yl]-6-(3-chloro-5-methylphenyl)-1,8-naphthyridin-3-yl}pyridin-2-amine;

4-44: 3-{5-[(4αS,8αS)-octahydro-1H-pyrido[3,4-b][1,4]oxazin-6-yl]-6-(3-chloro-5-methylphenyl)-1,8-naphthyridin-3-yl}pyridin-2-amine;

4-45: 3-{5-[(4αR,8αR)-octahydro-1H-pyrido[3,4-b][1,4]oxazin-6-yl]-6-(3,5-dichlorophenyl)-1,8-naphthyridin-3-yl}pyridin-2-amine;

4-46: 3-{5-[(4αS,8αS)-octahydro-1H-pyrido[3,4-b][1,4]oxazin-6-yl]-6-(3,5-dichlorophenyl)-1,8-naphthyridin-3-yl}pyridin-2-amine.

In some embodiments, provided herein is a pharmaceutically acceptable salt of a compound that is described in Table 4.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or altered metabolic pathways to reduce undesirable metabolites or reduced dosage requirements.

In some embodiments, the compounds of Formula (I) possess one or more stereocenters and each stereocenter exists independently in either the R or S configuration. For example, in some embodiments, the compound of Formula (I) exists in the R configuration when one stereocenter is present. In other embodiments, the compound of Formula (I) exists in the S configuration when one stereocenter is present. In some embodiments, the compound of Formula (I) exists in the RR configuration when two stereocenters are present. In some embodiments, the compound of Formula (I) exists in the RS configuration when two stereocenters are present. In some embodiments, the compound of Formula (I) exists in the SS configuration when two stereocenters are present. In some embodiments, the compound of Formula (I) exists in the SR configuration when two stereocenters are present.

The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers of compounds of Formula (I) is carried out using covalent diastereomeric derivatives of the compounds described herein. In another embodiment, diastereomers of compounds of Formula (I) are separated by separation/resolution techniques based upon differences in solubility. In other embodiments, separation of steroisomers of compounds of Formula (I) is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

Seaparation of individual enantiomers from a racemic mixture is possible by the use of chiral supercritical fluid chromatography (SFC) or chiral high performance liquid chromatography (HPLC). In some embodiments, enantiomers described herein are separated from each other by the use of chiral SFC or chrial HPLC. In some embodiments, compounds of Formula (I) that include one or more chiral centers (e.g. compounds of Formula (I) that include the moiety trans-octahydro-1H-pyrido[3,4-b]morpholin-6-yl) are separated into individual enantiomers using chiral SFC or chrial HPLC. A wide variety of conditions and suitable columns are available.

Daicel polysaccharide chiral stationary phases (CSPs) are among the columns used for chiral SFC separations. In some embodiments, Daicel analytical immobilised and coated CHIRALPAK and CHIRALCEL HPLC columns can be used for SFC analysis.

In some embodiments, screening for the suitability of using a SFC column is performed on the four main immobilised phases (CHIRALPAK IA, IB, IC and ID) and the four main coated columns (CHIRALPAK AD and AS and CHIRALCEL OD and OJ), with varying concentrations of organic modifier. A variety of column phases are available, including but not limited to OD and OJ, OX and OZ chlorinated phases, and a range of complementary cellulose based CHIRALCEL phases including OA, OB, OC, OF, OG and OK.

Non-limiting examples of chiral selectors contemplated for use in the seaparation of enantiomers include amylose tris (3,5-dimethylphenylcarbamate), cellulose tris (3,5-dimethylphenylcarbamate), cellulose tris (3,5-dichlorophenylcarbamate), amylose tris (3-chlorophenylcarbamate), amylose tris (3,5-dichlorophenylcarbamate), amylose tris (3-chloro, 4-methylphenylcarbamate), amylose tris ((S)-alpha-methylbenzylcarbamate), amylose tris (5-chloro-2-methylphenylcarbamate), cellulose tris (4-methylbenzoate), cellulose tris (4-chloro-3-methylphenylcarbamate), and cellulose tris (3-chloro-4-methylphenylcarbamate).

Non-limiting examples of chiral columns contemplated for use in the seaparation of enantiomers include CHIRALPAK IA SFC, CHIRALPAK AD-H SFC, CHIRALPAK IB SFC, CHIRALCEL OD-H SFC, CHIRALPAK IC SFC, CHIRALPAK ID SFC, CHIRALPAK IE SFC, CHIRALPAK IF SFC, CHIRALPAK AZ-H SFC, CHIRALPAK AS-H SFC, CHIRALPAK AY-H SFC, CHIRALCEL OJ-H SFC, CHIRALCEL OX-H SFC, and CHIRALCEL OZ-H SFC.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In some embodiments, the identity of and placement of susbtituents on the compounds described herein help to minimize undesired activity. For example, in some embodiments undesired activity includes undesired hERG inhibition. In some embodiments, the presence of a hydroxyl group and an adjacent cyano group on an aromatic ring reduces undesired hERG inhibition significantly as compared to the lack of both groups, the presence of a hydroxyl group without an adjacent cyano group, or the presence of a cyano group without an adjacent hydroxyl group. For example, in some embodiments significant reduction of undesired hERG inhibition is observed when $R^B$ is a substituted or unsubstituted 2-hydroxy-3-cyanophenyl.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

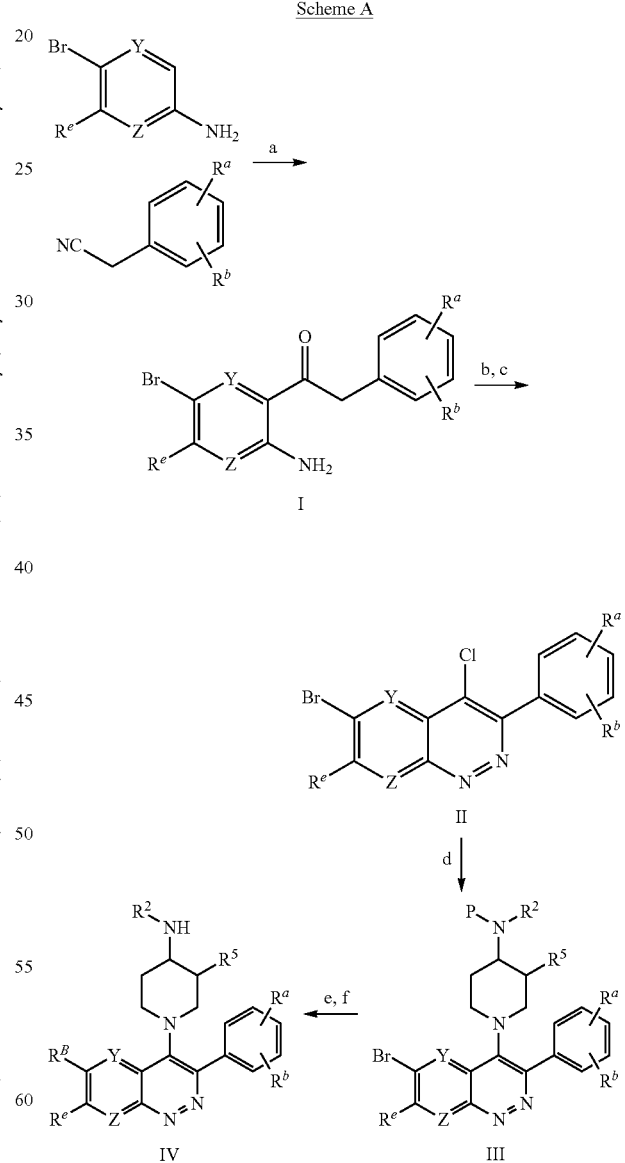

P = protecting group
a: BCl$_3$, AlCl$_3$. b: NaNO$_2$, HCl. c: POCl$_3$. d: a cyclic amine, Et$_3$N. e: R$^B$B(OH)$_2$, Pd.
f: deprotection Friedel-Crafts acylation of an aniline with an aryl acetonitrile in the presence of $BCl_3$ and $AlCl_3$ formed compound I. Compound I reacted with $NaNO_2$ in the presence of a strong acid such as HCl to form a cinnolin-4-ol, and followed by chlorination with $POCl_3$ leads to formation of compound II. A nucleophilic aromatic substitution with a corresponding cyclic amine in the presence of $Et_3N$ or DIEA yields compound III. $R^B$ was introduced by an organometallic coupling reaction such as Suzuki-Miyaura reaction with $R^B B(OH)_2$, or its boronic ester and subsquent removal of all protecting groups using appropriate deprotection methods such as acid, yield the compound IV.

In some other embodiments, compounds described herein are prepared as described in Scheme B.

Scheme B:

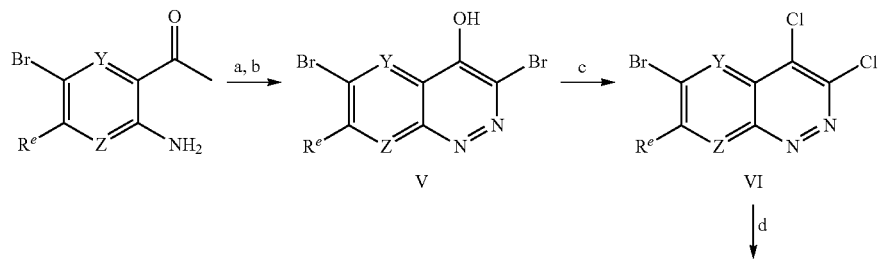

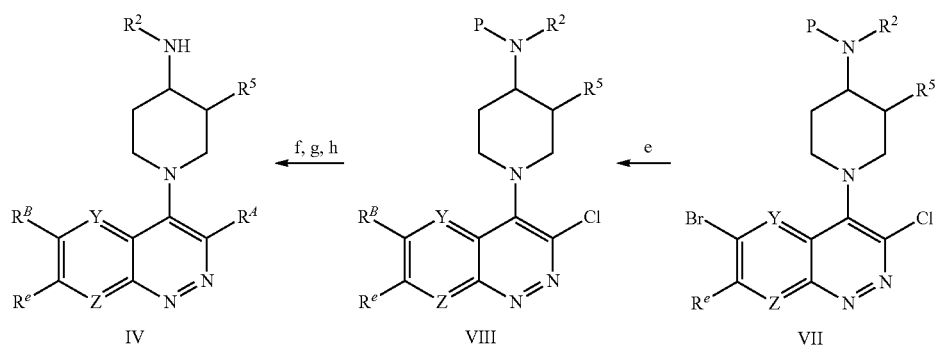

P = protecting group
a: $NaNO_2$, HCl. b: $Br_2$, NaOAc, AcOH. c: $POCl_3/PCl_5$. d: a cyclic amine, $Et_3N$. e: $R^B B(OH)_2$, Pd.
f: $R^4 B(OH)_2$, Pd, or $R^4 ZnBr$, Pd, or $R^4 H$, Pd, or $R^4 H$, $Et_3N$. g: deprotection. h: $R^2 X$, $Et_3N$, when $R^2$ = H Commercially available 1-(2-amino-5-bromophenyl) ethanone was treated with NaNO₂ in the presence of a strong acid such as HCl to form a cinnolin-4-ol, and followed by bromination leads to formation of compound V. Compound V was converted to compound VI under refluxing condition in the presence of POCl₃/PCl₅. A nucleophilic aromatic substitution with a corresponding cyclic amine in the presence of Et₃N or DIEA yields compound VII. Two consecutive but selective Suzuki-Miyaura reactions with R$^B$B(OH)₂ or its boronic ester and R$^A$(OH)₂, or its boronic ester and subsquent removal of all protecting groups using appropriate deprotection methods such as acid lead to formation of compound IV. Alkyls, substituted alkyl, or oxetanyl for R² of IV were also introduced by a SN₂ reaction or reductive amination if R² was hydrogen after deprotection or before deprotection. Alternatively, R$^A$ was introduced by a Negishi coupling reaction with a corresponding zinc reagent, or a Buchwald-Hartwig amination, or a nucleophilic aromatic substitution with a corresponding cyclic saturated amine in the presence of Et₃N.

In some other embodiments, the intermediate VIII is synthesized as outlined in Scheme C.

Scheme C

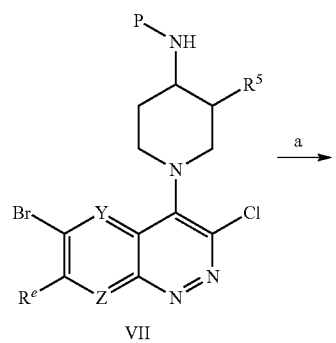

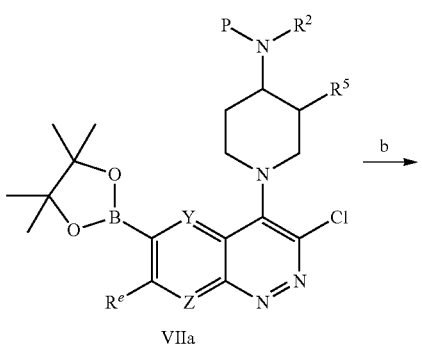

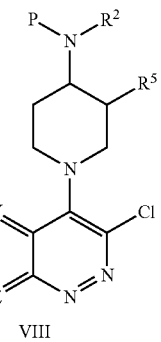

a: Bis(pinacolato)diboron, Pd, X-Phos, KOAc. b: R$^B$X, Pd.

Compound VII reacted with bis(pinacolato)diboron in the presence of a palladium catalyst such as Pd₂dba₃ and a ligand such as X-Phos to form the boronic ester VIIa, and followed by selective Suzuki-Miyaura reactions with R$^B$X (X=Cl, Br, OTf or I) leads to formation of compound VIII. Following the same route in Scheme B from VIII to IV, the final desired compounds were prepared.

In some embodiments, compounds described herein are prepared as described in Scheme D.

Scheme D

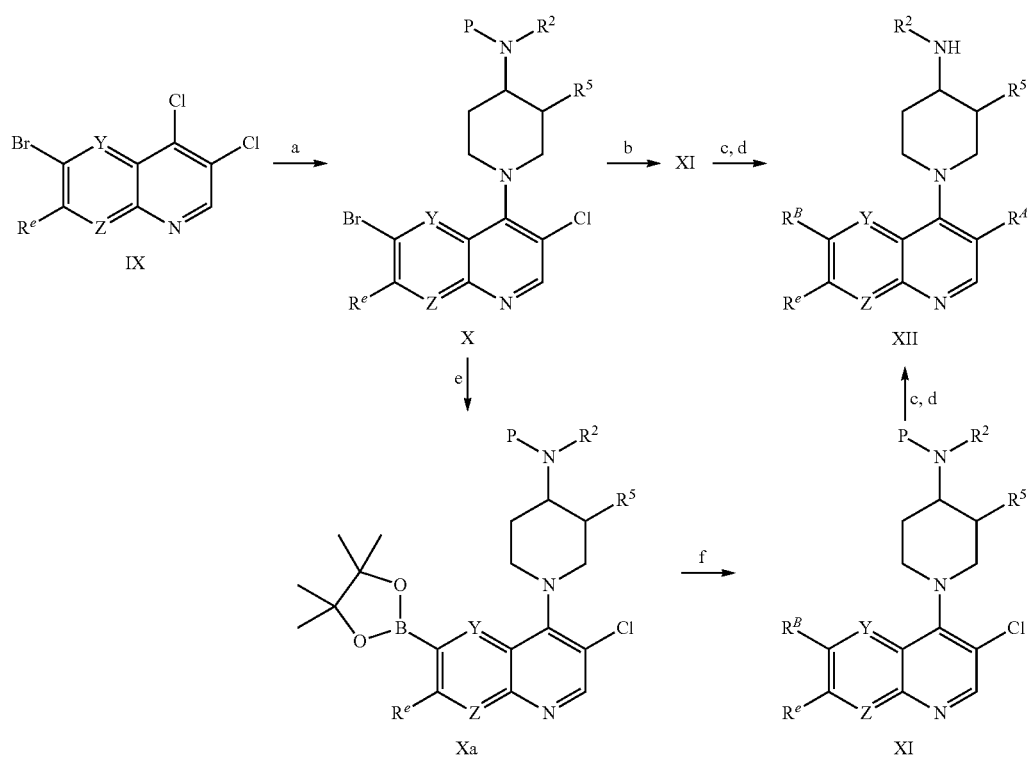

a: A cyclic amine, Et₃N. b: R^B B(OH)₂, Pd. c: R^A B(OH)₂, Pd. d: deprotection.
e: bis(pinacolate)diboron, Pd, X-Phos, KOAc. f: R^B X, Pd Compound IX was converted to compound X by a nucleophilic replacement with a corresponding cyclic amine over chloro in the presence of Et₃N or DIEA. Selective Suzuki-Miyaura reactions with $R^B B(OH)_2$ or its boronic ester yield XI, which was also prepared by a two step sequence through formation of the boronc ester (Xa) and selective Suzuki-Miyaura reactions with $R^B X$ (X=Cl, Br, or I). Suzuki-Miyaura reactions with $R^A(OH)_2$ or its boronic ester and removal of all protecting groups using appropriate deprotection methods such as acid lead to formation of compound XII.

In some embodiments, compounds described herein are prepared as described in Scheme E using V as the starting material.

Scheme E

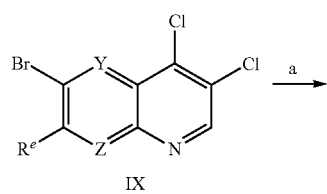

IX

-continued

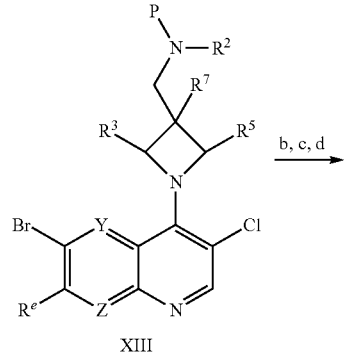

a: A cyclic amine, Et₃N. b: R^B B(OH)₂, Pd. c: R^A B(OH)₂, Pd. d: deprotection

Compound IX was converted to compound XIII by a nucleophilic aromatic substitution with a corresponding cyclic amine in the presence of Et₃N or DIEA. Two consecutive but selective Suzuki-Miyaura reactions with R^B B(OH)₂ and R^A B(OH)₂, and subsquent removal of all protecting groups using appropriate deprotection methods such as acid lead to formation of compound XIV. If it is necessary, R² substitution can be introduced at XIII where R² is a hydrogen, XIII can react with R²X (X=Br, I, OMs, OTf) under strong base such as NaH. If it is necessary, R² substitution can also be introduced on XIV where R² is hydrogen. A reductive amination with aldehyde or ketone can be conducted with reducing reagent such as NaBH(OAc)₃ or NaBH₄ to afford R² substituted XIV.

In some embodiments, compounds described herein are prepared as described in Scheme F.

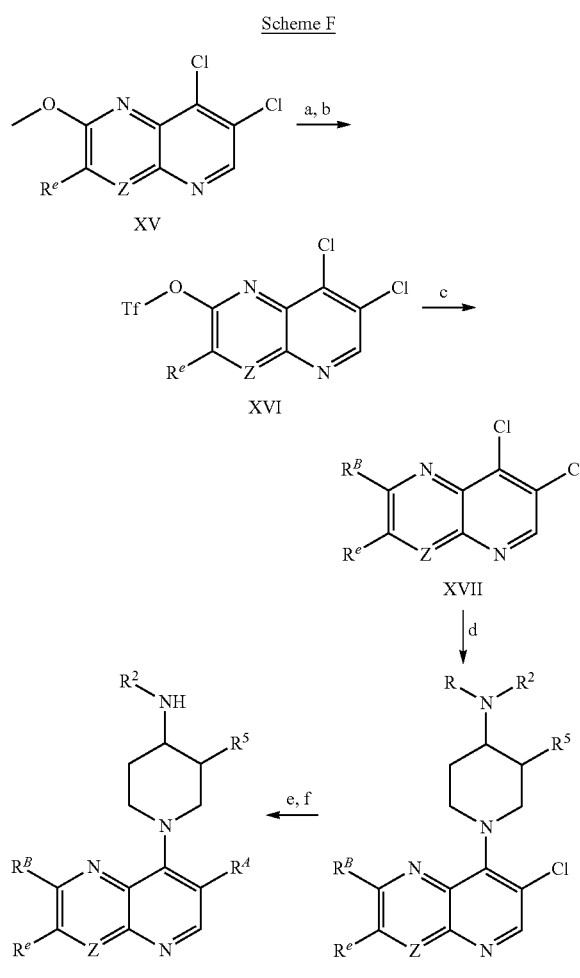

a: HCl. b: Tf₂O, Et₃N. c: R^B B(OH)₂, Pd. d: a cyclic amine, Et₃N. e: R^A(OH)₂, Pd. f: deprotection.

Compound XVI was prepared by a two step sequence through demethylation of XV under refluxing condition in 6N HCl and formation of the triflate with triflic anhydride in the presence of a base. Compound XVI undergoes a selective Suzuki-Miyaura reaction with R^B B(OH)₂ or its boronic ester to yield XVII. Compound XVII was converted to compound XVIII by a nucleophilic aromatic substitution with a corresponding cyclic amine in the presence of Et₃N. Suzuki-Miyaura reactions with R^A(OH)₂ or its boronic ester and removal of all protecting groups using appropriate deprotection methods such as acid lead to formation of compound XIX.

In some embodiments, compound XIX described herein is prepared as described in Scheme G.

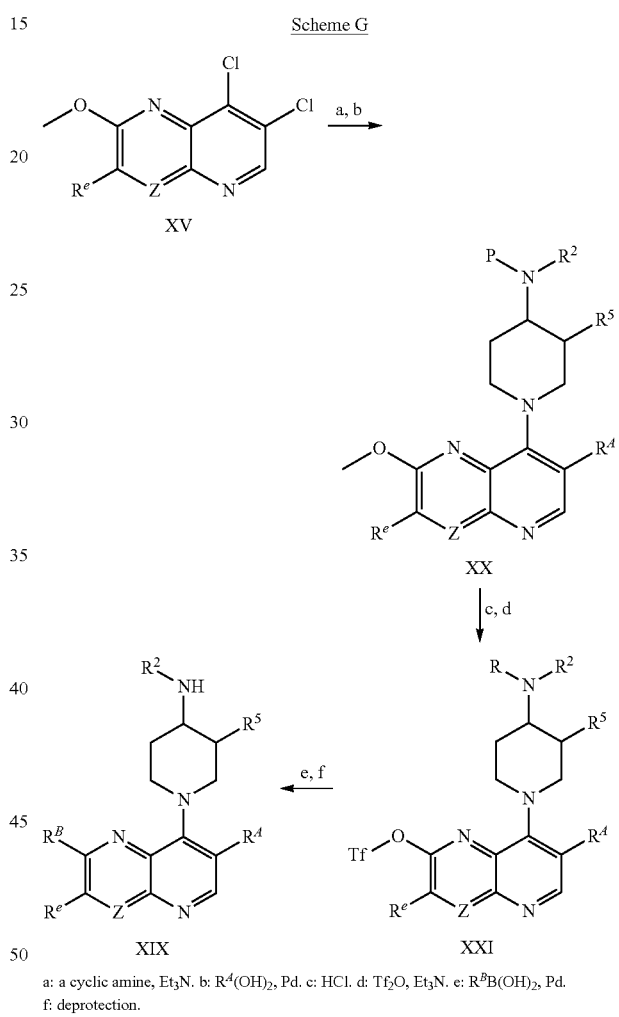

a: a cyclic amine, Et₃N. b: R^A(OH)₂, Pd. c: HCl. d: Tf₂O, Et₃N. e: R^B B(OH)₂, Pd. f: deprotection.

Compound XV was transformed to XX by a selective nucleophilic aromatic substitution with a corresponding cyclic amine in the presence of Et₃N and a Suzuki-Miyaura reaction with R^A(OH)₂ or its boronic ester. Compound XXI was prepared by a two step sequence through demethylation of XX under refluxing condition in 6N HCl and formation of the triflate with triflic anhydride in the presence of a base. Suzuki-Miyaura reactions with R^B B(OH)₂ and removal of all protecting groups using appropriate deprotection methods such as acid lead to formation of compound XIX.

In some embodiments, compound XIV described herein is prepared as described in Scheme H

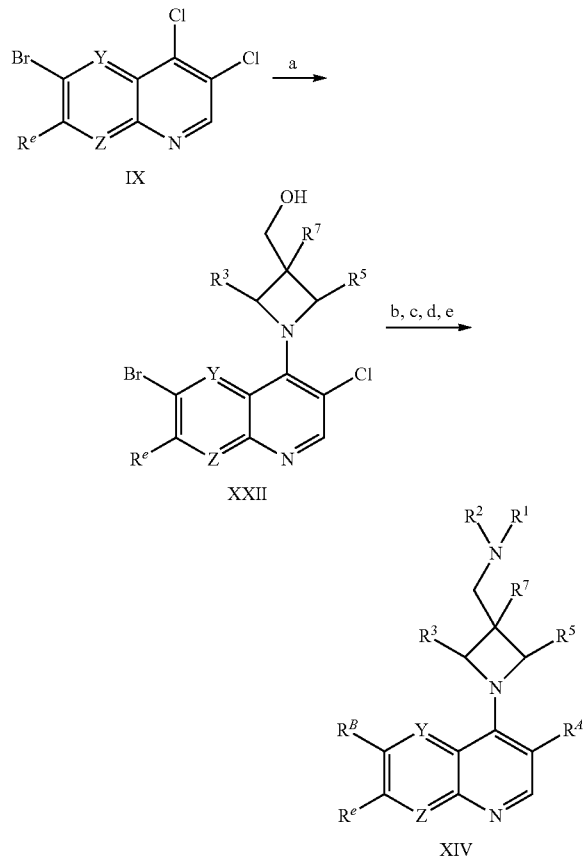

a: A cyclic amine, Et₃N. b: $R^B B(OH)_2$, Pd. c: $R^A B(OH)_2$, Pd. d: $CBr_4$, $PPh_3$
e: $R^2 R^1 NH$ Compound IX was transformed to XXII by a selective nucleophilic aromatic substitution with a corresponding cyclic amine in the presence of Et₃N, and two connective but selective Suzuki-Miyaura reactions with $R^B(OH)_2$ or its boronic ester and then $R^A(OH)_2$ or its boronic ester, followed by converting the free alcohol group to bromide or mesylate with the well known methods, then replacement of such group with $R^2R^1NH$ to yield XIV (if necessary, a deprotection of protecting group on $R^B$, $R^2$ or $R^1$ can be performed).

In some embodiments, the compounds obtained from the above mentioned methods are prepared as racemic or diastereomic mixtures. In some other embodiments, racemic mixtures of the compounds are separated to obtain optically pure (or optically enriched) isomers by the use of common chiral separation methods such as chiral HPLC, chiral supercritical fluid chromatographic system (SFC), simulated moving bed chromatography (SMB), and the like.

In some other embodiments, diastereomic mixtures of the compounds are separated to obtain optically pure (or optically enriched) isomers by the use of crystallization methods or common non-chiral chromatography methods such as silica gel chromatography or chiral chromatography methods such as chiral HPLC, chiral supercritical fluid chromatographic system (SFC), simulated moving bed chromatography (SMB), and the like.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH_2CH_2$—, —$CH_2CH_2CH_2$—, —$CH_2CH_2CH_2CH_2$—, and the like. In some embodiments, an alkylene is —$CH_2$—.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —$CH_2OH$, —$CH_2CH_2OH$, —$CH_2CH_2CH_2OH$, —$CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, and the like.

The term "alkenyl" refers to a type of alkyl group in which at least one carbon-carbon double bond is present. In one embodiment, an alkenyl group has the formula —C(R)═CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$ —C≡CCH$_2$CH$_3$, —CH$_2$C≡CH.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, a heteroalkyl is a $C_1$-$C_6$heteroalkyl includes 1-2 heteroatoms selected from O, N (e.g. —NH— or —N($C_1$-$C_4$alkyl)-), and S. In some embodiments, a heteroalkyl is a $C_1$-$C_6$heteroalkyl includes 1-2 O atoms. In some embodiments, a heteroalkyl is a $C_1$-$C_4$heteroalkyl. Examplary heteroalkyls include, but are not limited to, —CH$_2$OH, —CH$_2$OCH$_3$, —CH$_2$OCH$_2$CH$_3$, —CH$_2$CH$_2$OCH$_3$, —CH$_2$OCH$_2$CH$_2$OCH$_3$, —CH$_2$CH$_2$OCH$_2$CH$_2$OCH$_3$, —CH$_2$SH, —CH$_2$SCH$_3$, —CH$_2$SCH$_2$CH$_3$, —CH$_2$CH$_2$SCH$_3$, —CH$_2$SCH$_2$CH$_2$SCH$_3$, —CH$_2$CH$_2$SCH$_2$CH$_2$SCH$_3$, —CH$_2$NH$_2$CH$_2$NHCH$_3$, —CH$_2$N(CH$_3$)$_2$—CH$_2$N(CH$_2$CH$_3$)$_2$, and the like. In some embodiments, a heteroalkyl is —CH$_2$OCH$_3$, —CH$_2$OCH$_2$CH$_3$, —CH$_2$CH$_2$OCH$_3$, —CH$_2$OCH$_2$CH$_2$OCH$_3$, or —CH$_2$CH$_2$OCH$_2$CH$_2$OCH$_3$.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, a carbocycle is a monocyclic carbocycle or a bicyclic carbocycle. In some embodiments, a carbocycle is a monocyclic carbocycle. Carbocycles are non-aromatic or aromatic. Non-aromatice carbocyles are saturated or partially unsaturated. In some embodiments, a carbocycle is a bicyclic carbocycle. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicycicic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group in which one or more skeletal atoms of the cycloalkyl are selected from an atom other than carbon, e.g., oxygen, nitrogen (e.g. —NH—, —N(alkyl)-, sulfur, or combinations thereof. In some embodiments, a heterocycloalkyl is fused with an aryl or heteroaryl. In some embodiments, the heterocycloalkyl is oxiranyl, aziridinyl, oxetanyl, oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co- agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non- aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

Abbreviations:
BINAP: (2,2'-bis(diphenylphosphino)-1,1'-binaphthyl);
DCE: 1,2-dichloroethane;
DCM: dichloromethane;
DIEA or DIPEA: diisopropylethylamine;
EtOAc: ethyl acetate;
HATU: 1-[bis(dimethylamino)methylene]-1H-1,2,3-triazolo[4,5-b]pyridinium 3-oxid hexafluorophosphate;
IPA: isopropylalcohol;
NBS: N-bromosuccinimide;
NCS: N-chlorosuccinimide;
PTS: p-toluene sulfonic acid;
Pd(amphos)Cl$_2$: bis(di-tert-butyl(4-dimethylaminophenyl)phosphine)dichloropalladium(II);
Pd$_2$dba$_3$: tris(dibenzylideneacetone)dipalladium(0);
(pinB)$_2$: bis(pinacolato)diboron;
rt or RT: room temperature;
Rt: retention time;
SFC: supercritical fluid chromatography;
SST: somatostatin;
SSTR: somatostatin receptor;
TEA: trimethylamine;
TEA: trifluoroacetic acid;
Xphos: 2-dicyclohexylphosphino-2',4',6'-triisopropylbiphenyl;
hrs: hours;
h or hr: hour.

The following examples are provided for illustrative purposes only and not to limit the scope of the claims provided herein.

Synthesis of Compounds

Example 1

3-[4-(4-aminopiperidin-1-yl)-7-chloro-3-(3-fluoro-5-methylphenyl)cinnolin-6-yl]-5-fluorobenzamide (Compound No. 1-4)

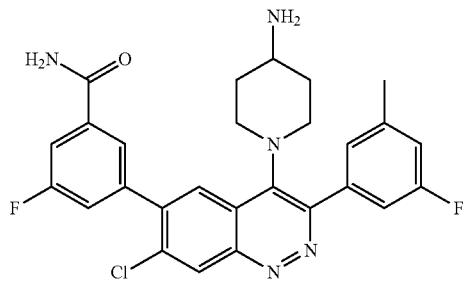 [SMILES: Cc1cc(F)cc(-c2nnc3cc(Cl)c(-c4cc(F)cc(C(N)=O)c4)cc3c2N2CCC(N)CC2)c1]

Step 1-1, preparation of 1-(2-amino-5-bromo-4-chloro-phenyl)-2-(3-fluoro-5-methyl-phenyl)-ethanone: To a solution of 1M-BCl$_3$ (17.2 mL, 18 mmol, in DCM) in DCE (30 mL) was added 4-Bromo-3-chloro-phenylamine (3.5 g, 16.9 mmol) under ice-cooling. After stirring for 30 min, the mixture was sequentially treated with (3-Fluoro-5-methyl-phenyl)-acetonitrile (5.0 g, 42 mmol) and AlCl$_3$ (2.5 g, 18 mmol). The reaction was refluxed for 2 days and cooled down to room temperature. The reaction was quenched with 2N-HCl (16 mL) and stirred for 1 h at 80° C. The reaction was extracted with DCM (2×), and the combined organic layers were dried with anhydrous Na$_2$SO$_4$ and concentrated. The residue was purified by column chromatography to afford the title compound (1.8 g, 30%). MS (M+H)$^+$=356.1

Step 1-2, preparation of 6-bromo-7-chloro-3-(3-fluoro-5-methyl-phenyl)-cinnolin-4-ol: To a suspension of 1-(2-amino-5-bromo-4-chloro-phenyl)-2-(3-fluoro-5-methyl-phenyl)-ethanone (1.7 g, 4.8 mmol) in 5N-HCl (20 mL) under ice cooling was slowly added NaNO$_2$ (510 mg, 7.3 mmol) in H$_2$O (3 mL). The reaction was stirred for 1.5 h at 85° C., and cooled to room temperature. The solid ppts were filtered, and the filtered solid was triturated in MeOH to produce fine solid powder. The solid product was filtered again, washed with MeOH, and dried to afford the title compound (1.1 g, 64%). MS (M+H)$^+$=367.0.

Step 1-3, preparation of 6-bromo-4,7-dichloro-3-(3-fluoro-5-methyl-phenyl)-cinnoline: A mixture of 6-bromo-7-chloro-3-(3-fluoro-5-methyl-phenyl)-cinnolin-4-ol (1.1 g, 3 mmol) and POCl$_3$ (10 mL) was stirred for 2.5 h at 100° C. During the reaction progress, the heterogenous solution became a clear solution. The reaction was cooled to room temperature, and slowly poured into ice (~40 g) under ice cooling. The solid ppts were collected, washed with H$_2$O, triturated in MeOH, filtered again, and dried to afford the title compound (1.1 g, 96%). MS (M+H)$^+$=385.3.

Step 1-4, preparation of {1-[6-bromo-7-chloro-3-(3-fluoro-5-methyl-phenyl)-cinnolin-4-yl]-piperidin-4-yl}-carbamic acid tert-butyl ester: 6-Bromo-4,7-dichloro-3-(3-fluoro-5-methyl-phenyl)-cinnoline (0.38 g, 0.98 mmol), piperidin-4-yl-carbamic acid tert-butyl ester (320 mg, 1.6 mmol), triethylamine (0.66 mL, 4.9 mmol), and IPA (6 mL) was filled into a seal tube, and the mixture was stirred for 20 h at 130° C. The reaction was cooled to room temperature, diluted with EtOAc, washed with 1N-HCl (2×), dried, and concentrated. The residue was purified by column chromatography to afford the title compound (0.21 g, 39%). MS (M+H)⁺=549.6.

Step 1-5, preparation of {1-[6-(3-carbamoyl-5-fluoro-phenyl)-7-chloro-3-(3-fluoro-5-methyl-phenyl)-cinnolin-4-yl]-piperidin-4-yl}-carbamic acid tert-butyl ester: A mixture of {1-[6-bromo-7-chloro-3-(3-fluoro-5-methyl-phenyl)-cinnolin-4-yl]-piperidin-4-yl}-carbamic acid tert-butyl ester (50 mg, 0.09 mmol), 3-carbamoyl-5-fluorobenzeneboronic acid (25 mg, 0.14 mmol), PdCl$_2$(t-Bu$_2$PPhNMe$_2$)$_2$ (6.5 mg, 0.009 mmol), and K$_2$CO$_3$ (25 mg, 0.18 mmol) in dioxane/H$_2$O (10/1=2 mL/0.2 mL) was degassed with N$_2$ for 5 min, and then sealed. The reaction mixture was stirred for 1 h at 80° C. and cooled to room temperature. The reaction was filtered through a pad of celite, and the volatile solvent was removed under vacuum. The residue was directly purified by column chromatography to afford the title compound (30 mg, 54%). MS (M+H)⁺=608.3.

Step 1-6, preparation of 3-[4-(4-amino-piperidin-1-yl)-7-chloro-3-(3-fluoro-5-methyl-phenyl)-cinnolin-6-yl]-5-fluoro-benzamide: A solution of {1-[6-(3-carbamoyl-5-fluoro-phenyl)-7-chloro-3-(3-fluoro-5-methyl-phenyl)-cinnolin-4-yl]-piperidin-4-yl}-carbamic acid tert-butyl ester (30 mg, 0.049 mmol) and TFA (0.3 mL) in DCM (1.5 mL) was stirred for 1 h at room temperature. After removal of the volatile solvent, the residue was directly purified by using a reverse phase C18 column to afford the title compound (15.5 mg, 62%). MS (M+H)⁺=508.4.

Step 1-7, preparation of HCl salt: The product described in Step 1-6 was dissolved in dioxane or DCM. The resulting solution was treated with 4N-HCl in dioxane (~2 eq.) and stirred for 10 min at room temperature. The solution was concentrated under high vacuum to give the final product as a HCl salt.

The following compounds were prepared in a similar manner as described in Example 1, substituting with appropriate reagents and substrates as required:

| Compound no. | MS (M + H)⁺ |
| --- | --- |
| 1-1 | 504.3 |
| 1-2 | 484.4 |
| 1-5 | 526.3 |
| 1-6 | 526.4 |
| 1-7 | 488.4 |
| 1-8 | 503.3 |
| 1-9 | 503.3 |
| 1-10 | 538.5 |
| 1-27 | 508.3 |
| 1-28 | 523.5 |
| 1-30 | 510.5 |
| 1-34 | 496.5 |

Example 2

3-[4-(4-aminopiperidin-1-yl)-3-(3-chloro-5-methyl-phenyl)cinnolin-6-yl]-2-hydroxybenzonitrile (Compound No. 1-18)

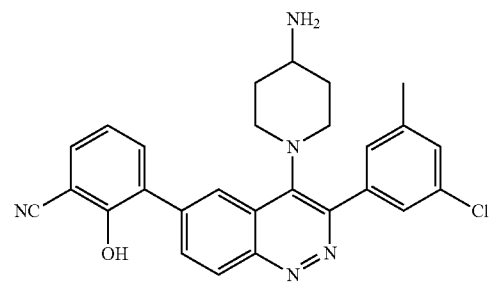 [SMILES: Cc1cc(Cl)cc(-c2nnc3ccc(-c4cccc(C#N)c4O)cc3c2N2CCC(N)CC2)c1]

Step 2-1, preparation of 6-bromo-cinnolin-4-ol: To a suspension of 1-(2-amino-5-bromo-phenyl)-ethanone (5.000 g, 23.35 mmol) in 5 N HCl (aq) (70 mL) at 0° C. was slowly added a solution of sodium nitrite (1.933 g, 28.01 mmol) in H$_2$O (5 mL). After stirring at 0° C. for 15 min, the reaction solution was heated at 85° C. for 1 hr. The mixture was cooled to RT and the solid was collected by vacuum filtration and washed with water to afford the title compound (3.947 g, 75.1% yield) as a brown solid. MS (M+H)⁺=225.2.

Step 2-2, preparation of 3,6-dibromo-cinnolin-4-ol: To a suspension of 6-bromo-cinnolin-4-ol (3.947 g, 17.54 mmol) and sodium acetate (2.589 g, 31.57 mmol) in AcOH (25 mL) at 100° C. was added a solution of bromine (1.4 mL, 27.16 mmol) in AcOH (18 mL). The mixture was heated at 100° C. for 1 hr. The mixture was cooled to RT and diluted with water (150 mL). The solid was collected by vacuum filtration and washed with water to afford the title compound (5.141 g, 96.5% yield) as a brown solid. MS (M+H)⁺=304.9.

Step 2-3, preparation of 6-bromo-3,4-dichloro-cinnoline: To 3,6-dibromo-cinnolin-4-ol (3.611 g, 11.88 mmol) was added POCl$_3$ (15 mL, 160.5 mmol) and PCl$_5$ (2.527 g, 12.14 mmol). The mixture was heated at 120° C. for 2 hr. The mixture was cooled to RT and poured into ice. The suspension was stirred for about 30 min until solid was crushed out. The solid was collected by vacuum filtration and washed with water to afford the title compound (3.119 g, 94.5% yield) as a brown solid. MS (M+H)⁺=279.0.

Step 2-4, preparation of [1-(6-bromo-3-chloro-cinnolin-4-yl)-piperidin-4-yl]-carbamic acid tert-butyl ester: A suspension of 6-bromo-3,4-dichloro-cinnoline (2.000 g, 7.197 mmol), piperidin-4-yl-carbamic acid tert-butyl ester (2.162 g, 10.79 mmol), and diisopropylethylamine (5.0 mL, 28.72 mmol) in IPA (20 mL) in a sealed tube was heated at 120° C. overnight. The mixture was concentrated and purified by silica gel column chromatography to afford the title compound (2.117 g, 66.6% yield) as a yellow solid. MS (M+H)⁺=443.4.

Step 2-5, preparation of {1-[3-chloro-6-(3-cyano-2-methoxymethoxy-phenyl)-cinnolin-4-yl]-piperidin-4-yl}-carbamic acid tert-butyl ester: To a mixture of [1-(6-bromo-3-chloro-cinnolin-4-yl)-piperidin-4-yl]-carbamic acid tert-butyl ester (0.400 g, 0.905 mmol), 2-methoxymethoxy-3-(4,4,5,5-tetramethyl-[1,3,2]dioxaborolan-2-yl)-benzonitrile (0.314 g, 1.086 mmol), tris(dibenzylideneacetone) dipalladium/tri-tert-butyl phosphonium tetrafluoroborate mixture (mole ratio: 1/1.2) (58.9 mg, 0.0452 mmol), and K$_3$PO$_4$·H$_2$O (0.834 g, 3.620 mmol) was added THF (6 mL) and water (0.6 mL). The mixture was bubbled with N₂ for 10 min and then stirred at RT for 1 hr. The organic layer was separated and the aqueous layer was extracted with EtOAc (1×). The combined organics were concentrated to dryness and the residue was purified by silica gel chromatography to afford the title compound (0.396 g, 83.6% yield) as a yellow solid. MS (M+H)⁺=524.3.

Step 2-6, preparation of {1-[3-(3-chloro-5-methyl-phenyl)-6-(3-cyano-2-methoxymethoxy-phenyl)-cinnolin-4-yl]-piperidin-4-yl}-carbamic acid tert-butyl ester: To a mixture of {1-[3-chloro-6-(3-cyano-2-methoxymethoxy-phenyl)-cinnolin-4-yl]-piperidin-4-yl}-carbamic acid tert-butyl ester (50.0 mg, 0.0954 mmol), 3-chloro-5-methylphenylboronic acid (19.5 mg, 0.114 mmol), Pd[t-Bu₂P(4-NMe₂C₆H₄)]₂Cl₂) (8.1 mg, 10 mol %), and K₂CO₃ (39.6 mg, 0.286 mmol) in a sealed tube was added dioxane (3 mL) and water (0.3 mL). The reaction mixture was bubbled with N₂ (g) for 10 min and then heated at 100° C. for 30 min. Due to unreacted starting material, more 3-chloro-5-methylphenylboronic acid (13.0 mg, 0.0763 mmol), Pd[t-Bu₂P(4-NMe₂C₆H₄)]₂Cl₂) (8.1 mg), and K₂CO₃ (39.6 mg) were added. After N₂ (g) bubbling for 5 min, the reaction was continued to heat at 95° C. for additional 30 min. The mixture was concentrated and purified by silica gel column chromatography and C₁₈ reversed-phase column chromatography (2$^{nd}$ purification). Pure fractions were combined, basified with saturated NaHCO₃ (aq), and concentrated to remove MeCN. The aqueous residue was extracted with DCM (2×) and the combined organics were dried over anhydrous Na₂SO₄ and concentrated to dryness to afford the title compound (34.8 mg, 59.4% yield) as a brown solid. MS (M+H)⁺=614.3.

Step 2-7, preparation of 3-[4-(4-amino-piperidin-1-yl)-3-(3-chloro-5-methyl-phenyl)-cinnolin-6-yl]-2-hydroxy-benzonitrile: To a solution of {1-[3-(3-chloro-5-methyl-phenyl)-6-(3-cyano-2-methoxymethoxy-phenyl)-cinnolin-4-yl]-piperidin-4-yl}-carbamic acid tert-butyl ester (34.8 mg, 0.0567 mmol) in dioxane (0.5 mL) was added 4 N HCl in dioxane (1.0 mL). The mixture was stirred at RT for 1 hr. The solid was collected by vacuum filtration and washed with dioxane and hexanes to afford the title compound as 2 HCl salt (25.7 mg, 84.4% yield) as an orange solid. MS (M+H)⁺=470.5.

The following compounds were prepared in a similar manner as described in Example 2, substituting with appropriate reagents and substrates as required:

| Compound no. | MS (M + H)⁺ |
| --- | --- |
| 1-11 | 524.3 |
| 1-12 | 522.4 |
| 1-13 | 474.2 |
| 1-14 | 478.2 |
| 1-15 | 474.2 |
| 1-16 | 469.5 |
| 1-17 | 454.4 |
| 1-19 | 474.3 |
| 1-20 | 458.4 |
| 1-21 | 490.4 |
| 1-22 | 488.4 |
| 1-23 | 503.3 |
| 1-24 | 503.4 |
| 1-29 | 463.2 |

Example 3

3-[7-chloro-3-(3-fluoro-5-methylphenyl)-4-{4-[(2-fluoroethyl)amino]piperidin-1-yl}cinnolin-6-yl]-5-fluorobenzamide (Compound No. 1-25)

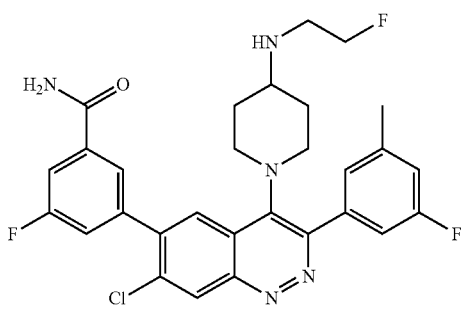 [SMILES: Cc1cc(F)cc(-c2nnc3cc(Cl)c(-c4cc(F)cc(C(N)=O)c4)cc3c2N2CCC(NCCF)CC2)c1]

Step 3-1, preparation of 3-[7-chloro-3-(3-fluoro-5-methylphenyl)-4-{4-[(2-fluoroethyl)amino]piperidin-1-yl}cinnolin-6-yl]-5-fluorobenzamide: A mixture of 3-[4-(4-amino-piperidin-1-yl)-7-chloro-3-(3-fluoro-5-methyl-phenyl)-cinnolin-6-yl]-5-fluoro-benzamide (10 mg, 0.019 mmol), 1-fluoro-2-iodoethane (35 mg, 1.9 mmol), and Et₃N (12 mL, 0.08 mmol) in IPA (1.5 mL) was filled into a seal tube and then stirred overnight at 125° C. After removal of the volatile solvent, the residue was purified by a reverse phase C18 column chromatography to afford the title compound, which was converted to HCl salt (3.0 mg, 25%) by the similar manner described in Step 1-7, Example 1. MS (M+H)⁺=554.4.

The following compounds were prepared in a similar manner as described in Example 3, substituting with appropriate reagents and substrates as required:

| Compound no. | MS (M + H)⁺ |
| --- | --- |
| 1-32 | 606.3 |
| 1-33 | 556.2 |

Example 4

3-[4-(4-amino-piperidin-1-yl)-3-(3,5-difluoro-phenyl)-quinolin-6-yl]-2-hydroxy-benzonitrile (Compound No. 2-2)

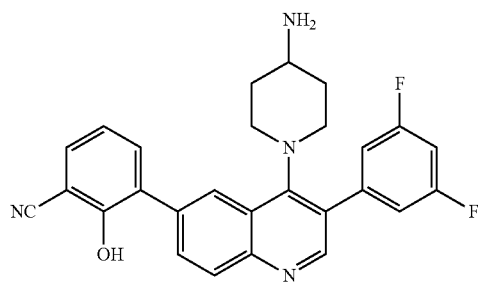 [SMILES: N#Cc1cccc(-c2ccc3ncc(-c4cc(F)cc(F)c4)c(N4CCC(N)CC4)c3c2)c1O]

Step 4-1, preparation of [1-(6-bromo-3-chloro-quinolin-4-yl)-piperidin-4-yl]-carbamic acid tert-butyl ester: To an anhydrous DMSO (40 mL) solution of 6-bromo-3,4-dichloro-quinoline (14.0 mmol, 3.9 g) was added N,N-diisopropylethylamine (10 mL) and piperidin-4-yl-carbamic acid tert-butyl ester (2.0 eq., 28 mmol, 5.6 g). N$_2$ was bubbled through the reaction solution for 5 min and the resulting solution was heated at 140° C. for 1 h. The reaction mixture was diluted with ethyl acetate and washed with water and brine. The organic layer was separated, dried with MgSO$_4$ and concentrated. The residue obtained was purified by silica gel chromatography eluting with ethyl acetate/hexane (0~50%) to give 4.0 g of the desired product as white solid. MS (M+H)$^+$=442.6.

Step 4-2A (Method A), preparation of 1-{3-chloro-6-[3-cyano-2-(2-methoxy-ethoxymethoxy)-phenyl]-quinolin-4-yl}-piperidin-4-yl)-carbamic acid tert-butyl ester: To a THF (5.0 mL) solution of [1-(6-bromo-3-chloro-quinolin-4-yl)-piperidin-4-yl]-carbamic acid tert-butyl ester (1.0 mmol, 440 mg) and 2-(2-methoxy-ethoxymethoxy)-3-(4,4,5,5-tetramethyl-[1,3,2]dioxaborolan-2-yl)-benzonitrile (1.4 eq., 1.4 mmol, 460 mg) was added PdCl$_2$dppf (0.1 eq., 0.1 mmol, 75 mg) and KOAc (3.0 eq., 3.0 mmol, 300 mg). N$_2$ was bubbled through the reaction solution for 5 min and 0.5 mL water was added. The resulting mixture was heated at 80° C. for 1 h. LCMS analysis showed about 50% of the starting material has been converted to the desired product. Additional 2-(2-methoxy-ethoxymethoxy)-3-(4,4,5,5-tetramethyl-[1,3,2]dioxaborolan-2-yl)-benzonitrile (1.4 eq., 1.4 mmol, 460 mg), PdCl$_2$dppf (0.1 eq., 0.1 mmol, 75 mg) and KOAc (3.0 eq., 3.0 mmol, 300 mg) were added and the resulting solution was heated at 80° C. for another 2 h. The reaction solution was combined with silica gel and concentrated. The residue obtained was purified by silica gel chromatography eluting with ethyl acetate/hexane (0~50%) to give 0.512 g of the desired product as white solid. MS (M+H)$^+$=567.6.

Step 4-2B (Method B), preparation of 1-{3-chloro-6-[3-cyano-2-(2-methoxy-ethoxymethoxy)-phenyl]-quinolin-4-yl}-piperidin-4-yl)-carbamic acid tert-butyl ester: 1) Step 4-2B-1, preparation of {1-[3-chloro-6-(4,4,5,5-tetramethyl-[1,3,2]dioxaborolan-2-yl)-quinolin-4-yl]-piperidin-4-yl}-carbamic acid tert-butyl ester: Pd$_2$(dba)$_3$ (0.05 eq., 0.35 mmol, 323 mg) and Xphos (0.10 eq., 0.70 mmol, 335 mg) were added to anhydrous dioxane (25 mL). N$_2$ was bubbled through the reaction solution for 5 min. [1-(6-bromo-3-chloro-quinolin-4-yl)-piperidin-4-yl]-carbamic acid tert-butyl ester (3.1 g, 7.07 mmol), bis(pincolato)diborane (1.5 eq., 10.6 mmol, 2.70 g) and KOAc (3.0 eq., 21.2 mmol, 2.1 g) were added under N$_2$. The reaction solution was heated at 100° C. for 4 h. Ethyl acetate (50 mL) was added to the reaction mixture and the resulting suspension was filtered. The filtrate obtained was concentrated and purified by silica gel chromatography eluting with ethyl acetate/hexane (0~40%) to give 2.26 g of {1-[3-chloro-6-(4,4,5,5-tetramethyl-[1,3,2]dioxaborolan-2-yl)-quinolin-4-yl]-piperidin-4-yl}-carbamic acid tert-butyl ester. MS (M+H)$^+$=488.5.

2) Step 4-2B-2, preparation of 1-{3-chloro-6-[3-cyano-2-(2-methoxy-ethoxymethoxy)-phenyl]-quinolin-4-yl}-piperidin-4-yl)-carbamic acid tert-butyl ester: To a dioxane (15 mL) solution of {1-[3-chloro-6-(4,4,5,5-tetramethyl-[1,3,2]dioxaborolan-2-yl)-quinolin-4-yl]-piperidin-4-yl}-carbamic acid tert-butyl ester (2.12 g, 4.34 mmol) and 3-bromo-2-(2-methoxy-ethoxymethoxy)-benzonitrile (1.3 eq., 5.6 mmol, 1.61 g) were added PdCl$_2$dppf (0.1 eq., 0.43 mmol, 320 mg) and KOAc (3.0 eq., 13.02 mmol, 1.28 g). N$_2$ was bubbled through the reaction solution for 5 min and 1.0 mL water was added. The reaction solution was heated at 100° C. for 1.5 h and LCMS analysis indicated that the starting material has been fully consumed. The reaction solution was worked up with water and brine, dried with Na$_2$SO$_4$, concentrated and purified by silica gel chromatography eluting with ethyl acetate/hexane (0~50%) to give 1.34 g of the desired product. MS (M+H)$^+$=567.5.

Step 4-3, preparation of {1-[6-[3-cyano-2-(2-methoxy-ethoxymethoxy)-phenyl]-3-(3,5-difluoro-phenyl)-quinolin-4-yl]-piperidin-4-yl}-carbamic acid tert-butyl ester: To a dioxane (5 mL) solution of (1-{3-chloro-6-[3-cyano-2-(2-methoxy-ethoxymethoxy)-phenyl]-quinolin-4-yl}-piperidin-4-yl)-carbamic acid tert-butyl ester (0.5 mmol, 283 mg) was added Pd(amphos)Cl$_2$ (0.1 eq., 0.05 mmol, 37 mg), 3,5-difluorophenyl boronic acid (3.0 eq., 1.5 mmol, 250 mg) and K$_2$CO$_3$ (4.0 eq., 2.0 mmol, 276 mg). N$_2$ was bubbled through the reaction solution for 5 min and 0.5 mL water was added. The resulting mixture was heated at 95° C. for 0.5 h and LCMS analysis showed that starting material was completely consumed. The reaction solution was concentrated with silica gel and purified by silica gel chromatography eluting with ethyl acetate/hexane (0~50%) to give 0.170 g of the desired product as white solid. MS (M+H)$^+$=645.6.

Step 4-4, preparation of 3-[4-(4-amino-piperidin-1-yl)-3-(3,5-difluoro-phenyl)-quinolin-6-yl]-2-hydroxy-benzonitrile: to the dichloromethane (5.0 mL) solution of {1-[6-[3-cyano-2-(2-methoxy-ethoxymethoxy)-phenyl]-3-(3,5-difluoro-phenyl)-quinolin-4-yl]-piperidin-4-yl}-carbamic acid tert-butyl ester (170 mg) was added triflurороacetic acid (2.0 mL) and the resulting mixture was stirred at ambient temperature for 2 h. The reaction solution was concentrated and purified by C18 reversed phase chromatography eluting with MeCN/water (0~40%). Pure fractions were combined, neutralized with saturated NaHCO$_3$, extracted with ethyl acetate and dried with MgSO$_4$. The organic solution was concentrated with HCl in ether (2.0 M) to give the final compound as HCl salt. MS (M+H)$^+$=457.5.

The following compounds were prepared in a similar manner as described in Example 4, substituting with appropriate reagents and substrates as required.

| Compound no. | Method | MS (M + H)$^+$ |
|---|---|---|
| 2-1 | A | 453.4 |
| 2-3 | A | 487.5 |
| 2-4 | A | 471.3 |
| 2-5 | A | 441.5 |
| 2-6 | A | 432.4 |
| 2-7 | B | 456.4 |
| 2-8 | A | 468.2 |
| 2-9 | A | 468.5 |
| 2-10 | A | 475.4 |
| 2-12 | A | 439.4 |
| 2-13 | A | 455.4 |
| 2-14 | A | 473.3 |
| 2-15 | A | 487.3 |
| 2-16 | A | 471.3 |
| 2-17 | A | 457.4 |
| 2-19 | A | 499.4 |
| 2-20 | A | 495.5 |
| 2-21 | A | 477.3 |
| 2-22 | A | 473.2 |
| 2-23 | A | 461.0 |
| 2-80 | A | 532.1 |

Example 5

3-[8-(4-aminopiperidin-1-yl)-7-(3-fluoro-5-methyl-phenyl)-1,5-naphthyridin-2-yl]-5-fluoro-2-hydroxy-benzonitrile (Compound No. 3-2)

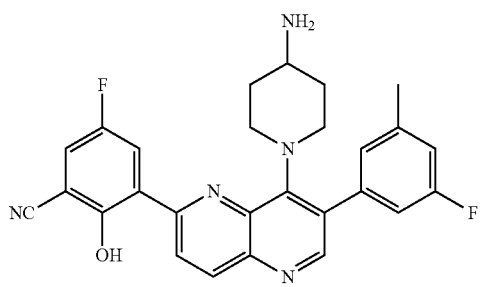 [SMILES: Cc1cc(F)cc(-c2cnc3ccc(-c4cc(F)cc(C#N)c4O)nc3c2N2CCC(N)CC2)c1]

Step 5-1, preparation of [1-(3-chloro-6-methoxy-[1,5]naphthyridin-4-yl)-piperidin-4-yl]-carbamic acid tert-butyl ester: A suspension of 7,8-dichloro-2-methoxy-[1,5]naphthyridine (1.000 g, 4.364 mmol), piperidin-4-yl-carbamic acid tert-butyl ester (1.311 g, 6.545 mmol), and DIEA (2.30 mL, 13.2 mmol) in IPA (20 mL) in a sealed tube was heated at 120° C. for 9 hr. Due to unreacted starting material, the reaction was continued for another 9 hr after more piperidin-4-yl-carbamic acid tert-butyl ester (1.311 g, 6.545 mmol) and DIEA (2.30 mL, 13.2 mmol) were added (repeated twice). The reaction was not complete (74% conversion) but stopped. The mixture was concentrated and purified by silica gel column chromatography to afford the title compound (1.0 g, 58.0% yield) as a light yellow solid. MS $(M+H)^+=393.2$.

Step 5-2, preparation of {1-[3-(3-fluoro-5-methyl-phenyl)-6-methoxy-[1,5]naphthyridin-4-yl]-piperidin-4-yl}-carbamic acid tert-butyl ester: To a mixture of [1-(3-chloro-6-methoxy-[1,5]naphthyridin-4-yl)-piperidin-4-yl]-carbamic acid tert-butyl ester (1.0 g, 2.53 mmol), 3-fluoro-5-methylphenylboronic acid (0.78 g, 5.06 mmol), Pd[t-Bu$_2$P(4-NMe$_2$C$_6$H$_4$)]$_2$Cl$_2$) (0.21 g, 0.25 mmol), and K$_2$CO$_3$ (1.05 g, 7.59 mmol) in a sealed tube was added dioxane (20 mL) and water (2 mL). The reaction mixture was bubbled with N$_2$ for 10 min and then heated at 100° C. for 1 hr. Due to unreacted starting material, the reaction was continued to heat at 100° C. for 1 hr after more 3-fluoro-5-methylphenylboronic acid (0.78 g, 5.06 mmol), Pd[t-Bu$_2$P(4-NMe$_2$C$_6$H$_4$)]$_2$Cl$_2$) (0.211 g, 0.253 mmol), and K$_2$CO$_3$ (1.049 g, 7.590 mmol) were added. The mixture was concentrated and purified by silica gel column chromatography and and then C$_{18}$ reversed-phase column chromatography. Pure fractions were combined, basified with saturated NaHCO$_3$ (aq) and concentrated to remove MeCN. The solid from aqueous residue was collected by vacuum filtration and washed with water to afford the title compound (0.8 g, 68.0% yield) as a light yellow solid. MS $(M+H)^+=467.2$.

Step 5-3, preparation of {1-[3-(3-fluoro-5-methyl-phenyl)-6-hydroxy-[1,5]naphthyridin-4-yl]-piperidin-4-yl}-carbamic acid tert-butyl ester: To {1-[3-(3-fluoro-5-methyl-phenyl)-6-methoxy-[1,5]naphthyridin-4-yl]-piperidin-4-yl}-carbamic acid tert-butyl ester (0.74 g, 1.58 mmol) was added 6 N HCl (aq) (20 mL) and the mixture was heated at reflux for 7 hr. The mixture was cooled to 0° C. and neutralized with solid NaOH. The solid was collected by vacuum filtration to afford the de-Boc product (0.47 g) as an off-white solid. MS $(M+H)^+=353.4$. To a suspension of the de-Boc product in THF (10 mL) was added TEA (0.19 mL, 1.4 mmol) and Boc$_2$O (0.32 mL, 1.4 mmol). The mixture was stirred at rt overnight. The mixture was quenched with water and the organic layer was separated, dried over anhydrous Na$_2$SO$_4$ and concentrated to dryness. The residue was triturated with MTBE and the solid was collected by vacuum filtration to afford the title compound (0.40 g, 58.5% yield) as a white solid. MS $(M+H)^+=453.3$.

Step 5-4, preparation of trifluoro-methanesulfonic acid 8-(4-tert-butoxycarbonylamino-piperidin-1-yl)-7-(3-fluoro-5-methyl-phenyl)-[1,5]naphthyridin-2-yl ester: To a solution of {1-[3-(3-fluoro-5-methyl-phenyl)-6-hydroxy-[1,5]naphthyridin-4-yl]-piperidin-4-yl}-carbamic acid tert-butyl ester (287.4 mg, 0.64 mmol) in DCM (7 mL) at 0° C. was added TEA (0.35 mL, 2.5 mmol), followed by slow addition of Tf$_2$O (0.21 mL, 1.2 mmol). The mixture was stirred at 0° C. for 10 min. The mixture was quenched with water and the organic layer was separated. The organic layer was concentrated and purified by silica gel column chromatography to afford the title compound (151.1 mg, 40.7% yield) as a brown solid. MS $(M+H)^+=585.3$.

Step 5-5, preparation of {1-[6-(3-Cyano-5-fluoro-2-methoxymethoxy-phenyl)-3-(3-fluoro-5-methyl-phenyl)-[1,5]naphthyridin-4-yl]-piperidin-4-yl}-carbamic acid tert-butyl ester: To a mixture of trifluoro-methanesulfonic acid 8-(4-tert-butoxycarbonylamino-piperidin-1-yl)-7-(3-fluoro-5-methyl-phenyl)-[1,5]naphthyridin-2-yl ester (57.8 mg, 0.0989 mmol), 5-fluoro-2-methoxymethoxy-3-(4,4,5,5-tetramethyl-[1,3,2]dioxaborolan-2-yl)-benzonitrile (60.7 mg, 0.198 mmol), tris(dibenzylideneacetone) dipalladium/tri-tert-butyl phosphonium tetrafluoroborate mixture (mole ratio: 1/1.2) (6.4 mg, 0.0049 mmol), and K$_3$PO$_4$.H$_2$O (91.1 mg, 0.396 mmol) was added THF (4 mL) and water (0.4 mL). The mixture was bubbled with N$_2$ (g) for 10 min and then stirred at RT for 2 hr. The organic layer was separated and the aqueous layer was extracted with EtOAc (1×). The combined organics were concentrated to dryness and the residue was purified by silica gel chromatography to afford the title compound (82.9 mg, 55.3% yield) as a yellow solid. MS $(M+H)^+=616.6$.

Step 5-6, preparation of 3-[8-(4-aminopiperidin-1-yl)-7-(3-fluoro-5-methylphenyl)-1,5-naphthyridin-2-yl]-5-fluoro-2-hydroxybenzonitrile: To {1-[6-(3-cyano-5-fluoro-2-methoxymethoxy-phenyl)-3-(3-fluoro-5-methyl-phenyl)-[1,5]naphthyridin-4-yl]-piperidin-4-yl}-carbamic acid tert-butyl ester (82.9 mg, 0.134 mmol) was added 4 N HCl in dioxane (2.0 mL). The mixture was stirred at rt for 1 hr. The mixture was concentrated to dryness and the residue was triturated with DCM. The solid was collected by vacuum filtration and washed with DCM and hexanes to afford the title compound as 2 HCl salt (68.3 mg, 93.7% yield) as a yellow solid. MS $(M+H)^+=472.3$.

The following compounds were prepared in a similar manner as described in Example 5, substituting with appropriate reagents and substrates as required:

| Compound no. | MS $(M + H)^+$ |
|---|---|
| 3-1 | 474.3 |
| 3-3 | 487.5 |
| 3-4 | 469.5 |
| 3-5 | 487.4 |

Example 6

3-[3-(3,5-dichlorophenyl)-4-{4-[(oxetan-3-yl)amino]piperidin-1-yl}cinnolin-6-yl]-5-fluorobenzamide (Compound No. 1-31)

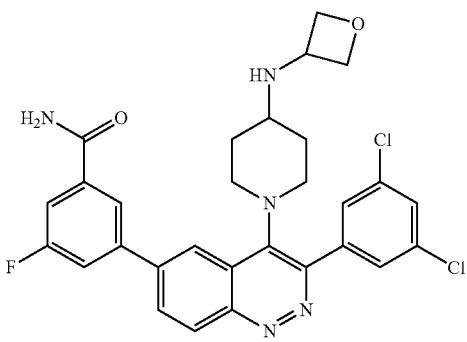 [SMILES: NC(=O)c1cc(F)cc(-c2ccc3nnc(-c4cc(Cl)cc(Cl)c4)c(N4CCC(NC5COC5)CC4)c3c2)c1]

Step 6-1, preparation of 3-[3-(3,5-dichlorophenyl)-4-{4-[(oxetan-3-yl)amino]piperidin-1-yl}cinnolin-6-yl]-5-fluorobenzamide: A sealed tube was charged with 3-[4-(4-aminopiperidin-1-yl)-3-(3,5-dichlorophenyl)cinnolin-6-yl]-5-fluorobenzamide (40 mg, 0.078 mmol), 3-oxetanone (45 mg, 0.62 mmol), NaOAc (7 mg, 0.078 mmol), sodium triacetoxyborohydride (66 mg, 0.31 mmol) and DCM (3 mL). The mixture was stirred overnight at 60° C. The reaction was cooled to rt and quenched with sat-NaHCO₃ (~1 mL). The reaction was diluted with DCM, washed with H₂O, dried with anhydrous MgSO₄, and concentrated. The residue was purified by a reverse phase C18 column chromatography to afford the title compound (9 mg, 20%). MS (M+H)⁺=566.5.

Example 7

3-(4-{3-[(ethylamino)methyl]azetidin-1-yl}-3-(3-fluoro-5-methylphenyl)quinolin-6-yl)-5-fluoro-2-hydroxybenzonitrile (Compound No. 2-18)

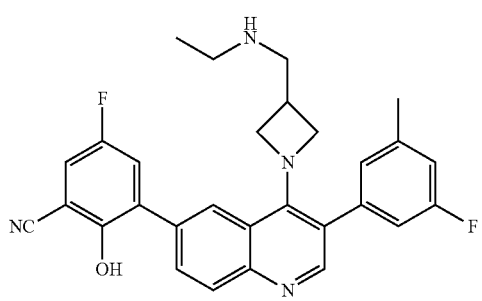 [SMILES: CCNCC1CN(c2c(-c3cc(C)cc(F)c3)cnc3ccc(-c4cc(F)cc(C#N)c4O)cc23)C1]

Step 7-1, preparation of [1-(6-bromo-3-chloro-quinolin-4-yl)-azetidin-3-ylmethyl]-carbamic acid tert-butyl ester: to an anhydrous MeCN (10 mL) solution of 6-bromo-3,4-dichloro-quinoline (2.0 mmol, 0.554 g) was added N,N-diisopropylethylamine (2 mL) and the HCl salt of 3-(boc-aminomethyl)azetidine (1.5 eq., 3.0 mmol, 0.666 g). The reaction solution was heated at 90° C. for 2 hrs. The reaction mixture was diluted with 50 mL ethyl acetate and washed with water (30 mL) and brine (10 mL). The organic layer was separated, dried with MgSO₄ and concentrated. The residue obtained was purified by silica gel chromatography eluting with ethyl acetate/hexane (0~50%) to give 0.6 g of the desired product as off-white solid. MS (M+H)⁺=426.0, 428.2.

Step 7-2, preparation of {1-[3-chloro-6-(3-cyano-5-fluoro-2-methoxymethoxy-phenyl)-quinolin-4-yl]-azetidin-3-ylmethyl}-carbamic acid tert-butyl ester: to a THF (5.0 mL) solution of [1-(6-bromo-3-chloro-quinolin-4-yl)-azetidin-3-ylmethyl]-carbamic acid tert-butyl ester (1.0 mmol, 427 mg) and 5-fluoro-2-(2-methoxy-ethoxymethoxy)-3-(4,4,5,5-tetramethyl-[1,3,2]dioxaborolan-2-yl)-benzonitrile (1.3 eq., 1.3 mmol, 412 mg) was added tris(dibenzylideneacetone)dipalladium/tri-tert-butyl phosphonium tetrafluoroborate mixture (mole ratio: 1/1.2) complex (0.05 eq., 0.05 mmol, 65 mg) and K₃PO₄·H₂O (3.0 eq., 3.0 mmol, 691 mg). N₂ was bubbled through the reaction solution for 5 min and 0.5 mL water was added. The resulting mixture was stirred at ambient temperature for 1 h. LCMS analysis showed complete consumption of starting material. The reaction solution was diluted with EtOAc (50 mL) and washed with brine. The organic layer was dried with Na₂SO₄, filtered and concentrated. The residue obtained was purified by silica gel chromatography eluting with ethyl acetate/hexane (0~50%) to give 460 mg of the desired product as oily foam. MS (M+H)⁺=527.3.

Step 7-3, preparation of {1-[6-(3-cyano-5-fluoro-2-methoxymethoxy-phenyl)-3-(3-fluoro-5-methyl-phenyl)-quinolin-4-yl]-azetidin-3-ylmethyl}-carbamic acid tert-butyl ester: to a dioxane (3 mL) solution of {1-[3-chloro-6-(3-cyano-5-fluoro-2-methoxymethoxy-phenyl)-quinolin-4-yl]-azetidin-3-ylmethyl}-carbamic acid tert-butyl ester (0.3 mmol, 160 mg) was added Pd[t-Bu₂P(4-NMe₂C₆H₄)]₂Cl₂) (0.2 eq., 0.06 mmol, 42 mg), 3-fluoro-5-methylphenyl boronic acid (4.0 eq., 1.2 mmol, 186 mg) and K₂CO₃ (5.0 eq., 1.5 mmol, 207 mg). N₂ was bubbled through the reaction solution for 5 min and 0.3 mL water was added. The resulting mixture was heated at 100° C. for 1 h and LCMS analysis showed that starting material was completely consumed. The reaction solution was diluted with ethyl acetate (20 mL) and washed with brine. The organic layer was dried with Na₂SO₄, filtered and concentrated. The residue obtained was purified by silica gel chromatography eluting with ethyl acetate/hexane (0~50%) to give 118 mg of the desired product as yellow foam. MS (M+H)⁺=601.4.

Step 7-4, preparation of {1-[6-(3-cyano-5-fluoro-2-methoxymethoxy-phenyl)-3-(3-fluoro-5-methyl-phenyl)-quinolin-4-yl]-azetidin-3-ylmethyl}-ethyl-carbamic acid tert-butyl ester: to an anhydrous DMF (0.5 mL) and THF (1.0 mL) solution of {1-[6-(3-cyano-5-fluoro-2-methoxymethoxy-phenyl)-3-(3-fluoro-5-methyl-phenyl)-quinolin-4-yl]-azetidin-3-ylmethyl}-carbamic acid tert-butyl ester (0.066 mmol, 40 mg) was added sodium hydride (60% dispersion in mineral oil) (4.0 eq., 0.254 mmol, 10.6 mg) and iodoethane (3.0 eq., 0.19 mmol, 0.0164 mL). The resulting solution was stirred at ambient temperature for 0.5 h. LCMS analysis showed about 60% converstion to the desired product. Additional sodium hydride (60% dispersion in mineral oil) (4.0 eq., 0.254 mmol, 10.6 mg) and iodoethane (3.0 eq., 0.19 mmol, 0.0164 mL) were added and the reaction mixture was stirred for another 1 h. The reaction solution was diluted with ethyal acetate (20 mL) and washed with brine (5 mL). The organic layer was dried with Na₂SO₄, filtered and concentrated. The residue obtained was purified by silica gel chromatography eluting with ethyl acetate/hexane (0~70%) to give 25 mg of the desired product. MS (M+H)⁺=629.6.

Step 7-5, preparation of 3-(4-{3-[(ethylamino)methyl]azetidin-1-yl}-3-(3-fluoro-5-methylphenyl)quinolin-6-yl)-5-fluoro-2-hydroxybenzonitrile: to a dichloromethane (0.5 mL) solution of fluoro-2-methoxymethoxy-phenyl)-3-(3-fluoro-5-methyl-phenyl)-quinolin-4-yl]-azetidin-3-ylmethyl}-ethyl-carbamic acid tert-butyl ester was added TFA (0.2 mL). The resulting solution was stirred at ambient temperature for 1 h. The reaction solution was concentrated and the residue obtained was purified by revers phase C18 chromatography eluting with MeCN/water (0~30%). Pure fractions were combined and concentrated to give 20 mg desired product as TFA salt. MS (M+H)$^+$=485.4.

The following compounds were prepared in a similar manner as described in Example 6, substituting with appropriate reaents and substrates as required:

| Compound no. | MS (M + H)$^+$ |
|---|---|
| 2-24 | 503.0 |
| 2-25 | 499.3 |
| 2-26 | 487.5 |
| 2-27 | 515.5 |
| 2-28 | 517.1 |
| 2-31 | 499.1 |

Example 8

3-[4-(3-cyclopropylaminomethyl-azetidin-1-yl)-3-(3-fluoro-5-methyl-phenyl)-quinolin-6-yl]-5-fluoro-2-hydroxy-benzonitrile (Compound No. 2-29)

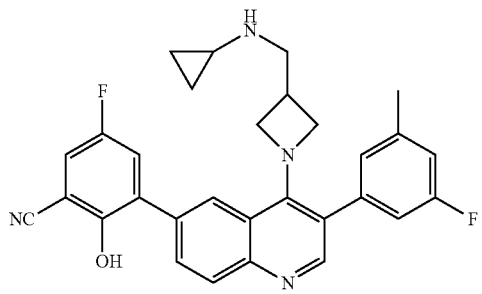 [SMILES: Cc1cc(F)cc(-c2cnc3ccc(-c4cc(F)cc(C#N)c4O)cc3c2N2CC(CNC3CC3)C2)c1]

Step 8-1, preparation of azetidin-3-yl-methanol: to an anhydrous dioxane (3 mL) solution of 3-hydroxymethyl-azetidine-1-carboxylic acid tert-butyl ester (5.34 mmol, 1.0 g) was added 4.0 M HCl in dixoane (6 mL) at ambient temperature. The reaction solution was stirred at the same temperature for 2 hrs. The reaction mixture was concentrated and dried under high vacuum to give 0.66 g of the HCl salt of the desired product as a colorless oil. This material was used for next step without further purification.

Step 8-2, preparation of [1-(6-bromo-3-chloro-quinolin-4-yl)-azetidin-3-yl]-methanol: to an anhydrous DMSO (25 mL) solution of 6-bromo-3,4-dichloro-quinoline (5.0 mmol, 1.38 g) was added N,N-diisopropylethylamine (4 mL) and azetidin-3-yl-methanol HCl salt (0.9 eq., 4.45 mmol, 560 mg). N$_2$ was bubbled through the reaction solution for 5 min and the resulting solution was heated at 140° C. for 1 h. The reaction mixture was diluted with ethyl acetate and washed with water and brine. The organic layer was separated, dried with Na$_2$SO$_4$ and concentrated. The residue obtained was purified by silica gel chromatography eluting with ethyl acetate/dichloromethane (0~50%) to give 818 mg of the desired product as white solid. MS (M+H)$^+$: 327.3, 329.2.

Step 8-3, preparation of 3-[3-chloro-4-(3-hydroxymethyl-azetidin-1-yl)-quinolin-6-yl]-5-fluoro-2-methoxymethoxy-benzonitrile: to a THF (8.0 mL) solution of [1-(6-bromo-3-chloro-quinolin-4-yl)-azetidin-3-yl]-methanol (1.58 mmol, 516 mg) and 5-fluoro-2-(2-methoxy-ethoxymethoxy)-3-(4,4,5,5-tetramethyl-[1,3,2]dioxaborolan-2-yl)-benzonitrile (1.2 eq., 1.9 mmol, 598 mg) was added tris(dibenzylideneacetone)dipalladium/tri-tert-butyl phosphonium tetrafluoroborate mixture (mole ratio: 1/1.2) complex (0.05 eq., 0.078 mmol, 102 mg) and K$_3$PO$_4$.H$_2$O (3.0 eq., 4.73 mmol, 1.10 g). N$_2$ was bubbled through the reaction solution for 5 min and 0.8 mL water was added. The resulting mixture was stirred at ambient temperature for 1 h. LCMS analysis showed complete consumption of starting material. The reaction solution was diluted with ethyl acetate (50 mL) and washed with brine. The organic layer was dried with Na$_2$SO$_4$, filtered and concentrated. The residue obtained was purified by silica gel chromatography eluting with ethyl acetate/dichloromethane (0~50%) to give 456 mg of the desired product as off-white solide. MS (M+H)$^+$=428.3.

Step 8-4, preparation of 5-fluoro-3-[3-(3-fluoro-5-methyl-phenyl)-4-(3-hydroxymethyl-azetidin-1-yl)-quinolin-6-yl]-2-methoxymethoxy-benzonitrile: to a dioxane (10 mL) solution of 3-[3-chloro-4-(3-hydroxymethyl-azetidin-1-yl)-quinolin-6-yl]-5-fluoro-2-methoxymethoxy-benzonitrile (1.065 mmol, 456 mg) was added Pd[t-Bu$_2$P(4-NMe$_2$C$_6$H$_4$)]$_2$Cl$_2$) (0.2 eq., 0.21 mmol, 151 mg), 3-fluoro-5-methylphenyl boronic acid (3.0 eq., 3.2 mmol, 492 mg) and K$_2$CO$_3$ (5.0 eq., 5.3 mmol, 735 mg). N$_2$ was bubbled through the reaction solution for 5 min and 1.0 mL water was added. The resulting mixture was heated at 100° C. for 1 h and LCMS analysis showed that starting material was fully consumed. The reaction solution was diluted with ethyl acetate (40 mL) and washed with brine. The organic layer was dried with Na$_2$SO$_4$, filtered and concentrated. The residue obtained was purified by silica gel chromatography eluting with ethyl acetate/dichloromethane (0~85%) to give 314 mg of the desired product as yellow foam. MS (M+H)$^+$=502.0.

Step 8-5, preparation of 3-[4-(3-bromomethyl-azetidin-1-yl)-3-(3-fluoro-5-methyl-phenyl)-quinolin-6-yl]-5-fluoro-2-methoxymethoxy-benzonitrile: to the dichloromethane solution (6 mL) of 5-fluoro-3-[3-(3-fluoro-5-methyl-phenyl)-4-(3-hydroxymethyl-azetidin-1-yl)-quinolin-6-yl]-2-methoxymethoxy-benzonitrile (200 mg, 0.40 mmol) was added tetrabromomethane (1.55 eq., 0.62 mmol, 216 mg) and triphenylphosphine (1.45 eq., 0.58 mmol, 154 mg) at 0° C. The resulting mixture was stirred at ambient temperature for 3 hrs and LCMS analysis showed that the reaction was not fully complete. Additional tetrabromomethane (0.5 eq., 0.21 mmol, 70 mg) and triphenylphosphine (0.48 eq., 0.19 mmol, 50 mg) were added at 0° C. and the reaction solution was stirred at ambient temperature for another 1 h. The reaction mixture was diluted with dichloromethane (40 mL), washed with sat. NaHCO$_3$ and brine, and dried with Na$_2$SO$_4$. The organic was concentrated and purified by silica gel chromatography eluting with ethyl acetate/hexane (0~40%) to give 151 mg of the desired product as white foam. MS (M+H)$^+$=564.4, 566.3.

Step 8-6, preparation of 3-[4-(3-cyclopropylaminomethyl-azetidin-1-yl)-3-(3-fluoro-5-methyl-phenyl)-quinolin-6-yl]-5-fluoro-2-methoxymethoxy-benzonitrile: to a MeCN solution (1 mL) of 3-[4-(3-bromomethyl-azetidin-1-yl)-3-(3-fluoro-5-methyl-phenyl)-quinolin-6-yl]-5-fluoro-2-methoxymethoxy-benzonitrile (0.05 mmol, 29 mg) was added NaHCO₃ (6.0 eq., 0.3 mmol, 25 mg) and cyclopropylamine (0.1 mL). The resulting mixture was heated at 90° C. for 4 hrs and LCMS showed the reaction was complete. The reaction solution was diluted with dichloromethane, washed with sat. NaHCO₃ and brine, and dried with Na₂SO₄. The organic was concentrated and purified by silica gel chromatography eluting with ethyl acetate/dichloromethane (0~10%) to give 18 mg of the desired product as yellow oil. MS (M+H)⁺=541.5.

Step 8-7, preparation of 3-[4-(3-cyclopropylaminomethyl-azetidin-1-yl)-3-(3-fluoro-5-methyl-phenyl)-quinolin-6-yl]-5-fluoro-2-hydroxy-benzonitrile: to a dichloromethane solution (0.5 mL) of 3-[4-(3-cyclopropylaminomethyl-azetidin-1-yl)-3-(3-fluoro-5-methyl-phenyl)-quinolin-6-yl]-5-fluoro-2-methoxymethoxy-benzonitrile was added trifluoroacetic acid (0.2 mL). The resulting mixture was stirred at ambient temperature for 1 h. The reaction solution was concentrated and the residue obtained was purified by revers phase C18 chromatography eluting with MeCN/water (0~30%). Pure fractions were combined and concentrated to give 13 mg of the desired product as TFA salt. MS (M+H)⁺=497.5.

Example 9

5-fluoro-3-[3-(3-fluoro-5-methyl-phenyl)-4-(3-pyrrolidin-1-ylmethyl-azetidin-1-yl)-quinolin-6-yl]-2-hydroxy-benzonitrile (Compound No. 2-30)

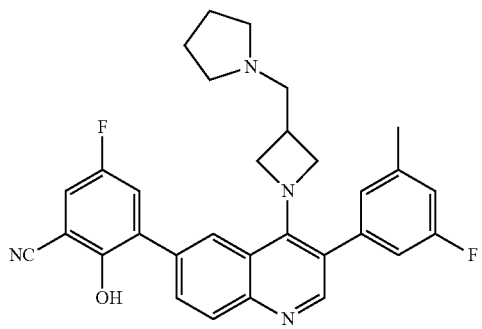 [SMILES: Cc1cc(F)cc(-c2cnc3ccc(-c4cc(F)cc(C#N)c4O)cc3c2N2CC(CN3CCCC3)C2)c1]

Step 9-1, preparation of methanesulfonic acid 1-[6-(3-cyano-5-fluoro-2-methoxymethoxy-phenyl)-3-(3-fluoro-5-methyl-phenyl)-quinolin-4-yl]-azetidin-3-yl methyl ester: to an anhydrous THF (2 mL) solution of 5-fluoro-3-[3-(3-fluoro-5-methyl-phenyl)-4-(3-hydroxymethyl-azetidin-1-yl)-quinolin-6-yl]-2-methoxymethoxy-benzonitrile (Step 8-4, 0.19 mmol, 95 mg) was added triethylamine (2.2 eq, 0.42 mmol, 0.058 mL) and methanesulfonyl chloride (2.2 eq., 0.42 mmol, 0.032 mL) at ambient temperature. After 1 h, the reaction solution was diluted with ethyl acetate, washed with sat. NH₄Cl and brine, and dried with Na₂SO₄. The organic layer was concentrated and purified by silica gel chromatography eluting with ethyl acetate/hexane (0~70%) to give 79 mg of the desired product as yellow oil. MS (M+H)⁺=580.2.

Step 9-2, preparation of 5-fluoro-3-[3-(3-fluoro-5-methyl-phenyl)-4-(3-pyrrolidin-1-ylmethyl-azetidin-1-yl)-quinolin-6-yl]-2-hydroxy-benzonitrile: to a DMF solution (1.5 mL) of methanesulfonic acid 1-[6-(3-cyano-5-fluoro-2-methoxymethoxy-phenyl)-3-(3-fluoro-5-methyl-phenyl)-quinolin-4-yl]-azetidin-3-yl methyl ester (39 mg, 0.069 mmol) was added pyrrolidine (20 eq., 1.4 mmol, 0.11 mL).

The resulting mixture was heated at 80° C. for 1.5 hrs and LCMS analysis showed complete consumption of starting material. The reaction solution was diluted with ethyl acetate, washed with sat. NaHCO₃ and brine, and dried with Na₂SO₄. The organic layer was concentrated and purified by silica gel chromatography eluting with methonal/dichloromethane (0~20%). Pure factions were combined and concentrated with HCl in EtOEt (2.0 M, 1 mL) to give 12.2 mg of the desired product as yellow solid. MS (M+H)⁺=511.6.

Example 10

3-[4-(4-aminopiperidin-1-yl)-3-(3,5-difluorophenyl)quinolin-6-yl]-2-(2-hydroxyethoxy)benzonitrile (Compound No. 2-65)

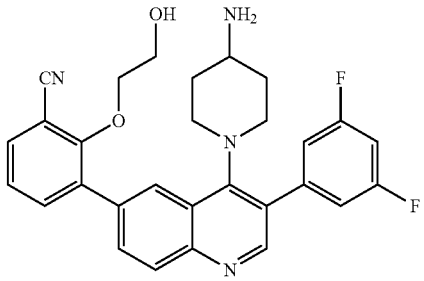 [SMILES: N#Cc1cccc(-c2ccc3ncc(-c4cc(F)cc(F)c4)c(N4CCC(N)CC4)c3c2)c1OCCO]

Step 10-1, preparation of {1-[6-(3-cyano-2-hydroxy-phenyl)-3-(3,5-difluoro-phenyl)-quinolin-4-yl]-piperidin-4-yl}-carbamic acid tert-butyl ester: to a DCM (20 mL) suspension of the HCl salt of 3-[4-(4-amino-piperidin-1-yl)-3-(3,5-difluoro-phenyl)-quinolin-6-yl]-2-hydroxy-benzonitrile (2-2) (2.0 mmol, 1.06 g) was added triethylamine (4.0 eq, 8.0 mmol, 1.14 mL) and di-tert-butyl dicarbonate (1.1 eq., 2.2 mmol, 0.51 mL) at ambient temperature. After 1 h, the reaction solution was diluted with ethyl acetate, washed with water and dried with MgSO₄. The organic layer was concentrated and dried under high vaccum to give 1.10 g of the desired product as yellow powder. This material was used for next step without further purification. MS (M+H)⁺=557.2.

Step 10-2, preparation of acetic acid 2-{2-[4-(4-tert-butoxycarbonylamino-piperidin-1-yl)-3-(3,5-difluoro-phenyl)-quinolin-6-yl]-6-cyano-phenoxy}-ethyl ester: to a DMF solution (2.0 mL) of {1-[6-(3-cyano-2-hydroxy-phenyl)-3-(3,5-difluoro-phenyl)-quinolin-4-yl]-piperidin-4-yl}-carbamic acid tert-butyl ester (112 mg, 0.20 mmol) was added K₂CO₃ (2.0 eq., 0.4 mmol, 52 mg) and ethyl 2-bromoacetate (5.5 eq., 1.1 mmol, 0.12 mL). The resulting mixture was heated at 80° C. for 1 h and LCMS analysis showed complete consumption of starting material. The reaction solution was diluted with ethyl acetate, washed with water and brine, and dried with Na₂SO₄. The organic layer was concentrated and purified by silica gel chromatography eluting with ethyl acetate/hexane (0~50%) to give 68 mg of the desired product. MS (M+H)⁺=643.5.

Step 10-3, preparation of {1-[6-[3-cyano-2-(2-hydroxyethoxy)-phenyl]-3-(3,5-difluoro-phenyl)-quinolin-4-yl]-piperidin-4-yl}-carbamic acid tert-butyl ester: to a THF solution (1.0 mL) of acetic acid 2-{2-[4-(4-tert-butoxycarbonylamino-piperidin-1-yl)-3-(3,5-difluoro-phenyl)-quinolin-6-yl]-6-cyano-phenoxy}-ethyl ester (68 mg, 0.11 mmol) was added MeOH (0.5 mL) and aqeous NaOH (4.0 M, 0.5 mL). The resulting mixture was stirred at ambient temperature for 0.5 h and LCMS analysis showed complete consumption of starting material. The reaction solution was diluted with ethyl acetate, washed with water and brine, and dried with Na$_2$SO$_4$. The organic layer was concentrated to give 68 mg of the desired product. This material was used for next step without futher purification. MS (M+H)$^+$=601.6.

Step 10-4, preparation of 3-[4-(4-aminopiperidin-1-yl)-3-(3,5-difluorophenyl)quinolin-6-yl]-2-(2-hydroxyethoxy)benzonitrile: to the MeOH solution (0.2 mL) of {1-[6-[3-cyano-2-(2-hydroxy-ethoxy)-phenyl]-3-(3,5-difluoro-phenyl)-quinolin-4-yl]-piperidin-4-yl}-carbamic acid tert-butyl ester was added HCl in dioxane (4.0 M, 1.5 mL). The resulting mixture was stirred at ambient temperature for 0.5 h and LCMS analysis showed complete consumption of starting material. MTBE (5 mL) was added to oil out the desired product and the clear layer was decanted. The resulting oil was concentrated with EtOH to give desired product as yellow solid. MS (M+H)$^+$=501.3.

Example 11

2-{2-[4-(4-aminopiperidin-1-yl)-3-(3,5-difluorophenyl)quinolin-6-yl]-6-cyanophenoxy}acetic acid (Compound No. 2-56)

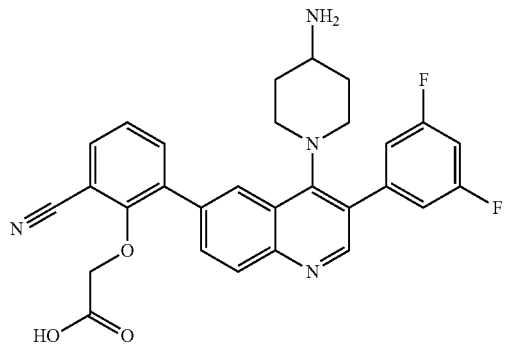 [SMILES: N#Cc1cccc(-c2ccc3ncc(-c4cc(F)cc(F)c4)c(N4CCC(N)CC4)c3c2)c1OCC(=O)O]

Step 11-1, preparation of {2-[4-(4-tert-butoxycarbonylamino-piperidin-1-yl)-3-(3,5-difluoro-phenyl)-quinolin-6-yl]-6-cyano-phenoxy}-acetic acid tert-butyl ester: to a DMF solution (1.0 mL) of {1-[6-(3-cyano-2-hydroxy-phenyl)-3-(3,5-difluoro-phenyl)-quinolin-4-yl]-piperidin-4-yl}-carbamic acid tert-butyl ester (56 mg, 0.10 mmol) was added K$_2$CO$_3$ (5.0 eq., 0.5 mmol, 70 mg) and t-butyl bromoacetate (2.0 eq., 0.2 mmol, 0.04 mL). The resulting mixture was heated at 80° C. for 0.5 h and LCMS analysis showed complete consumption of starting material. The reaction solution was diluted with ethyl acetate, washed with water and brine, and dried with Na$_2$SO$_4$. The organic layer was concentrated and purified by silica gel chromatography eluting with ethyl acetate/hexane (0~50%) to give 30 mg of the desired product. MS (M+H)$^+$=671.6.

Step 11-2, preparation of 2-{2-[4-(4-aminopiperidin-1-yl)-3-(3,5-difluorophenyl)quinolin-6-yl]-6-cyanophenoxy}acetic acid: to the dichloromethane (1.0 mL) solution of {2-[4-(4-tert-butoxycarbonylamino-piperidin-1-yl)-3-(3,5-difluoro-phenyl)-quinolin-6-yl]-6-cyano-phenoxy}-acetic acid tert-butyl ester (30 mg) was added trifluoroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in ether (2.0 M) to give 1.6 mg of the final compound as HCl salt. MS (M+H)$^+$=515.4.

The following compounds were prepared in a similar manner as described in Example 11, substituting with appropriate reagents and substrates as required:

| Compound no. | MS (M + H)$^+$ |
| --- | --- |
| 2-57 | 543.3 |
| 2-67 | 549.6 |
| 2-72 | 515.5 |
| 2-73 | 513.4 |
| 2-204 | 529.3 |
| 2-231 | 496.6 |

Example 2-67 was prepared via 2-73 with excess hydrogen chloride treatment.

Example 12 cis-3-{4-[4-amino-3-hydroxypiperidin-1-yl]-3-(3,5-difluorophenyl)quinolin-6-yl}-2-hydroxybenzonitrile (Compound No. 2-60)

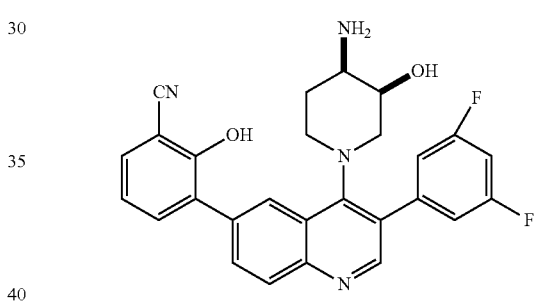

Step 12-1, preparation of cis-4-amino-piperidin-3-ol: to the dioxane solution (1.0 mL) of cis-4-amino-1-boc-3-hydroxypiperidine (1.0 mmol, 216 mg) was added HCl in dioxane (4.0 M, 2.0 mL). The resulting mixture was stirred at ambient temperature for 0.5 h and LCMS analysis showed complete consumption of starting material. The reaction solution was concentrated to give 160 mg of the HCl salt of the desired product. This material was used for next step without further purification. MS (M+H)$^+$=117.2.

Step 12-2, preparation of cis-4-amino-1-(6-bromo-3-chloro-quinolin-4-yl)-piperidin-3-ol: to an anhydrous DMSO (2.0 mL) solution of 6-bromo-3,4-dichloro-quinoline (0.6 mmol, 170 mg) was added N,N-diisopropylethylamine (0.4 mL) and HCl salt of cis-4-amino-piperidin-3-ol (1.16 eq., 130 mg, 0.69 mmol). N$_2$ was bubbled through the reaction solution for 5 min and the resulting solution was heated at 135° C. for 8 h. The reaction mixture was diluted with ethyl acetate and washed with water and brine. The organic layer was separated, dried with MgSO$_4$ and concentrated. The residue obtained was purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic was concentrated and dried under high vaccum to give 50 mg of the desired product as a white solid. MS (M+H)$^+$=356.1, 358.1.

Step 12-3, preparation of cis-3-[4-(4-amino-3-hydroxy-piperidin-1-yl)-3-chloro-quinolin-6-yl]-2-methoxymethoxy-benzonitrile: to a THF solution (2.0 mL) of cis-4-amino-1-(6-bromo-3-chloro-quinolin-4-yl)-piperidin-3-ol (50 mg, 0.14 mmol) was added 2-(2-methoxy-ethoxymethoxy)-3-(4,4,5,5-tetramethyl-[1,3,2]dioxaborolan-2-yl)-benzonitrile (1.5 eq., 0.2 mmol, 58 mg), tris(dibenzylideneacetone)dipalladium/tri-tert-butyl phosphonium tetrafluoroborate mixture (mole ratio: 1/1.2) (0.1 eq., 0.014 mmol, 14 mg), $K_3PO_4 \cdot H_2O$ (3.0 eq., 0.42 mmol, 97 mg). $N_2$ was bubbled through the reaction solution for 5 min and 0.2 mL water was added. The resulting mixture stirred at ambient temperature for 0.5 h and LCMS analysis showed 70% converstion to the desired product. 2-(2-Methoxy-ethoxymethoxy)-3-(4,4,5,5-tetramethyl-[1,3,2]dioxaborolan-2-yl)-benzonitrile (0.75 eq., 0.1 mmol, 29 mg), tris(dibenzylideneacetone)dipalladium/tri-tert-butyl phosphonium tetrafluoroborate mixture (mole ratio: 1/1.2) (0.05 eq., 0.007 mmol, 7 mg), and $K_3PO_4 \cdot H_2O$ (1.5 eq., 0.21 mmol, 45 mg) were added and the reaction mixture was stirred under $N_2$ for another 0.5 h. LCMS analysis showed complete consumption of starting material. The reaction mixture was diluted with ethyl acetate and washed with water and brine. The organic layer was separated, dried with $MgSO_4$ and concentrated to give crude product which was used for next step without further purication. MS $(M+H)^+=439.4$.

Step 12-4, preparation of cis-3-[4-(4-amino-3-hydroxy-piperidin-1-yl)-3-(3,5-difluoro-phenyl)-quinolin-6-yl]-2-methoxymethoxy-benzonitrile: to the dioxane solution (1.5 mL) of the crude material from step 12-3 was added Pd(amphos)$Cl_2$ (0.02 mmol, 14 mg), 3,5-difluorophenyl boronic acid (0.5 mmol, 75 mg) and $K_2CO_3$ (0.5 mmol, 70 mg). $N_2$ was bubbled through the reaction solution for 5 min and 0.15 mL water was added. The resulting mixture was heated at 95° C. for 1 h and LCMS analysis showed that starting material was completely consumed. The reaction mixture was diluted with ethyl acetate and washed with brine. The organic layer was separated, dried with $MgSO_4$ and concentrated. The residue obtained was purified by C18 reversed phase chromatography eluting with MeCN/water (0~40%). Pure fractions were combined, neutralized with saturated $NaHCO_3$/NaCl, extracted with ethyl acetate and dried with $MgSO_4$. The organic was concentrated and dried under high vaccum to give 26 mg of the desired product as a yellow solid. MS $(M+H)^+=517.4$.

Step 12-5, preparation of cis-3-{4-[4-amino-3-hydroxypiperidin-1-yl]-3-(3,5-difluorophenyl)quinolin-6-yl}-2-hydroxybenzonitrile: cis-3-[4-(4-amino-3-hydroxy-piperidin-1-yl)-3-(3,5-difluoro-phenyl)-quinolin-6-yl]-2-methoxymethoxy-benzonitrile (24 mg) was combined with 4.0 M HCl in dioxane (1.0 mL) and MeOH (0.1 mL). The resulting mixture was stirred at ambient temperature for 0.5 h. MTBE (1.5 mL) was added and to percipate out solid which was collected after filtration. The solid obtained was purified by C18 reversed phase chromatography eluting with MeCN/water (0~40%). Pure fractions were combined, neutralized with saturated $NaHCO_3$ and NaCl, extracted with ethyl acetate and dried with $MgSO_4$. The organic was concentrated and dried under high vaccum to give 26 mg of the desired product as a yellow solid. MS $(M+H)^+=473.3$.

The following compounds were prepared in a similar manner as described in Example 12, substituting with appropriate reagents and substrates as required, with or without using Step 12-5:

| Compound no. | MS (M + H)+ |
|---|---|
| 2-58 | 517.4 |
| 2-61 | 487.5 |
| 2-62 | 531.3 |
| 2-63 | 491.3 |
| 2-66 | 487.5 |
| 2-219 | 487.5 |

Example 13

1-[3-(3,5-difluorophenyl)-6-[5-fluoro-4-(oxetan-3-yloxy)pyridin-3-yl]quinolin-4-yl]piperidin-4-amine (Compound No. 2-74)

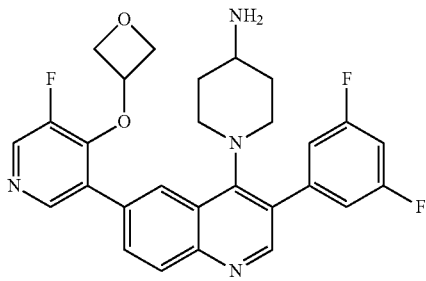 [SMILES: NC1CCN(c2c(-c3cc(F)cc(F)c3)cnc3ccc(-c4cncc(F)c4OC4COC4)cc23)CC1]

Step 13-1, preparation of [1-(3-bromo-6-chloro-quinolin-4-yl)-piperidin-4-yl]-carbamic acid tert-butyl ester: to an anhydrous DMSO (40 mL) solution of 3-bromo-4,6-dichloro-quinoline (10.0 mmol, 2.77 g) was added N,N-diisopropylethylamine (10 mL) and piperidin-4-yl-carbamic acid tert-butyl ester (2.0 eq., 20.0 mmol, 4.0 g). $N_2$ was bubbled through the reaction solution for 5 min and the resulting solution was heated at 135° C. for 2 h. The reaction mixture was diluted with ethyl acetate and washed with water and brine. The organic layer was separated, dried with $MgSO_4$ and concentrated. The residue obtained was purified by silica gel chromatography eluting with ethyl acetate/hexane (0~50%) to give 2.84 g of the desired product as white solid. MS $(M+H)^+=440.4, 442.4$.

Step 13-2, preparation of {1-[6-chloro-3-(3,5-difluorophenyl)-quinolin-4-yl]-piperidin-4-yl}-carbamic acid tert-butyl ester: to a THF solution (10 mL) of [1-(3-bromo-6-chloro-quinolin-4-yl)-piperidin-4-yl]-carbamic acid tert-butyl ester (1.2 g, 1.41 mmol) was added 3,5-difluorophenyl boronic acid (1.5 eq., 4.23 mmol, 677 mg), tris(dibenzylideneacetone)dipalladium/tri-tert-butyl phosphonium tetrafluoroborate mixture (mole ratio: 1/1.2) (0.05 eq., 0.07 mmol, 75 mg), $K_3PO_4 \cdot H_2O$ (3.0 eq., 4.2 mmol, 1.95 g). $N_2$ was bubbled through the reaction solution for 5 min and 1.0 mL water was added. The resulting mixture stirred at ambient temperature for 1 h and LCMS analysis showed 75% converstion to the desired product. Additional 3,5-difluorophenyl boronic acid (0.75 eq., 2.11 mmol, 340 mg), tris(dibenzylideneacetone)dipalladium/tri-tert-butyl phosphonium tetrafluoroborate mixture (mole ratio: 1/1.2) (0.025 eq., 0.035 mmol, 37 mg), and $K_3PO_4 \cdot H_2O$ (1.5 eq., 2.1 mmol, 0.97 g) were added and the reaction mixture was stirred at ambient temperature for another 1 h. The reaction mixture was diluted with ethyl acetate and washed with water and brine. The organic layer was separated, dried with $MgSO_4$ and concentrated. The residue obtained was purified by silica gel chromatography eluting with ethyl acetate/ hexane (0~50%) to give 1.12 g of the desired product as white solid. MS (M+H)⁺=474.2.

Step 13-3, preparation of {1-[3-(3,5-difluoro-phenyl)-6-(4,4,5,5-tetramethyl-[1,3,2]dioxaborolan-2-yl)-quinolin-4-yl]-piperidin-4-yl}-carbamic acid tert-butyl ester: to the dioxane solution (15 mL) of {1-[6-chloro-3-(3,5-difluoro-phenyl)-quinolin-4-yl]-piperidin-4-yl}-carbamic acid tert-butyl ester (0.9 g, 1.9 mmol) were added $Pd_2(dba)_3$ (0.05 eq., 0.0.09 mmol, 87 mg), Xphos (0.10 eq., 0.19 mmol, 91 mg), bis(pincolato)diborane (2.0 eq., 3.8 mmol, 965 mg) and KOAc (3.0 eq., 5.1 mmol, 560 mg). $N_2$ was bubbled through the reaction solution for 5 min and the resulting mixture was heated at 100° C. for 3 h. The reaction mixture was diluted with ethyl acetate and washed with water and brine. The organic layer was separated, dried with $Na_2SO_4$ and concentrated. The residue obtained was purified by silica gel chromatography eluting with ethyl acetate/hexane (0~50%) to give 0.87 g of the desired product as white solid. MS (M+H)⁺=566.5.

Step 13-4 preparation of (1-{3-(3,5-difluoro-phenyl)-6-[5-fluoro-4-(oxetan-3-yloxy)-pyridin-3-yl]-quinolin-4-yl}-piperidin-4-yl)-carbamic acid tert-butyl ester: to a THF solution (1.0 mL) of {1-[3-(3,5-difluoro-phenyl)-6-(4,4,5,5-tetramethyl-[1,3,2]dioxaborolan-2-yl)-quinolin-4-yl]-piperidin-4-yl}-carbamic acid tert-butyl ester (0.1 mmol, 56 mg) was added 3-bromo-5-fluoro-4-(oxetan-3-yloxy)-pyridine (1.2 eq., 0.12 mmol, 30 mg), tris(dibenzylideneacetone) dipalladium/tri-tert-butyl phosphonium tetrafluoroborate mixture (mole ratio: 1/1.2) (0.05 eq., 0.005 mmol, 6.5 mg), $K_3PO_4.H_2O$ (3.0 eq., 0.3 mmol, 69 mg). $N_2$ was bubbled through the reaction solution for 5 min and 0.1 mL water was added. The resulting mixture stirred at ambient temperature for 1 h. The reaction mixture was diluted with ethyl acetate and washed with saturated $NH_4Cl$, $NaHCO_3$ and brine. The organic layer was separated, dried with $Na_2SO_4$ and concentrated. The residue obtained was purified by silica gel chromatography eluting with ethyl acetate/hexane (0~50%) to give 18 mg of the desired product as white solid. MS (M+H)⁺=607.2.

Step 13-5, preparation of 1-{3-(3,5-difluoro-phenyl)-6-[5-fluoro-4-(oxetan-3-yloxy)-pyridin-3-yl]-quinolin-4-yl}-piperidin-4-ylamine: to the dichloromethane (0.5 mL) solution of (1-{3-(3,5-difluoro-phenyl)-6-[5-fluoro-4-(oxetan-3-yloxy)-pyridin-3-yl]-quinolin-4-yl}-piperidin-4-yl)-carbamic acid tert-butyl ester (18 mg) was added trifluroroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated $NaHCO_3$/NaCl, extracted with ethyl acetate and dried with $MgSO_4$. The organic solution was concentrated to give 7 mg of the final compound. MS (M+H)⁺=507.4.

The following compounds were prepared in a similar manner as described in Example 13, substituting with appropriate reagents and substrates as required:

| Compound no. | MS (M + H)⁺ |
|---|---|
| 2-75 | 497.5 |
| 2-76 | 515.5 |
| 2-77 | 456.6 |
| 2-132 | 513.3 |
| 2-181 | 462.2 |
| 2-241 | 548.2 |

The following compounds were prepared in a similar manner as described in Example 13 using appropriate susbtrates and reagents. For example, for the Suzuki couping described in Step 13-4 was carried out using $Pd(amphos)Cl_2$ as the catalyst in the presence of $K_2CO_3$ in dioxane/water upon heating at 100° C. and the Boc protecting group was removed with HCl or TFA:

| Compound no. | MS (M + H)⁺ |
|---|---|
| 2-141 | 506.3 |
| 2-142 | 473.1 |
| 2-169 | 446.3 |
| 2-99 | 493.3 |
| 2-177 | 457.4 |
| 2-178 | 446.4 |
| 2-179 | 492.3 |
| 2-187 | 453.3 |
| 2-211 | 431.5 |
| 2-250 | 446.0 |
| 2-229 | 489.4 |
| 2-234 | 504.2 |
| 2-242 | 511.5 |

Example 14

3-[4-(4-aminopiperidin-1-yl)-3-[3-fluoro-5-(oxetan-3-yloxy)phenyl]quinolin-6-yl]-2-hydroxybenzonitrile (Compound No. 2-69)

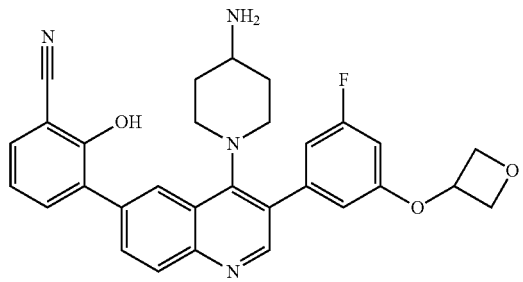 [SMILES: N#Cc1cccc(-c2ccc3ncc(-c4cc(F)cc(OC5COC5)c4)c(N4CCC(N)CC4)c3c2)c1O]

Step 14-1, preparation of {1-[6-chloro-3-(3-fluoro-5-hydroxy-phenyl)-quinolin-4-yl]-piperidin-4-yl}-carbamic acid tert-butyl ester: to a THF solution (10 mL) of [1-(3-bromo-6-chloro-quinolin-4-yl)-piperidin-4-yl]-carbamic acid tert-butyl ester (from step 13-1) (660 mg, 1.50 mmol) was added 3-fluoro-5-hydroxyphenyl boronic acid (1.5 eq., 2.25 mmol, 351 mg), tris(dibenzylideneacetone)dipalladium/tri-tert-butyl phosphonium tetrafluoroborate mixture (mole ratio: 1/1.2) (0.05 eq., 0.075 mmol, 75 mg), and $K_3PO_4.H_2O$ (3.0 eq., 4.5 mmol, 1.03 g). $N_2$ was bubbled through the reaction solution for 5 min and 1.0 mL water was added. The resulting mixture stirred at ambient temperature for 1 h and LCMS analysis showed complete converstion to the desired product. The reaction mixture was diluted with ethyl acetate and washed with water and brine. The organic layer was separated, dried with $MgSO_4$ and concentrated. The residue obtained was purified by silica gel chromatography eluting with ethyl acetate/hexane (0~50%) to give 561 mg of the desired product as white solid. MS (M+H)⁺=472.3.

Step 14-2, preparation of {1-[6-(3-cyano-2-methoxymethoxy-phenyl)-3-(3-fluoro-5-hydroxy-phenyl)-quinolin-4-yl]-piperidin-4-yl}-carbamic acid tert-butyl ester: to the dioxane solution (4 mL) of {1-[6-chloro-3-(3-fluoro-5-hydroxy-phenyl)-quinolin-4-yl]-piperidin-4-yl}- carbamic acid tert-butyl ester (0.64 mmol, 300 mg) was added Pd(amphos)Cl₂ (0.10 eq., 0.064 mmol, 45 mg), 2-methoxymethoxy-3-(4,4,5,5-tetramethyl-[1,3,2]dioxaborolan-2-yl)-benzonitrile (1.5 eq., 1.0 mmol, 289 mg) and K₂CO₃ (1.5 eq., 1.0 mmol, 138 mg). N₂ was bubbled through the reaction solution for 5 min and 0.40 mL water was added. The resulting mixture was heated at 95° C. for 1 h and LCMS analysis showed that starting material was completely consumed. The reaction mixture was diluted with ethyl acetate and washed with brine. The organic layer was separated, dried with MgSO₄ and concentrated. The residue obtained was purified by silica gel chromatography eluting with ethyl acetate/hexane (0~50%) to give 400 mg of the desired product as a yellow solid. MS (M+H)⁺=599.5.

Step 14-3, preparation of (1-{6-(3-Cyano-2-methoxymethoxy-phenyl)-3-[3-fluoro-5-(oxetan-3-yloxy)-phenyl]-quinolin-4-yl}-piperidin-4-yl)-carbamic acid tert-butyl ester: to the DMF solution (1.0 mL) of {1-[6-(3-cyano-2-methoxymethoxy-phenyl)-3-(3-fluoro-5-hydroxy-phenyl)-quinolin-4-yl]-piperidin-4-yl}-carbamic acid tert-butyl ester (0.16 mmol, 100 mg) was added 3-tosyloxyoxetane (10 eq., 1.6 mmol, 365 mg) and K₂CO₃ (10 eq., 1.6 mmol, 220 mg) portion-wise. The resulting mixture was heated at 80° C. for 5 hrs. The reaction mixture was diluted with ethyl acetate and washed with water and brine. The organic layer was separated, dried with MgSO₄ and concentrated. The residue obtained was purified by silica gel chromatography eluting with ethyl acetate/hexane (0~50%) to give 28 mg of the desired product as white solid. MS (M+H)⁺=655.2.

Step 14-4, preparation of 3-[4-(4-aminopiperidin-1-yl)-3-[3-fluoro-5-(oxetan-3-yloxy)phenyl]quinolin-6-yl]-2-hydroxybenzonitrile: to the dichloromethane (1 mL) solution of {(1-{6-(3-Cyano-2-methoxymethoxy-phenyl)-3-[3-fluoro-5-(oxetan-3-yloxy)-phenyl]-quinolin-4-yl}-piperidin-4-yl)-carbamic acid tert-butyl ester (28 mg) was added trifluroroacetic acid (0.2 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO₃, extracted with ethyl acetate and dried with MgSO₄. The organic solution was concentrated to give 8 mg of the final compound. MS (M+H)⁺=511.5.

The following compounds were prepared in a similar manner as described in Example 13, substituting with appropriate reagents and substrates as required:

| Compound no. | MS (M + H)⁺ |
|---|---|
| 2-68 | 497.5 |

Example 15

3-[4-(4-aminopiperidin-1-yl)-3-{3-fluoro-5-[(1E)-(methoxyimino)methyl]phenyl}quinolin-6-yl]-2-hydroxybenzonitrile (Compound No. 2-70)

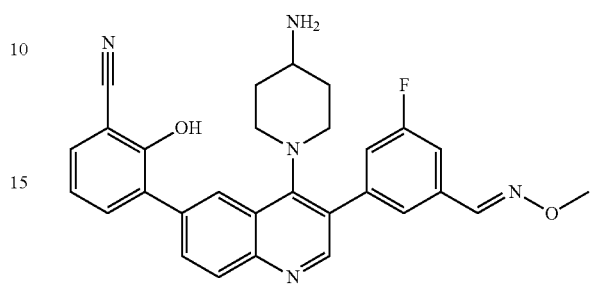

Step 15-1, preparation of {1-[6-chloro-3-(3-fluoro-5-formyl-phenyl)-quinolin-4-yl]-piperidin-4-yl}-carbamic acid tert-butyl ester: to a THF solution (10 mL) of [1-(3-bromo-6-chloro-quinolin-4-yl)-piperidin-4-yl]-carbamic acid tert-butyl ester (from step 13-1) (757 mg, 1.72 mmol) was added 3-fluoro-5-formylphenylboronic acid (1.5 eq., 2.58 mmol, 433 mg), tris(dibenzylideneacetone)dipalladium/tri-tert-butyl phosphonium tetrafluoroborate mixture (mole ratio: 1/1.2) (0.05 eq., 0.086 mmol, 86 mg), and K₃PO₄·H₂O (3.0 eq., 5.16 mmol, 1.18 g). N₂ was bubbled through the reaction solution for 5 min and 1.0 mL water was added. The resulting mixture stirred at ambient temperature for 1 h and LCMS analysis showed complete converstion to the desired product. The reaction mixture was diluted with ethyl acetate and washed with water and brine. The organic layer was separated, dried with MgSO₄ and concentrated. The residue obtained was purified by silica gel chromatography eluting with ethyl acetate/hexane (0~50%) to give 440 mg of the desired product as white solid. MS (M+H)⁺=484.4.

Step 15-2, preparation of {1-[6-(3-cyano-2-methoxymethoxy-phenyl)-3-(3-fluoro-5-formyl-phenyl)-quinolin-4-yl]-piperidin-4-yl}-carbamic acid tert-butyl ester: to the dioxane solution (5 mL) of {1-[6-chloro-3-(3-fluoro-5-formyl-phenyl)-quinolin-4-yl]-piperidin-4-yl}-carbamic acid tert-butyl ester (0.50 mmol, 241 mg) was added Pd(amphos)Cl₂ (0.10 eq., 0.05 mmol, 35 mg), 2-methoxymethoxy-3-(4,4,5,5-tetramethyl-[1,3,2]dioxaborolan-2-yl)-benzonitrile (1.5 eq., 0.75 mmol, 218 mg) and K₂CO₃ (1.5 eq., 0.75 mmol, 105 mg). N₂ was bubbled through the reaction solution for 5 min and 0.50 mL water was added. The resulting mixture was heated at 95° C. for 1 h and LCMS analysis showed that starting material was completely consumed. The reaction mixture was diluted with ethyl acetate and washed with brine. The organic layer was separated, dried with MgSO₄ and concentrated. The residue obtained was purified by silica gel chromatography eluting with ethyl acetate/hexane (0~50%) to give 270 mg of the desired product as a yellow solid. MS (M+H)⁺=611.3.

Step 15-3, preparation of (1-{6-(3-cyano-2-methoxymethoxy-phenyl)-3-[3-fluoro-5-(methoxyimino-methyl)-phenyl]-quinolin-4-yl}-piperidin-4-yl)-carbamic acid tert-butyl ester: to the dichloromethane solution (1.0 mL) of {1-[6-(3-cyano-2-methoxymethoxy-phenyl)-3-(3-fluoro-5-formyl-phenyl)-quinolin-4-yl]-piperidin-4-yl}-carbamic acid tert-butyl ester (0.05 mmol, 30 mg) was added the HCl salt of O-methyl-hydroxylamine (2.0 eq., 0.10 mmol, 9 mg) and pyridine (10 eq., 0.5 mmol, 0.02 mL). The resulting mixture was stirred at ambient temperature for 2 hrs and LCMS analysis showed that starting material was completely consumed. The crude reaction solution was used for next step without further purification. MS $(M+H)^+=640.5$.

Step 15-4, preparation of 3-[4-(4-aminopiperidin-1-yl)-3-{3-fluoro-5-[(1E)-(methoxyimino)methyl]phenyl}quinolin-6-yl]-2-hydroxybenzonitrile: the crude solution obtained from step 15-3 was added trifluroroacetic acid (0.4 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated $NaHCO_3/NaCl$, extracted with ethyl acetate and dried with $MgSO_4$. The organic solution was concentrated to give 6 mg of the final compound. MS $(M+H)^+=496.5$.

The following compounds were prepared in a similar manner as described in Example 15, substituting with appropriate reagents and substrates as required:

| Compound no. | MS (M + H)+ |
| --- | --- |
| 2-79 | 510.5 |

Example 16

3-[4-(4-aminopiperidin-1-yl)-3-{3-[(3,3-difluoroazetidin-1-yl)methyl]-5-fluorophenyl}quinolin-6-yl]-2-hydroxybenzonitrile (Compound No. 2-71)

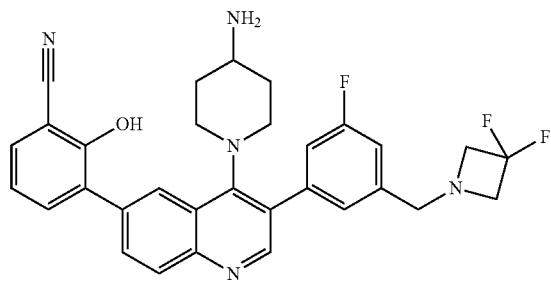 [SMILES: N#Cc1cccc(-c2ccc3ncc(-c4cc(F)cc(CN5CC(F)(F)C5)c4)c(N4CCC(N)CC4)c3c2)c1O]

Step 16-1, preparation of (1-{6-(3-cyano-2-methoxymethoxy-phenyl)-3-[3-(3,3-difluoro-azetidin-1-yl-methyl)-5-fluoro-phenyl]-quinolin-4-yl}-piperidin-4-yl)-carbamic acid tert-butyl ester: to the dichloromethane solution (1.0 mL) of {1-[6-(3-cyano-2-methoxymethoxy-phenyl)-3-(3-fluoro-5-formyl-phenyl)-quinolin-4-yl]-piperidin-4-yl}-carbamic acid tert-butyl ester (step 15-2) (0.05 mmol, 30 mg) was added the HCl salt of 3,3-difluoro-azetidine (6.0 eq., 0.30 mmol, 40 mg), triethyl amine (6 eq., 0.3 mmol 0.042 mL) and sodium triacetoxyborohydride (12 eq., 0.6 mmol, 130 mg). The resulting mixture was stirred at ambient temperature for 17 h. The reaction mixture was diluted with ethyl acetate and washed with sat. $NH_4Cl$. The organic layer was separated, dried with $MgSO_4$ and concentrated. The residue obtained was used for next step without further purfication. MS $(M+H)^+=688.4$.

Step 16-2, preparation of 3-[4-(4-aminopiperidin-1-yl)-3-{3-[(3,3-difluoroazetidin-1-yl)methyl]-5-fluorophenyl}quinolin-6-yl]-2-hydroxybenzonitrile: to the dichlormethane solution (1.0 mL) of crude product obtained from step 16-1 was added trifluroroacetic acid (0.2 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated $NaHCO_3/NaCl$, extracted with ethyl acetate and dried with $MgSO_4$. The organic solution was concentrated to give 7 mg of the final compound. MS $(M+H)^+=544.4$.

Example 17

3-[4-(4-aminopiperidin-1-yl)-3-(3,5-difluorophenyl)quinolin-6-yl]-2-(methoxy methoxy)benzonitrile (Compound No. 2-78)

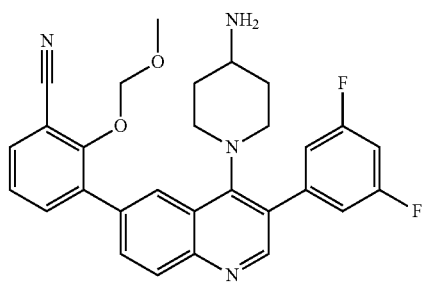 [SMILES: COCOc1c(C#N)cccc1-c1ccc2ncc(-c3cc(F)cc(F)c3)c(N3CCC(N)CC3)c2c1]

Step 17-1, preparation of 1-[6-chloro-3-(3,5-difluorophenyl)-quinolin-4-yl]-piperidin-4-ylamine: to the dichloromethane solution (4.0 mL) of {1-[6-chloro-3-(3,5-difluoro-phenyl)-quinolin-4-yl]-piperidin-4-yl}-carbamic acid tert-butyl ester (from Step 13-2) (0.5 mmol, 233 mg) was added trifluroroacetic acid (1.0 mL) and the resulting mixture was stirred at ambient temperature for 1 h. The reaction mixture was diluted with ethyl acetate and washed with saturated $NaHCO_3$. The organic layer was separated, dried with $MgSO_4$ and concentrated. The residue obtained was used for next step without further purifciation. MS $(M+H)^+=374.0$.

Step 17-2, preparation of 3-[4-(4-aminopiperidin-1-yl)-3-(3,5-difluorophenyl)quinolin-6-yl]-2-(methoxymethoxy) benzonitrile: to the dioxane solution (6 mL) of 1-[6-chloro-3-(3,5-difluoro-phenyl)-quinolin-4-yl]-piperidin-4-ylamine (0.50 mmol, 180 mg) was added $Pd(amphos)Cl_2$ (0.10 eq., 0.05 mmol, 34 mg), 2-methoxymethoxy-3-(4,4,5,5-tetramethyl-[1,3,2]dioxaborolan-2-yl)-benzonitrile (2.0 eq., 1.0 mmol, 289 mg) and $K_2CO_3$ (2.0 eq., 1.0 mmol, 138 mg). $N_2$ was bubbled through the reaction solution for 5 min and 0.60 mL water was added. The resulting mixture was heated at 95° C. for 1 h and LCMS analysis showed about 50% converstion to the desired product. $Pd(amphos)Cl_2$ (0.10 eq., 0.05 mmol, 34 mg), 2-methoxymethoxy-3-(4,4,5,5-tetramethyl-[1,3,2]dioxaborolan-2-yl)-benzonitrile (2.0 eq., 1.0 mmol, 289 mg) and $K_2CO_3$ (2.0 eq., 1.0 mmol, 138 mg) were added and the resulting mixture was heated for another 1 h. The reaction mixture was diluted with ethyl acetate and washed with brine. The organic layer was separated, dried with $MgSO_4$ and concentrated. The residue obtained was purified by C18 reversed phase chromatography eluting with MeCN/water (0~40%). Pure fractions were combined, neutralized with saturated $NaHCO_3/NaCl$, extracted with ethyl acetate and dried with $MgSO_4$. The organic solution was concentrated with HCl in ether (0.2 M, 0.7 mL) to give 55 mg of the desired product as HCl salt. MS (M+H)$^+$=501.3.

The following compounds were prepared in a similar manner as described in Example 17, substituting with appropriate reagents and substrates as required:

| Compound no. | MS (M + H)$^+$ |
|---|---|
| 2-194 | 519.4 |

Example 18

2-[4-(4-aminopiperidin-1-yl)-3-(3,5-difluorophenyl)quinolin-6-yl]-6-methoxyiminomethyl-phenol (Compound No. 2-81)

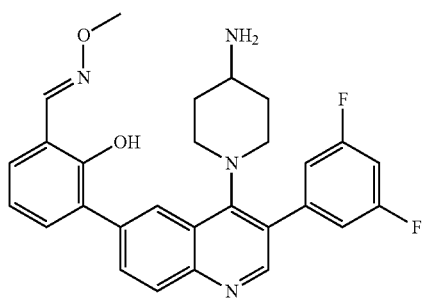 [SMILES: CO/N=C/c1cccc(-c2ccc3ncc(-c4cc(F)cc(F)c4)c(N4CCC(N)CC4)c3c2)c1O]

Step 18-1, preparation of {1-[3-(3,5-difluoro-phenyl)-6-(3-formyl-2-hydroxy-phenyl)-quinolin-4-yl]-piperidin-4-yl}-carbamic acid tert-butyl ester: to the dioxane solution (1 mL) of {1-[3-(3,5-difluoro-phenyl)-6-(4,4,5,5-tetramethyl-[1,3,2]dioxaborolan-2-yl)-quinolin-4-yl]-piperidin-4-yl}-carbamic acid tert-butyl ester (0.10 mmol, 57 mg) was added Pd(amphos)Cl$_2$ (0.10 eq., 0.01 mmol, 7.8 mg), 3-bromo-2-hydroxy-benzaldehyde (2.0 eq., 0.2 mmol, 40 mg) and K$_2$CO$_3$ (2.0 eq., 0.2 mmol, 28 mg). N$_2$ was bubbled through the reaction solution for 5 min and 0.1 mL water was added. The resulting mixture was heated at 95° C. for 1 h. The reaction mixture was diluted with ethyl acetate and washed with brine. The organic layer was separated, dried with MgSO$_4$ and concentrated. The residue obtained was purified by silica gel chromatography eluting with EtOAc/hexane (0~40%) to give 30 mg of the desired product. MS (M+H)$^+$=560.23.

Step 18-2, preparation of (1-{3-(3,5-difluoro-phenyl)-6-[2-hydroxy-3-(methoxyimino-methyl)-phenyl]-quinolin-4-yl}-piperidin-4-yl)-carbamic acid tert-butyl ester: to the dichloromethane solution (1.0 mL) of {1-[3-(3,5-difluoro-phenyl)-6-(3-formyl-2-hydroxy-phenyl)-quinolin-4-yl]-piperidin-4-yl}-carbamic acid tert-butyl ester (30 mg, 0.054 mmol) was added the HCl salt of O-methyl-hydroxylamine (2.0 eq., 0.10 mmol, 9 mg) and pyridine (10 eq., 0.5 mmol, 0.04 mL). The resulting mixture was stirred at ambient temperature for 2 h and LCMS analysis showed that starting material was completely consumed. The crude reaction solution was used for next step without further purification. MS (M+H)$^+$=589.5.

Step 18-3, preparation of 2-[4-(4-aminopiperidin-1-yl)-3-(3,5-difluorophenyl)quinolin-6-yl]-6-methoxyiminomethyl-phenol: the crude solution obtained from step 18-2 was added trifluroroacetic acid (0.5 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated to give 6 mg of the title compound. MS (M+H)$^+$=489.4.

The following compounds were prepared in a similar manner as described in Example 18, substituting with appropriate reagents and substrates as required:

| Compound no. | MS (M + H)$^+$ |
|---|---|
| 2-115 | 485.4 |
| 2-166 | 489.4 |
| 2-168 | 474.3 |
| 2-176 | 528.1 |
| 2-188 | 463.2 |
| 2-152 | 478.2 |
| 2-192 | 494.4 |
| 2-116 | 503.4 |
| 2-195 | 460.3 |
| 2-196 | 460.5 |
| 2-200 | 460.2 |
| 2-202 | 491.3 |
| 2-203 | 460.3 |
| 2-213 | 485.4 |
| 2-217 | 503.2 |

The following compounds were prepared similarly to example 18 except the Suzuki coupling was carried out using tris(dibenzylideneacetone)dipalladium/tri-tert-butyl phosphonium tetrafluoroborate mixture (mole ratio: 1/1.2) catalyst in the presence of K$_3$PO$_4$.H$_2$O in THF/water at ambient temperature:

| Compound no. | MS (M + H)$^+$ |
|---|---|
| 2-126 | 477.3 |
| 2-129 | 491.3 |

Example 19 methyl N-{2-[4-(4-aminopiperidin-1-yl)-3-(3,5-difluorophenyl)quinolin-6-yl]-4,6-difluorophenyl}carbamate (Compound No. 2-83)

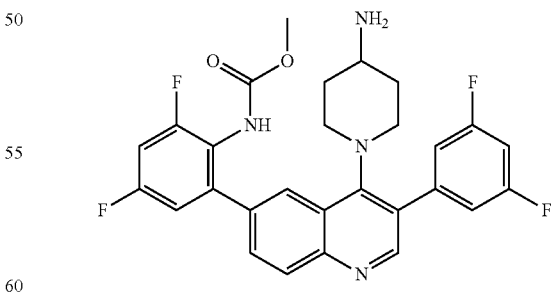

Step 19-1, preparation of {1-[6-(2-amino-3,5-difluoro-phenyl)-3-(3,5-difluoro-phenyl)-quinolin-4-yl]-piperidin-4-yl}-carbamic acid tert-butyl ester: to the dioxane solution (2 mL) of {1-[3-(3,5-difluoro-phenyl)-6-(4,4,5,5-tetramethyl-[1,3,2]dioxaborolan-2-yl)-quinolin-4-yl]-piperidin-4-yl}-carbamic acid tert-butyl ester (0.20 mmol, 112 mg) was added Pd(amphos)Cl$_2$ (0.10 eq., 0.02 mmol, 15 mg), 2-bromo-4,6-difluoro-phenylamine (2.0 eq., 0.4 mmol, 84 mg) and K$_2$CO$_3$ (2.0 eq., 0.4 mmol, 56 mg). N$_2$ was bubbled through the reaction solution for 5 min and 0.2 mL water was added. The resulting mixture was heated at 95° C. for 1 h. The reaction mixture was diluted with ethyl acetate and washed with brine. The organic layer was separated, dried with MgSO$_4$ and concentrated. The residue obtained was purified by silica gel chromatography eluting with EtOAc/hexane (0~40%) to give 62 mg of the desired product. MS (M+H)$^+$=567.4.

Step 19-2, preparation of {1-[6-(3,5-difluoro-2-methoxy-carbonylamino-phenyl)-3-(3,5-difluoro-phenyl)-quinolin-4-yl]-piperidin-4-yl}-carbamic acid tert-butyl ester: to the dichloromethane (1.0) solution of {1-[6-(2-amino-3,5-difluoro-phenyl)-3-(3,5-difluoro-phenyl)-quinolin-4-yl]-piperidin-4-yl}-carbamic acid tert-butyl ester (30 mg, 0.05 mmol) was added pyridine (13 eq., 0.0.65 mmol, 0.052 mL) and methyl chloroformate (6.0 eq., 0.30 mmol, 0.03 mL). The resulting mixture was stirred at ambient temperature for 2 h and LCMS analysis showed that starting material was completely consumed. The crude reaction solution was used for next step without further purification. MS (M+H)$^+$=625.6.

Step 19-3, preparation of methyl N-{2-[4-(4-aminopiperidin-1-yl)-3-(3,5-difluorophenyl)quinolin-6-yl]-4,6-difluorophenyl}carbamate: the crude solution obtained from step 19-2 was added trifluroroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in EtOEt to give 7 mg of the desired product as HCl salt. MS (M+H)$^+$=525.3.

The following compounds were prepared in a similar manner as described in Example 19, substituting with appropriate reagents and substrates as required:

| Compound no. | MS (M + H)$^+$ |
| --- | --- |
| 2-86 | 545.3 |
| 2-230 | 535.5 |

Example 20

3-(4-{3-[(1S)-1-aminopropyl]azetidin-1-yl}-3-(3-fluoro-5-methylphenyl)quinolin-6-yl)-5-fluoro-2-hydroxybenzonitrile (Compound No. 2-82)

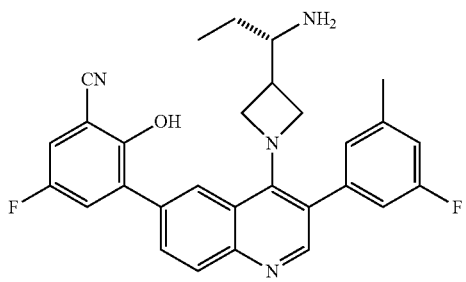 [SMILES: CC[C@H](N)C1CN(c2c(-c3cc(C)cc(F)c3)cnc3ccc(-c4cc(F)cc(C#N)c4O)cc23)C1]

Step 20-1, preparation of 3-[(R)-(2-methyl-propane-2-sulfinylimino)-methyl]-azetidine-1-carboxylic acid tert-butyl ester: To a solution of 3-formyl-azetidine-1-carboxylic acid tert-butyl ester (500.0 mg, 2.700 mmol) and (R)-2-methyl-propane-2-sulfinic acid amide (327.2 mg, 2.700 mmol) in DCM (5 mL) under nitrogen was added anhydrous copper (II) sulfate (948.0 mg, 5.940 mmol). The mixture was stirred at RT overnight. The mixture was filtered through Celite and the filtrate was concentrated in vacuo to dryness to afford the crude title compound as a colorless gum. (M+1)$^+$: 289.3.

Step 20-2, preparation of 3-[(S)-1-((R)-2-methyl-propane-2-sulfinylamino)-propyl]-azetidine-1-carboxylic acid tert-butyl ester: To a solution of the above crude 3-[((R)-2-methyl-propane-2-sulfinylimino)-methyl]-azetidine-1-carboxylic acid tert-butyl ester (2.700 mmol) (from Step 20-1) in DCM (20 mL) under nitrogen at −78° C. was added 0.9 M ethylmagnesium bromide solution in THF (4.5 mL, 4.05 mmol) dropwise. The mixture was stirred at −78° C. for 4 hr. The mixture was quenched with saturated NH$_4$Cl (aq) and warmed to RT. The mixture was extracted with DCM (1×) and the organic layer was concentrated in vacuo to dryness. The residue was purified by silica gel column chromatography to afford the title compound containing 32% of (R,R)-diastereomer (738.1 mg, 2.317 mmol, 85.8% yield) as a colorless gum. MS (M+1)$^+$: 319.2.

Step 20-3, preparation of 3-((S)-1-amino-propyl)-azetidine-1-carboxylic acid tert-butyl ester: To a solution of 3-[(S)-1-((R)-2-methyl-propane-2-sulfinylamino)-propyl]-azetidine-1-carboxylic acid tert-butyl ester (300.0 mg, 0.942 mmol) (from Step 20-2) in MeOH (5 mL) at 0° C. was added 4 N HCl solution in dioxane (0.31 mL) and the mixture was stirred at 0° C. for 5 hr. The mixture was quenched with saturated NaHCO$_3$ (aq) and extracted with DCM (2×). The combined organics were dried over anhydrous Na$_2$SO$_4$ and concentrated in vacuo to dryness to afford the crude title compound as an off-white gum. MS (M+1)$^+$: 215.0.

Step 20-4, preparation of 3-((S)-1-benzyloxycarbonylamino-propyl)-azetidine-1-carboxylic acid tert-butyl ester: To a solution of the crude 3-((S)-1-amino-propyl)-azetidine-1-carboxylic acid tert-butyl ester (from Step 20-3) in DCM (5 mL) was added carbonic acid benzyl ester 2,5-dioxo-pyrrolidin-1-yl ester (330.0 mg, 1.324 mmol) and the mixture was stirred at RT for 1 hr. The mixture was quenched with water and the organic layer was separated and concentrated in vacuo to dryness. The residue was purified by silica gel column chromatography to afford the title compound (222.2 mg, 0.638 mmol, 67.7% yield) as a colorless gum. MS (M+1)$^+$: 349.6.

Step 20-5, preparation of ((S)-1-azetidin-3-yl-propyl)-carbamic acid benzyl ester: To a solution of 3-((S)-1-benzyloxycarbonylamino-propyl)-azetidine-1-carboxylic acid tert-butyl ester (222.2 mg, 0.638 mmol) (from Step 3) in DCM (2.0 mL) was added TFA (0.5 mL). The mixture was stirred at RT for 30 min. The mixture was concentrated in vacuo to dryness and redissolved in EtOAc. The organic solution was washed with saturated NaHCO$_3$ (aq), dried over anhydrous Na$_2$SO$_4$ and concentrated in vacuo to dryness to afford the crude title compound (158.4 mg, 100% yield) as a light yellow gum. MS (M+1)$^+$: 249.2.

Example 21

3-{4-[(3R,4R)-4-amino-3-fluoropiperidin-1-yl]-3-(3,5-difluorophenyl)quinolin-6-yl}-2-hydroxybenzonitrile (Compound No. 2-59)

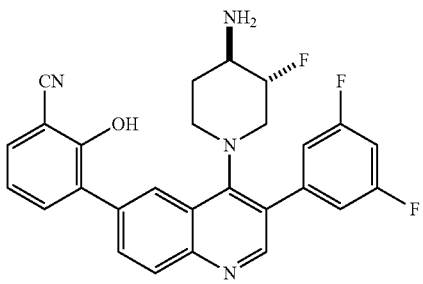

Step 21-1, preparation of {1-[6-(3-cyano-2-methoxymethoxy-phenyl)-3-(3,5-difluoro-phenyl)-quinolin-4-yl]-3-fluoro-piperidin-4-yl}-carbamic acid tert-butyl ester: to the dioxane solution (1.0 mL) of {1-[6-chloro-3-(3,5-difluoro-phenyl)-quinolin-4-yl]-3-fluoro-piperidin-4-yl}-carbamic acid tert-butyl ester (prepared similar to step 13-2) (0.08 mmol, 40 mg) was added Pd(amphos)Cl$_2$ (0.25 eq., 0.02 mmol, 15 mg), 2-methoxymethoxy-3-(4,4,5,5-tetramethyl-[1,3,2]dioxaborolan-2-yl)-benzonitrile (2.0 eq., 0.16 mmol, 47 mg) and K$_2$CO$_3$ (2.3 eq., 0.18 mmol, 25 mg). N$_2$ was bubbled through the reaction solution for 5 min and 0.10 mL water was added. The resulting mixture was heated at 100° C. for 1 h and LCMS analysis showed that starting material was completely consumed. The reaction mixture was diluted with ethyl acetate and washed with brine. The organic layer was separated, dried with Na$_2$SO$_4$ and concentrated. The residue obtained was purified by silica gel chromatography eluting with ethyl acetate/hexane (0~50%) to give 25 mg of the desired product as a yellow solid. MS (M+H)$^+$=619.6.

Step 21-2, preparation of 3-{4-[(3R,4R)-4-amino-3-fluoropiperidin-1-yl]-3-(3,5-difluorophenyl)quinolin-6-yl}-2-hydroxybenzonitrile: to the dichlormethane solution (1.5 mL) of {1-[6-(3-cyano-2-methoxymethoxy-phenyl)-3-(3,5-difluoro-phenyl)-quinolin-4-yl]-3-fluoro-piperidin-4-yl}-carbamic acid tert-butyl ester was added trifluroroacetic acid (0.5 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated to give 8 mg of the final compound. MS (M+H)$^+$=475.3.

Compound 2-92 was prepared similar to Compound 2-59 except the Suzuki coupling was carried out using Pd(amphos)Cl$_2$ catalyst in the presence of K$_2$CO$_3$ in dioxane/water upon heating at 100° C. (M+H)$^+$=481.5.

Example 22

3-[4-(4-aminopiperidin-1-yl)-3-(3,5-difluorophenyl)quinolin-6-yl]-2-[(2-methoxyethoxy)methoxy]benzonitrile (Compound No. 2-87)

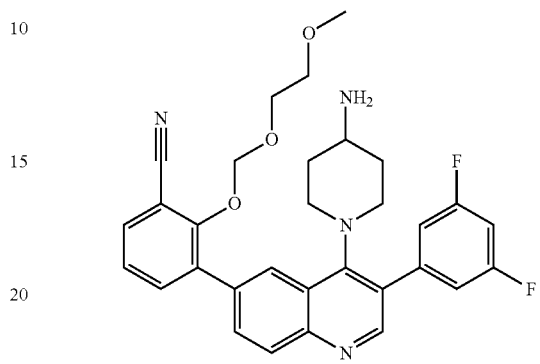

Step 22-1, preparation of tert-butyl N-[1-(6-{3-cyano-2-[(2-methoxyethoxy)methoxy]phenyl}-3-(3,5-difluorophenyl)quinolin-4-yl)piperidin-4-yl]carbamate: to a dichloromethane solution (5.0 mL) of {1-[6-(3-cyano-2-hydroxy-phenyl)-3-(3,5-difluoro-phenyl)-quinolin-4-yl]-piperidin-4-yl}-carbamic acid tert-butyl ester (300 mg, 0.54 mmol) was added N,N-diisopropylethylamine (1.5 eq., 0.81 mmol, 0.133 mL) and 2-methoxyethoxymethyl chloride (1.1 eq., 0.60 mmol, 0.0675 mL) at 0° C. The resulting mixture was stirred at the same temperature for 2 h. The reaction solution was diluted with dichloromethane, washed with saturated NH$_4$Cl, and dried with Na$_2$SO$_4$. The organic layer was concentrated and purified by silica gel chromatography eluting with ethyl acetate/hexane (0~50%) to give 187 mg of the desired product. MS (M+H)$^+$=645.6.

Step 22-2, preparation of 3-[4-(4-aminopiperidin-1-yl)-3-(3,5-difluorophenyl)quinolin-6-yl]-2-[(2-methoxyethoxy)methoxy]benzonitrile: to the dichloromethane (5.0 mL) solution of tert-butyl N-[1-(6-{3-cyano-2-[(2-methoxyethoxy)methoxy]phenyl}-3-(3,5-difluorophenyl)quinolin-4-yl)piperidin-4-yl]carbamate (187 mg, 0.29 mmol) was added trifluroroacetic acid (0.5 mL) and the resulting mixture was stirred at 0° C. for 0.5 h. Addditional 0.5 mL trifluroroacetic acid was added and the reaction solution was stirred at 0° C. for 1 h. The reaction solution was diluted with dichloromethane, washed with sasturated NaHCO$_3$, dired with Na$_2$SO$_4$ and concentrated. The residue obtained was purified by C18 reversed phase chromatography eluting with MeCN/water (0~40%). Pure fractions containing the desired product were combined, neutralized with saturated NaHCO$_3$/NaCl, extracted with ethyl acetate and dried with MgSO$_4$. MS (M+H)$^+$=545.4.

Example 23 trans-3-{4-amino-3-methoxypiperidin-1-yl]-3-(3,5-difluorophenyl)quinolin-6-yl}-2-(methoxymethoxy)benzonitrile (Compound No. 2-84)

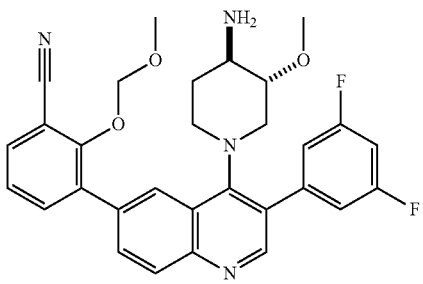

Step 23-1, preparation of trans-tert-butyl N-(1-{6-[3-cyano-2-(methoxymethoxy)phenyl]-3-(3,5-difluorophenyl)quinolin-4-yl}-3-methoxypiperidin-4-yl)carbamate: to the dioxane solution (6.6 mL) of trans-tert-butyl N-{1-[6-chloro-3-(3,5-difluorophenyl)quinolin-4-yl]-3-methoxypiperidin-4-yl}carbamate (0.686 mmol, 346 mg) (prepared similar to the compound described in Example 13, Step 13-2 but using trans-tert-butyl N-(3-methoxypiperidin-4-yl)carbamate) was added Pd(amphos)Cl$_2$ (0.20 eq., 0.13 mmol, 97 mg), 2-methoxymethoxy-3-(4,4,5,5-tetramethyl-[1,3,2]dioxaborolan-2-yl)-benzonitrile (2.0 eq., 1.36 mmol, 418 mg) and K$_2$CO$_3$ (3.0 eq., 2.06 mmol, 284 mg). N$_2$ was bubbled through the reaction solution for 5 min and 0.66 mL water was added. The resulting mixture was heated at 100° C. for 1 h and LCMS analysis showed that starting material was completely consumed. The reaction mixture was diluted with ethyl acetate and washed with brine. The organic layer was separated, dried with Na$_2$SO$_4$ and concentrated. The residue obtained was purified by silica gel chromatography eluting with ethyl acetate/hexane (0~50%) to give 273 mg of the desired product as a yellow foam. MS (M+H)$^+$=631.5.

Step 23-2, preparation of trans-3-{4-amino-3-methoxypiperidin-1-yl]-3-(3,5-difluorophenyl)quinolin-6-yl}-2-(methoxymethoxy)benzonitrile: to the dichloromethane (5.0 mL) solution of trans-tert-butyl N-(1-{6-[3-cyano-2-(methoxymethoxy)phenyl]-3-(3,5-difluorophenyl)quinolin-4-yl}-3-methoxypiperidin-4-yl)carbamate (188 mg, 0.30 mmol) was added trifluroroacetic acid (0.23 mL) in 1.0 mL dichloromethane at 0° C. After 0.5 h, addditional 0.5 mL trifluroroacetic acid was added and the reaction solution was stirred at 0° C. for 1 h. The reaction solution was diluted with dichloromethane, washed with sasturated NaHCO$_3$, dired with Na$_2$SO$_4$ and concentrated. The residue obtained was purified by silica gel chromatography eluting with MeOH/DCM (0~10%) to give 24 mg of the desired product. MS (M+H)$^+$=531.1.

Example 24

2-[4-(4-aminopiperidin-1-yl)-3-(3-fluoro-5-methylphenyl)quinolin-6-yl]6-(azetidine-1-carbonyl)phenol (Compound No. 2-88)

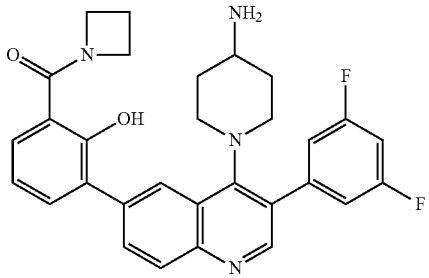 [SMILES: NC1CCN(c2c(-c3cc(F)cc(F)c3)cnc3ccc(-c4cccc(C(=O)N5CCC5)c4O)cc23)CC1]

Step 24-1, preparation of 2-(azetidine-1-carbonyl)-6-bromophenol: to the DMF solution (5 mL) of 3-bromo-2-hydroxybenzonic acid (1.0 mmol, 217 mg) was added triethyl amine (3.0 eq., 3.0 mmol, 0.415 mL), HATU (1.5 eq., 1.5 mmol, 570 mg) and the HCl salt of azetidine (1.5 eq., 1.5 mmol, 141 mg). The resulting mixture was stirred at ambient temperature for 1 h. The reaction mixture was diluted with ethyl acetate, washed with water and brine. The organic layer was separated, dried with Na$_2$SO$_4$ and concentrated. The residue obtained was purified by silica gel chromatography eluting with ethyl acetate/hexane (0~50%) to give 95 mg of the desired product as a yellow foam. MS (M+H)$^+$=631.5.

Step 24-2, preparation of tert-butyl N-(1-{6-[3-(azetidine-1-carbonyl)-2-hydroxyphenyl]-3-(3-fluoro-5-methylphenyl)quinolin-4-yl}piperidin-4-yl)carbamate: to the dioxane solution (2.0 mL) of 2-(azetidine-1-carbonyl)-6-bromophenol (0.2 mmol, 52 mg) was added added Pd(amphos)Cl$_2$ (0.10 eq., 0.02 mmol, 14 mg), tert-butyl N-{1-[3-(3-fluoro-5-methylphenyl)-6-(tetramethyl-1,3,2-dioxaborolan-2-yl)quinolin-4-yl]piperidin-4-yl}carbamate (1.0 eq., 0.2 mmol, 112 mg) (prepared similar to the compound described in Example 13, Step 13-3) and K$_2$CO$_3$ (2.5 eq., 0.5 mmol, 67 mg). N$_2$ was bubbled through the reaction solution for 5 min and 0.20 mL water was added. The resulting mixture was heated at 100° C. for 1 h and LCMS analysis showed that starting material was completely consumed. The reaction mixture was diluted with ethyl acetate and washed with brine. The organic layer was separated, dried with Na$_2$SO$_4$ and concentrated. The residue obtained was purified by silica gel chromatography eluting with ethyl acetate/hexane (0~50%) to give 40 mg of the desired product. MS (M+H)$^+$=611.4.

Step 24-3, preparation of 2-[4-(4-aminopiperidin-1-yl)-3-(3-fluoro-5-methylphenyl)quinolin-6-yl]6-(azetidine-1-carbonyl)phenol: to the dichloromethane (1.0 mL) solution of tert-butyl N-(1-{6-[3-(azetidine-1-carbonyl)-2-hydroxyphenyl]-3-(3-fluoro-5-methylphenyl)quinolin-4-yl}piperidin-4-yl)carbamate (40 mg) was added trifluroroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in EtOEt (2.0 M, 0.5 mL) to give 8 mg of the final compound as HCl salt. MS (M+H)$^+$=511.5.

Example 25

3-[4-(4-aminopiperidin-1-yl)-3-(3,5-difluorophenyl)quinolin-6-yl]-5-chloro-4-fluoro-2-hydroxybenzonitrile (Compound No. 2-147)

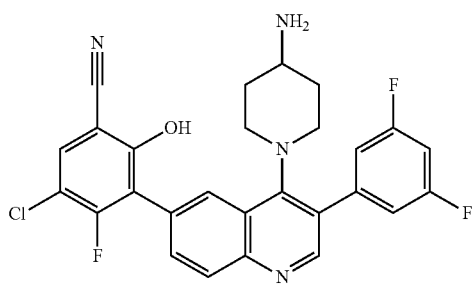 [SMILES: N#Cc1cc(Cl)c(F)c(-c2ccc3ncc(-c4cc(F)cc(F)c4)c(N4CCC(N)CC4)c3c2)c1O]

Step 25-1, preparation of 3-bromo-5-chloro-4-fluoro-2-hydroxybenzonitrile: to the dichloromethane solution (15 mL) of 4-chloro-2,5-difluorophenol (803 mg, 4.46 mmol) was added bromine (1.2 eq., 5.35 mmol, 0.28 mL) in 5 mL dichloromethane drop-wise. The resulting mixture was heated at 40° C. in a sealed tube for 2 h. The reaction solution was diluted with dichloromethane, washed with brine, dried with Na$_2$SO$_4$, and concentrated. The residue obtained was slurred in ethyl acetate/hexane (1:4) for 1 h and filtered to give 940 mg of the desired product.

Step 25-2, preparation of 3-bromo-5-chloro-4-fluoro-2-[(2-methoxyethoxy)methoxy]benzonitrile: to the dichloromethane solution (40 mL) of 3-bromo-5-chloro-4-fluoro-2-hydroxybenzonitrile (940 mg, 3.76 mmol) was was added N,N-diisopropylethylamine (1.5 eq., 5.64 mmol, 0.93 mL) and 2-methoxyethoxymethyl chloride (1.5 eq., 5.64 mmol, 0.64 mL) at 0° C. The resulting mixture was stirred at the same temperature for 2 h. The reaction solution was diluted with dichloromethane, washed with saturated NH$_4$Cl, and dried with Na$_2$SO$_4$. The organic layer was concentrated and purified by silica gel chromatography eluting with ethyl acetate/hexane (0~15%) to give 939 mg of the desired product as white solid.

Step 25-3, preparation of tert-butyl N-[1-(6-{3-chloro-5-cyano-2-fluoro-6-[(2-methoxyethoxy)methoxy]phenyl}-3-(3,5-difluorophenyl)quinolin-4-yl)piperidin-4-yl]carbamate: to a THF solution (2.0 mL) of tert-butyl N-{1-[3-(3,5-difluoro-phenyl)-6-(tetramethyl-1,3,2-dioxaborolan-2-yl)quinolin-4-yl]piperidin-4-yl}carbamate (0.21 mmol, 121 mg, step 13-3) was added 3-bromo-5-chloro-4-fluoro-2-[(2-methoxyethoxy)methoxy]benzonitrile (2.0 eq., 0.21 mmol, 142 mg), tris(dibenzylideneacetone)dipalladium/tri-tert-butyl phosphonium tetrafluoroborate mixture (mole ratio: 1/1.2) (0.05 eq., 0.01 mmol, 14 mg), K$_3$PO$_4$.H$_2$O (3.0 eq., 0.63 mmol, 148 mg). N$_2$ was bubbled through the reaction solution for 5 min and 0.2 mL water was added. The resulting mixture stirred at ambient temperature for 1 h. The reaction mixture was diluted with ethyl acetate and washed with saturated NH$_4$Cl, NaHCO$_3$ and brine. The organic layer was separated, dried with Na$_2$SO$_4$ and concentrated. The residue obtained was purified by silica gel chromatography eluting with ethyl acetate/hexane (0~40%) to give 24 mg of the desired product as a yellow solid. MS (M+H)$^+$=697.5.

Step 25-4, preparation of 3-[4-(4-aminopiperidin-1-yl)-3-(3,5-difluorophenyl)quinolin-6-yl]-5-chloro-4-fluoro-2-hydroxybenzonitrile: to the dichloromethane (1.0 mL) solution of tert-butyl N-[1-(6-{3-chloro-2,5-difluoro-6-[(2-methoxyethoxy)methoxy]phenyl}-3-(3,5-difluorophenyl)quinolin-4-yl)piperidin-4-yl]carbamate (24 mg) was added trifluoroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in EtOEt (2.0 M, 0.2 mL) to give 4.4 mg of the final compound as HCl salt. MS (M+H)$^+$=509.2.

The following compounds were prepared in a similar manner as described in Example 25, substituting with appropriate reagents and substrates as required:

| Compound no. | MS (M + H)$^+$ |
| --- | --- |
| 2-150 | 486.3 |
| 2-161 | 498.3 |
| 2-134 | 502.2 |

Example 26

1-{2-[4-(4-aminopiperidin-1-yl)-3-(3,5-difluorophenyl)quinolin-6-yl]-4,6-difluorophenyl}-3-methoxyurea (Compound No. 2-139)

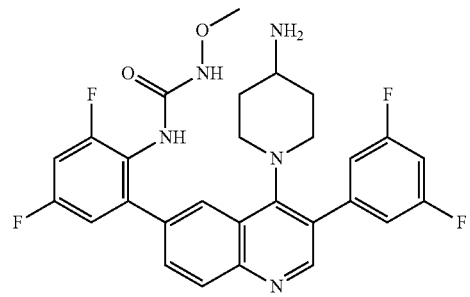 [SMILES: CONC(=O)Nc1c(F)cc(F)cc1-c1ccc2ncc(-c3cc(F)cc(F)c3)c(N3CCC(N)CC3)c2c1]

Step 26-1, preparation of tert-butyl N-{1-[6-(2-amino-3,5-difluorophenyl)-3-(3,5-difluorophenyl)quinolin-4-yl]piperidin-4-yl}carbamate: to the dioxane solution (2.0 mL) of tert-butyl N-{1-[3-(3,5-difluoro-phenyl)-6-(tetramethyl-1,3,2-dioxaborolan-2-yl)quinolin-4-yl]piperidin-4-yl}carbamate (1.0 eq., 0.2 mmol, 112 mg, Step 13-3) was added added Pd(amphos)Cl$_2$ (0.10 eq., 0.02 mmol, 14 mg), 2-bromo-4,6-difluoro-phenylamine (0.4 mmol, 80 mg) and K$_2$CO$_3$ (2.5 eq., 0.5 mmol, 67 mg). N$_2$ was bubbled through the reaction solution for 5 min and 0.20 mL water was added. The resulting mixture was heated at 100° C. for 1 h and LCMS analysis showed that starting material was completely consumed. The reaction mixture was diluted with ethyl acetate and washed with brine. The organic layer was separated, dried with Na$_2$SO$_4$ and concentrated. The residue obtained was purified by silica gel chromatography eluting with ethyl acetate/hexane (0~50%) to give 29 mg of the desired product. MS (M+H)$^+$=567.4.

Step 26-2, preparation of tert-butyl N-{1-[6-(3,5-difluoro-2-isocyanatophenyl)-3-(3,5-difluorophenyl)quinolin-4-yl]

piperidin-4-yl}carbamate: tert-butyl N-{1-[6-(2-amino-3,5-difluorophenyl)-3-(3,5-difluorophenyl)quinolin-4-yl]piperidin-4-yl}carbamate (29 mg, 0.051 mmol) was dissolved in 0.5 mL dichloromethane followed by the addition of triethyl amine (2.2 eq., 0.11 mmol, 0.016 mL). The resulting mixture was added to the dichloromethane solution (0.5 mL) of triphosgene (0.4 eq., 0.02 mmol, 6.0 mg) at 0° C. drop-wise. After 15 min, the reaction solution was warmed up to ambient temperature and stirred for 0.5 h. The crude reaction solution was used for next step without further purification.

Step 26-3, preparation of tert-butyl N-[1-(6-{3,5-difluoro-2-[(methoxycarbamoyl)amino]phenyl}-3-(3,5-difluorophenyl)quinolin-4-yl)piperidin-4-yl]carbamate: to the anhydrous DMF solution (1.0 mL) of O-methyl-hydroxylamine HCl salt (3.0 eq., 0.15 mmol, 13 mg) was added triethyl amine (4.4 eq., 0.20 mmol, 0.032 mL). The resulting suspension was cooled down to 0° C., and the crude reaction solution from step 26-2 was added drop-wise. The reaction solution was stirred at ambient temperature for 10 min and LCMS analysis showed that starting material was completely consumed. The reaction mixture was diluted with ethyl acetate and washed with water and brine. The organic layer was separated, dried with MgSO$_4$, concentrated and dried under high vaccum to give 23 mg of the desired product. This material was used for next step without further purification. MS (M+H)$^+$=640.4.

Step 26-4, preparation of 1-{2-[4-(4-aminopiperidin-1-yl)-3-(3,5-difluorophenyl)quinolin-6-yl]-4,6-difluorophenyl}-3-methoxyurea: to the dichloromethane (1.0 mL) solution of tert-butyl N-[1-(6-{3,5-difluoro-2-[(methoxycarbamoyl)amino]phenyl}-3-(3,5-difluorophenyl)quinolin-4-yl)piperidin-4-yl]carbamate (23 mg) was added trifluroroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in EtOEt (2.0 M, 0.5 mL) to give 8.0 mg of the final compound as HCl salt. MS (M+H)$^+$=540.4.

The following compounds were prepared using similar methods as described in Example 26 and substituting with appropriate reagents and substrates as required. Compound 2-215, 2-237 were prepared by treating the corresponding aniline intermediates with 3-methoxy-1-(4-nitrophenyl)urea in dioxane as an alternative step of Step 26-2.

| Compound no. | MS (M + H)$^+$ |
|---|---|
| 2-164 | 552.3 |
| 2-172 | 519.5 |
| 2-174 | 534.3 |
| 2-175 | 544.5 |
| 2-182 | 504.4 |
| 2-183 | 519.4 |
| 2-185 | 514.5 |
| 2-186 | 535.4 |
| 2-189 | 529.3 |
| 2-191 | 579.4 |
| 2-198 | 550.6 |
| 2-199 | 534.4 |
| 2-206 | 575.6 |
| 2-207 | 566.2 |
| 2-210 | 532.2 |
| 2-212 | 504.4 |
| 2-215 | 515.4 |
| 2-216 | 564.3 |
| 2-222 | 525.4 |
| 2-223 | 518.5 |
| 2-226 | 501.3 |
| 2-228 | 550.6 |
| 2-233 | 604.5 |
| 2-236 | 566.3 |
| 2-237 | 543.2 |
| 2-238 | 596.9 |
| 2-239 | 515.4 |
| 2-240 | 500.1 |

Example 27 methyl N-{2-[4-(4-aminopiperidin-1-yl)-3-(3,5-difluorophenyl)quinolin-6-yl]-6-cyanophenyl}carbamate (Compound No. 2-148)

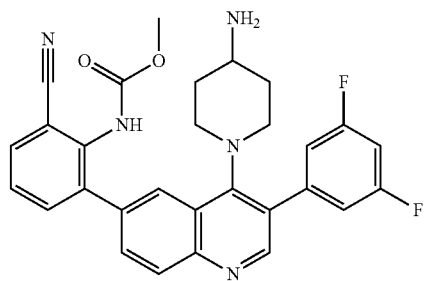 [SMILES: COC(=O)Nc1c(C#N)cccc1-c1ccc2ncc(-c3cc(F)cc(F)c3)c(N3CCC(N)CC3)c2c1]

Step 27-1 preparation of methyl N-{2-[4-(4-{[(tert-butoxy)carbonyl]amino}piperidin-1-yl)-3-(3,5-difluorophenyl)quinolin-6-yl]-6-cyanophenyl}carbamate: the dichloromethane solution (0.9 mL) of tert-butyl N-{1-[6-(3-cyano-2-isocyanatophenyl)-3-(3,5-difluorophenyl)quinolin-4-yl]piperidin-4-yl}carbamate (0.065 mmol, prepared silmiliar to Example 26, step 26-2) was added into 1.0 mL MeOH at 0° C. and the resulting mixture was stirred at ambient temperature for 0.5 h. The reaction solution was concentrated and dried under high vaccum to give 25 mg of the desired product. This material was used for next step without further purification. MS (M+H)$^+$=614.5.

Step 27-2, preparation of methyl N-{2-[4-(4-aminopiperidin-1-yl)-3-(3,5-difluorophenyl)quinolin-6-yl]-6-cyanophenyl}carbamate: to the dichloromethane (1.0 mL) solution of methyl N-{2-[4-(4-{[(tert-butoxy)carbonyl]amino}piperidin-1-yl)-3-(3,5-difluorophenyl)quinolin-6-yl]-6-cyanophenyl}carbamate (25 mg) was added trifluroroacetic acid (0.3 mL) and the resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in EtOEt (2.0 M, 0.5 mL) to give 5.8 mg of the final compound as HCl salt. MS (M+H)$^+$=514.5.

The following compounds were prepared using similar methods as described in Example 27 and substituting with appronriate reagents and substrates as required

| Compound no. | MS (M + H)+ |
| --- | --- |
| 2-165 | 537.5 |
| 2-167 | 526.3 |
| 2-171 | 504.3 |
| 2-173 | 519.4 |
| 2-125 | 515.5 |
| 2-180 | 550.5 |
| 2-184 | 520.4 |
| 2-197 | 521.4 |
| 2-123 | 543.4 |
| 2-205 | 546.4 |
| 2-209 | 503.4 |
| 2-214 | 489.4 |
| 2-218 | 540.2 |
| 2-235 | 551.2 |

Example 28 methyl trans-4-amino-1-[6-(3-cyano-2-hydroxyphenyl)-3-(3,5-difluorophenyl)quinolin-4-yl]piperidine-3-carboxylate (Compound No. 2-143)

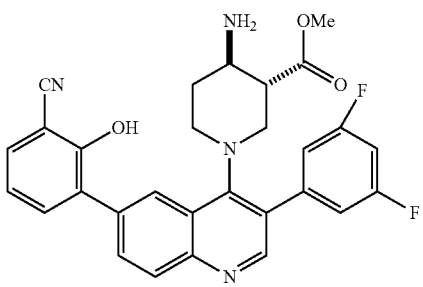

Step 28-1, preparation of methyl trans-1-(6-bromo-3-chloroquinolin-4-yl)-4-{[(tert-butoxy)carbonyl]amino}piperidine-3-carboxylate: from 6-bromo-3,4-dichloroquinoline (225.1 mg, 0.813 mmol) and methyl trans-tert-butoxy)carbonyl]amino}piperidine-3-carboxylate (140.0 mg, 0.542 mmol), the title compound was prepared as a light brown solid using a similar method to the one described in "Example 4, Step 4-1". MS (M+1)+=499.8.

Step 28-2, preparation of methyl trans-4-{[(tert-butoxy)carbonyl]amino}-1-{3-chloro-6-[3-cyano-2-(methoxymethoxy)phenyl]quinolin-4-yl}piperidine-3-carboxylate: from methyl trans-1-(6-bromo-3-chloroquinolin-4-yl)-4-{[(tert-butoxy)carbonyl]amino}piperidine-3-carboxylate (108.0 mg, 0.217 mmol) and 2-(methoxymethoxy)-3-(tetramethyl-1,3,2-dioxaborolan-2-yl)benzonitrile (74.8 mg, 0.260 mmol), the title compound was prepared as a light brown gum using a similar method to the one described in "Example 12, Step 12-3". MS (M+1)+=581.1.

Step 28-3, preparation of methyl trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylate: from methyl trans-4-{[(tert-butoxy)carbonyl]amino}-1-{3-chloro-6-[3-cyano-2-(methoxymethoxy)phenyl]quinolin-4-yl}piperidine-3-carboxylate (125.9 mg, 0.217 mmol) and (3,5-difluorophenyl)boronic acid (51.4 mg, 0.326 mmol), the title compound was prepared as a light yellow gum using a similar method to the one described in "Example 12, Step 12-4". MS (M+1)+=659.5.

Step 28-4, preparation of methyl trans-4-amino-[6-(3-cyano-2-hydroxyphenyl)-3-(3,5-difluorophenyl)quinolin-4-yl]piperidine-3-carboxylate: From methyl trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylate (14.0 mg, 0.0213 mmol), the title compound was prepared as a yellow solid using a similar method to the one described in "Example 5, Step 5-6". MS (M+1)+=515.5.

The following compounds were prepared using similar methods as described in Example 28 and substituting with appropriate reagents and substrates as required.

| Compound no. | MS (M + H)+ |
| --- | --- |
| 2-170 | 515.6 |
| 2-94 | 482.4 |

Example 29 trans-4-amino-1-{6-[3-cyano-2-(methoxymethoxy)phenyl]-3-(3,5-difluorophenyl)quinolin-4-yl}piperidine-3-carboxylic acid (Compound No. 2-145)

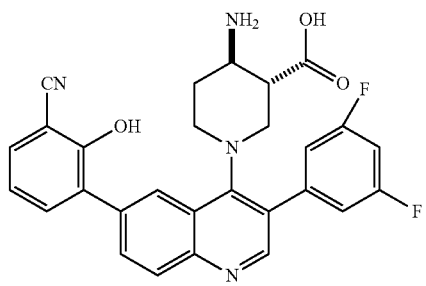

Step 29-1, preparation of trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylic acid: to a solution of methyl trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylate (106.0 mg, 0.161 mmol) in a mixed solvent of THF/MeOH/H$_2$O (3:1:1, 2 mL) at 0° C. was added lithium hydroxide monohydrate (33.8 mg, 0.805 mmol). The mixture was stirred at ambient temperature for 4 hr. The mixture was neutralized with 1 N HCl (aq) and concentrated to remove organic solvent. The aqueous residue was diluted with water and acidified with 1 N HCl (aq) to pH 3. The solid was collected by vacuum filtration and washed with water to afford the title compound (74.4 mg, 0.115 mmol, 71.4% yield) as a yellow solid. (M+1)+=645.3.

Step 29-2, preparation of trans-4-amino-1-{6-[3-cyano-2-(methoxymethoxy)phenyl]-3-(3,5-difluorophenyl)quinolin-4-yl}piperidine-3-carboxylic acid: from trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylic acid (15.0 mg, 0.0233 mmol), the title compound was prepared as a yellow solid using a similar method to the one described in "Example 5, Step 5-6". MS (M+1)+=501.2.

Example 30 trans-4-Amino-1-[6-(3-cyano-2-hydroxyphenyl)-3-(3,5-difluorophenyl)quinolin-4-yl]piperidine-3-carboxamide (Compound No. 2-146)

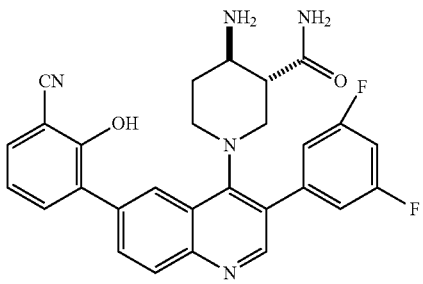

Step 30-1, preparation of tert-butyl N-trans-3-carbamoyl-1-{6-[3-cyano-2-(methoxymethoxy)phenyl]-3-(3,5-difluorophenyl)quinolin-4-yl}piperidin-4-yl]carbamate: To a solution of trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylic acid (30.0 mg, 0.0465 mmol) and 1-[bis(dimethylamino)methylene]-1H-1,2,3-triazolo[4,5-b]pyridinium 3-oxide hexafluorophosphate (26.5 mg, 0.0617 mmol) in DMF (2 mL) in a sealed tube was added diisopropylethylamine (0.12 mL, 0.689 mmol). After stirring at RT for 5 min, ammonium chloride (24.9 mg, 0.465 mmol) was added. The mixture was stirred at RT overnight. The mixture was purified by reversed-phase column chromatography (neutralized with saturated NaHCO$_3$ (aq)) to afford the title compound (19.4 mg, 0.0301 mmol, 64.7% yield) as a yellow solid. MS (M+1)$^+$=644.1.

Step 30-2, preparation of trans-4-amino-1-[6-(3-cyano-2-hydroxyphenyl)-3-(3,5-difluorophenyl)quinolin-4-yl]piperidine-3-carboxamide: from tert-butyl N-[trans-3-carbamoyl-1-{6-[3-cyano-2-(methoxymethoxy)phenyl]-3-(3,5-difluorophenyl)quinolin-4-yl}piperidin-4-yl]carbamate (19.4 mg, 0.0301 mmol), the title compound was prepared as a yellow solid using a similar method to the one described in "Example 5, Step 5-6". MS (M+1)$^+$=500.3.

The following compounds were prepared in a similar manner as described in Example 30, substituting with appropriate reagents and substrates as required.

| Compound no. | MS (M + H)$^+$ |
|---|---|
| 2-151 | 527.9 |

Example 31 trans-4-Amino-1-[6-(3-cyano-2-hydroxyphenyl)-3-(3,5-difluorophenyl)quinolin-4-yl]-N-methylpiperidine-3-carboxamide (Compound No. 2-149)

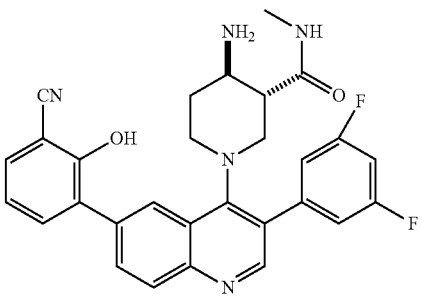

Step 31-1, Preparation of tert-butyl N-[trans-1-{6-[3-cyano-2-(methoxymethoxy)phenyl]-3-(3,5-difluorophenyl)quinolin-4-yl}-3-{[(4-methoxyphenyl)methyl](methyl)carbamoyl}piperidin-4-yl]carbamate: from trans-4-{[(tert-butoxy)carbonyl]amino}-1-{6-[3-cyano-2-(methoxymethoxy)phenyl]-3-(3,5-difluorophenyl)quinolin-4-yl}piperidine-3-carboxylic acid (28.4 mg, 0.0441 mmol) and [(4-methoxyphenyl)methyl](methyl)amine (8.7 mg, 0.0575 mmol), the title compound was prepared as a yellow solid using a similar method to the one described in "Example 24, Step 24-1". MS (M+1)$^+$=778.4.

Step 31-2, preparation of trans-4-amino-1-[6-(3-cyano-2-hydroxyphenyl)-3-(3,5-difluorophenyl)quinolin-4-yl]-N-methylpiperidine-3-carboxamide: to tert-butyl N-[trans-1-{6-[3-cyano-2-(methoxymethoxy)phenyl]-3-(3,5-difluorophenyl)quinolin-4-yl}-3-{[(4-methoxyphenyl)methyl](methyl)carbamoyl}piperidin-4-yl]carbamate (28.0 mg, 0.0360 mmol) was added (methylsulfanyl)benzene (0.05 mL) and 2,2,2-trifluoroacetic acid (0.25 mL). The mixture was heated at 80° C. overnight. The mixture was concentrated in vacuo to dryness and the residue was purified by reversed-phase column chromatography (neutralized with saturated NaHCO$_3$ (aq)) to afford the title compound (15.9 mg, 0.0310 mmol, 86.1% yield) as a yellow solid. MS (M+1)$^+$=514.0.

Example 32 trans-6-[3-(3,5-difluorophenyl)-4-{octahydro-1H-pyrido[3,4-b]morpholin-6-yl}quinolin-6-yl]-4-fluoro-2,3-dihydro-1H-1,3-benzodiazol-2-one (Compound No. 2-80)

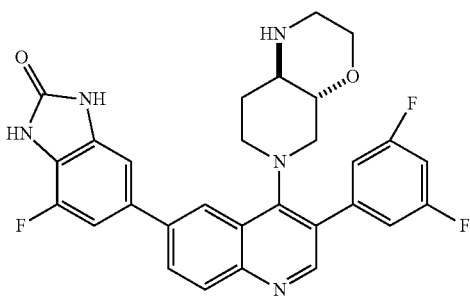

Step 32-1, preparation of trans-tert-butyl 6-(6-bromo-3-chloroquinolin-4-yl)-octahydro-1H-pyrido[3,4-b]morpholine-1-carboxylate: from 6-bromo-3,4-dichloroquinoline (137 mg, 0.495 mmol) and trans-tert-butyl octahydro-1H-pyrido[3,4-b]morpholine-1-carboxylate (100 mg, 0.413 mmol), the title compound was prepared as a brown gum using a similar method to the one described in "Example 4, Step 4-1". MS (M+1)$^+$=484.4.

Step 32-2, preparation of trans-tert-butyl 6-[3-chloro-6-(7-methyl-2-oxo-2,3-dihydro-1H-1,3-benzodiazol-5-yl)quinolin-4-yl]-octahydro-1H-pyrido[3,4-b]morpholine-1-carboxylate: from trans-tert-butyl 6-(6-bromo-3-chloroquinolin-4-yl)-octahydro-1H-pyrido[3,4-b]morpholine-1-carboxylate (112 mg, 0.232 mmol) and (77 mg, 0.278 mmol), the title compound was prepared as a yellow solid using a method similar to the one described in "Example 4, Step 4-3". MS (M+1)$^+$=554.4.

Step 32-3, trans-tert-butyl 6-[3-(3,5-difluorophenyl)-6-(7-fluoro-2-oxo-2,3-dihydro-1H-1,3-benzodiazol-5-yl)quinolin-4-yl]-octahydro-1H-pyrido[3,4-b]morpholine-1-carboxylate: from trans-tert-butyl 6-[3-chloro-6-(7-fluoro-2-oxo-2,3-dihydro-1H-1,3-benzodiazol-5-yl)quinolin-4-yl]-octahydro-1H-pyrido[3,4-b]morpholine-1-carboxylate (123 mg, 0.223 mmol) and 3,-5-difluorophenyl boronic acid (70 mg, 0.443 mmol), the title compound was prepared as a yellow solid using a method similar to the one described in "Example 4, Step 4-3". MS (M+1)$^+$: 632.5.

Step 32-4, preparation of trans-6-[3-(3,5-difluorophenyl)-4-{octahydro-1H-pyrido[3,4-b]morpholin-6-yl}quinolin-6-yl]-4-fluoro-2,3-dihydro-1H-1,3-benzodiazol-2-one: from trans-tert-butyl 6-[3-(3,5-difluorophenyl)-6-(7-fluoro-2-oxo-2,3-dihydro-1H-1,3-benzodiazol-5-yl)quinolin-4-yl]-octahydro-1H-pyrido[3,4-b]morpholine-1-carboxylate (76 mg, 0.120 mmol) and HCl in dioxane (4.0 M, 3.0 mL), the title compound was prepared as a yellow solid using a method similar to the one described in "Example 5, Step 5-6". MS (M+1)$^+$=532.1.

Example 33 trans-6-[3-(3,5-difluorophenyl)-4-{octahydro-1H-pyrido[3,4-b]morpholin-6-yl}quinolin-6-yl]pyridine-2-carboxamide (Compound No. 2-85)

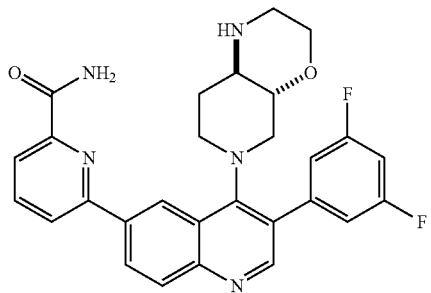

Step 33-1, preparation of trans-1-benzyl 6-tert-butyl octahydro-1H-pyrido[3,4-b]morpholine-1,6-dicarboxylate: to the dichloromethane solution (5.0 mL) of trans-tert-butyl octahydro-1H-pyrido[3,4-b]morpholine-6-carboxylate (400 mg, 1.81 mmol) was added benzyloxycarbonyl N-succinimide (1.3 eq., 2.35 mmol, 583 mg) and the resulting mixture was stirred at ambient temperature for overnight. The reaction solution was concentrated and purified by silica gel chromatography eluting with ethyl acetate/hexane (0~40%) to give 540 mg of the desired product as a colorless oil. MS (M+1)$^+$=377.4.

Step 33-2, preparation of trans-benzyl octahydro-1H-pyrido[3,4-b]morpholine-1-carboxylate: to the dioxane solution (1.5 mL) of trans-1-benzyl 6-tert-butyl octahydro-1H-pyrido[3,4-b]morpholine-1,6-dicarboxylate (500 mg, 1.33 mmol) was added HCl in dioxane (3.5 mL, 4.0 M) and the resulting mixture was stirred at ambient temperature for 2 h. The resulting suspension was filtered and solid was collected after washing with hexane to give 375.5 mg of the desired product as HCl salt. MS (M+1)$^+$=277.0.

Step 33-3, preparation of trans-benzyl 6-(3-bromo-6-chloroquinolin-4-yl)-octahydro-1H-pyrido[3,4-b]morpholine-1-carboxylate: to an anhydrous DMSO (5.0 mL) solution of 3-bromo-4,6-dichloro-quinoline (1.2 eq., 1.44 mmol, 399 mg) was added N,N-diisopropylethylamine (1.0 mL) and HCl salt of trans-benzyl octahydro-1H-pyrido[3,4-b]morpholine-1-carboxylate (1.20 mmol, 376 mg). N$_2$ was bubbled through the reaction solution for 5 min and the resulting solution was heated at 130° C. for overnight. The reaction mixture was diluted with dichloromethane and washed with water and brine. The organic layer was separated, dried with Na$_2$SO$_4$ and concentrated. The residue obtained was purified by C18 reverse phase chromatography eluting with MeCN/water (0~40%). Pure fractions were combined, neutralized with saturated NaHCO$_3$/NaCl, extracted with ethyl acetate and dried with MgSO$_4$. The organic solution was concentrated and dried under high vaccum to give 239 mg of the desired product. MS (M+H)$^+$=516.3.

Step 33-4, preparation of trans-benzyl 6-[6-chloro-3-(3,5-difluorophenyl)quinolin-4-yl]-octahydro-1H-pyrido[3,4-b]morpholine-1-carboxylate: from trans-benzyl 6-(3-bromo-6-chloroquinolin-4-yl)-octahydro-1H-pyrido[3,4-b]morpholine-1-carboxylate (239 mg, 0.464 mmol) and 3,-5-difluorophenyl boronic acid (2.0 eq., 0.928 mmol, 147 mg,), the title compound was prepared as a white solid using a method similar to the one described in "Example 13, Step 13-2". MS (M+1)$^+$=550.5.

Step 33-5, preparation of trans-benzyl 6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate: from trans-benzyl 6-[6-chloro-3-(3,5-difluorophenyl)quinolin-4-yl]-octahydro-1H-pyrido[3,4-b]morpholine-1-carboxylate (130 mg, 0.236 mmol), the title compound was prepared using a method similar to the one described in "Example 13, Step 13-3". The reaction solution was diluted with ethyl acetate, washed with water, dired with Na$_2$SO$_4$ and concentrated. This material was used for next step without further purification. MS (M+1)$^+$=642.5.

Step 33-6, preparation of trans-benzyl 6-[6-(6-carbamoylpyridin-2-yl)-3-(3,5-difluorophenyl)quinolin-4-yl]-octahydro-1H-pyrido[3,4-b]morpholine-1-carboxylate: from trans-benzyl 6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.118 mmol) and 6-bromopyridine-2-carboxylic acid amide (0.263 mmol, 55 mg), the title compound was prepared as white solid using a method similar to the one described in "Example 12, Step 12-4". MS (M+1)$^+$=636.4.

Step 33-7, preparation of trans-6-[3-(3,5-difluorophenyl)-4-{octahydro-1H-pyrido[3,4-b]morpholin-6-yl}quinolin-6-yl]pyridine-2-carboxamide: trans-benzyl 6-[6-(6-carbamoylpyridin-2-yl)-3-(3,5-difluorophenyl)quinolin-4-yl]-octahydro-1H-pyrido[3,4-b]morpholine-1-carboxylate (30.4 mg) was combined with trifluoroacetic acid (0.5 mL) and thioanisole (0.1 mL) and the resulting mixture was stirred at 60° C. for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in ether (2.0 M, 0.5 mL) give 23 mg of the desired product as a HCl salt. MS (M+H)$^+$=502.4.

The following compounds were prepared in a similar manner as described in Example 33, substituting with appropriate reagents and substrates as required. Compound 2-251 was prepared by use of MOM protected 2-bromo-3-hydroxy-isonicotinonitrile. Compound 2-256 was prepared by use of 3,4-dimethoxybenzyl protected 3-bromo-5-fluoropyridin-4-ol.

| Compound no. | MS (M + H)$^+$ |
|---|---|
| 2-100 | 535.4 |
| 2-245 | 477.4 |
| 2-247 | 488.4 |
| 2-249 | 477.4 |
| 2-251 | 500.4 |
| 2-252 | 557.3 |
| 2-255 | 475.2 |
| 2-256 | 493.3 |
| 2-257 | 505.2 |

Example 34 trans-2-[3-(3,5-difluorophenyl)-4-{octahydro-1H-pyrido[3,4-b]morpholin-6-yl}quinolin-6-yl]-6-fluorophenol (Compound No. 2-144)

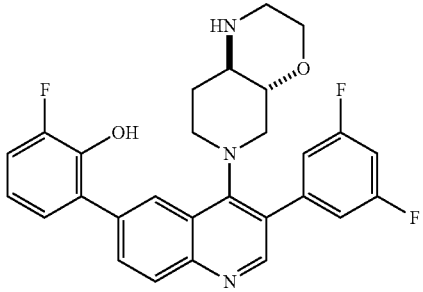

Step 34-1, preparation of trans-benzyl 6-[3-(3,5-difluorophenyl)-6-(3-fluoro-2-hydroxyphenyl)quinolin-4-yl]-octahydro-1H-pyrido[3,4-b]morpholine-1-carboxylate: from trans-benzyl 6-[6-chloro-3-(3,5-difluorophenyl)quinolin-4-yl]-octahydro-1H-pyrido[3,4-b]morpholine-1-carboxylate (Example 33, step 33-4) (50 mg, 0.09 mmol) and 3-fluoro-2-hydroxyphenyl-boronic acid (2.0 eq., 0.18 mmol, 28 mg), the title compound was prepared as a white solid using a method similar to the one described in "Example 12, Step 12-4". MS (M+1)$^+$=626.4.

Step 34-2, preparation of trans-2-[3-(3,5-difluorophenyl)-4-{octahydro-1H-pyrido[3,4-b]morpholin-6-yl}quinolin-6-yl]-6-fluorophenol: from trans-benzyl 6-[3-(3,5-difluorophenyl)-6-(3-fluoro-2-hydroxyphenyl)quinolin-4-yl]-octahydro-1H-pyrido[3,4-b]morpholine-1-carboxylate (30 mg), the title compound was prepared as white solid using a method similar to the one described in "Example 33, Step 33-7". MS (M+1)$^+$=492.4.

Example 35

2-{4-[trans-octahydro-1H-pyrido[3,4-b]morpholin-6-yl]-3-(3,5-difluorophenyl)quinolin-6-yl}-6-(methoxyiminomethyl)phenol (Compound No. 2-243)

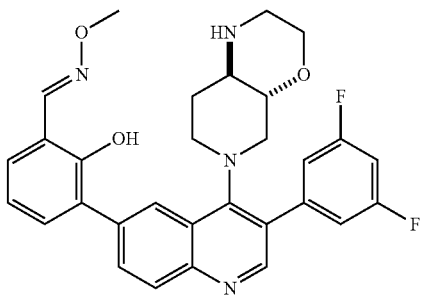

Step 35-1, preparation of 3-bromo-2-(methoxymethoxy)benzaldehyde: to a dichloromethane solution (100 mL) of 3-bromo-2-hydroxybenzaldehyde (4.144 g, 20 mmol) was added N,N-diisopropylethylamine (1.5 eq., 30 mmol, 4.95 mL) and methoxymethyl chloride (1.5 eq., 30 mmol, 2.28 mL) at 0° C. The resulting mixture was stirred at ambient temperature for 1 h. The reaction solution was diluted with dichloromethane, washed with saturated NH$_4$Cl, and dried with Na$_2$SO$_4$. The organic layer was concentrated and purified by silica gel chromatography eluting with ethyl acetate/hexane (0~25%) to give 4.575 g of the desired product. MS (M+H)$^+$=245.2, 246.9.

Step 35-2, preparation of 2-(methoxymethoxy)-3-(tetramethyl-1,3,2-dioxaborolan-2-yl)benzaldehyde: to anhydrous dioxane (30 mL) solution of 3-bromo-2-(methoxymethoxy)benzaldehyde (10 mml, 2.45 g) were added Pd(dppf)Cl$_2$ (0.10 eq., 1.0 mmol, 731 mg), bis(pincolato)diborane (2.0 eq., 20 mmol, 5.08 g) and KOAc (3.0 eq., 30 mmol, 2.94 g). N$_2$ was bubbled through the reaction solution for 5 min. The reaction solution was heated at 80° C. for 2 h. Additional Pd(dppf)Cl$_2$ (0.05 eq., 0.5 mmol, 350 mg), bis(pincolato) diborane (1.0 eq., 10 mmol, 2.5 g) were added and bubbled with N2. The resulting solution was heated at 80° C. for 24 h. The reaction solution was filtered through a celite pad and concentrated. The residue obtained was purified by silica gel chromatography eluting with ethyl acetate/hexane (0~5%) to give 6.01 g of the title compound.

Step 35-3, preparation of benzyl-trans-6-[3-(3,5-difluorophenyl)-6-[3-formyl-2-(methoxymethoxy)phenyl]quinolin-4-yl]-octahydro-1H-pyrido[3,4-b]morpholine-1-carboxylate: from benzyl-trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.166 mmol) and 2-(methoxymethoxy)-3-(tetramethyl-1,3,2-dioxaborolan-2-yl)benzaldehyde (0.33 mmol), the title compound was prepared as white solid using a method similar to the one described in "Example 12, Step 12-4". MS (M+1)$^+$=680.4.

Step 35-4, preparation of 3-{4-[trans-octahydro-1H-pyrido[3,4-b]morpholin-6-yl]-3-(3,5-difluorophenyl)quinolin-6-yl}-2-hydroxybenzaldehyde: benzyl-trans-6-[3-(3,5-difluorophenyl)-6-[3-formyl-2-(methoxymethoxy)phenyl]quinolin-4-yl]-octahydro-1H-pyrido[3,4-b]morpholine-1-carboxylate (30 mg, 0.044 mmol) was combined with trifluoroacetic acid (0.4 mL) and thioanisole (0.02 mL). The resulting mixture was heated at 60° C. for 1 h and then cooled down to ambient temperature. MTBE was added and the solid crashed out was collected after filtration. This material was used for next step without purification. MS (M+1)⁺=502.4.

Step 35-5, preparation of 2-{4-[trans-octahydro-1H-pyrido[3,4-b]morpholin-6-yl]-3-(3,5-difluorophenyl)quinolin-6-yl}-6-(methoxyiminomethyl)phenol: from 3-{4-[trans-octahydro-1H-pyrido[3,4-b]morpholin-6-yl]-3-(3,5-difluorophenyl)quinolin-6-yl}-2-hydroxybenzaldehyde (20 mg), the title compound was prepared using a method similar to the one described in "Example 18, Step 18-2". MS (M+1)⁺=531.4.

The following compounds were prepared in a similar manner as described in Example 35, substituting with appropriate reagents and substrates as required:

| Compound no. | MS (M + H)⁺ |
| --- | --- |
| 2-221 | 527.3 |
| 2-253 | 505.4 |

Example 36

2-{2-[4-(4-aminopiperidin-1-yl)-3-(3,5-difluorophenyl)quinolin-6-yl]-6-cyanophenoxy}acetic acid (Compound No. 2-201)

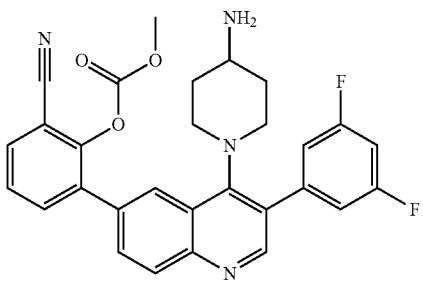 [SMILES: COC(=O)Oc1c(C#N)cccc1-c1ccc2ncc(-c3cc(F)cc(F)c3)c(N3CCC(N)CC3)c2c1]

Step 36-1, preparation of 2-[4-(4-{[(tert-butoxy)carbonyl]amino}piperidin-1-yl)-3-(3,5-difluorophenyl)quinolin-6-yl]-6-cyanophenyl methyl carbonate: to a DCM solution (3.0 mL) of {1-[6-(3-cyano-2-hydroxy-phenyl)-3-(3,5-difluoro-phenyl)-quinolin-4-yl]-piperidin-4-yl}-carbamic acid tert-butyl ester (167 mg, 0.30 mmol) was added pyridine (8.0 eq., 0.0.24 mmol, 0.19 mL) and methyl chloroformate (4.0 eq., 1.2 mmol, 0.090 mL) at 0° C. The resulting mixture was heated at 80 the same temperature for 0.5 h and LCMS analysis showed complete consumption of starting material. The reaction solution was diluted with ethyl acetate, washed with water and brine, and dried with Na₂SO₄. The organic layer was concentrated and purified by silica gel chromatography eluting with ethyl acetate/hexane (0~50%) to give 135 mg of the desired product. MS (M+H)⁺=615.4.

Step 36-2, preparation of 2-[4-(4-aminopiperidin-1-yl)-3-(3,5-difluorophenyl)quinolin-6-yl]-6-cyanophenyl methyl carbonate: to the dichloromethane (2.0 mL) solution of 2-[4-(4-{[(tert-butoxy)carbonyl]amino}piperidin-1-yl)-3-(3,5-difluorophenyl)quinolin-6-yl]-6-cyanophenyl methyl carbonate (135 mg) was added trifluroroacetic acid (20 eq., 4.4 mmol, 0.34 mL) and the resulting mixture was stirred at ambient temperature for 3 h. MTBE was added to the reaction solution and solid product crashed out. The solid collected was purified by C18 reversed phase chromatography eluting with MeCN/water (0~80%). Pure fractions were combined, neutralized with saturated NaHCO₃/NaCl, extracted with MTBE and dried with MgSO₄. The organic solution was concentrated with HCl in ether (2.0 M trifluroroacetic acid to give 55 mg of the final compound as TFA salt. MS (M+H)⁺=515.4.

Example 37

3-{4-[cis-4-amino-3-hydroxypiperidin-1-yl]-3-(3-fluoro-5-methylphenyl)quinolin-6-yl}-2-(2-methoxyethoxy)benzonitrile (Compound No. 2-224)

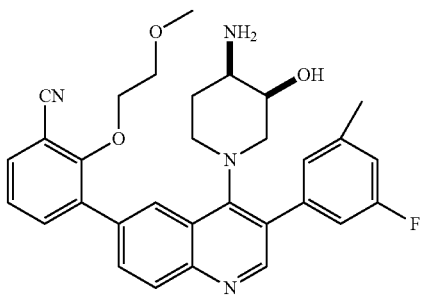 [SMILES: COCCOc1c(C#N)cccc1-c1ccc2ncc(-c3cc(C)cc(F)c3)c(N3CC[C@@H](N)[C@@H](O)C3)c2c1]

Step 37-1, preparation of benzyl trans-4-amino-3-hydroxypiperidine-1-carboxylate: to a 1-L sealed tube, was placed benzyl 7-oxa-3-azabicyclo[4.1.0]heptane-3-carboxylate (40 g, 171.48 mmol, 1.00 equiv), ethanol (400 mL), ammonium (400 mL). The resulting solution was stirred overnight at 70° C. in an oil bath. The mixture was concentrated and then diluted with 700 mL of water. The organics were extracted out with 3×300 mL of ethyl acetate and the organic layers ewere combined and dried over anhydrous sodium sulfate and concentrated under vacuum. This resulted in 27 g (63%) of desired product as yellow oil. MS (M+H)⁺=251.1.

Step 37-2, preparation of benzyl trans-4-[[(tert-butoxy)carbonyl]amino]-3-hydroxypiperidine-1-carboxylate: to a 1-L round-bottom flask, was placed benzyl trans-4-amino-3-hydroxypiperidine-1-carboxylate (27 g, 107.87 mmol, 1.00 equiv), dichloromethane (300 mL), (Boc)₂O (23.5 g, 107.67 mmol, 1.00 equiv), triethylamine (16.4 g, 162.07 mmol, 1.50 equiv). The resulting solution was stirred overnight at room temperature and concentrated. The residue was purified via a silica gel column eluting with ethyl acetate/petroleum ether (2:1). The fractions containing the desired product were combined and concentrated under vacuum. This resulted in 24 g (63%) of benzyl trans-4-[[(tert-butoxy)carbonyl]amino]-3-hydroxypiperidine-1-carboxylate as yellow oil. MS (M+H)⁺=351.2.

Step 37-3, preparation of tert-butyl N-[trans-3-hydroxypiperidin-4-yl]carbamate: to a 1-L round-bottom flask purged and maintained with an inert atmosphere of nitrogen, was placed benzyl trans-4-[[(tert-butoxy)carbonyl]amino]-3-hydroxypiperidine-1-carboxylate (24 g, 68.49 mmol, 1.00 equiv), methanol (400 mL) and palladium on carbon (2.4 g, 10%). The resulting solution was stirred at room temperature under H₂ atomasphere for 2 h. The solids were filtered out. The mixture was concentrated under vacuum. This resulted in 14.5 g (98%) of tert-butyl N-[trans-3-hydroxypiperidin-4-yl]carbamate as a white solid. MS (M+H)⁺=217.1.

Step 37-4, preparation of N-[trans-1-(6-bromo-3-chloroquinolin-4-yl)-3-hydroxypiperidin-4-yl]carbamate: to a 250-mL round-bottom flask purged and maintained with an inert atmosphere of nitrogen, was placed 6-bromo-3,4-dichloroquinoline (8.5 g, 30.69 mmol, 1.00 equiv), NMP (80 mL), DIEA (7.9 g, 61.13 mmol, 2.00 equiv), tert-butyl N-[trans-3-hydroxypiperidin-4-yl]carbamate (7.9 g, 36.53 mmol, 1.20 equiv). The resulting solution was stirred overnight at 130° C. in an oil bath, cooled to rt and then diluted with 300 mL of water, and extracted with 3×100 mL of ethyl acetate. The organic layers were combined and washed with 2×300 mL of brine, dried over anhydrous sodium sulfate and concentrated after filtration of solids. The residue was purified via a silica gel column eluting with ethyl acetate/petroleum ether (1:2). The fractions containing desired product were combined and concentrated under vacuum resulting in 9 g (64%) of title compound as a white solid. MS $(M+H)^+=456.1$.

Step 37-5, preparation of tert-butyl N-[1-(6-bromo-3-chloroquinolin-4-yl)-3-oxopiperidin-4-yl]carbamate: to a 500-mL 3-necked round-bottom flask, was placed tert-butyl N-[trans-1-(6-bromo-3-chloroquinolin-4-yl)-3-hydroxypiperidin-4-yl]carbamate (9 g, 19.70 mmol, 1.00 equiv), dichloromethane (150 mL), was added Dess-Martin periodinane (13 g, 1.50 equiv) in several portions. The resulting solution was stirred for 2 h at rt, then quenched with 10 mL of $Na_2S_2O_3$ aqueous solution. The mixture was extracted with 3×200 mL of dichloromethane and the combined organic layers were washed with 2×200 mL of brine, dried over anhydrous sodium sulfate and concentrated after removal of solids through filtration resulting in 9 g (100%) of title compound as a white solid. MS $(M+H)^+=454.0$.

Step 37-6, preparation of tert-butyl N-[cis-1-(6-bromo-3-chloroquinolin-4-yl)-3-hydroxypiperidin-4-yl]carbamate: to a 500-mL 3-necked round-bottom flask purged and maintained with an inert atmosphere of nitrogen, was placed tert-butyl N-[(1-(6-bromo-3-chloroquinolin-4-yl)-3-oxopiperidin-4-yl]carbamate (9 g, 19.79 mmol, 1.00 equiv), anhydrous oxolane (100 mL). The flask was cooled to −78° C., followed by the addition of L-selectride (25.7 mL, 1.30 equiv) dropwise. The resulting solution was stirred for 2 h at −60° C., then quenched by the addition of 30 mL of ethanol. The mixture was diluted with 200 mL of saturated aqueous $NH_4Cl$. After solids were filtered out, the resulting solution was extracted with 3×200 mL of dichloromethane and combined organic layers were dried over anhydrous sodium sulfate and concentrated after removal of the solids The crude was purified by Prep HPLC on a C18 column resulting in 5 g (55%) of the title compound as a white solid. MS $(M+H)^+=456.1$.

Step 37-7, preparation of cis-4-amino-1-(6-bromo-3-chloroquinolin-4-yl)piperidin-3-ol: to a 250-mL round-bottom flask, was placed tert-butyl N-[cis-1-(6-bromo-3-chloroquinolin-4-yl)-3-hydroxypiperidin-4-yl]carbamate (4.8 g, 10.51 mmol, 1.00 equiv), dichloromethane (50 mL). This was followed by the addition of trifluoroacetic acid (6 mL) dropwise with stirring at 0° C. The resulting solution was stirred for 2 h at room temperature. The resulting mixture was concentrated under vacuum resulting in 4.5 g (91%) of cis-4-amino-1-(6-bromo-3-chloroquinolin-4-yl)piperidin-3-ol as yellow oil of TFA salt. MS $(M+H)^+=356.0$.

Step 37-8, preparation of benzyl N-[(cis-1-(6-bromo-3-chloroquinolin-4-yl)-3-hydroxypiperidin-4-yl]carbamate: to cis-4-amino-1-(6-bromo-3-chloroquinolin-4-yl)piperidin-3-ol (4.5 g, 9.56 mmol, 1.00 equiv) in dichloromethane (80 mL) at 0° C., triethylamine (5 g, 49.41 mmol, 5.00 equiv) was added dropwise with stirring, followed by addition of Cbz-OSu (3 g, 1.20 equiv) in several portions. The resulting solution was stirred for an additional 3 h at rt and then diluted with 300 mL of $H_2O$. The mixture was extracted with 3×100 mL of dichloromethane and combined organic layers were washed with 200 mL of brine, dried over anhydrous sodium sulfate and concentrated under vacuum after filtration of the solids which gave to 3.57 g (76%) of the title compound as a light yellow solid. MS $(M+H)^+=490.0$.

Step 37-9, preparation of benzyl N-[cis-1-[3-chloro-6-(3-cyano-2-hydroxyphenyl)quinolin-4-yl]-3-hydroxypiperidin-4-yl]carbamate: from benzyl N-[cis-1-(6-bromo-3-chloroquinolin-4-yl)-3-hydroxypiperidin-4-yl]carbamate (98 mg, 0.20 mmol) and 3-cyano-2-hydroxyphenyl boronic acid (0.5 mg, 0.81 mmol), the title compound was prepared using a similar method to the one described in "Example 7, Step 7-2". The reaction solution was diluted with ethyl acetate, washed with water and brine, dried with $MgSO_4$, and concentrated. The crude was used for next step without further purification. MS $(M+1)^+=529.2$.

Step 37-10, preparation of benzyl N-[cis-1-{3-chloro-6-[3-cyano-2-(2-methoxyethoxy)phenyl]quinolin-4-yl}-3-hydroxypiperidin-4-yl]carbamate: from crude benzyl N-[cis-1-[3-chloro-6-(3-cyano-2-hydroxyphenyl)quinolin-4-yl]-3-hydroxypiperidin-4-yl]carbamate and methoxyethyl bromide (0.8 mmol, 0.125 mL), the title compound was prepared using a similar method to the one described in "Example 10, Step 10-2". MS $(M+1)^+=587.4$.

Step 37-11, preparation of benzyl N-[cis-1-{6-[3-cyano-2-(2-methoxyethoxy)phenyl]-3-(3-fluoro-5-methylphenyl)quinolin-4-yl}-3-hydroxypiperidin-4-yl]carbamate: from benzyl N-[cis-1-{3-chloro-6-[3-cyano-2-(2-methoxyethoxy)phenyl]quinolin-4-yl}-3-hydroxypiperidin-4-yl]carbamate (0.078 mmol, 46 mg) and 3-fluoro-5-methyl-phenylboronic acid (0.235 mmol, 36 mg), the title compound was prepared using a similar method to the one described in "Example 12, Step 12-4". MS $(M+1)^+=661.4$.

Step 37-12, preparation of 3-{4-[cis-4-amino-3-hydroxypiperidin-1-yl]-3-(3-fluoro-5-methylphenyl)quinolin-6-yl}-2-(2-methoxyethoxy)benzonitrile: from benzyl N-[cis-1-{6-[3-cyano-2-(2-methoxyethoxy)phenyl]-3-(3-fluoro-5-methylphenyl)quinolin-4-yl}-3-hydroxypiperidin-4-yl]carbamate (0.05 mmo, 32 mg), the title compound was prepared using a similar method to the one described in "Example 33, Step 33-7". MS $(M+1)^+=527.3$.

The following compounds were prepared in a similar manner as described in Example 37, substituting with appropriate reagents and substrates as required. Compound 2-220 was prepared from 2-219 using the alkylation conditions described in Step 37-10 and followed by removal of protecting group as described in Step 37-12.

| Compound no. | MS $(M + H)^+$ |
| --- | --- |
| 2-220 | 545.3 |
| 2-225 | 531.2 |
| 2-232 | 549.5 |

Example 38 cis-4-amino-1-(6-{3-fluoro-2-[(hydroxyimino)
methyl]phenyl}-3-(3-fluoro-5-methylphenyl)quino-
lin-4-yl)piperidin-3-ol (Compound No. 2-227)

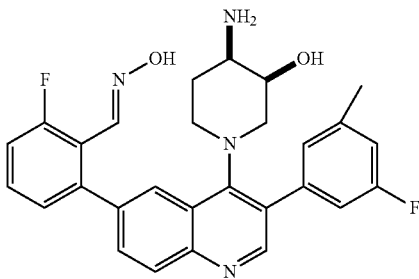 [SMILES: Cc1cc(F)cc(-c2cnc3ccc(-c4cccc(F)c4/C=N/O)cc3c2N2CC[C@@H](N)[C@@H](O)C2)c1]

Step 38-1, preparation of tert-butyl N-[cis-1-[3-chloro-6-(3-fluoro-2-formylphenyl)quinolin-4-yl]-3-hydroxypiperidin-4-yl]carbamate: to a 50-mL round-bottom flask purged and maintained with an inert atmosphere of nitrogen, was placed tert-butyl N-[cis-1-(6-bromo-3-chloroquinolin-4-yl)-3-hydroxypiperidin-4-yl]carbamate (120 mg, 0.26 mmol, 1.00 equiv, prepared in "Example 37, step 37-6"), tetrahydrofuran/$H_2O$ (3 mL), (3-fluoro-2-formylphenyl)boronic acid (177.6 mg, 1.06 mmol, 4.00 equiv), $K_3PO_4$ (168 mg, 0.79 mmol, 3.00 equiv), $Pd_2(dba)_3$ chloroform (14.4 mg, 0.05 equiv), P(t-Bu)$_3$ (7.2 mg, 0.10 equiv). The resulting solution was stirred for 4 h at 30° C. and then concentrated under vacuum. The residue was purified by a silica gel column eluting with ethyl acetate/petroleum ether (1:3) which resulted in 100 mg (76%) of the title compound as a light yellow solid. MS $(M+1)^+$=500.2.

Step 38-2, preparation of N-[cis-1-[6-(3-fluoro-2-formylphenyl)-3-(3-fluoro-5-methylphenyl)quinolin-4-yl]-3-hydroxypiperidin-4-yl]carbamate: to a 8-mL vial purged and maintained with an inert atmosphere of nitrogen, was placed tert-butyl N-[cis-1-[3-chloro-6-(3-fluoro-2-formylphenyl)quinolin-4-yl]-3-hydroxypiperidin-4-yl]carbamate (100 mg, 0.20 mmol, 1.00 equiv), (3-fluoro-5-methylphenyl)boronic acid (62 mg, 0.40 mmol, 2.00 equiv), Pd(amphos)Cl$_2$ (9 mg, 0.05 equiv), $K_3PO_4$ (65 mg, 0.31 mmol, 3.00 equiv), toluene/$H_2O$ (2 mL). The resulting solution was stirred for 10 h at 100° C. and then concentrated under vacuum. The residue was purified by a silica gel column eluting with ethyl acetate/petroleum ether (1:3) yielding 60 mg (52%) of the title compound as a light yellow solid. MS $(M+1)^+$=574.2.

Step 38-3, preparation of tert-butyl N-[cis-1-(6-[3-fluoro-2-[(hydroxyimino)methyl]phenyl]-3-(3-fluoro-5-methylphenyl)quinolin-4-yl)-3-hydroxypiperidin-4-yl]carbamate: to a 8-mL vial, was placed tert-butyl N-[cis-1-[6-(3-fluoro-2-formylphenyl)-3-(3-fluoro-5-methylphenyl)quinolin-4-yl]-3-hydroxypiperidin-4-yl]carbamate (60 mg, 0.10 mmol, 1.00 equiv), methanol (2 mL), pyridine (41 mg, 0.52 mmol, 3.00 equiv), HO—NH$_2$.HCl (15 mg, 2.00 equiv). The resulting solution was stirred for 2 h at rt and then concentrated under vacuum resulting in 80 mg (crude) of title compound as a light yellow solid. MS $(M+1)^+$=589.3.

Step 38-4, preparation of cis-4-amino-1-(6-{3-fluoro-2-(hydroxyiminomethyl)phenyl}-3-(3-fluoro-5-methylphenyl)quinolin-4-yl)piperidin-3-ol: to a 8-mL vial, was placed tert-butyl N-[cis-1-(6-[3-fluoro-2-[(hydroxyimino)methyl]phenyl]-3-(3-fluoro-5-methylphenyl)quinolin-4-yl)-3-hydroxypiperidin-4-yl]carbamate (80 mg, 0.14 mmol, 1.00 equiv), dichloromethane (1 mL), trifluoroacetic acid (0.25 mL). The resulting solution was stirred for 2 h at rt and then concentrated under vacuum. The crude was purified by Prep-HPLC resulting in 28.5 mg (40%) of the title product as a yellow solid. MS $(M+1)^+$=489.2.

Example 39

5-{4-[trans-octahydro-1H-pyrido[3,4-b]morpholin-6-yl]-3-(3,5-difluorophenyl)quinolin-6-yl}-4-hydroxy-pyridine-3-carbonitrile (Compound No. 2-254)

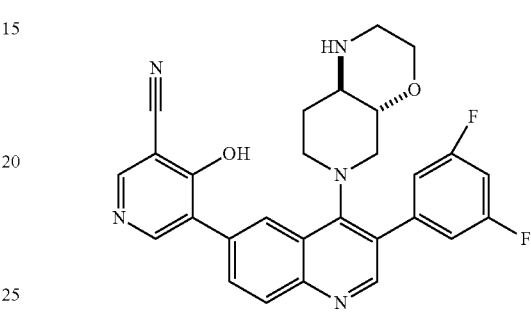

Step 39-1, preparation of 5-bromo-4-hydroxypyridine-3-carbonitrile: to the HOAc solution (2.2 mL) of 4-hydroxypyridine-3-carbonitrile (1.0 mmol, 120 mg) was added Br$_2$ (1.2 eq., 1.2 mmol, 0.062 mL) in 1.0 mL HOAc. The resulting solution was heated at 90° C. for 4 h. The reaction solution was concentrated and slurred in i-PrOH (3 mL) and filtered to give 100 mg of the desired product. MS $(M+1)^+$=199.1.

Step 39-2, preparation of 5-bromo-4-oxo-1-(prop-2-en-1-yl)-1,4-dihydropyridine-3-carbonitrile: to the DMF solution (1.0 mL) of 5-bromo-4-hydroxypyridine-3-carbonitrile (77 mg, 0.4 mmol) was added K$_2$CO$_3$ (2.0 eq., 0.8 mmol, 110 mg) and allyl bromide (1.5 eq., 0.6 mmol, 0.052 mL). The resulting mixture was heated at 70° C. for 0.5 h. The reaction mixture was diluted with ethyl acetate and washed with water and brine. The organic layer was separated, dried with MgSO$_4$, concentrated and purified by silica gel chromatography eluting with ethyl acetate/DCM (0~50%) to give 35 mg of the desired product. MS $(M+H)^+$=239.1.

Step 39-3, preparation of benzyl trans-6-{6-[5-cyano-4-oxo-1-(prop-2-en-1-yl)-1,4-dihydropyridin-3-yl]-3-(3,5-difluorophenyl)quinolin-4-yl}-octahydro-1H-pyrido[3,4-b]morpholine-1-carboxylate: from 5-bromo-4-oxo-1-(prop-2-en-1-yl)-1,4-dihydropyridine-3-carbonitrile (0.07 mmol, 17 mg) and trans-benzyl 6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.1 mmol, prepared in Example 33, step 33-5), the title compound was prepared using a similar method to the one described in "Example 12, Step 12-4". The reaction mixture was diluted with ethyl acetate and washed with water and brine. The organic layer was separated, dried with MgSO$_4$, concentrated. The crude material obtained was used for next step without purification. MS $(M+1)^+$: 674.5.

Step 39-4, preparation of benzyl trans-6-[6-(5-cyano-4-hydroxypyridin-3-yl)-3-(3,5-difluorophenyl)quinolin-4-yl]-octahydro-1H-pyrido[3,4-b]morpholine-1-carboxylate: to the THF solution (1.0 mL) of crude trans-6-{6-[5-cyano-4-oxo-1-(prop-2-en-1-yl)-1,4-dihydropyridin-3-yl]-3-(3,5-difluorophenyl)quinolin-4-yl}-octahydro-1H-pyrido[3,4-b]

morpholine-1-carboxylate was added Pd$_2$(dba)$_3$ (0.1 eq., 0.007 mmol, 7.0 mg), dppb (0.2 eq., 0.014 mmol, 7.0 mg) and thiosalicylic acid (4.5 eq., 0.32 mmol, 50 mg). The resulting solution was stirred under N$_2$ for 1 h. The reaction mixture was diluted with ethyl acetate and washed with water and brine. The organic layer was separated, dried with MgSO$_4$, concentrated. The crude material obtained was used for next step without purification. MS (M+1)$^+$=634.4.

Step 39-5, preparation of 5-{4-[trans-octahydro-1H-pyrido[3,4-b]morpholin-6-yl]-3-(3,5-difluorophenyl)quinolin-6-yl}-4-hydroxypyridine-3-carbonitrile: from crude benzyl trans-6-[6-(5-cyano-4-hydroxypyridin-3-yl)-3-(3,5-difluorophenyl)quinolin-4-yl]-octahydro-1H-pyrido[3,4-b]morpholine-1-carboxylate, the title compound was prepared using a similar method to the one described in "Example 33, Step 33-7". MS (M+1)$^+$=500.4.

Example 40

2-{4-[trans-octahydro-1H-pyrido[3,4-b]morpholin-6-yl]-3-(3,5-difluorophenyl)quinolin-6-yl}-4-methylpyridin-3-ol (Compound No. 2-258)

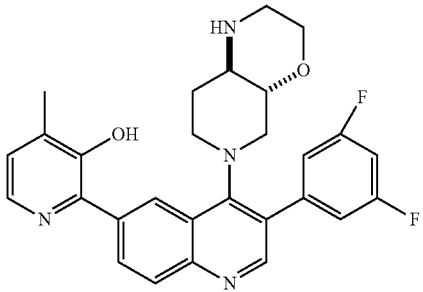

Step 40-1, preparation of 2-bromo-3-(methoxymethoxy)-4-methylpyridine: to the dichloromethane solution (3.0 mL) of 2-bromo-4-methyl-pyridin-3-ol (0.516 mmol, 100 mg) was added DIPEA (1.5 eq., 0.774 mmol, 0.13 mL) and chloromethyl methyl ether (1.5 eq., 0.774 mmol, 0.06 mL) at 0° C. The resulting mixture was stirred at rt for 1 h. The reaction solution was diluted with dichloromethane, washed with water, dried with Na$_2$SO$_4$, and concentrated. The residue obtained was purified by silica gel chromatography eluting with ethyl acetate/hexane (0~25%) to give 80 mg of the title product. MS (M+H)$^+$=232.2.

Step 40-2, preparation of tert-butyl trans-6-(3-bromo-6-chloroquinolin-4-yl)-octahydro-1H-pyrido[3,4-b]morpholine-1-carboxylate: to an anhydrous DMSO (8 mL) solution of 3-bromo-4,6-dichloro-quinoline (5.78 mmol, 1.6 g) was added N,N-diisopropylethylamine (4.0 eq., 23.1 mmol, 3.82 mL) and tert-butyl trans-octahydro-1H-pyrido[3,4-b]morpholine-1-carboxylate (1.0 eq., 5.78 mmol, 1.4 g). N$_2$ was bubbled through the reaction solution for 5 min and the resulting solution was heated at 140° C. for 6 h. The reaction mixture was diluted with ethyl acetate and washed with water and brine. The organic layer was separated, dried with MgSO$_4$ and concentrated. The residue obtained was purified by silica gel chromatography eluting with ethyl acetate/hexane (0~50%) to give 1.31 g of the title product as white solid. MS (M+H)$^+$=482.2.

Step 40-3, preparation of tert-butyl trans-6-[6-chloro-3-(3,5-difluorophenyl)quinolin-4-yl]-octahydro-1H-pyrido[3,4-b]morpholine-1-carboxylate: to a THF solution (25 mL) of tert-butyl trans-6-(3-bromo-6-chloroquinolin-4-yl)-octahydro-1H-pyrido[3,4-b]morpholine-1-carboxylate (2.05 g, 4.24 mmol) was added 3,5-difluoro-phenylboronic acid (2.0 eq., 6.48 mmol, 1.34 g), tris(dibenzylideneacetone)dipalladium/tri-tert-butyl phosphonium tetrafluoroborate mixture (mole ratio: 1/1.2) (0.05 eq., 0.21 mmol, 276 mg), and K$_3$PO$_4$.H$_2$O (4.0 eq., 17.0 mmol, 3.9 g). N$_2$ was bubbled through the reaction solution for 5 min and 2.5 mL water was added. The resulting mixture stirred at ambient temperature for 1 h and LCMS analysis showed complete converstion to the desired product. The reaction mixture was diluted with ethyl acetate and washed with water and brine. The organic layer was separated, dried with MgSO$_4$ and concentrated. The residue obtained was purified by silica gel chromatography eluting with ethyl acetate/hexane (0~50%) to give 1.80 g of the title product as white solid. MS (M+H)$^+$=516.3.

Step 40-4, preparation of tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate: Pd$_2$(dba)$_3$ (0.05 eq., 0.0.01 mmol, 9.2 mg) and Xphos (0.10 eq., 0.02 mmol, 9.6 mg), tert-butyl trans-6-[6-chloro-3-(3,5-difluorophenyl)quinolin-4-yl]-octahydro-1H-pyrido[3,4-b]morpholine-1-carboxylate (0.2 mmol, 103 mg), bis(pincolato)diborane (2.0 eq., 0.4 mmol, 102 g) and KOAc (3.0 eq., 0.6 mmol, 59 mg) were added to anhydrous dioxane (2 mL). N$_2$ was bubbled through the reaction solution for 5 min. The reaction solution was heated at 100° C. for 1 h and LCMS analysis showed complete consumption of starting material. The crude reaction solution was used for next step without further treatment. MS (M+H)$^+$=608.4.

Step 40-5, preparation of tert-butyl trans-6-[3-(3,5-difluorophenyl)-6-[3-(methoxymethoxy)-4-methylpyridin-2-yl]quinolin-4-yl]-octahydro-1H-pyrido[3,4-b]morpholine-1-carboxylate: to the crude solution from step 40-4 was added 2-bromo-3-(methoxymethoxy)-4-methylpyridine (3.0 eq., 0.6 mmol, 139 mg), Pd(Amphos)Cl$_2$ (0.15 eq., 0.03 mmol, 21 mg), K$_2$CO$_3$ (3.0 eq., 0.6 mmol, 83 mg) and H$_2$O (0.2 mL). N$_2$ was bubbled through the reaction solution for 5 min. The reaction solution was heated at 100° C. for 1 h and LCMS analysis showed complete consumption of starting material. The reaction mixture was diluted with ethyl acetate and washed with water and brine. The organic layer was separated, dried with Na$_2$SO$_4$ and concentrated. The residue obtained was purified by silica gel chromatography eluting with ethyl acetate/hexane (0~50%) to give 55 mg of the desired product. MS (M+H)$^+$=633.5.

Step 40-6, preparation of 2-{4-[trans-octahydro-1H-pyrido[3,4-b]morpholin-6-yl]-3-(3,5-difluorophenyl)quinolin-6-yl}-4-methylpyridin-3-ol: to the dichloromethane solution (1.0 mL) of tert-butyl trans-6-[3-(3,5-difluorophenyl)-6-[3-(methoxymethoxy)-4-methylpyridin-2-yl]quinolin-4-yl]-octahydro-1H-pyrido[3,4-b]morpholine-1-carboxylate (55 mg) was added TFA (0.25 mL). The resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with Na$_2$SO$_4$. The organic solution was concentrated with HCl in EtOEt (2.0 M, 1.0 mL) to give 34 mg of the final compound as HCl salt. MS (M+H)$^+$=489.4.

The following compounds were prepared in a similar manner as described in Example 40, substituting with appropriate reagents and substrates as required. Compound 2-259 was prepared from 2-bromo-3-[(3,4-dimethoxyphenyl)

methoxy]pyridine and removal of protecting group was achieved by heating in TFA at 90° C. in the presemce of thioanisole.

| Compound no. | MS (M + H)+ |
|---|---|
| 2-259 | 493.4 |
| 2-263 | 475.1 |

Example 41

N-[(3-{4-[trans-octahydro-1H-pyrido[3,4-b]morpholin-6-yl]-3-(3,5-difluorophenyl)quinolin-6-yl}pyridin-2-yl)methylidene]hydroxylamine (Compound No. 2-264)

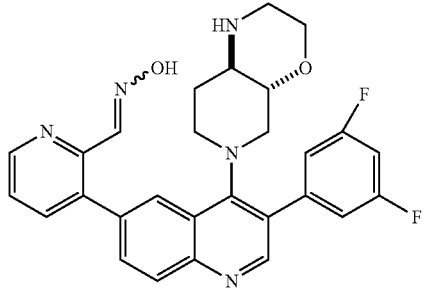

Step 41-1, preparation of tert-butyl trans-6-[3-(3,5-difluorophenyl)-6-(2-formylpyridin-3-yl)quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.2 mmol crude, "Example 40, step 40-4") and 3-bromo-2-formylpyridine (1.25 eq., 0.25 mmol, 50 mg), the title compound was prepared using a similar method to the one described in "Example 40, Step 40-5". The reaction mixture was diluted with ethyl acetate and washed with water and brine. The organic layer was separated, dried with Na$_2$SO$_4$ and concentrated. The residue obtained was purified by silica gel chromatography eluting with ethyl acetate/hexane (0~50%) to give 64 mg of the desired product. MS (M+1)+=587.5.

Step 41-2, preparation of tert-butyl trans-6-[3-(3,5-difluorophenyl)-6-{2-[(hydroxyimino)methyl]pyridin-3-yl}quinolin-4-yl]-octahydro-1H-pyrido[3,4-b]morpholine-1-carboxylate: to the dichloromethane solution (1.0 mL) of tert-butyl trans-6-[3-(3,5-difluorophenyl)-6-(2-formylpyridin-3-yl)quinolin-4-yl]-octahydro-1H-pyrido[3,4-b]morpholine-1-carboxylate (64 mg) was added pyridine (8.0 eq., 0.88 mmol, 0.07 mL) and HCl salt of hydroxylamine (4.0 eq., 0.44 mmol, 32 mg). The resulting mixture was stirred at ambient temperature for 1 h. LCMS analysis showed full consumption of starting material and formation of desired product. The reaction solution was used for next step without further purification.

Step 41-3, preparation of N-[(3-{4-[trans-octahydro-1H-pyrido[3,4-b]morpholin-6-yl]-3-(3,5-difluorophenyl)quinolin-6-yl}pyridin-2-yl)methylidene]hydroxylamine: to the crude dichloromethane solution from step 41-4 was added TFA (0.75 mL). The resulting mixture was stirred at ambient temperature for 0.5 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with Na$_2$SO$_4$. The organic solution was concentrated with HCl in EtOEt (2.0 M, 1.0 mL) to give 42 mg of the title compound as HCl salt. MS (M+H)+=502.4.

The following compounds were prepared in a similar manner as described in Example 41, substituting with appropriate reagents and substrates as required.

| Compound no. | MS (M + H)+ |
|---|---|
| 2-260 | 505.3 |
| 2-266 | 531.3 |

Example 42

2-{4-[trans-octahydro-1H-pyrido[3,4-b]morpholin-6-yl]-3-(3,5-difluorophenyl)quinolin-6-yl}-3-aminopyridine-4-carbonitrile (Compound No. 2-262)

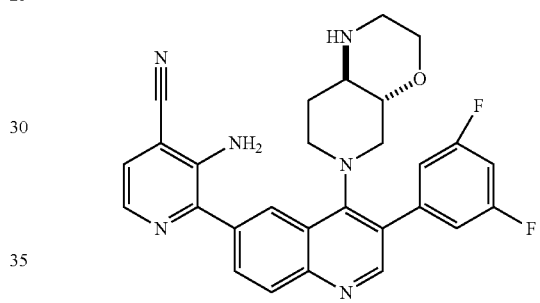

Step 42-1, preparation of tert-butyl trans-6-[6-(4-cyano-3-fluoropyridin-2-yl)-3-(3,5-difluorophenyl)quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.3 mmol crude, "Example 40, step 40-4") and 2-chloro-3-fluoro-4-cyanopyridine (3.0 eq., 1.0 mmol, 156 mg), the title compound was prepared using a similar method to the one described in "Example 40, Step 40-5". The reaction mixture was diluted with ethyl acetate and washed with water and brine. The organic layer was separated, dried with Na$_2$SO$_4$ and concentrated. The residue obtained was used for next step without purification. MS (M+1)+=602.5.

Step 42-2, preparation of tert-butyl trans-6-[6-(4-cyano-3-{[(2,4-dimethoxyphenyl)methyl]amino}pyridin-2-yl)-3-(3,5-difluorophenyl)quinolin-4-yl]-octahydro-1H-pyrido[3,4-b]morpholine-1-carboxylate: to the DMSO solution (3.0 mL) of crude tert-butyl trans-6-[6-(4-cyano-3-fluoropyridin-2-yl)-3-(3,5-difluorophenyl)quinolin-4-yl]-octahydro-1H-pyrido[3,4-b]morpholine-1-carboxylate was added DIPEA and 2,4-dimethoxybenzylamine (0.3 mL). The resulting mixture was heated at 130° C. for 3 h. The reaction mixture was diluted with ethyl acetate and washed with water and brine. The organic layer was separated, dried with Na$_2$SO$_4$ and concentrated. The residue obtained was purified by silica gel chromatography eluting with ethyl acetate/hexane (0~50%) to give 150 mg of the title compound. MS (M+1)+=749.5.

Step 42-3, preparation of 2-{4-[trans-octahydro-1H-pyrido[3,4-b]morpholin-6-yl]-3-(3,5-difluorophenyl)quinolin-6-yl}-3-aminopyridine-4-carbonitrile: tert-butyl trans-6-[6-(4-cyano-3-{[(2,4-dimethoxyphenyl)methyl]amino}pyridin-2-yl)-3-(3,5-difluorophenyl)quinolin-4-yl]-octahydro-1H-pyrido[3,4-b]morpholine-1-carboxylate (150 mg) was combined with TFA (3.0 mL) and thioanisole (0.2 mL). The resulting mixture was heated at 60° C. for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with MgSO$_4$. The organic solution was concentrated with HCl in EtOEt (2.0 M, 1.0 mL) to give 44 mg of the title compound as HCl salt. MS (M+H)$^+$=499.2.

The following compounds were prepared in a similar manner as described in Example 42, substituting with appropriate reagents and substrates as required.

| Compound no. | MS (M + H)$^+$ |
| --- | --- |
| 2-282 | 495.4 |

Example 43

3-{4-[trans-octahydro-1H-pyrido[3,4-b]morpholin-6-yl]-3-(3,5-difluorophenyl)quinolin-6-yl}pyridin-2-amine (Compound No. 2-246)

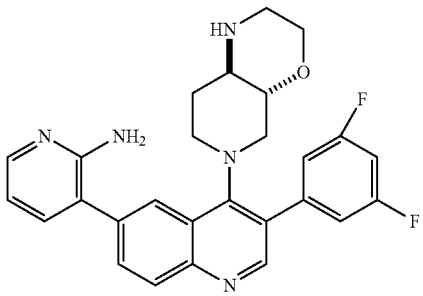

Step 43-1, preparation of tert-butyl trans-6-[6-(2-aminopyridin-3-yl)-3-(3,5-difluorophenyl)quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.2 mmol crude, "Example 40, step 40-4") and 3-bromo-2-aminopyridine (2.0 eq., 0.4 mmol, 71 mg), the title compound was prepared using a similar method to the one described in "Example 40, Step 40-5". The reaction mixture was diluted with ethyl acetate and washed with water and brine. The organic layer was separated, dried with Na$_2$SO$_4$ and concentrated. The residue obtained was used for next step without purification. The residue obtained was purified by silica gel chromatography eluting with ethyl acetate/hexane (0~50%) to give 70 mg of the title compound. MS (M+1)$^+$=574.6.

Step 43-2, preparation of 3-{4-[trans-octahydro-1H-pyrido[3,4-b]morpholin-6-yl]-3-(3,5-difluorophenyl)quinolin-6-yl}pyridin-2-amine: to the dichloromethane solution (1.0 mL) of tert-butyl trans-6-[6-(2-aminopyridin-3-yl)-3-(3,5-difluorophenyl)quinolin-4-yl]-octahydro-1H-pyrido[3,4-b]morpholine-1-carboxylate (70 mg) was added TFA (0.25 mL). The resulting mixture was stirred at ambient temperature for 1 h. The reaction solution was concentrated and purified by C18 reversed phase chromatography eluting with MeCN/water (0~40%). Pure fractions were combined, neutralized with saturated NaHCO$_3$/NaCl, extracted with ethyl acetate and dried with Na$_2$SO$_4$. The organic solution was concentrated with HCl in EtOEt (2.0 M, 1.0 mL) to give 44 mg of the title compound as HCl salt. MS (M+H)$^+$=474.2.

The following compounds were prepared in a similar manner as described in Example 43, substituting with appropriate reagents and substrates as required.

| Compound no. | MS (M + H)$^+$ |
| --- | --- |
| 2-261 | 502.4 |
| 2-265 | 492.4 |
| 2-268 | 519.3 |
| 2-267 | 514.5 |
| 2-283 | 474.0 |
| 2-284 | 504.4 |

Example 44

5-{4-[trans-octahydro-1H-pyrido[3,4-b]morpholin-6-yl]-3-(3,5-difluorophenyl)quinolin-6-yl}-4-aminopyridine-3-carbonitrile (Compound No. 2-244)

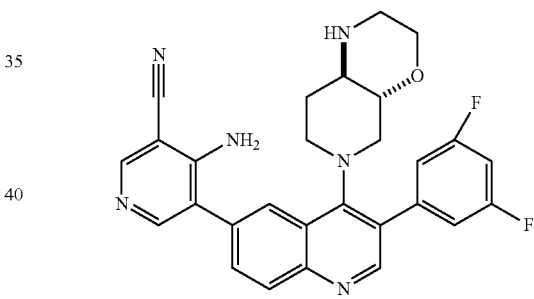

Step 44-1, preparation of tert-butyl trans-6-[6-(4-amino-5-cyanopyridin-3-yl)-3-(3,5-difluorophenyl)quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.15 mmol crude, "Example 40, step 40-4") and 4-amino-5-bromonicotinonitrile (1.5 eq., 0.23 mmol, 47 mg), the title compound was prepared using a similar method to the one described in "Example 40, Step 40-5". The reaction mixture was diluted with ethyl acetate and washed with water and brine. The organic layer was separated, dried with Na$_2$SO$_4$ and concentrated. The residue obtained was used for next step without purification. The residue obtained was purified by silica gel chromatography eluting with ethyl acetate/hexane (0~50%) to give 53 mg of the desired product. MS (M+1)$^+$=599.4.

Step 44-2, preparation of 5-{4-[trans-octahydro-1H-pyrido[3,4-b]morpholin-6-yl]-3-(3,5-difluorophenyl)quinolin-6-yl}-4-aminopyridine-3-carbonitrile: to the dichloromethane solution (1.0 mL) of tert-butyl trans-6-[6-(4-amino-5-cyanopyridin-3-yl)-3-(3,5-difluorophenyl)

quinolin-4-yl]-octahydro-1H-pyrido[3,4-b]morpholine-1-carboxylate (53 mg) was added TFA (0.25 mL). The resulting mixture was stirred at ambient temperature for 1 h. The reaction solution was concentrated and purified by C18 reversed phase chromatography eluting with MeCN/water (0~40%). Pure fractions were combined, neutralized with saturated NaHCO₃/NaCl, extracted with ethyl acetate and dried with Na₂SO₄. The organic solution was concentrated with HCl in ethyl ether (2.0 M, 1.0 mL) to give 44 mg of the final compound as HCl salt. MS (M+H)⁺=499.4.

Example 45

2-{4-[trans-octahydro-1H-pyrido[3,4-b]morpholin-6-yl]-3-(3,5-difluorophenyl)quinolin-6-yl}-4-[(methoxyimino)methyl]pyridin-3-amine (Compound No. 2-269)

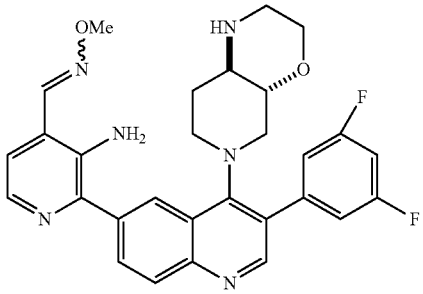

Step 45-1, preparation of tert-butyl trans-6-[6-(3-amino-4-formylpyridin-2-yl)-3-(3,5-difluorophenyl)quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.15 mmol crude, "Example 40, step 40-4") and 3-amino-2-bromopyridine-4-crbaldehyde (2.0 eq., 0.30 mmol, 64 mg), the title compound was prepared using a similar method to the one described in "Example 40, Step 40-5". The reaction mixture was diluted with ethyl acetate and washed with water and brine. The organic layer was separated, dried with Na₂SO₄ and concentrated. The residue obtained was purified by silica gel chromatography eluting with MeOH/DCM (0~3%) to give 60 mg of the desired product. MS (M+1)⁺=602.5.

Step 45-2, preparation of tert-butyl trans-6-(6-{3-amino-4-[(methoxyimino)methyl]pyridin-2-yl}-3-(3,5-difluorophenyl)quinolin-4-yl)-octahydro-1H-pyrido[3,4-b]morpholine-1-carboxylate: to the dichloromethane solution (1.0 mL) of tert-butyl trans-6-[3-(3,5-difluorophenyl)-6-(2-formylpyridin-3-yl)quinolin-4-yl]-octahydro-1H-pyrido[3,4-b]morpholine-1-carboxylate (60 mg) was added pyridine (8.0 eq., 0.80 mmol, 0.08 mL) and HCl salt of methoxyamine (4.0 eq., 0.40 mmol, 32 mg). The resulting mixture was stirred at rt for 1 h. LCMS analysis showed full consumption of starting material and formation of desired product. The reaction solution was used for next step without further purification. MS (M+1)⁺=631.5.

Step 45-3, preparation of 2-{4-[trans-octahydro-1H-pyrido[3,4-b]morpholin-6-yl]-3-(3,5-difluorophenyl)quinolin-6-yl}-4-[(methoxyimino)methyl]pyridin-3-amine: to the crude dichloromethane solution from step 45-2 was added TFA (1.0 mL). The resulting mixture was stirred at ambient temperature for 0.5 h. The reaction solution was concentrated and purified by C18 reversed phase chromatography eluting with MeCN/water (0~40%). Pure fractions were combined, neutralized with saturated NaHCO₃/NaCl, extracted with ethyl acetate and dried with Na₂SO₄. The organic solution was concentrated with HCl in ethyl ether (2.0 M, 1.0 mL) to give 47 mg of the title compound as HCl salt. MS (M+H)⁺=531.4.

Example 46

3-{4-[trans-octahydro-1H-pyrido[3,4-b]morpholin-6-yl]-3-(3,5-difluorophenyl)quinolin-6-yl}pyridin-2-ol (Compound No. 2-248)

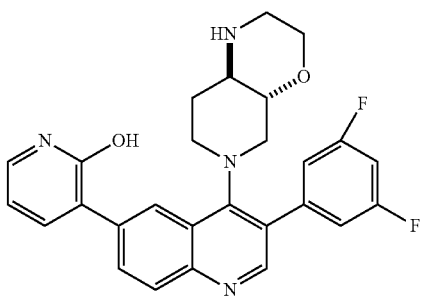

Step 46-1, preparation of 3-bromo-2-[(3,4-dimethoxyphenyl)methoxy]pyridine: to the THF solution (5.0 mL) of 3-bromo-2-hydroxypyridine (2.0 mmol, 348 mg) was added PPh₃ (1.5 eq., 3.0 mmol, 786 mg), 3,4-dimethoxybenzyl alcohol (1.2 eq., 2.4 mmol, 0.356 mL) and diisopropyl azodicarboxylate (DIAD) (1.2 eq., 2.4 mmol, 0.46 mL) at 0° C. The resulting mixture was then stirred at rt for 4 h. The reaction mixture was diluted with ethyl acetate and washed with water and brine. The organic layer was separated, dried with Na₂SO₄ and concentrated. The residue obtained was purified by silica gel chromatography eluting with EtOAc/hexane (0~30%) to give 227 mg of the title compound. MS (M+1)⁺=324.0.

Step 46-2, preparation of tert-butyl trans-6-[3-(3,5-difluorophenyl)-6-{2-[(3,4-dimethoxyphenyl)methoxy]pyridin-3-yl}quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.42 mmol, concentrated crude after workup and drying with Na₂SO₄, "Example 40, step 40-4") and 3-bromo-2-[(3,4-dimethoxyphenyl)methoxy]pyridine (1.66 eq., 0.69 mmol, 227 mg), the title compound was prepared using a similar method to the one described in "Example 40, Step 40-5". The reaction mixture was diluted with ethyl acetate and washed with water and brine. The organic layer was separated, dried with Na₂SO₄ and concentrated. The residue obtained was used for next step without purification. The residue obtained was purified by silica gel chromatography eluting with ethyl acetate/hexane (0~50%) to give 86 mg of the title compound. MS (M+1)⁺=725.7.

Step 46-3, preparation of 3-{4-[trans-octahydro-1H-pyrido[3,4-b]morpholin-6-yl]-3-(3,5-difluorophenyl)quinolin-6-yl}pyridin-2-ol: tert-butyl (4aR,8aR)-6-[3-(3,5-difluorophenyl)-6-{2-[(3,4-dimethoxyphenyl)methoxy]pyridin-3-yl}quinolin-4-yl]-octahydro-1H-pyrido[3,4-b]morpholine-1-carboxylate (86 mg) was combined with TFA (1.5 mL) and thioanisole (0.3 mL). The resulting mixture was stirred at 90° C. for 22 h. The reaction solution was concentrated and purified by C18 reversed phase chromatography eluting with MeCN/water (0~40%). Pure fractions were combined, neutralized with saturated NaHCO₃/NaCl, extracted with ethyl acetate and dried with Na₂SO₄. The organic solution was concentrated with HCl in ethyl ether (2.0 M, 1.0 mL) to give 18 mg of the title compound as HCl salt. MS (M+H)⁺=475.2.

Example 47

3-[5-(4-aminopiperidin-1-yl)-6-(3,5-difluorophenyl)-1,8-naphthyridin-3-yl]-2-hydroxybenzonitrile (Compound No. 4-1)

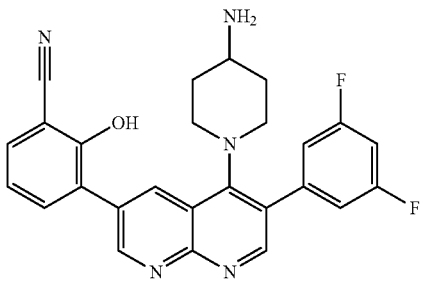 [SMILES: N#Cc1cccc(-c2cnc3ncc(-c4cc(F)cc(F)c4)c(N4CCC(N)CC4)c3c2)c1O]

Step 47-1, preparation of 6-bromo-3-chloro-1,8-naphthyridin-4-ol: to a solution of 6-bromo-1,8-naphthyridin-4-ol (1.14 g, 5.07 mmol) in acetic acid (20 mL) was added NCS (0.81 g, 6.08 mmol). The mixture was heated at 100° C. for 1 hr and then cooled to RT. The solid was collected by vacuum filtration and washed with acetic acid and water to afford the title compound (0.73 g, 2.79 mmol, 55.1% yield) as a brown solid. (M+1)⁺=259.0.

Step 47-2, preparation of 6-bromo-3,4-dichloro-1,8-naphthyridine: to 6-bromo-3-chloro-1,8-naphthyridin-4-ol (0.73 g, 2.79 mmol) was added POCl₃ (3 mL) and the mixture was heated at 130° C. for 25 min. The mixture was poured into an ice and the solid was collected by vacuum filtration and washed with water to afford the title compound (0.66 g, 2.36 mmol, 84.6% yield) as a brown solid. (M+1)⁺=279.0.

Step 47-3, preparation of tert-butyl N-[1-(6-bromo-3-chloro-1,8-naphthyridin-4-yl)piperidin-4-yl]carbamate: to a mixture of 6-bromo-3,4-dichloro-1,8-naphthyridine (0.657 g, 2.364 mmol) and piperidin-4-yl-carbamic acid tert-butyl ester (0.916 g, 3.546 mmol) in a sealed tube was added DMSO (8 mL) and DIEA (1.2 mL, 6.892 mmol). The mixture was heated at 130° C. overnight. The mixture was diluted with water and the solid was collected by vacuum filtration and washed with water. The crude solid was purified by silica gel column chromatography to afford the title compound (0.92 g, 2.09 mmol, 88.3% yield) as a light orange solid. (M+1)⁺=441.3.

Step 47-4, preparation of tert-butyl N-(1-{3-chloro-6-[3-cyano-2-(methoxymethoxy)phenyl]-1,8-naphthyridin-4-yl}piperidin-4-yl)carbamate: to a mixture of tert-butyl N-[1-(6-bromo-3-chloro-1,8-naphthyridin-4-yl)piperidin-4-yl]carbamate (0.275 g, 0.622 mmol), 2-methoxymethoxy-3-(4,4,5,5-tetramethyl-[1,3,2]dioxaborolan-2-yl)-benzonitrile (0.216 g, 0.747 mmol), tris(dibenzylideneacetone)dipalladium/tri-tert-butyl phosphonium tetrafluoroborate mixture (mole ratio: 1/1.2) (40.5 mg, 0.031 mmol), and K₃PO₄.H₂O (0.57 g, 2.49 mmol) in a sealed tube was added THF (5 mL) and water (0.5 mL). The mixture was bubbled with N₂ (g) for 10 min and then stirred at rt for 45 min. The mixture was concentrated and purified by silica gel column chromatography to afford the title compound (211.4 mg, 0.40 mmol, 64.8% yield) as a medium brown solid. MS (M+1)⁺=524.4.

Step 47-5, preparation of tert-butyl N-(1-{6-[3-cyano-2-(methoxymethoxy)phenyl]-3-(3,5-difluorophenyl)-1,8-naphthyridin-4-yl}piperidin-4-yl)carbamate: to a mixture of tert-butyl N-(1-{3-chloro-6-[3-cyano-2-(methoxymethoxy)phenyl]-1,8-naphthyridin-4-yl}piperidin-4-yl)carbamate (106.8 mg, 0.20 mmol), 3,5-difluorophenylboronic acid (64.4 mg, 0.41 mmol), Pd[t-Bu₂P(4-NMe₂C₆H₄)]₂Cl₂) (14.4 mg, 0.02 mmol), and K₂CO₃ (84.6 mg, 0.61 mmol) in a sealed tube was added dioxane (3 mL) and water (0.3 mL).). The mixture was bubbled with N₂ (g) for 10 min and then heated at 100° C. for 50 min. The mixture was concentrated and purified by silica gel column chromatography to give the title compound (104.8 mg, 0.17 mmol, 85.3% yield) as a brown gum. MS (M+1)⁺=602.6.

Step 47-6, preparation of 3-[5-(4-amino-piperidin-1-yl)-6-(3,5-difluorophenyl)-1,8-naphthyridin-3-yl]-2-hydroxy-benzonitrile: to a solution of tert-butyl N-(1-{6-[3-cyano-2-(methoxymethoxy)phenyl]-3-(3,5-difluorophenyl)-1,8-naphthyridin-4-yl}piperidin-4-yl)carbamate (104.8 mg, 0.17 mmol) in DCM (0.8 mL) was added TFA (0.2 mL). The mixture was stirred at RT for 1 hr. The mixture was concentrated and purified by C₁₈ reversed-phase column chromatography to afford the title compound (55.5 mg, 0.12 mmol, 69.5% yield) as a yellow solid. MS (M+1)⁺=458.2.

The following compounds were prepared in a similar manner as described in Example 47, substituting with appropriate reagents and substrates as required.

| Compound no. | MS (M + H)⁺ |
| --- | --- |
| 4-2 | 454.0 |
| 4-3 | 472.0 |
| 4-4 | 470.4 |

Example 48

3-[3-(3-fluoro-5-methylphenyl)-4-[3-(morpholin-3-yl)azetidin-1-yl]quinolin-6-yl]-2-hydroxybenzonitrile (Compound No. 2-270)

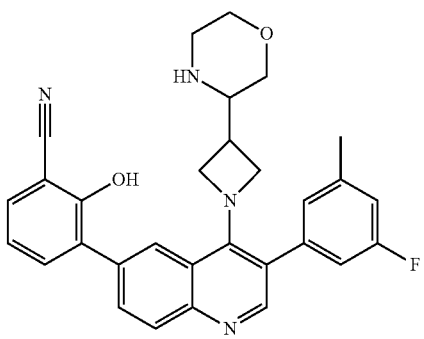 [SMILES: Cc1cc(F)cc(-c2cnc3ccc(-c4cccc(C#N)c4O)cc3c2N2CC(C3COCCN3)C2)c1]

Step 48-1, preparation of benzyl 3-{1-[(tert-butoxy)carbonyl]azetidin-3-yl}morpholine-4-carboxylate: to the dichloromethane solution (5.0 mL) of tert-butyl 3-(morpholin-3-yl)azetidine-1-carboxylate (200 mg, 0.82 mmol) was added N-(benzyloxycarbonyloxy)succinimide (1.5 eq., 1.24 mmol, 310 mg). The resulting mixture was stirred at ambient temperature for overnight. The reaction solution was diluted with dichloromethane, washed with water, dried with Na$_2$SO$_4$, and concentrated. The residue was purified by by silica gel column chromatography to give the title compound 286 mg as colorless oil. MS (M+1)$^+$=377.5.

Step 48-2, preparation of benzyl 3-(azetidin-3-yl)morpholine-4-carboxylate: benzyl 3-{1-[(tert-butoxy)carbonyl]azetidin-3-yl}morpholine-4-carboxylate (286 mg) was combined with HCl in dioxane (4.0 M, 4.0 mL) and the resulting mixture was stirred at ambient temperature for 1 h. The reaction mixture was concentrated to give the title compound 200 mg as HCl salt. MS (M+1)$^+$=277.1.

Step 48-3, preparation of benzyl 3-[1-(3-bromo-6-chloroquinolin-4-yl)azetidin-3-yl]morpholine-4-carboxylate: from benzyl 3-(azetidin-3-yl)morpholine-4-carboxylate (0.72 mmol) and 3-bromo-4,6-dichloro-quinoline (1.40 eq., 1.0 mmol), the title compound was prepared using a similar method to the one described in "Example 40, Step 40-2". MS (M+1)$^+$=516.2.

Step 48-4, preparation of benzyl 3-{1-[6-chloro-3-(3-fluoro-5-methylphenyl)quinolin-4-yl]azetidin-3-yl}morpholine-4-carboxylate: from benzyl 3-[1-(3-bromo-6-chloroquinolin-4-yl)azetidin-3-yl]morpholine-4-carboxylate (50 mg), the title compound was prepared using a similar method to the one described in "Example 40, Step 40-3". The reaction crude was worked up, dried, concentrated and used for next step without further purification. MS (M+1)$^+$=546.5.

Step 48-5, preparation of benzyl 3-{1-[6-(3-cyano-2-hydroxyphenyl)-3-(3-fluoro-5-methylphenyl)quinolin-4-yl]azetidin-3-yl}morpholine-4-carboxylate: from crude benzyl 3-{1-[6-(3-cyano-2-hydroxyphenyl)-3-(3-fluoro-5-methylphenyl)quinolin-4-yl]azetidin-3-yl}morpholine-4-carboxylate and 3-cyano-2-hydroxyphenyl-boronic acid (5.0 eq., 0.5 mmol, 75 mg), the title compound was prepared as a white solid using a method similar to the one described in "Example 12, Step 12-4". The reaction crude was worked up, dried, concentrated and used for next step without further purification. MS (M+1)$^+$=629.4.

Step 48-6, preparation of 3-[3-(3-fluoro-5-methylphenyl)-4-[3-(morpholin-3-yl)azetidin-1-yl]quinolin-6-yl]-2-hydroxybenzonitrile: from crude benzyl 3-{1-[6-(3-cyano-2-hydroxyphenyl)-3-(3-fluoro-5-methylphenyl)quinolin-4-yl]azetidin-3-yl}morpholine-4-carboxylate (50 mg), the title compound was prepared using a method similar to the one described in "Example 33, Step 33-7". MS (M+1)$^+$=495.5.

The following compounds were prepared in a similar manner as described in Example 48, substituting with appropriate reagents and substrates as required.

| Compound no. | MS (M + H)$^+$ |
|---|---|
| 2-271 | 499.3 |

Example 49

2-{4-[trans-octahydro-1H-pyrido[3,4-b]morpholin-6-yl]-3-(3,5-difluorophenyl)quinolin-6-yl}-4-ethynylpyridin-3-amine (Compound No. 2-277)

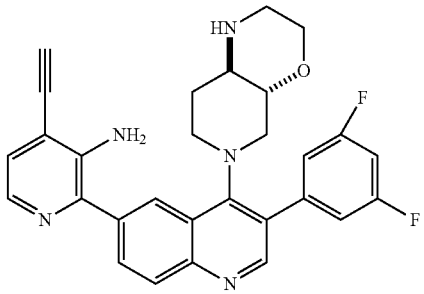

Step 49-1, preparation of tert-butyl trans-6-[6-(3-amino-4-chloropyridin-2-yl)-3-(3,5-difluorophenyl)quinolin-4-yl]-octahydro-1H-pyrido[3,4-b]morpholine-1-carboxylate: from tert-butyl trans-6-[3-(3,5-difluorophenyl)-6-(tetramethyl-1,3,2-dioxaborolan-2-yl)quinolin-4-yl]-octahydro-1H-pyrido[3,4-b]morpholine-1-carboxylate (0.275 mmol crude, "Example 40, step 40-4") and 2-bromo-4-chloropyridin-3-aminopyridine (2.0 eq., 0.55 mmol, 120 mg), the title compound was prepared using a similar method to the one described in "Example 40, Step 40-5". The reaction mixture was diluted with ethyl acetate and washed with water and brine. The organic layer was separated, dried with Na$_2$SO$_4$ and concentrated. The residue obtained was purified by silica gel chromatography eluting with ethyl acetate/hexane (0~50%) to give 82 mg of the desired product. MS (M+1)$^+$=608.3.

Step 49-2, tert-butyl trans-6-(6-{3-amino-4-[2-(trimethylsilyl)ethynyl]pyridin-2-yl}-3-(3,5-difluorophenyl)quinolin-4-yl)-octahydro-1H-pyrido[3,4-b]morpholine-1-carboxylate: to the toluene solution of tert-butyl trans-6-[6-(3-amino-4-chloropyridin-2-yl)-3-(3,5-difluorophenyl)quinolin-4-yl]-octahydro-1H-pyrido[3,4-b]morpholine-1-carboxylate (26 mg, 0.041 mmol) and 1-tributylstannyl-2-trimethylsilylacetlene (3.0 eq., 0.123 mmol, 0.048 mL) was added Pd(Amphos)Cl$_2$ (0.2 eq., 5.9 mg). N$_2$ was bubbled through the reaction solution for 5 min and heated at 100° C. for 8 h. The reaction mixture was diluted with ethyl acetate and washed with water and brine. The organic layer was separated, dried with Na$_2$SO$_4$ and concentrated. The residue obtained was purified by silica gel chromatography eluting with ethyl acetate/hexane (0~50%) to give 16 mg of the title compound. MS (M+1)$^+$=670.6.

Step 49-3, preparation of 2-{4-[trans-octahydro-1H-pyrido[3,4-b]morpholin-6-yl]-3-(3,5-difluorophenyl)quinolin-6-yl}-4-ethynylpyridin-3-amine: to the THF/MeOH solution (2:1, 3.0 mL) was added tert-butyl trans-6-(6-{3-amino-4-[2-(trimethylsilyl)ethynyl]pyridin-2-yl}-3-(3,5-difluorophenyl)quinolin-4-yl)-octahydro-1H-pyrido[3,4-b]morpholine-1-carboxylate (16 mg, 0.024 mmol) and K$_2$CO$_3$ (3.0 eq., 10 mg) at 0° C. The resulting mixture was stirred at the same temperature for 0.5 h. The mixture was filtered and concentrated. The residue obtained was dissolved in dichloromethane (1.0 mL) and TFA (0.2 mL) was added. The reaction mixture was stirred at ambient temperature for 0.5 h. The mixture was concentrated and purified by C18 reversed-phase column chromatography to afford the title compound. MS (M+1)⁺=498.4.

The following compounds were prepared in a similar manner as described in Example 49, substituting with appropriate reagents and substrates as required.

| Compound no. | MS (M + H)⁺ |
|---|---|
| 2-272 | 512.4 |
| 2-274 | 498.3 |

Example 50

1-(3-{4-[trans-octahydro-1H-pyrido[3,4-b]morpholin-6-yl]-3-(3,5-difluorophenyl)quinolin-6-yl}pyridin-2-yl)-3-methoxyurea (Compound No. 2-273)

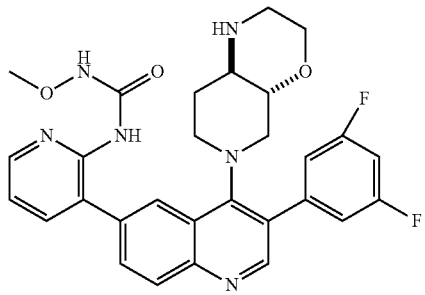

Step 50-1, preparation of tert-butyl trans-6-[3-(3,5-difluorophenyl)-6-{2-[(methoxycarbamoyl)amino]pyridin-3-yl}quinolin-4-yl]-octahydro-1H-pyrido[3,4-b]morpholine-1-carboxylate: from tert-butyl trans-6-[6-(2-aminopyridin-3-yl)-3-(3,5-difluorophenyl)quinolin-4-yl]-octahydro-1H-pyrido[3,4-b]morpholine-1-carboxylate (92 mg, 0.16 mmol, "Example 43, step 43-1"), the title compound was prepared using a similar method to the one described in "Example 26, Step 26-3". MS (M+1)⁺=647.3.

Step 50-2, preparation of 1-(3-{4-[trans-octahydro-1H-pyrido[3,4-b]morpholin-6-yl]-3-(3,5-difluorophenyl)quinolin-6-yl}pyridin-2-yl)-3-methoxyurea: from tert-butyl trans-6-[3-(3,5-difluorophenyl)-6-{2-[(methoxycarbamoyl)amino]pyridin-3-yl}quinolin-4-yl]-octahydro-1H-pyrido[3,4-b]morpholine-1-carboxylate (43 mg), the title compound was prepared using a similar method to the one described in "Example 26, Step 26-4". MS (M+1)⁺=547.4.

Example 51

Chiral SFC Separation of Compound 2-19 to 2-190 and 2-193

The two enantiomers of 3-{4-[trans-octahydro-1H-pyrido[3,4-b]morpholin-6-yl]-3-(3,5-difluorophenyl)quinolin-6-yl}-2-hydroxybenzonitrile (2-19, 2.1 g) are 3-{4-[(4aS,8aS)-octahydro-1H-pyrido[3,4-b]morpholin-6-yl]-3-(3,5-difluorophenyl)quinolin-6-yl}-2-hydroxybenzonitrile (2-190) and 3-{4-[(4αR,8αR)-octahydro-1H-pyrido[3,4-b]morpholin-6-yl]-3-(3,5-difluorophenyl)quinolin-6-yl}-2-hydroxybenzonitrile (2-193). The two enantiomers were seaparated by chiral SFC using the conditions described as below. Thar SFC 350, Column: CHIRALPAK AD-H, 50×250 mm, 5 um; Mobile Phase A: CO2; Mobile Phase B: MeOH containing 0.1% diethylamine; Flow rate: 150g/min; Gradient: 50% B; Injection volume: 1 mL (57.5 mg/mL in MeOH); cycle time: 4 min; Detector, 220 nm. This resulted in collection of peak 1 (enantiomer A; Rt=1.924 min; 837.7 mg) as a light yellow solid and peak 2 (enantiomer B, Rt=3.493 min; 830.1 mg) as a light yellow solid.

MS (M+1)⁺=499.2 for both 2-190 and 2-193.

Example A-1

Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2

Oral Solution

To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3

Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100 -500 mg.

Example A-4

Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

Example A-5

Topical Gel Composition

To prepare a pharmaceutical topical gel composition, a compound of Formula (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1

SSTR Assays

Functional Assay for SSTR2 Agonists

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology*, 2005,2.2.1-2.2). Human SSTR2 intracellular cAMP assay is described below. The human SSTR1, 3, 4 and 5 assays follow the same protocol of SSTR2.

cAMP Assay Protocol:

Four days prior to the assay, 5,000 Chinese hamster ovary cells (CHO-K1, ATCC #CCL-61) stably expressing the human SSTR2 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.2 mg/mL hygromycin B (GoldBio #31282-04-9). The cells are cultured at 37° C., 5% $CO_2$ and 95% humidity. On the day of the assay, the media is aspirated and the cells are treated with 50 µL of 1.6 µM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 µL of lysis buffer (HRTF cAMP kit, Cisbio). The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipluations are in GraphPad Prism v6.

Illustrative biological activity of compounds is demonstrated in the following table by evaluating the inhibition of cAMP activities via human SST2R, where A means <10 nM; B means ≥10 nM and <100 nM; C means ≤100 nM and <1000 nM; D means ≥1000 nM

| Compound no. | $EC_{50}$ |
|---|---|
| 1-1 | A |
| 1-2 | A |
| 1-3 | C |
| 1-4 | A |
| 1-5 | A |
| 1-6 | A |
| 1-7 | A |
| 1-8 | A |
| 1-9 | B |
| 1-10 | A |
| 1-11 | A |
| 1-12 | A |
| 1-13 | A |
| 1-14 | A |
| 1-15 | B |
| 1-16 | A |
| 1-17 | A |
| 1-18 | A |
| 1-19 | A |
| 1-20 | B |
| 1-21 | A |
| 1-22 | A |
| 1-23 | A |
| 1-24 | A |
| 1-25 | A |
| 1-26 | A |
| 1-27 | A |
| 1-28 | A |
| 1-29 | A |
| 1-30 | A |
| 1-31 | A |
| 1-32 | A |
| 1-33 | A |
| 1-34 | A |
| 2-1 | A |
| 2-2 | A |
| 2-3 | A |
| 2-4 | A |
| 2-5 | A |
| 2-6 | A |
| 2-7 | A |
| 2-8 | A |
| 2-9 | A |
| 2-10 | A |
| 2-11 | B |
| 2-12 | B |
| 2-13 | B |
| 2-14 | B |
| 2-15 | C |
| 2-16 | A |
| 2-17 | B |
| 2-18 | A |
| 2-19 | A |
| 2-20 | A |
| 2-21 | B |
| 2-22 | B |
| 2-23 | C |
| 2-24 | A |
| 2-25 | A |
| 2-26 | A |
| 2-27 | A |
| 2-28 | A |
| 2-29 | A |
| 2-30 | A |
| 2-31 | A |
| 2-33 | B |
| 2-35 | C |
| 2-38 | A |
| 2-39 | C |
| 2-40 | A |
| 2-41 | B |
| 2-42 | A |
| 2-43 | A |
| 2-44 | C |
| 2-45 | B |
| 2-46 | A |
| 2-47 | C |
| 2-48 | A |
| 2-49 | A |
| 2-50 | B |
| 2-51 | B |
| 2-52 | B |
| 2-53 | A |

-continued

| Compound no. | EC$_{50}$ |
|---|---|
| 2-54 | A |
| 2-55 | A |
| 2-56 | B |
| 2-57 | B |
| 2-58 | A |
| 2-59 | A |
| 2-60 | A |
| 2-61 | B |
| 2-62 | A |
| 2-63 | A |
| 2-64 | A |
| 2-65 | A |
| 2-66 | B |
| 2-67 | A |
| 2-68 | B |
| 2-69 | B |
| 2-70 | B |
| 2-71 | C |
| 2-72 | A |
| 2-73 | B |
| 2-74 | C |
| 2-75 | A |
| 2-76 | C |
| 2-77 | A |
| 2-78 | A |
| 2-79 | C |
| 2-80 | A |
| 2-81 | A |
| 2-82 | B |
| 2-83 | A |
| 2-84 | A |
| 2-85 | A |
| 2-86 | C |
| 2-87 | B |
| 2-88 | B |
| 2-92 | C |
| 2-94 | B |
| 2-99 | A |
| 2-100 | B |
| 2-115 | A |
| 2-116 | A |
| 2-123 | A |
| 2-125 | A |
| 2-126 | A |
| 2-129 | B |
| 2-132 | B |
| 2-134 | A |
| 2-139 | A |
| 2-141 | B |
| 2-142 | A |
| 2-143 | A |
| 2-144 | A |
| 2-145 | C |
| 2-146 | D |
| 2-147 | B |
| 2-148 | A |
| 2-149 | C |
| 2-150 | A |
| 2-151 | C |
| 2-152 | A |
| 2-161 | A |
| 2-164 | A |
| 2-165 | A |
| 2-166 | A |
| 2-167 | A |
| 2-168 | A |
| 2-169 | A |
| 2-170 | C |
| 2-171 | A |
| 2-172 | A |
| 2-173 | A |
| 2-174 | A |
| 2-175 | B |
| 2-176 | A |
| 2-177 | A |
| 2-178 | A |
| 2-179 | A |

-continued

| Compound no. | EC$_{50}$ |
|---|---|
| 2-180 | A |
| 2-181 | A |
| 2-182 | A |
| 2-183 | A |
| 2-184 | A |
| 2-185 | A |
| 2-186 | A |
| 2-187 | A |
| 2-188 | A |
| 2-189 | A |
| 2-191 | A |
| 2-192 | A |
| 2-194 | A |
| 2-195 | A |
| 2-196 | A |
| 2-197 | A |
| 2-198 | A |
| 2-199 | A |
| 2-200 | A |
| 2-201 | A |
| 2-202 | A |
| 2-203 | A |
| 2-204 | A |
| 2-205 | A |
| 2-206 | A |
| 2-207 | A |
| 2-209 | A |
| 2-210 | A |
| 2-211 | A |
| 2-212 | A |
| 2-213 | B |
| 2-214 | A |
| 2-215 | B |
| 2-216 | A |
| 2-217 | A |
| 2-218 | A |
| 2-219 | A |
| 2-220 | A |
| 2-221 | A |
| 2-222 | A |
| 2-223 | A |
| 2-224 | A |
| 2-225 | A |
| 2-226 | A |
| 2-227 | A |
| 2-228 | A |
| 2-229 | A |
| 2-230 | A |
| 2-231 | A |
| 2-232 | A |
| 2-233 | A |
| 2-234 | A |
| 2-235 | A |
| 2-236 | A |
| 2-237 | A |
| 2-238 | A |
| 2-239 | B |
| 2-240 | B |
| 2-241 | A |
| 2-242 | A |
| 2-243 | A |
| 2-244 | A |
| 2-245 | A |
| 2-246 | A |
| 2-247 | A |
| 2-248 | A |
| 2-249 | A |
| 2-250 | A |
| 2-251 | C |
| 2-251 | A |
| 2-252 | A |
| 2-253 | A |
| 2-254 | B |
| 2-255 | B |
| 2-256 | B |
| 2-257 | B |
| 2-258 | A |

-continued

| Compound no. | EC$_{50}$ |
|---|---|
| 2-259 | A |
| 2-260 | A |
| 2-261 | B |
| 2-262 | A |
| 2-263 | A |
| 2-264 | A |
| 2-265 | A |
| 2-266 | A |
| 2-267 | B |
| 2-268 | B |
| 2-269 | A |
| 2-270 | A |
| 2-271 | B |
| 2-272 | A |
| 2-273 | A |
| 2-274 | A |
| 2-275 | A |
| 2-277 | A |
| 2-282 | A |
| 2-283 | B |
| 3-1 | A |
| 3-2 | A |
| 3-3 | A |
| 3-4 | A |
| 3-5 | A |
| 3-9 | A |
| 3-10 | A |
| 4-1 | B |
| 4-2 | A |
| 4-3 | A |
| 4-4 | A |

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (AIIb), or a pharmaceutically acceptable salt, solvate, diastereomeric mixture, or individual enantiomers thereof:

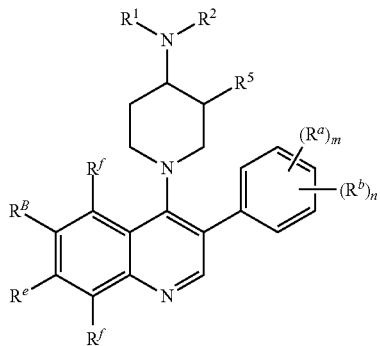

Formula (AIIb)

wherein:
each $R^a$ and $R^b$ is independently hydrogen, halogen, unsubstituted or substituted $C_1$-$C_6$alkyl, unsubstituted or substituted $C_1$-$C_6$fluoroalkyl, unsubstituted or substituted $C_1$-$C_6$heteroalkyl, unsubstituted or substituted monocyclic carbocycle, unsubstituted or substituted monocyclic heterocycle, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$ or —C(=NOR$^{15}$)R$^{15}$;

m is 1 or 2; n is 0, 1 or 2;

or if one $R^a$ and one $R^b$ are on adjacent atoms then the adjacent $R^a$ and $R^b$ groups are taken together with the intervening atoms to which they are attached to form an unsubstituted or substituted 5- or 6-membered monocyclic carbocycle or an unsubstituted or substituted 5- or 6-membered monocyclic heterocycle;

$R^B$ is an unsubstituted or substituted ring B that is an unsubstituted or substituted phenyl or an unsubstituted or substituted pyridinyl, wherein if the ring B is substituted then the ring B is substituted with p $R^c$ and q $R^d$;

each $R^c$ and $R^d$ is independently hydrogen, halogen, unsubstituted or substituted $C_1$-$C_6$alkyl, unsubstituted or substituted $C_1$-$C_6$fluoroalkyl, unsubstituted or substituted monocyclic carbocycle, unsubstituted or substituted monocyclic heterocycle, —CN, —OH, —OR$^{14}$, —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, —C(=NOR$^{15}$)R$^{15}$, —N(R$^{15}$)SO$_2$R$^{14}$, —C(=O)NR$^{15}$S(=O)$_2$R$^{14}$, —S(=O)$_2$NR$^{15}$C(=O)R$^{14}$, —C(=NR$^{15}$)N(R$^{15}$)$_2$, —NR$^{15}$C(=NR$^{15}$)N(R$^{15}$)$_2$, —NR$^{15}$C(=CR$^{14}$R$^{15}$)N(R$^{15}$)$_2$, —C(=O)NR$^{15}$C(=NR$^{15}$)N(R$^{15}$)$_2$ or, —C(=O)NR$^{15}$C(=CR$^{14}$R$^{15}$)N(R$^{15}$)$_2$;

p is 1 or 2; q is 0, 1 or 2;

or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle;

$R^e$ is hydrogen, halogen, $C_1$-$C_4$alkyl, $C_1$-$C_4$fluoroalkyl, —CN, OH, or —OR$^{14}$;

each $R^f$ is independently hydrogen, halogen, $C_1$-$C_4$alkyl, $C_1$-$C_4$fluoroalkyl, —CN, —OH, or —OR$^{14}$;

$R^1$ and $R^2$ are independently hydrogen, unsubstituted or substituted $C_1$-$C_6$alkyl, unsubstituted or substituted $C_1$-$C_6$ heteroalkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;

or $R^1$ and $R^2$ are taken together with the nitrogen atom to which they are attached to form ring C that is an unsubstituted or substituted N-containing $C_2$-$C_8$heterocycloalkyl;

$R^5$ is selected from the group consisting of hydrogen, halogen, —OH, —OR$^{14}$, —SR$^{14}$, —S(=O)R$^{14}$, —S(=O)$_2$R$^{14}$, —N(R$^{15}$)$_2$, —CN, —C(=O)OR$^{15}$, —C(=O)N(R$^{15}$)$_2$, unsubstituted or substituted $C_1$-$C_6$alkyl, unsubstituted or substituted $C_1$-$C_6$heteroalkyl, and unsubstituted or substituted $C_1$-$C_6$fluoroalkyl;

or $R^2$ and $R^5$ are taken together with the intervening atoms to which they are attached to form an unsubstituted or substituted 4-7 membered saturated N-containing heterocyclic ring;

each $R^{14}$ is independently selected from unsubstituted or substituted $C_1$-$C_6$alkyl, unsubstituted or substituted $C_1$-$C_6$heteroalkyl, unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

each R$^{15}$ is independently selected from hydrogen, unsubstituted or substituted C$_1$-C$_6$alkyl, unsubstituted or substituted C$_1$-C$_6$heteroalkyl, unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

or two R$^{15}$ on the same N atom are taken together with the N atom to which they are attached to form an unsubstituted or substituted N-containing heterocycle;

wherein each substituted alkyl, substituted fluoroalkyl, substituted heteroalkyl, substituted carbocycle, and substituted heterocycle is substituted with one or more R$^s$ groups independently selected from the group consisting of halogen, C$_1$-C$_6$alkyl, monocyclic carbocycle, monocyclic heterocycle, —CN, —OR$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

each R$^{16}$ is independently selected from hydrogen, C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl; or two R$^{16}$ groups are taken together with the N atom to which they are attached to form a N-containing heterocycle;

each R$^{17}$ is independently selected from C$_1$-C$_6$alkyl, C$_1$-C$_6$heteroalkyl, C$_3$-C$_6$cycloalkyl, C$_2$-C$_6$heterocycloalkyl, phenyl, benzyl, 5-membered heteroaryl and 6-membered heteroaryl.

2. The compound of claim 1, or a pharmaceutically acceptable salt, solvate, diastereomeric mixture, or individual enantiomers thereof, wherein:

R$^e$ is hydrogen, F, Cl, Br, —CH$_3$, —CH$_2$CH$_3$, —CH$_2$F, —CHF$_2$, —CF$_3$, —CN, —OH, —OCH$_3$, —OCH$_2$CH$_3$, or —OCF$_3$;

each R$^f$ is independently hydrogen, F, Cl, Br, —CH$_3$, —CH$_2$CH$_3$, —CH$_2$F, —CHF$_2$, —CF$_3$, —CN, —OH, —OCH$_3$, —OCH$_2$CH$_3$, or —OCF$_3$.

3. The compound of claim 2, or a pharmaceutically acceptable salt, solvate, diastereomeric mixture, or individual enantiomers thereof, wherein:

each R$^a$ is independently hydrogen, halogen, unsubstituted or substituted C$_1$-C$_4$alkyl, unsubstituted or substituted C$_1$-C$_4$fluoroalkyl, unsubstituted or substituted C$_1$-C$_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$ or; and each R$^b$ is independently hydrogen, halogen, unsubstituted or substituted C$_1$-C$_4$alkyl, unsubstituted or substituted C$_1$-C$_4$fluoroalkyl, unsubstituted or substituted C$_1$-C$_4$heteroalkyl, —CN, —OH, or —O-(unsubstituted or substituted C$_1$-C$_4$alkyl).

4. The compound of claim 2, or a pharmaceutically acceptable salt, solvate, diastereomeric mixture, or individual enantiomers thereof, wherein:

each R$^a$ is independently hydrogen, halogen, unsubstituted or substituted C$_1$-C$_4$alkyl, unsubstituted or substituted C$_1$-C$_4$fluoroalkyl, unsubstituted or substituted C$_1$-C$_4$heteroalkyl, —CN, —OH, —OR$^{14}$, —CO$_2$R$^{15}$, —CH$_2$CO$_2$R$^{15}$, —C(=O)N(R$^{15}$)$_2$, —CH$_2$C(=O)N(R$^{15}$)$_2$, —N(R$^{15}$)$_2$, or —CH$_2$N(R$^{15}$)$_2$; and each R$^b$ is independently hydrogen, halogen, unsubstituted or substituted C$_1$-C$_4$alkyl, unsubstituted or substituted C$_1$-C$_4$heteroalkyl, —CN, or —O-(unsubstituted or substituted C$_1$-C$_4$alkyl).

5. The compound of claim 2, or a pharmaceutically acceptable salt, solvate, diastereomeric mixture, or individual enantiomers thereof, wherein:

each R$^a$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, —OCF$_3$, —CH$_2$CH$_2$OH, —CO$_2$H, —CO$_2$CH$_3$, —CO$_2$CH$_2$CH$_3$, —CH$_2$CO$_2$H, —CH$_2$CO$_2$CH$_3$, —CH$_2$CO$_2$CH$_2$CH$_3$, —C(=O)NH$_2$, —C(=O)NHCH$_3$, —C(=O)N(CH$_3$)$_2$, —CH$_2$C(=O)NH$_2$, —CH$_2$C(=O)NHCH$_3$, —CH$_2$C(=O)N(CH$_3$)$_2$, —NH$_2$, —NHCH$_3$, —N(CH$_3$)$_2$, —CH$_2$NH$_2$, —CH$_2$NHCH$_3$, or —CH$_2$N(CH$_3$)$_2$;

each R$^b$ is independently hydrogen, F, Cl, Br, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)(CH$_2$CH$_3$), —C(CH$_3$)$_3$, —CH$_2$OH, —CH$_2$CN, —CH$_2$F, —CHF$_2$, —CF$_3$, —CN, —OH, —OCH$_3$, —OCH$_2$CH$_3$, or —OCF$_3$.

6. The compound of claim 1, or a pharmaceutically acceptable salt, solvate, diastereomeric mixture, or individual enantiomers thereof, wherein:

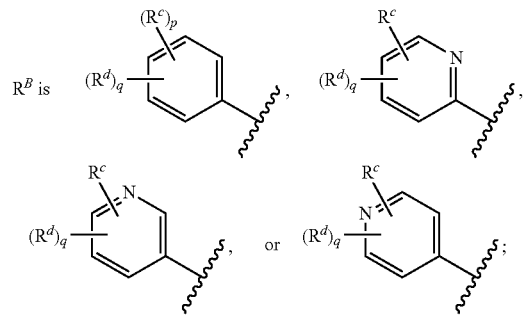

each R$^c$ is independently hydrogen, halogen, unsubstituted or substituted C$_1$-C$_4$alkyl, unsubstituted or substituted C$_1$-C$_4$fluoroalkyl, —CN, —OH, —OR$^{14}$, —CO$_2$R$^{15}$, —CH$_2$CO$_2$R$^{15}$, —C(=O)N(R$^{15}$)$_2$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SR$^{14}$, —S(=O)R$^{14}$, —SO$_2$R$^{14}$, —SO$_2$N(R$^{15}$)$_2$, or N(R$^{15}$)SO$_2$R$^{14}$; and R$^d$ is independently hydrogen, halogen, unsubstituted or substituted C$_1$-C$_4$alkyl, unsubstituted or substituted C$_1$-C$_4$fluoroalkyl, unsubstituted or substituted monocyclic 4-7-membered heterocycle, —CN, —OH, —O-(unsubstituted or substituted C$_1$-C$_4$alkyl), —O-(unsubstituted or substituted C$_1$-C$_4$heteroalkyl), —C(=O)R$^{15}$, —OC(=O)R$^{15}$, —CO$_2$R$^{15}$, —CH$_2$CO$_2$R$^{15}$, —C(=O)N(R$^{15}$)$_2$, —OC(=O)N(R$^{15}$)$_2$, —NR$^{15}$C(=O)N(R$^{15}$)$_2$, —NR$^{15}$C(=O)OR$^{14}$, —NR$^{15}$C(=O)NR$^{15}$OR$^{14}$, —C(=O)NR$^{15}$OR$^{15}$, —CH$_2$C(=O)N(R$^{15}$)$_2$, —N(R$^{15}$)$_2$, —CH$_2$N(R$^{15}$)$_2$, —CH(CF$_3$)N(R$^{15}$)$_2$, —NR$^{15}$C(=O)R$^{14}$, —CH$_2$NR$^{15}$C(=O)R$^{14}$, —SO$_2$N(R$^{15}$)$_2$, —C(=NOR$^{15}$)R$^{15}$, —N(R$^{15}$)SO$_2$R$^{14}$, —C(=O)NR$^{15}$S(=O)$_2$R$^{14}$, —S(=O)$_2$NR$^{15}$C(=O)R$^{14}$, or —C(=NR$^{15}$)N(R$^{15}$)$_2$;

or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic carbocycle or an unsubstituted or substituted 5- or 6-membered monocyclic heterocycle.

7. The compound of claim 1, or a pharmaceutically acceptable salt, solvate, diastereomeric mixture, or individual enantiomers thereof, wherein:
each $R^c$ is independently hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2OH$, —$CH_2CN$, —$CH_2F$, —$CHF_2$, —$CF_3$, —$CN$, —$OH$, —$OCH_3$, —$OCH_2CH_3$, —$OCF_3$, —$CO_2H$, —$CO_2CH_3$, —$CO_2CH_2CH_3$, —$CH_2CO_2H$, —$CH_2CO_2CH_3$, —$CH_2CO_2CH_2CH_3$, —$C(=O)NH_2$, —$C(=O)NHCH_3$, —$C(=O)NHOCH_3$, —$C(=O)N(CH_3)_2$, —$SO_2N(CH_3)_2$, —$C(=NOH)H$, —$C(=NOCH_3)H$, —$CH_2C(=O)NH_2$, —$CH_2C(=O)NHCH_3$, —$CH_2C(=O)N(CH_3)_2$, —$NH_2$, —$NHCH_3$, —$N(CH_3)_2$, —$NHCO_2CH_3$, —$NHSO_2CH_3$, —$CH_2NH_2$, —$CH_2NHCH_3$, —$CH_2N(CH_3)_2$, $CH(CF_3)NH_2$, azetidinyl, or pyrrolidinyl;
each $R^d$ is independently hydrogen, F, Cl, Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2OH$, —$CH_2CN$, —$CH_2F$, —$CHF_2$, —$CF_3$, pyrrolyl, imidazolyl, pyrazolyl, triazolyl, tetrazolyl, —$CN$, —$OH$, —$OCH_3$, —$OCH_2CH_3$, —$OCF_3$, —$OCH_2OCH_3$, —$OCH_2OCH_2CH_3$, —$OCH_2CH_2OH$, —$C(=O)NHOCH_3$, —$C(=NOH)H$, —$C(=NOCH_3)H$, —$CH_2C(=O)NH_2$, —$NH_2$, $NHCO_2CH_3$, $NHSO_2CH_3$, $NH(C=O)NHCH_3$, $NH(C=O)NHOCH_3$, or $CH(CF_3)NH_2$;
or if one $R^c$ and one $R^d$ are on adjacent atoms of ring B then the adjacent $R^c$ and $R^d$ groups are taken together with the intervening atoms to which they are attached to form an unsubstituted or substituted 5- or 6-membered monocyclic heterocycle.

8. The compound of claim 1, or a pharmaceutically acceptable salt, solvate, diastereomeric mixture, or individual enantiomers thereof, wherein:
each $R^a$ is independently hydrogen, F, Cl, Br, —$CH_3$, —$CHF_2$, —$CHF_2$, —$CF_3$, —$CN$, —$OH$, —$OCH_3$, —$OCF_3$, or —$CH_2CH_2OH$;
each $R^b$ is independently hydrogen, F, Cl, Br, —$CH_3$, —$CHF_2$, —$CHF_2$, —$CF_3$, —$CN$, —$OCH_3$, or —$OCF_3$;
each $R^c$ is independently hydrogen, F, Cl, Br, —$CH_3$, —$CHF_2$, —$CHF_2$, —$CF_3$, pyrrolyl, imidazolyl, pyrazolyl, triazolyl, tetrazolyl, —$CN$, —$OH$, —$OCH_3$, —$OCF_3$, —$NH_2$, —$C(=O)NH_2$, —$CONHCH_3$, —$C(=NOH)H$, —$C(=NOCH_3)H$, —$SO_2CH_3$, —$SO_2N(CH_3)_2$, azetidinyl, or pyrrolidinyl;
each $R^d$ is independently hydrogen, F, Cl, Br, —$CH_3$, —$CH_2F$, —$CHF_2$, —$CF_3$, —$CN$, —$OH$, —$OCH_3$, —$OCF_3$, —$OCH_2OCH_3$, —$CH_2OH$, —$OCH_2CH_2OH$, —$C(=O)NH_2$, —$C(=O)NHOCH_3$, —$NH_2$, —$NHCO_2CH_3$, —$NH(C=O)NHOCH_3$, or $CH_2(C=O)NH_2$;
or if one $R^c$ and one $R^d$ are on adjacent atoms of ring B then the adjacent $R^c$ and $R^d$ groups are taken together with the intervening atoms to which they are attached to form an unsubstituted or substituted 5-membered monocyclic heterocycle.

9. The compound of claim 1, or a pharmaceutically acceptable salt, solvate, diastereomeric mixture, or individual enantiomers thereof, wherein:
$R^1$ hydrogen;
$R^2$ is hydrogen, unsubstituted or substituted $C_1$-$C_6$alkyl, unsubstituted or substituted $C_1$-$C_6$fluoroalkyl, unsubstituted or substituted $C_3$-$C_6$cycloalkyl or substituted or unsubstituted $C_2$-$C_6$heterocycloalkyl;
or $R^1$ and $R^2$ are taken together with the nitrogen atom to which they are attached to form ring C that is an unsubstituted or substituted N-containing $C_2$-$C_6$heterocycloalkyl;
$R^5$ is selected from the group consisting of hydrogen, halogen, —$OH$, —$OR^{14}$, —$S(=O)_2R^{14}$, —$N(R^{15})_2$, —$CN$, —$C(=O)OR^{15}$, —$C(=O)N(R^{15})_2$, unsubstituted or substituted $C_1$-$C_6$alkyl, and unsubstituted or substituted $C_1$-$C_6$fluoroalkyl;
or $R^2$ and $R^5$ are taken together with the intervening atoms to which they are attached to form an unsubstituted or substituted 4- to 7-membered saturated N-containing heterocyclic ring.

10. The compound of claim 1, or a pharmaceutically acceptable salt, solvate, diastereomeric mixture, or individual enantiomers thereof, wherein:

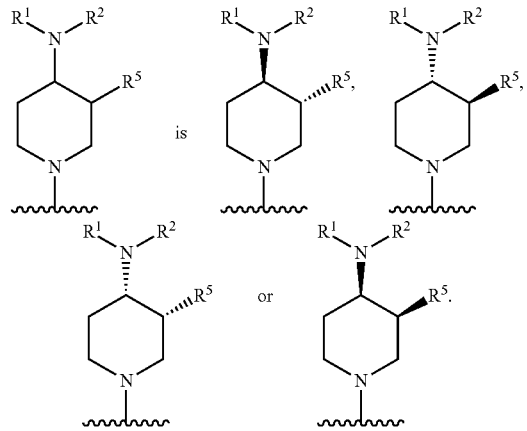

11. The compound of claim 10, or a pharmaceutically acceptable salt, solvate, diastereomeric mixture, or individual enantiomers thereof, wherein:
$R^1$ hydrogen;
$R^2$ is hydrogen, —$CH_3$, —$CH_2CH_3$, —$CH_2CH_2OH$, —$CH_2CH_2OCH_3$, $CH_2CH_2F$, —$CH_2CH_2NH_2$, —$CH_2CH_2NHCH_3$, —$CH_2CH_2N(CH_3)_2$, —$CH_2CH_2CH_3$, —$CH(CH_3)_2$, cyclopropyl, —$CH_2CH_2CH_2F$, $CH_2CH_2CH_2OH$, $CH_2CH_2CH_2OCH_3$, —$CH_2CH_2CH_2CH_3$, —$CH_2CH(CH_3)_2$, —$CH(CH_3)(CH_2CH_3)$, —$C(CH_3)_3$, cyclobutyl, cyclopentyl, cyclohexyl, oxetanyl, tetrahydrofuranyl, or tetrahydropyranyl;
or $R^1$ and $R^2$ are taken together with the nitrogen atom to which they are attached to form ring C that is an unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl;
$R^5$ is hydrogen, F, Cl, Br, —$OH$, —$OCH_3$, —$NH_2$, —$NHCH_3$, —$N(CH_3)_2$, —$OCH_2CH_3$, —$OCF_3$, —CH₃, —CH₂CH₃, —CH₂F, —CHF₂, —CF₃, —CN,
—C(=O)OCH₃, —C(=O)NH₂, —C(=O)NHCH₃, or
—C(=O)N(CH₃)₂;

or R² and R⁵ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

12. The compound of claim 1, wherein the compound has the following structure of Formula (AVb), or a pharmaceutically acceptable salt, solvate, diastereomeric mixture, or individual enantiomers thereof:

Formula (AVb)

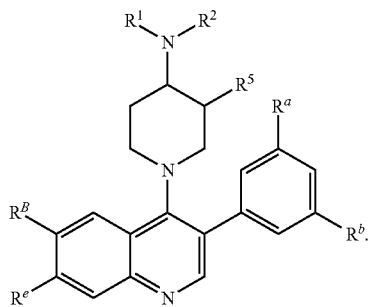

13. The compound of claim 12, wherein the compound of Formula (AVb) has the one of the following structures, or a pharmaceutically acceptable salt, solvate, diastereomeric mixture, or individual enantiomers thereof:

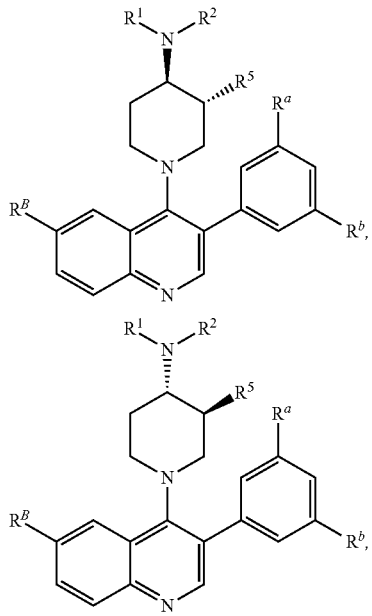

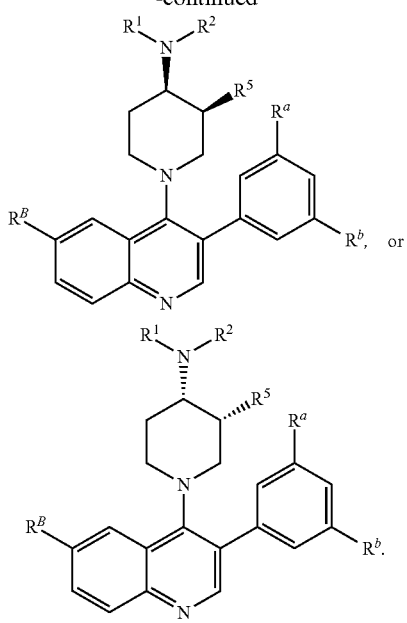

14. The compound of claim 12, or a pharmaceutically acceptable salt, solvate, diastereomeric mixture, or individual enantiomers thereof, wherein:

$R^B$ is 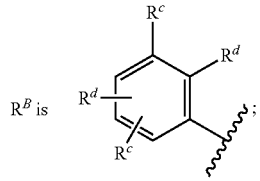;

R¹ hydrogen;

R² is hydrogen, methyl, ethyl, 2-fluoroethyl, 2-hydroxyethyl, 2-methoxyethyl, n-propyl, i-propyl, cyclopropyl, 3-fluoropropyl, 3-methoxypropyl, n-butyl, i-butyl, sec-butyl, cyclobutyl, or tert-butyl, or oxetanyl;

R⁵ is hydrogen, F, Cl, Br, —OH, —OCH₃, —NH₂, —NHCH₃, —N(CH₃)₂, —OCH₂CH₃, —OCF₃, —CH₃, —CH₂CH₃, —CH₂F, —CHF₂, —CF₃, —CN, —C(=O)OCH₃, —C(=O)NH₂, —C(=O)NHCH₃, or —C(=O)N(CH₃)₂;

or R² and R⁵ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

15. The compound of claim 12, or a pharmaceutically acceptable salt, solvate, diastereomeric mixture, or individual enantiomers thereof, wherein:

$R^B$ is 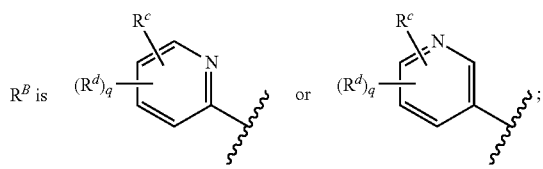

R¹ hydrogen;
R² is hydrogen, methyl, ethyl, 2-fluoroethyl, 2-hydroxyethyl, 2-methoxyethyl, n-propyl, i-propyl, cyclopropyl, 3-fluoropropyl, 3-methoxypropyl, n-butyl, i-butyl, sec-butyl, cyclobutyl, tert-butyl, or oxetanyl;
$R^5$ is hydrogen, F, Cl, Br, —OH, —OCH₃, —NH₂, —NHCH₃, —N(CH₃)₂, —OCH₂CH₃, —OCF₃, —CH₃, —CH₂CH₃, —CH₂F, —CHF₂, —CF₃, —CN, —C(=O)OCH₃, —C(=O)NH₂, —C(=O)NHCH₃, or —C(=O)N(CH₃)₂;
or $R^2$ and $R^5$ are taken together with the intervening atoms to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl.

16. The compound of claim 12, or a pharmaceutically acceptable salt, solvate, diastereomeric mixture, or individual enantiomers thereof, wherein:
$R^a$ is hydrogen, F, Cl, Br, —CH₃, —CH₂F, —CHF₂, —CF₃, —CN, —OH, —OCH₃, —OCF₃, —CH₂OH or —CH₂CH₂OH;
$R^b$ is hydrogen, F, Cl, Br, —CH₃, —CH₂F, —CHF₂, —CF₃, —CN, —OH, —OCH₃, or —OCF₃;
each $R^c$ is independently hydrogen, F, Cl, Br, —CH₃, —CH₂F, —CHF₂, —CF₃, pyrrolyl, imidazolyl, pyrazolyl, triazolyl, tetrazolyl, —CN, —OH, —OCH₃, —OCF₃, —NH₂, —C(=O)NH₂, —C(=NOH)H, —C(=NOCH₃)H, —SO₂CH₃, —SO₂N(CH₃)₂, azetidinyl, or pyrrolidinyl;
each $R^d$ is independently hydrogen, F, Cl, Br, —CH₃, —CH₂F, —CHF₂, —CF₃, —CN, —OH, —OCH₃, —OCF₃, —OCH₂OCH₃, —CH₂OH, —OCH₂CH₂OH, —C(=O)NH₂, —C(=O)NHOCH₃, —NH₂, —NHCO₂CH₃, —NH(C=O)NHOCH₃, or —CH₂(C=O)NH₂;
$R^e$ is hydrogen, F, Cl, Br, —CH₃, —CH₂F, —CHF₂, —CF₃, —CN, —OH, —OCH₃, or —OCF₃;
R¹ hydrogen;
R² is hydrogen;
$R^5$ is hydrogen, F, Cl, Br, —OH, —OCH₃, —NH₂, —NHCH₃, —N(CH₃)₂, —OCH₂CH₃, —OCF₃, —CH₃, —CH₂CH₃, —CH₂F, —CHF₂, —CF₃, —CN, —C(=O)OCH₃, —C(=O)NH₂, —C(=O)NHCH₃, or —C(=O)N(CH₃)₂;
or $R^2$ and $R^5$ are taken together with the intervening atoms to which they are attached to form an unsubstituted or substituted monocyclic 6-membered heterocyclic ring selected from unsubstituted or substituted piperidinyl, unsubstituted or substituted morpholinyl, unsubstituted or substituted thiomorpholinyl, or unsubstituted or substituted piperazinyl.

17. The compound of claim 12, or a pharmaceutically acceptable salt, solvate, diastereomeric mixture, or individual enantiomers thereof, wherein:
$R^a$ is hydrogen, F, Cl, —CH₃, —CF₃, —CN, —OH, —CH₂OH, —CH₂CH₂OH, —OCH₃, or —OCF₃;
$R^b$ is hydrogen, F, Cl, —CH₃, —CF₃, —CN, —OH, —OCH₃, or —OCF₃;
each $R^c$ is independently hydrogen, F, Cl, —CH₃, —CF₃, —CN, —OH, —NH₂, —OCH₃, —OCF₃, —C(=O)NH₂, —C(=NOH)H, or —C(=NOCH₃)H;
each $R^d$ is independently hydrogen, F, Cl, —CH₃, —CF₃, —CN, —OH, —NH₂, —OCH₃, —OCF₃;
R¹ hydrogen;
R² is hydrogen;
$R^5$ is hydrogen;
or $R^2$ and $R^5$ are taken together with the intervening atoms to which they are attached to form an unsubstituted or substituted morpholinyl.

18. A pharmaceutical composition comprising a compound of claim 1, or a pharmaceutically acceptable salt, solvate, diastereomeric mixture, or individual enantiomers thereof, and at least one pharmaceutically acceptable excipient.

19. A method of modulating somatostatin receptor subtype 2 (SSTR2) activity in a mammal comprising administering a compound of claim 1, or a pharmaceutically acceptable salt, solvate, diastereomeric mixture, or individual enantiomers thereof, to the mammal.

20. A method of treating acromegaly, a neuroendocrine tumor, pain, or combinations thereof, in a mammal comprising administering a compound of claim 1, or a pharmaceutically acceptable salt, solvate, diastereomeric mixture, or individual enantiomers thereof, to the mammal in need thereof.

* * * * *

UNITED STATES PATENT AND TRADEMARK OFFICE
CERTIFICATE OF CORRECTION

PATENT NO. : 9,896,432 B2
APPLICATION NO. : 15/647758
DATED : February 20, 2018
INVENTOR(S) : Jian Zhao et al.

Page 1 of 1

It is certified that error appears in the above-identified patent and that said Letters Patent is hereby corrected as shown below:

In the Specification

• Column 1, Lines 15-17: "This invention was made with the support of the United States government under SBIR Grant No. 1R44NS092231-01 by the National Institutes of Health." should read
-- This invention was made with government support under grant number NS092231 awarded by the National Institutes of Health. The government has certain rights in the invention. --.

In the Claims

• Claim 3: Column 335, Lines 50-51: "—$SO_2R^{14}$, —$SO_2N(R^{15})_2$ or; and" should read -- —$SO_2R^{14}$, or —$SO_2N(R^{15})_2$; and --.

• Claim 8: Column 337, Line 47: "—CHF," should read -- —$CH_2F$, --.
• Claim 8: Column 337, Line 50: "—CHF," should read -- —$CH_2F$, --.
• Claim 8: Column 337, Line 52: "—CHF," should read -- —$CH_2F$, --.

• Claim 14: Column 340, Line 46: "cyclobutyl, or tert-butyl, or oxetanyl;" should read -- cyclobutyl, tert-butyl, or oxetanyl; --.

Signed and Sealed this
Seventh Day of July, 2020

Andrei Iancu
*Director of the United States Patent and Trademark Office*